US012773450B2

(12) United States Patent
Amara et al.

(10) Patent No.: US 12,773,450 B2
(45) Date of Patent: Oct. 27, 2026

(54) CORONAVIRUS VACCINES, COMPOSITIONS, AND METHODS RELATED THERETO

(71) Applicant: EMORY UNIVERSITY, Atlanta, GA (US)

(72) Inventors: Rama Rao Amara, Atlanta, GA (US); Sailaja Gangadhara, Atlanta, GA (US); Nanda Kishore Routhu, Atlanta, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 892 days.

(21) Appl. No.: 17/918,431

(22) PCT Filed: Apr. 21, 2021

(86) PCT No.: PCT/US2021/028444

§ 371 (c)(1),
(2) Date: Oct. 12, 2022

(87) PCT Pub. No.: WO2021/216743

PCT Pub. Date: Oct. 28, 2021

(65) Prior Publication Data

US 2023/0143228 A1 May 11, 2023

Related U.S. Application Data

(60) Provisional application No. 63/143,191, filed on Jan. 29, 2021, provisional application No. 63/084,065, filed on Sep. 28, 2020, provisional application No. 63/044,711, filed on Jun. 26, 2020, provisional application No. 63/012,920, filed on Apr. 21, 2020.

(51) Int. Cl.

| | |
|---|---|
| ***C07K 14/165*** | (2006.01) |
| ***A61K 39/215*** | (2006.01) |
| ***C12N 15/86*** | (2006.01) |
| *A61K 39/00* | (2006.01) |

(52) U.S. Cl.

CPC ............ *A61K 39/215* (2013.01); *C12N 15/86* (2013.01); *A61K 2039/53* (2013.01); *C12N 2770/20022* (2013.01); *C12N 2770/20023* (2013.01); *C12N 2770/20034* (2013.01)

(58) Field of Classification Search

None

See application file for complete search history.

(56) References Cited

U.S. PATENT DOCUMENTS

2017/0067030 A1 3/2017 Wimmer et al.
2020/0061185 A1 2/2020 Graham et al.

FOREIGN PATENT DOCUMENTS

WO 2018081318 5/2018
WO 2018115527 A2 6/2018
WO 2018170347 A2 9/2018

OTHER PUBLICATIONS

Altenburg et al. Modified Vaccinia Virus Ankara (MVA) as Production Platform for Vaccines against Influenza and Other Viral Respiratory Diseases, Viruses, 2014, 6.
Andersen et al. The proximal origin of SARS-CoV-2, Nat Med, 2020, 26(4):450-452.
Chen et al. The SARS-CoV-2 Vaccine Pipeline: an Overview, Current Tropical Medicine Reports (2020) 7:61-64.
Corbett et al. SARS-CoV-2 mRNA Vaccine Design Enabled by Prototype Pathogen Preparedness, Nature, 2020, 586(7830): 567-571.
Geovax et al. GeoVax Progresses in Coronavirus (COVID-19) Vaccine Development, 2020 available at https://www.geovax.com/news/geovax-progresses-in-coronavirus-covid -. . . .
Grifoni et al. A Sequence Homology and Bioinformatic Approach Can Predict Candidate Targets for Immune Responses to SARS-CoV-2, 2020, Cell Host & Microbe, 27, 671-680.
Kirchdoefer, Stabilized coronavirus spikes are resistant to conformational changes induced by receptor recognition or proteolysis, Sci Rep, 2018, 8(1):15701.
Mteus et al. Selective and cross-reactive SARS-CoV-2 T cell epitopes in unexposed humans, Mateus et al., Science 370, 89-94 (2020).
Perlman et al. Coronaviruses post-SARS: update on replication and pathogenesis, Nat Rev Microbiol, 2009, 7 (6):439-50.
Polack et al. Safety and Efficacy of the BNT162b2 mRNA Covid-19 Vaccine, N Engl J Med, 2021, 385 (19):1761-1773.
Walls et al. Structure, Function, and Antigenicity of the SARSCoV-2 Spike Glycoprotein, Cell, 2020, 180, 1-12.
Wrapp et al. Cryo-EM structure of the 2019-nCoV spike in the prefusion conformation, Science, 367, 1260-1263 (2020).
Walls, Alexandra C., et al. "Structure, function, and antigenicity of the SARS-CoV-2 spike glycoprotein." Cell 181.2 (2020): 281-292.
Andersen, Kristian G., et al. "The proximal origin of SARS-CoV-2." Nature medicine 26.4 (2020): 450-452.
Altenburg, Arwen F., et al. "Modified vaccinia virus ankara (MVA) as production platform for vaccines against influenza and other viral respiratory diseases." Viruses 6.7 (2014): 2735-2761.
Shihab, Hashem A., et al. "GTB-an online genome tolerance browser." BMC bioinformatics 18.1 (2017): 1-6.

(Continued)

*Primary Examiner* — Michael D Pak

(57) ABSTRACT

This disclosure relates to methods of promoting immune responses against coronavirus, such as SARS-CoV-2, and compositions related thereto. In certain embodiments, this disclosure relates to methods of vaccinating for coronavirus comprising administering to the subject a composition disclosed herein. In certain embodiments, the composition comprises a recombinant virus such as recombinant MVA that encodes a coronavirus spike protein. In certain embodiments, the coronavirus spike protein comprises a proline mutation at position 986. In certain embodiments, the coronavirus spike protein comprises a proline mutation at position 987.

11 Claims, 12 Drawing Sheets

Specification includes a Sequence Listing.

(56) References Cited

OTHER PUBLICATIONS

Ng, Pauline C., and Steven Henikoff. "Predicting the effects of amino acid substitutions on protein function." Annual review of genomics and human genetics 7.1 (2006): 61-80.

Teng, S., E. Michonova-Alexova, and E. Alexov. "Approaches and resources for prediction of the effects of non-synonymous single nucleotide polymorphism on protein function and interactions." Current pharmaceutical biotechnology 9.2 (2008): 123-133.

Saldaño, Tadeo E., et al. "Evolutionary conserved positions define protein conformational diversity." PLoS Computational Biology 12.3 (2016): e1004775.

Marks, Debora S., Thomas A. Hopf, and Chris Sander. "Protein structure prediction from sequence variation." Nature biotechnology 30.11 (2012): 1072-1080.

Mackenzie, Craig O., and Gevorg Grigoryan. "Protein structural motifs in prediction and design." Current opinion in structural biology 44 (2017): 161-167.

Mackenzie, Craig O., Jianfu Zhou, and Gevorg Grigoryan. "Tertiary alphabet for the observable protein structural universe." Proceedings of the National Academy of Sciences 113.47 (2016): E7438-E7447.

Joseph, Agnel Praveen, and Alexandre G. de Brevern. "From local structure to a global framework: recognition of protein folds." Journal of The Royal Society Interface 11.95 (2014): 20131147.

Wei, Leyi, and Quan Zou. "Recent progress in machine learning-based methods for protein fold recognition." International journal of molecular sciences 17.12 (2016): 2118.

Wyatt, Linda S., et al. "Highly attenuated smallpox vaccine protects mice with and without immune deficiencies against pathogenic vaccinia virus challenge." Proceedings of the National Academy of Sciences 101.13 (2004): 4590-4595.

Shimizu, Yoshihiro, et al. "Cell-free translation reconstituted with purified components." Nature biotechnology 19.8 (2001): 751-755.

Asahara, Haruichi, and Shaorong Chong. "In vitro genetic reconstruction of bacterial transcription initiation by coupled synthesis and detection of RNA polymerase holoenzyme." Nucleic acids research 38.13 (2010): e141-e141.

Needleman, Saul B., and Christian D. Wunsch. "A general method applicable to the search for similarities in the amino acid sequence of two proteins." Journal of molecular biology 48.3 (1970): 443-453.

Smith, Temple F., and Michael S. Waterman. "Comparison of biosequences." Advances in applied mathematics 2.4 (1981): 482-489.

Gribskov, Michael, and Richard R. Burgess. "Sigma factors from *E. coli*, B. subtilis, phage SP01, and phage T4 are homologous proteins." Nucleic Acids Research 14.16 (1986): 6745-6763.

Schwarz, R. and Dayhoff, M. Matrices for Detecting Distant Relationships. In: Dayhoff, M., Ed., Atlas of Protein Sequences, National Biomedical Research Foundation, (1979) 353-358.

Wang, Yuancheng, et al. "2A self-cleaving peptide-based multi-gene expression system in the silkworm *Bombyx mori*." Scientific reports 5.1 (2015): 16273, 1-10.

Lv, H et al., Cross-reactive antibody response between SARS-CoV-2 and SARS-CoV infections. BioRxiv. Mar. 17, 2020, pp. 1-20.

Chen et al., Recombinant Modified Vaccinia Virus Ankara Expressing the Spike Glycoprotein of Severe Acute Respiratory Syndrome Coronavirus Induces Protective Neutralizing Antibodies Primarily Targeting the Receptor Binding Region. Journal of Virology. 2005, vol. 79, No. 5, pp. 2678-2688.

Xiong et al., A thermostable, closed SARS-CoV-2 spike protein trimer. Nature Structural and Molecular Biology. Oct. 2020, vol. 27, pp. 934-941.

International Search Report and Written Opinion issued in PCT/US2021/028444, mailed Oct. 13, 2021.

| Scoring criterion | | Number of Syncytia |
|---|---|---|
| Grade 0 | None | 0 |
| Grade 1 | Mild | 0-5 |
| Grade 2 | Moderate | 5-10 |
| Grade 3 | Severe | 10-15 |
| | Animal ID | Type 2 pneumocyte hyperplasia | Alveolar septal thickening | Fibrosis | Perivascular cuffing | Peribronchiolar hyperplasia | Syncytia formation | Total Score |
|---|---|---|---|---|---|---|---|---|
| MVA-Wt (Control) | RTb18 | 3 | 2 | 0 | 2 | 2 | 1 | 10 |
| | RTr17 | 0 | 1 | 0 | 2 | 2 | 1 | 6 |
| | RWb18 | 2 | 2 | 0 | 2 | 2 | 1 | 9 |
| | RVo17 | 1 | 1 | 3 | 2 | 1 | No | 8 |
| | RUp17 | 2 | 2 | 0 | 2 | 1 | No | 7 |
| MVA-S (Vaccine) | RAw17 | 0 | 0 | 0 | 0 | 0 | 0 | 0 |
| | RCc18 | 0 | 1 | 0 | 2 | 1 | 0 | 4 |
| | RKp17 | 0 | 1 | 0 | 2 | 2 | 0 | 5 |
| | RSt17 | 1 | 1 | 0 | 1 | 1 | 0 | 4 |
| | RSu17 | 2 | 2 | 0 | 2 | 2 | 0 | 8 |
FIG. 9
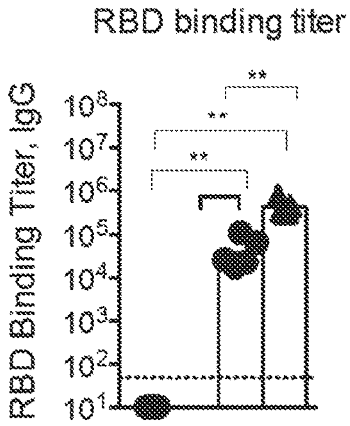
FIG. 10A
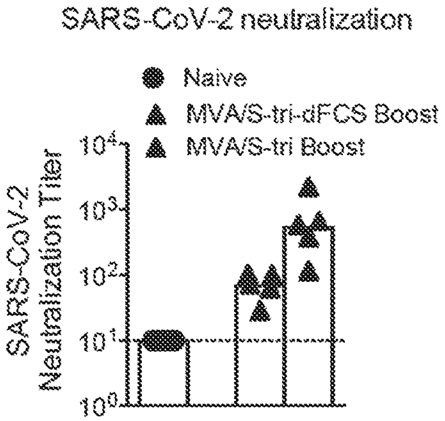
FIG. 10B
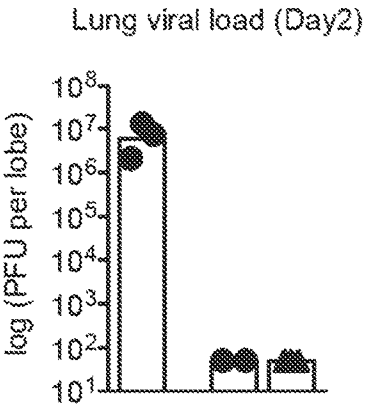
FIG. 10C

CORONAVIRUS VACCINES, COMPOSITIONS, AND METHODS RELATED THERETO

CROSS-REFERENCE TO RELATED APPLICATIONS

This application claims the benefit of U.S. Provisional Application No. 63/012,920 filed Apr. 21, 2020, U.S. Provisional Application No. 63/044,711 filed Jun. 26, 2020, U.S. Provisional Application No. 63/084,065 filed Sep. 28, 2020, and U.S. Provisional Application No. 63/143,191 filed Jan. 29, 2021. The entirety of each of these applications is hereby incorporated by reference for all purposes.

STATEMENT REGARDING FEDERALLY SPONSORED RESEARCH OR DEVELOPMENT

This invention was made with government support under AI148378 awarded by the National Institutes of Health. The government has certain rights in this invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 20121PCT_ST25.txt. The text file is 240 KB, was created on Apr. 20, 2021, and is being submitted electronically via EFS-Web.

BACKGROUND

About 10% of common colds are due to certain coronavirus (CoV) strains associated with mild symptoms. More dangerous human strains such as severe acute respiratory syndrome associated coronavirus (SARS-CoV-1) and SARS-CoV-2 (also referred to as COVID-19) are believed to result from coronavirus strains jumping to humans by secondary zoonotic transfers, e.g., from bats to cats and cats to humans. In humans, SARS-CoV-2 can be transferred from individuals who have mild symptoms or are asymptomatic and has caused numerous deaths worldwide. Thus, there is a need to find an effective vaccine.

The SARS-CoV-2 genome has about 30 kb that can be directly read by ribosomes with host cells. The RNA forms a ribonucleoprotein complex within virus particles having a viral lipid envelope membrane made up of membrane (M) glycoproteins, trimeric spike (S) glycoproteins and envelope (E) proteins. The trimeric units of the spike protein contain a receptor binding domain and a fusion domain that anchors it into lipid membrane.

Walls et al. report that the SARS-CoV-2 spike protein is involved in viral cell entry by recognizing human ACE2. Cell, 2020, 180, 1-12.

Andersen et al. report six receptor binding domain amino acids L455, F486, Q493, S494, N501 and Y505 are involved in binding to ACE2 receptors in SARS-CoV-2. Nat Med, 2020.

Altenburg et al. report modified vaccinia virus Ankara (MVA) as a production platform for vaccines against influenza and other viral respiratory diseases. Viruses, 2014, 6(7):2735-61.

Graham et al. report prefusion coronavirus spike proteins and uses. See WO 2018/081318.

References cited herein are not an admission of prior art.

SUMMARY

This disclosure relates to methods of promoting immune responses against coronavirus, such as SARS-CoV-2, and compositions related thereto. In certain embodiments, this disclosure relates to methods of vaccinating for coronavirus comprising administering to the subject a composition disclosed herein. In certain embodiments, the composition comprises a recombinant virus such as recombinant MVA that encodes a coronavirus spike protein. In certain embodiments, the coronavirus spike protein comprises a proline mutation at position 986. In certain embodiments, the coronavirus spike protein comprises a proline mutation at position 987.

In certain embodiments, this disclosure relates to methods of vaccinating or immunizing a human subject comprising administering an effective amount of coronavirus spike protein, a virus-like particle comprising a coronavirus spike protein, a nucleic acid and/or recombinant virus that encodes a coronavirus spike protein or segment thereof as disclosed herein under conditions such that a spike protein and/or virus-like particles with a spike protein are formed in the subject.

In certain embodiments, this disclosure relates to methods of vaccinating or immunizing a human subject comprising administering an effective amount of coronavirus spike protein, a virus-like particle comprising a coronavirus spike protein, a nucleic acid and/or recombinant virus that encodes a coronavirus spike protein or segment thereof as disclosed herein in combination with a nucleic acid encoding a T cell stimulating chimeric protein under conditions such that a spike protein and/or virus-like particles with a spike protein are formed in the subject.

In certain embodiments, this disclosure contemplates pharmaceutical compositions comprising a coronavirus spike protein or segment thereof as disclosed herein and variants thereof. In certain embodiments, this disclosure contemplates pharmaceutical compositions comprising virus-like particles having a coronavirus spike protein or segment thereof as disclosed herein and variants thereof. In certain embodiments, this disclosure contemplates pharmaceutical compositions comprising a nucleic acid and/or recombinant virus that encodes a coronavirus spike protein or segment thereof as disclosed herein and variants thereof.

In certain embodiments, this disclosure contemplates nucleic acids, recombinant vectors, viral vectors, and bacterial plasmids encoding a coronavirus spike protein or segment thereof as disclosed herein which forms trimeric protein complexes and uses in vaccination methods disclosed herein.

In certain embodiments, this disclosure relates to cells and other expression vectors and expression systems for use in producing a coronavirus spike protein or segment thereof as disclosed herein and trimeric coronavirus spike proteins or segment thereof as disclosed herein, or variants thereof.

BRIEF DESCRIPTION OF THE SEVERAL VIEWS OF THE DRAWINGS

FIG. 9 shows data on the pathology score of lungs of MVA/S vaccinated and MVA/Wt immunized rhesus macaques 10 days post infection.

FIGS. 10A-C shows data indicating MVA-based vaccines (MVA-S-tri and MVA-S-tri-dFCS) induces a robust neutralizing antibody response and provides protection against SARS-CoV-2 challenge in mice.

FIG. 10A shows data where six-week-old female BALB/c mice were immunized either with MVA-S-tri (circles) or MVA-S-tri-dFCS (upward triangle) vaccines via intramuscular route at weeks 0 and 4. Immunized mice were infected with 10^5 PFU SARS-CoV-2 MA10. Endpoint IgG titers against SARS-CoV-2 RBD measured in serum collected at week 2 post-boost immunizations.

FIG. 10B shows data on neutralization titer against live mNeonGreen SARS-CoV-2 virus. The dotted line represents the limit of detection.

FIG. 10C shows data on lung SARS-CoV-2 (MA10) viral titers of vaccinated animals compared to unvaccinated.

DETAILED DISCUSSION

Figure 1A:
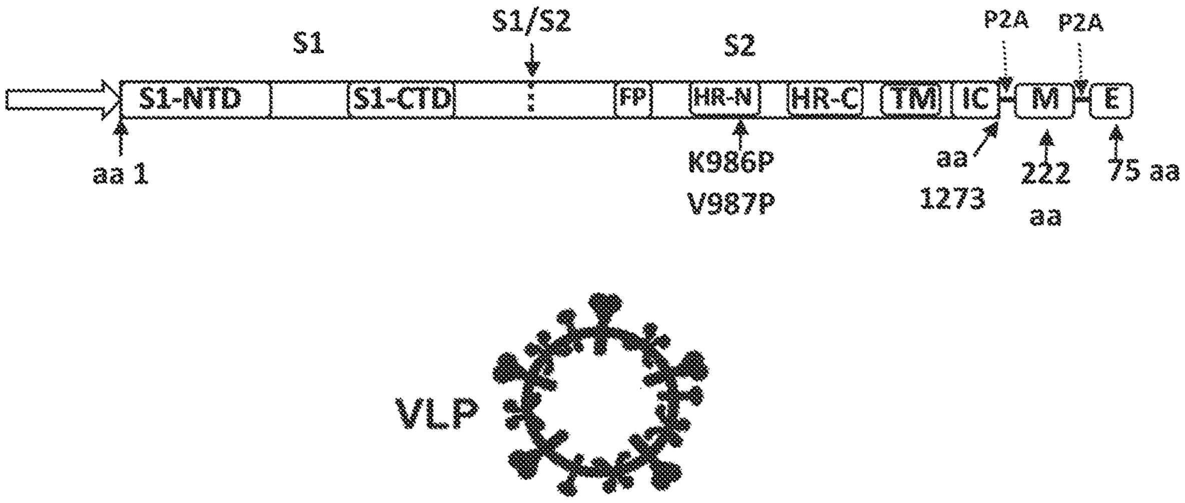
FIG. 1A illustrates a recombinant nucleic acid that encodes the spike protein of SARS-CoV-2 as a full-length protein displayed on VLPs (S-VLP) expressed within an MVA construct. In the s2 domain, the amino acids at positions 986 and 987 are mutated to proline. This expresses the full-length coronavirus S protein (aa 1 to 1273) followed by membrane protein (M; aa 1 to 222) and envelope glycoprotein (E; aa 1 to 75). The S, M and E are expresses as a single transcript from a single mH5 promoter using Porcine 2A sequences between S and M, and M and E. This construct is designed to produce VLPs that will display S, M and E proteins on the VLP membrane. Two point-mutations were introduced at positions 986 (K986P) and 987 (V987P) to introduce prolines. These mutations stabilize the protein in pre-fusion confirmation. The spike protein of SARS-CoV-2 is expressed as a trimer on the surface of the virion. Multimeric expression of the antigen in the form of virus-like particles (VLPs) generates antibodies by focusing the response away from unwanted epitopes. NTD—N terminal domain; CTD—C terminal domain; FP—Fusion peptide; HR-N—Heptad repeat N; HR-C—Heptad repeat C; TM—Transmembrane anchor; IC—intracellular tail, M—membrane protein; E—Envelope protein; P2A—Porcine 2A; aa—amino acid.
Figure 1B:
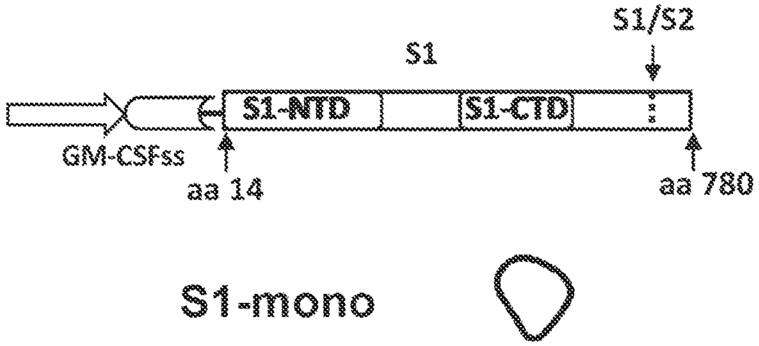
FIG. 1B illustrates a recombinant nucleic acid that encodes the spike protein of SARS-CoV-2 with a truncated spike ACE2 receptor domain (S) lacking the fusion domain. GM-CSFss refers to a GM-CSF signal sequence. This expresses the amino acids 14-780 of the S protein (contains S1 and part of S2). The first 13 amino acids of the spike protein were replaced with the GM-CSF secretory signal sequence to enhance protein secretion. The protein is expected to be secreted out of the cell as a monomer.
Figure 1C:
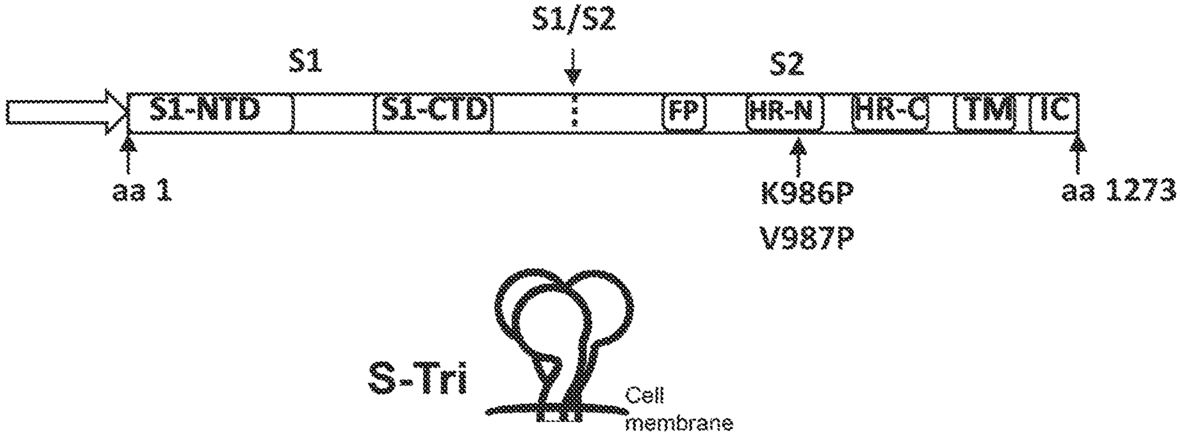
FIG. 1C illustrates a recombinant nucleic acid that encodes the spike protein of SARS-CoV-2 for forming a trimeric complex (S-Tri) in a lipid membrane for coating on cells. This expresses the full-length S protein (aa 1 to 1273) under the control of mH5 promoter. This leads to expression of a trimeric S protein that will be anchored on a membrane but will not make VLPs.
Figure 1D:
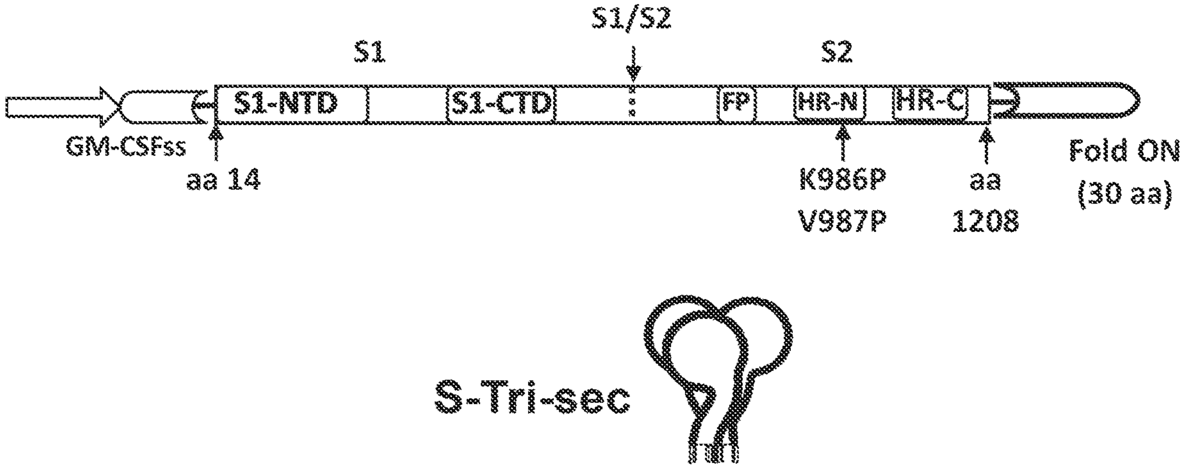
FIG. 1D illustrates a recombinant nucleic acid that encodes the spike protein of SARS-CoV-2 with a self-folding sequence on the C-terminus for forming a trimeric complex (S-Tri-sec). This expresses the amino acids 14-1208 of the S protein (contains most of S without transmembrane and cytoplasmic tail regions). The first 13 amino acids of the spike protein were replaced with the GM-CSF secretory signal sequence to enhance protein secretion. A Fold-on trimerization sequence downstream of S at position 1208 was added. This protein is secreted out of the cell as a stabilized trimeric protein. GM-CSFss refers to a GM-CSF signal sequence.

Before the present disclosure is described in greater detail, it is to be understood that this disclosure is not limited to embodiments described, and as such may, of course, vary. It is also to be understood that the terminology used herein is for describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. As such, the terms "a", "an", "one or more" and "at least one" can be used interchangeably. Similarly, the terms "comprising", "including" and "having" can be used interchangeably. It is further noted that the claims may be drafted to exclude any optional element.

"Subject" refers to any animal, preferably a human patient, livestock, rodent, monkey or domestic pet. The term is used herein to encompasses apparently healthy, non-infected individuals or a patient who is known to be infected with, diagnosed with, a pathogen.

As used herein, the term "combination with" when used to describe administration with an additional treatment means that the agent may be administered prior to, together with, or after the additional treatment, or a combination thereof.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide. The term "consisting of" in reference to a peptide having an amino acid sequence refers a peptide having the exact number of amino acids in the sequence and not more or having not more than a rage of amino acids expressly specified in the claim. In certain embodiments, the disclosure contemplates that the "N-terminus of a peptide may consist of an amino acid sequence," which refers to the N-terminus of the peptide having the exact number of amino acids in the sequence and not more or having not more than a rage of amino acids specified in the claim however the C-terminus may be connected to additional amino acids, e.g., as part of a larger peptide. Similarly, the disclosure contemplates that the "C-terminus of a peptide may consist of an amino acid sequence," which refers to the C-terminus of the peptide having the exact number of amino acids in the sequence and not more or having not more than a rage of amino acids specified in the claim however the N-terminus may be connected to additional amino acids, e.g., as part of a larger peptide.

The terms "protein" and "peptide" refer to polymers comprising amino acids joined via peptide bonds and are used interchangeably. Amino acids may be naturally or non-naturally occurring. A "chimeric protein" or "fusion protein" is a molecule in which different portions of the protein are derived from different origins such that the entire molecule is not naturally occurring. A chimeric protein may contain amino acid sequences from the same species of different species as long as they are not arranged together in the same way that they exist in a natural state. Examples of a chimeric protein include sequences disclosed herein that are contain one, two or more amino acids attached to the C-terminal or N-terminal end that are not identical to any naturally occurring protein, such as in the case of adding an amino acid containing an amine side chain group, e.g., lysine, an amino acid containing a carboxylic acid side chain group such as aspartic acid or glutamic acid, a polyhistidine tag, e.g. typically four or more histidine amino acids. Contemplated chimeric proteins include those with self-cleaving peptides such as P2A-GSG. See Wang. Scientific Reports 5, Article number: 16273 (2015).

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, this disclosure contemplates that chimeric proteins disclosed herein may be variants. Variants may include 1 or 2 amino acid substitutions or conserved substitutions. Variants may include 3 or 4 amino acid substitutions or conserved substitutions. Variants may include 5 or 6 or more amino acid substitutions or conserved substitutions. Variant include those with not more than 1% or 2% of the amino acids are substituted. Variant include those with not more than 3% or 4% of the amino acids are substituted. Variants include proteins with greater than 80%, 89%, 90%, 95%, 98%, or 99% identity or similarity.

Variant peptides can be produced by mutating a vector to produce appropriate codon alternatives for polypeptide translation. Active variants and fragments can be identified with a high probability using computer modeling. Shihab et al. report an online genome tolerance browser. BMC Bioinformatics, 2017, 18(1):20. Ng et al. report methods of predicting the effects of amino acid substitutions on protein function. Annu Rev Genomics Hum Genet, 2006, 7:61-80. Teng et al. Approaches and resources for prediction of the effects of non-synonymous single nucleotide polymorphism on protein function and interactions. Curr Pharm Biotechnol, 2008, 9(2): 123-33.

Desired amino acid substitutions (whether conservative or non-conservative) can be determined by those skilled in the art at the time such substitutions are desired. Guidance in determining which and how many amino acid residues may be substituted, inserted or deleted without abolishing biological activity may be found using computer programs well known in the art, for example, RaptorX, ESyPred3D, HHpred, Homology Modeling Professional for HyperChem, DNAStar, SPARKS-X, EVfold, Phyre, and Phyre2 software. See also Saldano et al. Evolutionary Conserved Positions Define Protein Conformational Diversity, PLoS Comput Biol. 2016, 12(3):e1004775; Marks et al. Protein structure from sequence variation, Nat Biotechnol. 2012, 30(11): 1072-80; Mackenzie et al. Curr Opin Struct Biol, 2017, 44:161-167 Mackenzie et al. Proc Natl Acad Sci USA. 113(47):E7438-E7447 (2016); Joseph et al. J R Soc Interface, 2014, 11(95):20131147, Wei et al. Int. J. Mol. Sci. 2016, 17(12), 2118. Variants can be tested in functional assays. Certain variants have less than 10%, and preferably less than 5%, and still more preferably less than 2% changes (whether substitutions, deletions, and so on).

Sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG (SEQ ID NO: 32) and GGGGT (SEQ ID NO: 33) have a sequence identity of 4 out of 5 or 80%. For example, the polypeptides GGGPPP (SEQ ID NO: 34) and GGGAPPP (SEQ ID NO: 35) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q. The amino acid groups are also considered conserved substitutions.

Percent identity can be determined, for example, by comparing sequence information using the GAP computer program, version 6.0, available from the University of Wisconsin Genetics Computer Group (UWGCG). The GAP program utilizes the alignment method of Needleman and Wunsch (J Mol Biol 1970 48:443), as revised by Smith and Waterman (Adv Appl Math 1981 2:482). Briefly, the GAP program defines identity as the number of aligned symbols (i.e., nucleotides or amino acids) which are identical, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (Nucl Acids Res 1986 14:6745), as described by Schwartz and Dayhoff (eds., Atlas of Protein Sequence and Structure, National Biomedical Research Foundation, Washington, D.C. 1979, pp. 353-358); (2) a penalty of 3.0 for each gap and an additional 0.10 penalty for each symbol in each gap; and (3) no penalty for end gaps.

The term "recombinant vector" when made in reference to vectors and nucleic acids refers to a nucleic acid molecule that is comprised of segments of nucleic acid joined together by means of molecular biological techniques. The term recombinant nucleic acid is distinguished from the natural recombinants that result from crossing-over between homologous chromosomes. Recombinant nucleic acids as used herein are an unnatural union of nucleic acids from nonhomologous sources, usually from different organisms.

The terms "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

In certain embodiments, a vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

Protein "expression systems" refer to in vivo and in vitro (cell free) systems. Systems for recombinant protein expression typically utilize somatic cells transfected with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vector, these extracts and components can synthesize proteins of interest. Cell-free systems typically do not contain proteases and enable labelling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (at1D), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

Coronavirus Vaccines

In certain embodiments, this disclosure relates to methods of vaccinating or immunizing a human subject comprising administering an effective amount of a coronavirus spike protein, a trimeric spike protein complex, a virus-like particle comprising a coronavirus spike protein, a nucleic acid and/or recombinant virus that encodes a coronavirus spike protein or segment thereof as disclosed herein under conditions such that spike protein, trimeric complex, and/or virus-like particles with spike protein are formed in the subject.

In certain embodiments, this disclosure contemplates pharmaceutical compositions comprising a coronavirus spike protein, trimeric complex, or segment thereof as disclosed herein and variants thereof. In certain embodiments, this disclosure contemplates pharmaceutical compositions comprising virus-like particles having a coronavirus spike protein or segment thereof as disclosed herein and variants thereof. In certain embodiments, this disclosure contemplates pharmaceutical compositions comprising a nucleic acid and/or recombinant virus that encodes a coronavirus spike protein or segment thereof as disclosed herein and variants thereof.

In certain embodiments, this disclosure contemplates nucleic acids, recombinant vectors, viral vectors, and bacterial plasmids encoding a coronavirus spike protein or segment thereof as disclosed herein which form trimeric protein complexes and uses in vaccination methods disclosed herein.

In certain embodiments, this disclosure contemplates non-naturally occurring coronavirus spike protein, or nucleic acid having a sequence encoding a mutation, comprising a proline mutation at position 986. In certain embodiments, the coronavirus spike protein, or nucleic acid having a sequence encoding a mutation, further comprises a proline mutation at position 987. In certain embodiments, the coronavirus spike protein comprises amino acid sequence (SEQ ID NO: 1)

MF VFLVLLPLVSSQCVNLTTRTQLPPAY-TNSFTRGVYYPDKVFRSSVLHSTQDLF LPFF-SNVTWF-HAIHVSGTNGTKRFDNPVLPFNDGVYFASTEKSNII RGWIFGTTLDSKTQS LLIVNNATNV-VIKVCEFQFCNDPFLGVYYHKNNKSWMESEFRVYS-SANNCTFEYVSQPF LMDLEGKQGNFKNL-REFVFKNIDGYFKIYSKHTPINLVRDLPQGFSALEPLV DLPIGINIT RFQTLLALHR-SYLTPGDSSSGWTAGAAAYYVGYLQPRT-FLLKYNENGTITDAVDCALD PLSETKCTLKSFTVEKGIYQTSNFRVQPTE-SIVRFPNITNLCPFGEVFNATRFASVYAWNR KRISNC-VADYSVLYNSASFSTFKCYGVSPTKLNDLCFTNVY-ADSFVIRGDEVRQIAPGQT GKIADYNYKLPDDFTGCVIAWNSNNLD SKVGGNY-NYLYRLFRKSNLKPFERDISTEIYQ AGSTPCNGVEG-FNCYFPLQ SYGFQPTNGVGYQPYRVVVLSFELL-HAPATVCGPKKSTNL VKNKCVNFNFNGLTGTGVLTESNKKFLPFQQFGR-DIADTTDAVRDPQTLEILDITPCSFG GVSVITPGTNTSNQVAVLYQDVNCTEVPVAI-HADQLTPTWRVYSTGSNVFQTRAGCLIG AEHVNN-SYECDIPIGAGICASYQTQTNSPRRARSVASQSIIAY-TMSLGAENSVAYSNNSIA IPTNFTISVTTEILPVSMTKT SVDCTMYICGD-STECSNLLLQYGSFCTQLNRALTGIAVEQ DKNTQEVFAQVKQIYKTPPIKDFGGFNF SQILPDP SKP SKRSFIEDLLFNKVTLADAGFIK QYGDCLGDI-AARDLICAQKFNGLTVLPPLLTDEMIAQYTSAL-LAGTITSGWTFGAGAAL QIPFAMQMAYRFN-GIGVTQNVLYENQKLIANQFNSAIGKIQDSLS STASALGKLQDVVN QNAQALNTLVKQLSSNFGAIS-SVLNDILSRLDPP (spike sequence amino acids 1 to 987) or variants thereof. In certain embodiments, the amino acid position of a coronavirus protein is in relation to SEQ ID NO: 1.

In certain embodiments, this disclosure contemplates non-naturally occurring coronavirus spike protein, or nucleic acid having a sequence encoding a mutation, comprising a mutation in the furin cleavage site at position 682, 683, 684 or 685, In certain embodiments, the mutation in the furin cleavage site is at position 682. In certain embodiments, the coronavirus spike protein comprises a serine mutation at position 682. In certain embodiments, this disclosure contemplates non-naturally occurring coronavirus spike protein, or nucleic acid having a sequence encoding a mutation, comprising a proline mutation at position 986. In certain embodiments, the coronavirus spike protein, or nucleic acid having a sequence encoding a mutation, further comprises a proline mutation at position 987. In certain embodiments, the coronavirus spike protein comprises amino acid sequence (SEQ ID NO: 23)

MFVFLVLLPLVS SQCVNLTTRTQLPPAY-TNSFTRGVYYPDKVFRS SVLHSTQDLF LPFF-SNVTWF-HAIHVSGTNGTKRFDNPVLPFNDGVYFASTEKSNI IRGWIFGTTLDSKTQS LLIVNNATNV-VIKVCEFQFCNDPFLGVYYHKNNKSWMESEFRVYS-SANNCTFEYVSQPF LMDLEGKQGNFKNL-REFVFKNIDGYFKIYSKHTPINLVRDLPQGFSALEPLV DLPIGINIT RFQTLLALHR-SYLTPGDSSSGWTAGAAAYYVGYLQPRT-FLLKYNENGTITDAVDCALD PLSETKCTLKSFTVEKGIYQTSNFRVQPTE-SIVRFPNITNLCPFGEVFNATRFASVYAWNR KRISNC-VADYSVLYNSASFSTFKCYGVSPTKLNDLCFTNVY-ADSFVIRGDEVRQIAPGQT GKIADYNYKLPDDFTGCVIAWNSNNLD SKVGGNY-NYLYRLFRKSNLKPFERDISTEIYQ AGSTPCNGVEG-FNCYFPLQ SYGFQPTNGVGYQPYRVVVL SFELL-HAPATVCGPKKSTNL VKNKCVNFNFNGLTGTGVLTESNKKFLPFQQFGR-DIADTTDAVRDPQTLEILDITPCSFG GVSVITPGTNTSNQVAVLYQDVNCTEVPVAI-HADQLTPTWRVYSTGSNVFQTRAGCLIG AEHVNN-SYECDIPIGAGICASYQTQTNSPSRARSVASQSIIAY-TMSLGAENSVAYSNNSIA IPTNFTISVTTEILPVSMTKTSVDCTMYICGD-STECSNLLLQYGSFCTQLNRALTGIAVEQ DKNTQEVFAQVKQIYKTPPIKDFGGFNFSQIL-PDPSKPSKRSFIEDLLFNKVTLADAGFIK QYGDCLG-DIAARDLICAQKFNGLTVLPPLLTDEMIAQYTSAL-LAGTITSGWTFGAGAAL QIPFAMQMAYRFNGIGVTQNVLYENQKLIANQFN-SAIGKIQDSLSSTASALGKLQDVVN QNAQAL-NTLVKQLSSNFGAISSVLNDILSRLDPP (spike sequence amino acids 1 to 987) or variants thereof.

In certain embodiments, this disclosure contemplates non-naturally occurring coronavirus spike protein, or nucleic acid having a sequence encoding a mutation, comprising a lysine mutation at position 484, an asparagine mutation at position 417, a tyrosine mutation at position 501, or combinations thereof and a mutation in the furin cleavage site at position 682, 683, 684 or 685, a serine mutation at position 682, a proline mutation at position 986, a proline mutation at position 987, or combinations thereof.

In certain embodiments, this disclosure contemplates non-naturally occurring coronavirus spike protein, or nucleic acid having a sequence encoding a mutation, comprising a mutation at position 484. In certain embodiments, this disclosure contemplates non-naturally occurring coronavirus spike protein, or nucleic acid having a sequence encoding a mutation, comprising a lysine mutation at position 484 optionally in combination with other mutations below. In certain embodiments, this disclosure contemplates non-naturally occurring coronavirus spike protein, or nucleic acid having a sequence encoding a mutation, comprising a mutation in the furin cleavage site at position 682, 683, 684 or 685. In certain embodiments, the mutation in the furin cleavage site is at position 682. In certain embodiments, the coronavirus spike protein, or nucleic acid having a sequence encoding a mutation, comprising a serine mutation at position 682. In certain embodiments, this disclosure contemplates non-naturally occurring coronavirus spike protein, or nucleic acid having a sequence encoding a mutation, comprising a proline mutation at position 986. In certain embodiments, the coronavirus spike protein further comprises a proline mutation at position 987.

In certain embodiments, the coronavirus spike protein comprises amino acid sequence (SEQ ID NO: 28)

MFVFLVLLPLVSSQCVNLTTRTQLPPAY-
TNSFTRGVYYPDKVFRS SVLHSTQDLF LPFF-
SNVTWF-
HAIHVSGTNGTKRFDNPVLPFNDGVYFASTEKSNII
RGWIFGTTLDSKTQS LLIVNNATNV-
VIKVCEFQFCNDPFLGVYYHKNNKSWMESEFRVYS-
SANNCTFEYVSQPF LMDLEGKQGNFKNL-
REFVFKNIDGYFKIYSKHTPINLVRDLPQGF
SALEPLVDLPIGINIT RFQTLLALHR-
SYLTPGDSSSGWTAGAAAYYVGYLQPRT-
FLLKYNENGTITDAVDCALD
PLSETKCTLKSFTVEKGIYQTSNFRVQPTE-
SIVRFPNITNLCPFGEVFNATRFASVYAWNR KRISNC-
VADYSVLYNSASFSTFKCYGVSPTKLNDLCFTNVY-
ADSFVIRGDEVRQIAPGQT
GKIADYNYKLPDDFTGCVIAWNSNNLDSKVGGNY-
NYLYRLFRKSNLKPFERDISTEIYQ
AGSTPCNGVKGFN-
CYFPLQSYGFQPTNGVGYQPYRVVVL SFELL-
HAPATVCGPKKSTNL
VKNKCVNFNFNGLTGTGVLTESNKKFLPFQQFGR-
DIADTTDAVRDPQTLEILDITPCSFG
GVSVITPGTNTSNQVAVLYQDVNCTEVPVAI-
HADQLTPTWRVYSTGSNVFQTRAGCLIG AEHVNN-
SYECDIPIGAGICASYQTQTNSPSRARSVASQSIIAY-
TMSLGAENSVAYSNNSIA
IPTNFTISVTTEILPVSMTKTSVDCTMYICGD-
STECSNLLLQYGSFCTQLNRALTGIAVEQ
DKNTQEVFAQVKQIYKTPPIKDFGGFNFSQIL-
PDPSKPSKRSFIEDLLFNKVTLADAGFIK QYGDCLG-
DIAARDLICAQKFNGLTVLPPLLTDEMIAQYTSAL-
LAGTITSGWTFGAGAAL
QIPFAMQMAYRFNGIGVTQNVLYENQKLIANQFN-
SAIGKIQDSLSSTASALGKLQDVVN QNAQAL-
NTLVKQLSSNFGAISSVLNDILSRLDPP (spike sequence amino acids 1 to 987) or variants thereof.

In certain embodiments, this disclosure contemplates non-naturally occurring coronavirus spike protein, or nucleic acid having a sequence encoding a mutation, comprising a mutation at position 417. In certain embodiments, this disclosure contemplates non-naturally occurring coronavirus spike protein, or nucleic acid having a sequence encoding a mutation, comprising an asparagine mutation at position 417 optionally in combination with other mutations below. In certain embodiments, this disclosure contemplates non-naturally occurring coronavirus spike protein, or nucleic acid having a sequence encoding a mutation, comprising a mutation in the furin cleavage site at position 682, 683, 684 or 685, In certain embodiments, the mutation in the furin cleavage site is at position 682. In certain embodiments, the coronavirus spike protein, or nucleic acid having a sequence encoding a mutation, comprising a serine mutation at position 682. In certain embodiments, this disclosure contemplates non-naturally occurring coronavirus spike protein, or nucleic acid having a sequence encoding a mutation, comprising a proline mutation at position 986. In certain embodiments, the coronavirus spike protein further comprises a proline mutation at position 987.

In certain embodiments, the coronavirus spike protein comprises amino acid sequence (SEQ ID NO: 29)

MFVFLVLLPLVSSQCVNLTTRTQLPPAY-
TNSFTRGVYYPDKVFRS SVLHSTQDLF LPFF-
SNVTWF-
HAIHVSGTNGTKRFDNPVLPFNDGVYFASTEKSNII
RGWIFGTTLDSKTQS LLIVNNATNV-
VIKVCEFQFCNDPFLGVYYHKNNKSWMESEFRVYS-
SANNCTFEYVSQPF LMDLEGKQGNFKNL-
REFVFKNIDGYFKIYSKHTPINLVRDLPQGFSALEPL
VDLPIGINIT RFQTLLALHR-
SYLTPGDSSSGWTAGAAAYYVGYLQPRT-
FLLKYNENGTITDAVDCALD
PLSETKCTLKSFTVEKGIYQTSNFRVQPTE-
SIVRFPNITNLCPFGEVFNATRFASVYAWNR KRISNC-
VADYSVLYNSASFSTFKCYGVSPTKLNDLCFTNVY-
ADSFVIRGDEVRQIAPGQT
GNIADYNYKLPDDFTGCVIAWNSNNLD SKVGGNY-
NYLYRLFRKSNLKPFERDISTEIYQ AGSTPCNGVEG-
FNCYFPLQSYGFQPTNGVGYQPYRVVVLSFELL-
HAPATVCGPKKSTNL
VKNKCVNFNFNGLTGTGVLTESNKKFLPFQQFGR-
DIADTTDAVRDPQTLEILDITPCSFG
GVSVITPGTNTSNQVAVLYQDVNCTEVPVAI-
HADQLTPTWRVYSTGSNVFQTRAGCLIG AEHVNN-
SYECDIPIGAGICASYQTQTNSPSRARSVASQSIIAY-
TMSLGAENSVAYSNNSIA
IPTNFTISVTTEILPVSMTKTSVDCTMYICGD-
STECSNLLLQYGSFCTQLNRALTGIAVEQ
DKNTQEVFAQVKQIYKTPPIKDFGGFNF SQILPDP
SKP SKRSFIEDLLFNKVTLADAGFIK QYGDCLGDI-
AARDLICAQKFNGLTVLPPLLTDEMIAQYTSAL-
LAGTITSGWTFGAGAAL QIPFAMQMAYRFN-
GIGVTQNVLYENQKLIANQFNSAIGKIQDSLS
STASALGKLQDVVN QNAQALNTLVKQLSSNFGAIS-
SVLNDILSRLDPP (spike sequence amino acids 1 to 987) or variants thereof.

In certain embodiments, this disclosure contemplates non-naturally occurring coronavirus spike protein, or nucleic acid having a sequence encoding a mutation, comprising a mutation at position 501. In certain embodiments, this disclosure contemplates non-naturally occurring coronavirus spike protein, or nucleic acid having a sequence encoding a mutation, comprising a tyrosine mutation at position 501 optionally in combination with other mutations below. In certain embodiments, this disclosure contemplates non-naturally occurring coronavirus spike protein, or nucleic acid having a sequence encoding a mutation, comprising a mutation in the furin cleavage site at position 682, 683, 684 or 685, In certain embodiments, the mutation in the furin cleavage site is at position 682. In certain embodiments, the coronavirus spike protein, or nucleic acid having a sequence encoding a mutation, comprising a serine mutation at position 682. In certain embodiments, this disclosure contemplates non-naturally occurring coronavirus spike protein, or nucleic acid having a sequence encoding a mutation, comprising a proline mutation at position 986. In certain embodiments, the coronavirus spike protein further comprises a proline mutation at position 987.

In certain embodiments, the coronavirus spike protein comprises amino acid sequence (SEQ ID NO: 30)

MFVFLVLLPLVSSQCVNLTTRTQLPPAY-TNSFTRGVYYPDKVFRSSVLHSTQDLF LPFF-SNVTWF-HAIHVSGTNGTKRFDNPVLPFNDGVYFASTEKSNII RGWIFGTTLDSKTQS LLIVNNATNV-VIKVCEFQFCNDPFLGVYYHKNNKSWMESEFRVYS-SANNCTFEYVSQPF LMDLEGKQGNFKNL-REFVFKNIDGYFKIYSKHTPINLVRDLPQGFSALEPL VDLPIGINIT RFQTLLALHR-SYLTPGDSSSGWTAGAAAYYVGYLQPRT-FLLKYNENGTITDAVDCALD PLSETKCTLKSFTVEKGIYQTSNFRVQPTE-SIVRFPNITNLCPFGEVFNATRFASVYAWNR KRISNC-VADYSVLYNSASFSTFKCYGVSPTKLNDLCFTNVY-ADSFVIRGDEVRQIAPGQT GKIADYNYKLPDDFTGCVIAWNSNNLDSKVGGNY-NYLYRLFRKSNLKPFERDISTEIYQ AGSTPCNGVEG-FNCYFPLQ SYGFQPTYGVGYQPYRVVVLSFELL-HAPATVCGPKKSTNL VKNKCVNFNFNGLTGTGVLTESNKKFLPFQQFGR-DIADTTDAVRDPQTLEILDITPCSFG GVSVITPGTNTSNQVAVLYQDVNCTEVPVAI-HADQLTPTWRVYSTGSNVFQTRAGCLIG AEHVNN-SYECDIPIGAGICASYQTQTNSPSRARSVASQSIIAY-TMSLGAENSVAYSNNSIA IPTNFTISVTTEILPVSMTKTSVDCTMYICGD-STECSNLLLQYGSFCTQLNRALTGIAVEQ DKNTQEVFAQVKQIYKTPPIKDFGGFNFSQIL-PDPSKPSKRSFIEDLLFNKVTLADAGFIK QYGDCLG-DIAARDLICAQKFNGLTVLPPLLTDEMIAQYTSAL-LAGTITSGWTFGAGAAL QIPFAMQMAYRFNGIGVTQNVLYENQKLIANQFN-SAIGKIQDSLS STASALGKLQDVVN QNAQAL-NTLVKQLSSNFGAISSVLNDILSRLDPP (spike sequence amino acids 1 to 987) or variants thereof.

In certain embodiments, the coronavirus spike protein further comprises a heterologous N-terminal signal sequence.

In certain embodiments, the coronavirus spike protein further comprises a C-terminal trimerization sequence.

In certain embodiments, the coronavirus spike protein comprises amino acid sequence (SEQ ID NO: 2)

MFVFLVLLPLVSSQCVNLTTRTQLPPAY-TNSFTRGVYYPDKVFRSSVLHSTQDLF LPFF-SNVTWF-HAIHVSGTNGTKRFDNPVLPFNDGVYFASTEKSNII RGWIFGTTLDSKTQS LLIVNNATNV-VIKVCEFQFCNDPFLGVYYHKNNKSWMESEFRVYS-SANNCTFEYVSQPF LMDLEGKQGNFKNL-REFVFKNIDGYFKIYSKHTPINLVRDLPQGFSALEPL VDLPIGINIT RFQTLLALHR-SYLTPGDSSSGWTAGAAAYYVGYLQPRT-FLLKYNENGTITDAVDCALD PLSETKCTLKSFTVEKGIYQTSNFRVQPTE-SIVRFPNITNLCPFGEVFNATRFASVYAWNR KRISNC-VADYSVLYNSASFSTFKCYGVSPTKLNDLCFTNVY-ADSFVIRGDEVRQIAPGQT GKIADYNYKLPDDFTGCVIAWNSNNLDSKVGGNY-NYLYRLFRKSNLKPFERDISTEIYQ AGSTPCNGVEG-FNCYFPLQ SYGFQPTNGVGYQPYRVVVLSFELL-HAPATVCGPKKSTNL VKNKCVNFNFNGLTGTGVLTESNKKFLPFQQFGR-DIADTTDAVRDPQTLEILDITPCSFG GVSVITPGTNTSNQVAVLYQDVNCTEVPVAI-HADQLTPTWRVYSTGSNVFQTRAGCLIG AEHVNN-SYECDIPIGAGICASYQTQTNSPRRARSVASQSIIAY-TMSLGAENSVAYSNNSIA IPTNFTISVTTEILPVSMTKTSVDCTMYICGD-STECSNLLLQYGSFCTQLNRALTGIAVEQ DKNTQEVFAQVKQIYKTPPIKDFGGFNFSQIL-PDPSKPSKRSFIEDLLFNKVTLADAGFIK QYGDCLG-DIAARDLICAQKFNGLTVLPPLLTDEMIAQYTSAL-LAGTITSGWTFGAGAAL QIPFAMQMAYRFNGIGVTQNVLYENQKLIANQFN-SAIGKIQDSLSSTASALGKLQDVVN QNAQAL-NTLVKQLSSNFGAISSVLNDILSRLDPPE-AEVQIDRLITGRLQSLQTYVTQQLIR AAEIRASANLAATKM-SECVLGQSKRVDFCGKGYHLMSFPQSAPHGVVFLH VTYVPAQE KNFTTAPAICHDGKAHF-PREGVFVSNGTH-WFVTQRNFYEPQIITTDNTFVSGNCDVVIGI VNNTVYDPLQPELDSFKEELDKYFKNHT-SPDVDLGDISGINASVVNIQKEIDRLNEVAKN LNESL-IDLQELGKYEQYIKWPWYIWLGFIAGLI-AIVMVTIMLCCMTSCC SCLKGCCSCGS CCKFDEDDSEPVLKGVKLHYT (S-Tri) or variants thereof.

In certain embodiments, the coronavirus spike protein comprises a coronavirus M protein sequence downstream from the C-terminal end of the coronavirus spike protein sequence, and wherein the M protein sequence and the coronavirus spike sequence are separated by a self-cleaving sequence. In certain embodiments, the coronavirus spike protein comprises a coronavirus E protein sequence downstream from the C-terminal end of the M protein sequence, and wherein the E protein sequence and the coronavirus M protein sequence are separated by a self-cleaving sequence.

In certain embodiments, the coronavirus spike protein comprises amino acid sequence (SEQ ID NO: 3)

MFVFLVLLPLVSSQCVNLTTRTQLPPAY-TNSFTRGVYYPDKVFRSSVLHSTQDLF LPFF-SNVTWF-HAIHVSGTNGTKRFDNPVLPFNDGVYFASTEKSNII RGWIFGTTLDSKTQS LLIVNNATNV-VIKVCEFQFCNDPFLGVYYHKNNKSWMESEFRVYS-SANNCTFEYVSQPF LMDLEGKQGNFKNL-REFVFKNIDGYFKIYSKHTPINLVRDLPQGFSALEPL VDLPIGINIT RFQTLLALHR-SYLTPGDSSSGWTAGAAAYYVGYLQPRT-FLLKYNENGTITDAVDCALD PLSETKCTLKSFTVEKGIYQTSNFRVQPTE-SIVRFPNITNLCPFGEVFNATRFASVYAWNR KRISNC-VADYSVLYNSASFSTFKCYGVSPTKLNDLCFTNVY-ADSFVIRGDEVRQIAPGQT GKIADYNYKLPDDFTGCVIAWNSNNLDSKVGGNY-NYLYRLFRKSNLKPFERDISTEIYQ AGSTPCNGVEG-FNCYFPLQ SYGFQPTNGVGYQPYRVVVL SFELL-HAPATVCGPKKSTNL VKNKCVNFNFNGLTGTGVLTESNKKFLPFQQFGR-DIADTTDAVRDPQTLEILDITPCSFG GVSVITPGTNTSNQVAVLYQDVNCTEVPVAI-HADQLTPTWRVYSTGSNVFQTRAGCLIG AEHVNN-SYECDIPIGAGICASYQTQTNSPRRARSVASQSIIAY-TMSLGAENSVAYSNNSIA IPTNFTISVTTEILPVSMTKTSVDCTMYICGD-STECSNLLLQYGSFCTQLNRALTGIAVEQ DKNTQEVFAQVKQIYKTPPIKDFGGFNFSQIL-PDPSKPSKRSFIEDLLFNKVTLADAGFIK QYGDCLG-DIAARDLICAQKFNGLTVLPPLLTDEMIAQYTSAL-

LAGTITSGWTFGAGAAL
QIPFAMQMAYRFNGIGVTQNVLYENQKLIANQFN-
SAIGKIQDSLS STASALGKLQDVVN QNAQAL-
NTLVKQLSSNFGAISSVLNDILSRLDPPE-
AEVQIDRLITGRLQSLQTYVTQQLIR
AAEIRASANLAATKMSECVLGQ
SKRVDFCGKGYHLMSFPQSAPHGVVFLHVTYVPAQE
KNFTTAPAICHDGKAHFPREGVFVSNGTH-
WFVTQRNFYEPQIITTDNTFVSGNCDVVIGI
VNNTVYDPLQPELDSFKEELDKYFKNHT-
SPDVDLGDISGINASVVNIQKEIDRLNEVAKN LNESL-
IDLQELGKYEQYIKWPWYIWLGFIAGLI-
AIVMVTIMLCCMTSCC SCLKGCCSCGS
CCKFDEDDSEPVLKGVKLHYTGS-
GATNFSLLKQAGDVEENPGPMADSNGTITVEELKKL
LEQWNLVIGFLFLTWICLLQFAYANRNRFLY-
IIKLIFLWLLWPVTLACFVLAAVYRINWI TGGIAIA-
MACLVGLMWLSYFIASFRLFARTRSMW SFNPET-
NILLNVPLHGTILTRPLLESE
LVIGAVILRGHLRIAGHHLGRCDIKDLPKEIT-
VATSRTLSYYKLGASQRVAGDSGFAAYS RYRI-
GNYKLNTDHSSSSDNIALLVQGSGATNFSLLKQAGD-
VEENPGPMYSFVSEETGTLI
VNSVLLFLAFVVFLLVTLAILTALRLCAYCC-
NIVNVSLVKP SFYVYSRVKNLNS SRVPDL LV (S-VLP)
or variants thereof.

With specific regard to coronavirus proteins disclosed herein, any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

In certain embodiments, this disclosure relates to virus-like particles comprising a coronavirus spike protein disclosed herein.

In certain embodiments, this disclosure relates nucleic acids comprising a sequence encoding a coronavirus spike protein disclosed herein in operable combination with a heterologous promotor.

In certain embodiments, the nucleic acid the sequence encoding a coronavirus spike protein comprises (SEQ ID NO: 4)

ATGTGGTTACAAGGACTACTAT-
TACTAGGTACTGTTGCCTGTTCAATTTCACA
ATGTGTAAATCTAACTACAAGAACTCAAT-
TACCGCCTGCCTATACTAATTCTTTTACA AGAG-
GAGTATATTATCCTGATAAAGTTTTTAGATCTTCTGT-
ATTACATTCTACACAAG
ATTTGTTTTTACCATTTTTCTCTAATGT-
TACTTGGTTTCATGCAATACATGTATCTGGA ACT-
AATGGAACAAAAAGATTTGATAATCCAGTAT-
TACCTTTTAATGATGGAGTTTAT
TTTGCTTCTACTGAAAAATCTAATATAATTAGAG-
GATGGATATTTGGAACTACATTA GAT-
TCTAAAACACAATCTCTACTAATTGT-
TAATAATGCAACTAATGTAGTTATAAAA
GTATGTGAATTTCAATTTTGTAATGATC CAT-
TTTTGGGAGTTTATTATCATAAAAATA
ATAAGTCTTGGATGGAATCTGAATTCAGAGTATAT-
TCTTCTGCTAATAATTGTACATT TGAATATGTATCT-
CAACCATTTTTGATGGATTTG-
GAAGGAAAACAAGGAAACTTTAA
AAATTTGAGAGAATTTGTTTTTAAAAATATTGATG-
GATACTTTAAAATCTATTCTAA ACATACTCCAAT-
TAATCTAGTAAGAGATTTGCCTCAAGGAT-
TTTCTGCTTTAGAACC ACTAGTAGATTTGC
CTATAGGAATTAATATTACTAGATTTCAAACATTATT-
AGC TTTA CATAGATCTTATTTGACACCTGGAGAT-
TCTTCTTCTGGATGGACTGCAGGAGCTGCA GCTT-
ATTATGTTGGATATTTGCAACCAAGAACATTTTTGT
TAAAATATAATGAAAAT GGAACTATAACA-
GATGCAGTTGATTGTGCTTTAGATCCTCTATCT-
GAAACTAAATGT ACTTTAAAATCTTT-
TACTGTAGAAAAAGGAATCTATCAAACATCTAACTT-
TAGAGTA
CAACCAACTGAATCTATTGTTAGATTTC-
CAAATATAACAAATCTATGTCCTTTTGGA
GAAGTTTTTAATGCAACTAGAT-
TTGCTTCTGTATATGCATGGAATAGAAAAAGAATA
TCTAATTGCGTAGCTGATTATTCTGTATTATATAAT-
TCTGCATCTTTTTCTACTTTTAA ATGTTATG-
GAGTATCTCCAACAAAATTGAATGATCTATGTTT-
TACTAATGTTTATGCA
GATTCTTTTGTAATAAGAGGAGATGAAGTTA-
GACAAATAGCTCCTGGACAAACAGG
AAAAATAGCAGATTATAATTATAAATTACCAGAT-
GATTTCACTGGATGCGTAATTGC TTGGAAT-
TCTAATAATTTGGATTCTAAAGTAGGAGGAAAT-
TATAATTATTTGTATAG
ATTGTTTAGAAAATCTAATTTGAAACCTTTT-
GAAAGAGATATTTCTACAGAAATCTA TCAAGCAG-
GATCTACTCCATGTAATGGAGTTGAAGGTTTTAAT-
TGTTATTTTCCACTA
CAATCTTATGGATTTCAACCTACAAATGGAGTAG-
GATATCAACCATATAGAGTAGTT GTATTATC TTTT-
GAATTATTACATGCACCAGCTACAGTATGTGGACC
TAAAAAATCT ACTAATTTGGT-
TAAAAATAAGTGCGTAAACTTTAACTTTAATGGAT-
TAACTGGAACA GGAGTTTTAACT-
GAATCTAATAAGAAATTTTTGCCTTTTCAACAATT
TGGAAGAGAT ATTGCTGATACTACA-
GATGCAGTAAGAGATCCTCAAACTTTAGAAATAT-
TGGATATT ACACCATGTTCTTTTGGAG-
GAGTTTCTGTAATAACACCAGGAACTAATACATCT
AAT CAAGTTGCTGTATTATATCAAGATGTTAAT-
TGTACTGAAGTTCCTGTAGCAATTCATG CTGAT-
CAATTAACTCCAACATGGAGAGTATATTCTACTG-
GATCTAATGTTTTTCAAA
CAAGAGCTGGATGTCTAATTGGAGCAGAA-
CATGTAAATAATTCTTATGAATGTGATATTCCTATAG-
GAGCTGGAATATGTGCATCTTATCAAACT-
CAAACAAATTCTCCAAGAA
GAGCTAGATCTGTTGCATCTCAATCTATAATTGCT-
TATACAATGTCTTTAGGAGCTGA AAATTCTGTAG-
CATATTCTAATAATTCTATTGCAATTCCTACTAACTT-
TACTATTTCT
GTAACTACAGAAATATTGCCAGTTTC-
TATGACTAAAACATCTGTAGATTGTACAATG
TATATATGTGGAGATTCTACTGAATGTTCTAATTTGC-
TACTACAATATGGATCTTTTT GTACTCAATT-
GAATAGAGCTTTAACAGGAATAGCAGTAGAACAA-
GATAAAAATACA
CAAGAAGTTTTTGCTCAAGTAAAACAAATC-
TATAAAACTCCACCTATAAAAGATTTT GGAGGTTT-
TAATTTTTCTCAAATATTGCCA-
GATCCTTCTAAACCTTCTAAAAGATCTT
TTATTGAAGATTTGTTGTTTAATAAGGTTACATT-

AGCAGATGCTGGTTTTATAAAACA ATATGGAGAT-TGTTTAGGAGATATTGCAGCTAGAGATTTGAT-TTGTGC TCAAAAGTT TAATGGATTAACTGTATTACCACCTCTACTAACA-GATGAAATGATAGCACAATATAC ATCTGCATTATT-AGCTGGAACTATTACATCTGGATGGACTTTTG-GAGCTGGAGCAGC TTTACAAATACCATTTGCTATGCAAATGGCATATA-GATTCAATGGAATTGGAGTTAC TCAAAATGTAT-TATATGAAAATCAAAAACTAATTGCTAATCAATT-CAATTCTGCAAT TGGAAAAATTCAAGATTCTCTATCTTCTACAG-CATCTGCTTTAGGAAAACTACAAGA TGTTGTAAAT-CAAAATGCACAAGCTTTAAATACTCTAGT-TAAACAACTATCTTCTAA TTTTGGAGCTATTTCTTCTGTTTTAAATGATATAT-TGTCTAGACTAGATCCACCT (encoding spike sequence amino acids 1 to 987) or variants with great than 85% identity thereto. In certain embodiments, variants are synonymous or non-synonymous codons.

Recombinant Nucleic Acids and Viral Vectors

In certain embodiments, the disclosure relates to recombinant viral vectors, recombinant vectors, and recombinant plasmids comprising nucleic acids encoding coronavirus spike proteins disclosed herein. In certain embodiments, this disclosure relates to expression systems comprising nucleic acids and vectors disclosed herein.

Nucleic acids, vectors, and expression constructs can be introduced in vivo via lipofection (DNA transfection via liposomes prepared from synthetic cationic lipids). Synthetic cationic lipids can be used to prepare liposomes to encapsulate a nucleic acid, vector, or expression construct of the disclosure. A nucleic acid, vector, or expression construct can also be introduced as naked DNA or RNA using methods known in the art, such as transfection, microinjection, electroporation, calcium phosphate precipitation, and by biolistic methods.

If a recombinant virus vector of this disclosure is constructed starting with a vaccinia virus, the majority of the nucleic acid molecules and proteins in the recombinant virus vector will come from vaccinia virus and thus the final recombinant virus vector can be referred to, for example, as a recombinant vaccinia virus vector or a vaccinia-based recombinant virus vector. In certain embodiments, the recombinant virus vector is selected from the group consisting of a recombinant poxvirus vector, a recombinant vaccinia virus vector, a recombinant chordopoxvirus vector, a recombinant iridovirus vector, a recombinant adenovirus vector, a recombinant adeno-associated virus vector, a recombinant SV40 virus vector, a recombinant Epstein-Barr virus vector, a recombinant herpes virus vector, and a recombinant JC virus vector.

In certain embodiments, this disclosure contemplates that methods disclosed herein are used with recombinant virus, preferably recombinant modified vaccinia virus Ankara (MVA). MVA is an attenuated strain of vaccinia virus originally developed as a vaccine for smallpox. The ability of MVA to infect mammalian, including human host cells, is restricted due to known deletions in the virus genome. In addition to the safe use in human vaccinations, Wyatt et al. report mice with severe combined immunodeficiency disease remained healthy when inoculated with MVA. Proc Natl Acad Sci USA. 2004, 101(13):4590-5.

MVA can be engineered in deleted regions to express heterologous genes to induce protective immunity to other viruses. Combined DNA and recombinant modified vaccinia Ankara (MVA62B) vaccines can produce virus-like particles that display membrane-bound trimeric forms of envelope proteins. As a result of extensive passage in cell culture, the MVA virus genome contains six major deletions, referred to as Del I, II, III, IV, V and VI. Historically, the region around Del II and Del III has been used for insertion of heterologous nucleic acid sequences.

As used herein, the term heterologous is a comparative term, and refers to a molecule that is from an organism different from that to which it is being referenced or that is made synthetically. The molecule can be a protein or a nucleic acid sequence (i.e., RNA or DNA). For example, a heterologous nucleic acid sequence in a recombinant virus vector refers to the fact that the heterologous nucleic acid sequence is or may be from an organism other than the base virus used to construct the recombinant virus vector. As a further example, a heterologous nucleic acid sequence in a recombinant vaccinia virus vector refers to the fact that the heterologous nucleic acid sequence is from an organism other than vaccinia virus or that was made synthetically.

A heterologous nucleic acid sequence can be inserted at any location in a recombinant virus vector genome, as long as such insertion does not unintentionally alter the functioning of the resulting recombinant virus vector. For example, a nucleic acid sequence can be inserted into a non-essential region. Such non-essential regions include, but are not limited to, naturally occurring deletions within the viral genome (e.g., Del I, II, III, etc. of modified vaccinia virus Ankara (MVA)), intergenic regions or non-essential genes. A non-essential region is a genomic region, the alteration of which has no, or almost no, discernible effect on viral replication and the production of progeny virus. One example of a non-essential region is a non-essential gene such as, for example, the vaccinia virus hemagglutinin gene.

Alternatively, a nucleic acid sequences can be inserted into an essential region of the genome (e.g., an essential gene). It will be appreciated that interruption of an essential region will result in a recombinant virus vector unable to complete the virus life cycle and produce progeny virus. However, such recombinant virus vectors can produce progeny virus when grown in cells that provide the missing function. Such a cell can be referred to as a complementing cell because it provides the function usually provided by the essential gene. That is, it "complements" the recombinant virus vector. Conversely, a cell that is unable to provide the missing viral function can be referred to as a non-commenting cell. Such culture systems are contemplated herein. At least one heterologous nucleic acid sequence may be inserted into the gene required for expression of post-replicative viral genes.

Methods of Use

This disclosure relates to methods of promoting immune responses against coronavirus, such as SARS-CoV-2, and compositions related thereto. In certain embodiments, this disclosure relates to methods of vaccinating for coronavirus, such as SARS-CoV-2, comprising administering to the subject a composition disclosed herein. In certain embodiments, the composition comprises a coronavirus spike protein, VLP containing the same, or a recombinant virus such as recombinant MVA that encodes a coronavirus, such as SARS-CoV-2 spike protein. In certain embodiments, the coronavirus spike protein comprises a proline mutation at position 986. In certain embodiments, the coronavirus spike protein comprises a proline mutation at position 987.

In certain embodiments, this disclosure relates to methods of vaccinating or immunizing comprising administering to a human subject an effective amount of coronavirus spike protein, a virus-like particle comprising a coronavirus spike protein, a nucleic acid and/or recombinant virus that encodes a coronavirus spike protein or segment thereof as disclosed herein under conditions such that spike protein and/or virus-like particles with spike protein are formed in the subject.

In certain embodiments, the methods are conducted in combination with an adjuvant. In certain embodiments, methods include using a coronavirus spike protein, trimeric complex or virus-like particle or nucleic acid encoding the same in combination with an adjuvant.

In certain embodiments, administering is to the skin, muscle, or buccal cavity. In certain embodiments, administration is by syringe, microneedle, topically, or using pressurized devices, e.g., device comprising a nozzle to push a solution into tissue by means of pressure, e.g., spring-powered without the use of a needle (needle-free devices).

DNA-based vaccines typically use bacterial plasmids to express protein immunogens in vaccinated hosts. Recombinant DNA technology is used to clone cDNAs encoding immunogens of interest into eukaryotic expression plasmids. Vaccine plasmids are then amplified in bacteria, purified, and directly inoculated into the hosts being vaccinated. DNA typically is inoculated by a needle injection of DNA in saline, or by a gene gun device that delivers DNA-coated gold beads into skin. The plasmid DNA is taken up by host cells, the vaccine protein is expressed, processed and presented in the context of self-major histocompatibility (MHC) class I and class II molecules, and an immune response against the DNA-encoded immunogen is generated.

In certain embodiments the present disclosure is a method to generate an immune response against coronavirus spike protein, a virus-like particle comprising a coronavirus spike protein, a nucleic acid and/or recombinant virus that encodes a coronavirus spike protein or segment thereof as disclosed herein. Such a response can be a CD8+ T cell immune response or an antibody response. More particularly, the present disclosure relates to “prime and boost” immunization regimes in which the immune response induced by administration of a priming composition is boosted by administration of a boosting composition. The present disclosure is based on experimental demonstration that effective priming can be achieved using modified vaccinia Ankara (MVA) vectors, following boosting with coronavirus spike protein, a virus-like particle comprising a coronavirus spike protein, a nucleic acid and/or recombinant virus that encodes a coronavirus spike protein or segment thereof as disclosed herein.

A major protective component of the immune response against a number of pathogens is mediated by T lymphocytes of the CD8+ type, also known as cytotoxic T lymphocytes (CTL). An important function of CD8+ cells is secretion of gamma interferon (IFNγ), and this provides a measure of CD8+ T cell immune response. A second component of the immune response is antibody directed to the proteins of the pathogen.

It is contemplated that a vaccination regime using needle-free, intradermal, intramuscular, or mucosal immunization for both prime and boost can be employed, constituting a general immunization regime suitable for inducing CD8+ T cells and also eliciting an antibody response, e.g., in humans. An immune response to coronavirus spike protein, trimeric complex or virus-like particle thereof may be primed by immunization with plasmid DNA, recombinant virus, or by infection with an infectious agent.

A further aspect of this disclosure provides a method of inducing a CD8+ T cell immune response to a coronavirus spike protein, trimeric complex or virus-like particle thereof in an individual, and also eliciting an antibody response.

A further aspect provides for use of coronavirus spike protein, trimeric complex or virus-like particle thereof as disclosed herein, in the manufacture of a medicament for administration to a mammal to boost a CD8+ T cell immune response and also eliciting an antibody response. Such a medicament is generally for administration following prior administration of a priming composition comprising nucleic acid and/or recombinant virus encoding the antigen.

The priming composition may comprise DNA encoding a coronavirus spike protein, trimeric complex or virus-like particle thereof, such DNA being in the form of a circular plasmid that is not capable of replicating in mammalian cells. Any selectable marker should preferably not be resistance to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present disclosure, administration of a priming composition is followed by boosting with a boosting composition, or first and second boosting compositions, the first and second boosting compositions being the same or different from one another.

In certain embodiments, the subject is a human subject. In certain embodiments, the human subject is of advanced age or elderly e.g., more than 45, 55, or 65 years old.

In certain embodiments, an “effective amount” in the context of administration of a therapy to a subject refers to the amount of a therapy which is sufficient to achieve one, two, three, four, or more of the following effects: (i) reduce or ameliorate the severity of a viral infection, disease or symptom associated therewith; (ii) reduce the duration of a viral infection, disease or symptom associated therewith; (iii) prevent the progression of a viral infection, disease or symptom associated therewith; (iv) cause regression of a viral infection, disease or symptom associated therewith; (v) prevent the development or onset of a viral infection, disease or symptom associated therewith; (vi) prevent the recurrence of a viral infection, disease or symptom associated therewith; (vii) reduce or prevent the spread of a viral from one cell to another cell, one tissue to another tissue, or one organ to another organ; (viii) prevent or reduce the spread of a viral from one subject to another subject; (ix) reduce organ failure associated with a viral infection; (x) reduce hospitalization of a subject; (xi) reduce hospitalization length; (xii) increase the survival of a subject with a viral infection or disease associated therewith; (xiii) eliminate a viral infection or disease associated therewith; (xiv) inhibit or reduce viral replication; (xv) inhibit or reduce the entry of an virus into a host cell(s); (xvi) inhibit or reduce replication of the virus genome; (xvii) inhibit or reduce synthesis of virus proteins; (xviii) inhibit or reduce assembly of virus particles; (xix) inhibit or reduce release of virus particles from a host cell(s); (xx) reduce virus titer; and/or (xxi) enhance or improve the prophylactic or therapeutic effect(s) of another therapy.

In certain embodiments, the effective amount does not result in complete protection from a coronavirus infection but results in a lower titer or reduced number of viruses compared to an untreated subject with a viral infection. In certain embodiments, the effective amount results in a 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of virus relative to an untreated subject with a viral infection. Benefits of a reduction in the titer, number or total burden of virus include, but are not limited to, less severe symptoms of the infection, fewer symptoms of the infection and a reduction in the length of the disease associated with the infection.

Compositions described herein may be delivered to a subject by a variety of routes. These include, but are not limited to, intranasal, intratracheal, oral, intradermal, intramuscular, intraperitoneal, transdermal, intravenous, conjunctival and subcutaneous routes. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, a composition is not formulated for administration by injection.

In certain embodiments, immunogenic compositions disclosed herein are administered intradermally. In certain embodiments, this disclosure contemplates administration using a transdermal patch for diffusion of the drug across the skin or by microneedle injection. In certain embodiments, it may be desirable to introduce the pharmaceutical compositions into the lungs by any suitable route. Pulmonary administration can also be employed, e.g., by use of an inhaler or nebulizer, and formulation with an aerosolizing agent for use as a spray.

In certain embodiments, this disclosure contemplates a combination vaccine that is designed to induce a strong neutralizing antibody response and broad cytotoxic CD8 T cell response against the SARS-CoV-2 providing long-lasting protection against SARS-CoV-2 and other SARS corona viruses. To achieve one combine DNA and modified vaccinia Ankara (MVA) vaccines such that both neutralizing antibodies and CD8 T cells are induce. The DNA and MVA immunogens express nucleocapsid, membrane and envelope proteins and a string of conserved epitopes from other proteins of SARS-CoV-2. In certain embodiments, priming with a DNA or MVA construct disclosed herein plus chimeric construction disclosed herein and boosting with DNA or MVA constructs disclosed herein. The DNA or MVA constructs for the priming and boosting may be the same or different. T cell epitopes in DNA and MVA vaccines promotes T cells against SARS corona viruses that could potentially provide protection even when the virus escapes from antibody responses providing induction of high levels of neutralizing antibodies and CD8 T cells with fewer immunizations.

In certain embodiments, this disclosure relates to vaccination methods using nucleic acids encoding T cell stimulating chimeric proteins. In certain embodiments, this disclosure relates to methods of vaccinating or immunizing a human subject comprising administering an effective amount of coronavirus spike protein, a virus-like particle comprising a coronavirus spike protein, a nucleic acid and/or recombinant virus that encodes a coronavirus spike protein or segment thereof as disclosed herein in combination with a nucleic acid encoding a T cell stimulating chimeric protein under conditions such that a spike protein and/or virus-like particles with a spike protein are formed in the subject.

In certain embodiments, this disclosure relates to a vaccination method comprising administering a corona virus vaccine such as a DNA or RNA vaccine encoding a corona virus spike protein of fragment thereof and preferably a DNA or MVA coronavirus construct disclosed herein in combination with chimeric sequences such as a nucleic acid encoding SdRBD-N-M (SEQ ID NO: 24), N-M, SdRBD-N-M_dTM (SEQ ID NO: 25), N-M_dTM, NSP3-4-6 (SEQ ID NO: 26) NSP3-4-6_dTM (SEQ ID NO: 27) or variants or combinations thereof (wherein d/delta is deleted) for the purpose of stimulating T cell responses.

In certain embodiments, this disclosure relates to a vaccination method comprising administering a prime and boost, wherein the prime is a corona virus vaccine such as a DNA or RNA vaccine encoding a corona virus spike protein of fragment thereof and preferably a DNA or MVA coronavirus construct disclosed herein in combination with chimeric sequences such as a nucleic acid encoding SdRBD-N-M (SEQ ID NO: 24), N-M, SdRBD-N-M_dTM (SEQ ID NO: 25), N-M_dTM, NSP3-4-6 (SEQ ID NO: 26), NSP3-4-6_dTM (SEQ ID NO: 27) or variants or combinations thereof (wherein d/delta is deleted) for the purpose of stimulating T cell responses; and the boost is a corona virus vaccine such as a DNA or RNA vaccine encoding a corona virus spike protein of fragment thereof and preferably a DNA or MVA coronavirus construct disclosed herein. In certain embodiments the prime is a DNA coronavirus construct, and the boost is an MVA coronavirus construct.

In certain embodiments, this disclosure relates to a vaccination method comprising administering a prime and boost, wherein the prime is a corona virus vaccine such as a DNA or RNA vaccine encoding a corona virus spike protein of fragment thereof and preferably a DNA or MVA coronavirus construct disclosed herein in combination with chimeric sequences such as a nucleic acid encoding SdRBD-N-M (SEQ ID NO: 24) or variants or combinations thereof (wherein d/delta is deleted) for the purpose of stimulating T cell responses, and the boost is MVA/S-tri-dFCS or variants optionally comprising mutations E484K, K417N, N501Y, or combinations thereof.

In certain embodiments, this disclosure relates to a vaccination method comprising administering a prime and boost, wherein the prime is a corona virus vaccine such as a DNA or RNA vaccine encoding a corona virus spike protein of fragment thereof and preferably a DNA or MVA coronavirus construct disclosed herein in combination with chimeric sequences such as a nucleic acid encoding SdRBD-N-M_dTM (SEQ ID NO: 25) or variants or combinations thereof (wherein d/delta is deleted) for the purpose of stimulating T cell responses, and the boost is MVA/S-tri-dFCS or variants optionally comprising mutations E484K, K417N, N501Y, or combinations thereof.

In certain embodiments, this disclosure relates to a vaccination method comprising administering a prime and boost, wherein the prime is a corona virus vaccine such as a DNA or RNA vaccine encoding a corona virus spike protein of fragment thereof and preferably a DNA or MVA coronavirus construct disclosed herein in combination with chimeric sequences such as a nucleic acid encoding NSP3-4-6 (SEQ ID NO: 26) or variants or combinations thereof (wherein d/delta is deleted) for the purpose of stimulating T cell responses, and the boost is MVA/S-tri-dFCS or variants optionally comprising mutations E484K, K417N, N501Y, or combinations thereof.

In certain embodiments, this disclosure relates to a vaccination method comprising administering a prime and boost, wherein the prime is a corona virus vaccine such as a DNA or RNA vaccine encoding a corona virus spike protein of fragment thereof and preferably a DNA or MVA coronavirus construct disclosed herein in combination with chimeric sequences such as a nucleic acid encoding NSP3-4-6_dTM (SEQ ID NO: 27) or variants or combinations thereof (wherein d/delta is deleted) for the purpose of stimulating T cell responses; and the boost is MVA/S-tri-dFCS or variants optionally comprising mutations E484K, K417N, N501Y, or combinations thereof.

In certain embodiments, this disclosure relates to a vaccination method comprising administering a DNA or MVA or combination of a DNA and MVA coronavirus construct disclosed herein.

In certain embodiments, this disclosure relates to a vaccination method comprising administering a prime and boost, wherein the prime is a DNA or MVA or combination of a DNA and MVA coronavirus construct disclosed herein and the boost is a DNA or MVA or combination of a DNA and MVA coronavirus construct disclosed herein.

In certain embodiments, this disclosure relates to a vaccination method comprising administering a prime and boost, wherein the prime is any coronavirus vaccine, e.g., mRNA vaccines viral vector coronavirus vaccines conventionally known by their supplier/brand name such as the Pfizer-BioNTech COVID-19 vaccine, Moderna COVID-19 vaccine, Johnson & Johnson's Janssen COVID-19 vaccine, AstraZeneca COVID-19 vaccine, and Novavax COVID-19 vaccine and the boost is a corona virus vaccine such as a DNA or RNA vaccine encoding a corona virus spike protein of fragment thereof and preferably a DNA or MVA or combination of a DNA and MVA coronavirus construct disclosed herein.

In certain embodiments, the boost is in combination with chimeric sequences such as a nucleic acid encoding SdRBD-N-M (SEQ ID NO: 24), N-M, SdRBD-N-M_dTM (SEQ ID NO: 25), N-M_dTM, NSP3-4-6 (SEQ ID NO: 26), NSP3-4-6_dTM (SEQ ID NO: 27) or variants or combinations thereof (wherein d/delta is deleted) for the purpose of stimulating T cell responses.

In certain embodiments, the boost is vaccine comprises mutation E484K, K417N, N501Y, or combinations thereof. In certain embodiments, the boost is MVA/S-tri-dFCS or variants optionally comprising mutations E484K, K417N, N501Y, or combinations thereof.

In certain embodiments, the boost is administered more than one or two weeks after the prime. In certain embodiments, the boost is administered more than one or two months after the prime. In certain embodiments, the boost is administered more than six months after the prime. In certain embodiments, the boost is administered more than one year after the prime.

Spike Protein of SARS-CoV-2

Four forms (FIG. 1A-D) of SARS-CoV-2 spike protein are disclosed, i.e., full-length protein displayed on VLPs like in the virus (S-VLP), soluble monomeric S1 (S1-Mono), trimeric S protein displayed on the membrane but does not produce VLPs (S-Tri) and stabilized soluble S Trimer (S-Trisec). See FIGS. 1A-D.

Figure 2A:
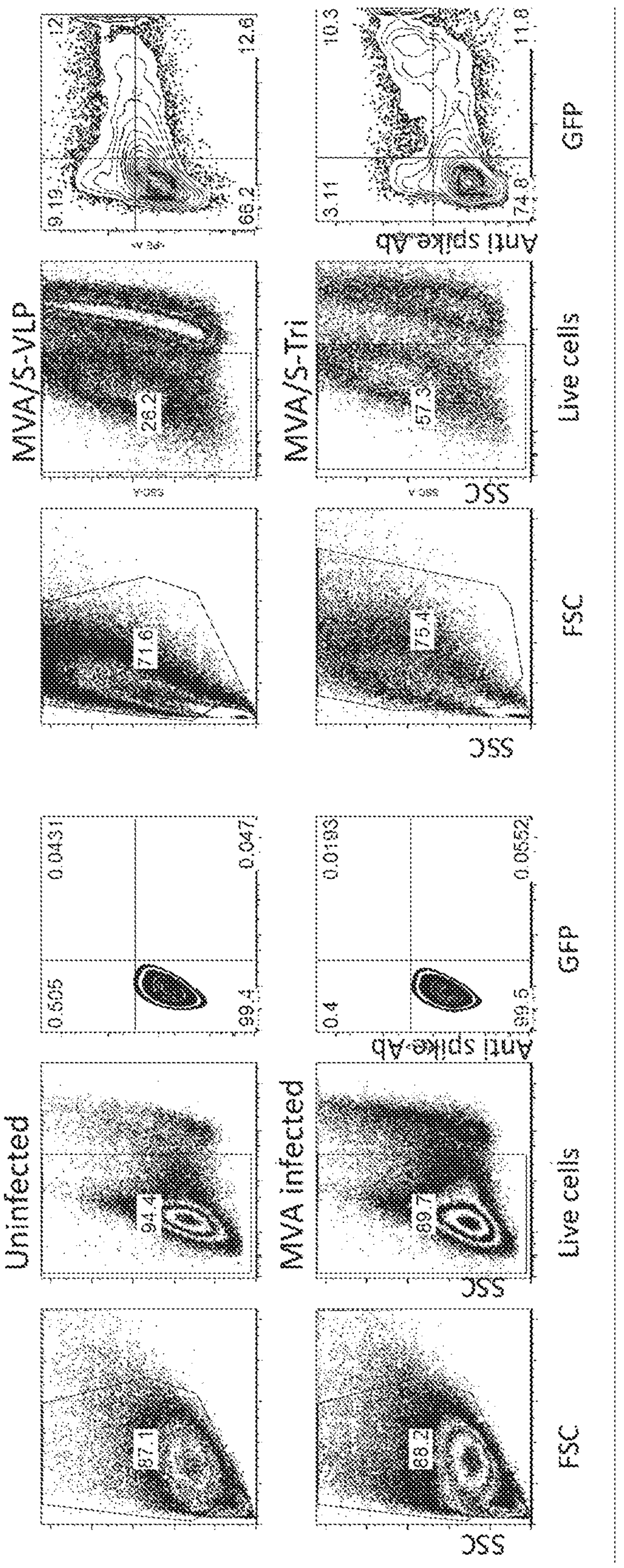
FIG. 2A shows flow cytometry data indicating the expression of full-length spike protein. DF-1 cells were infected with wild type MVA and transfected with pLW-73-MVA/S-Tri or MVA/S-VLP DNA expression plasmids. Polyclonal rabbit serum was used to detect spike protein.
Figure 2B:
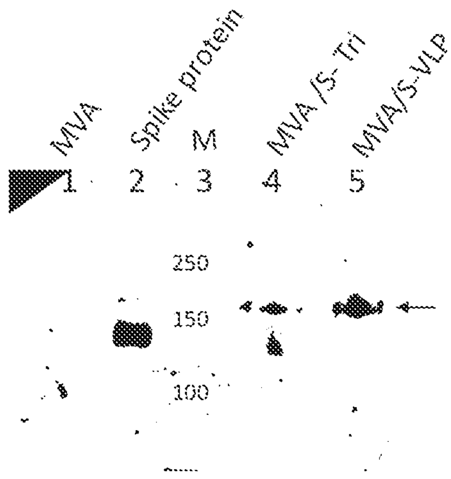
FIG. 2B shows a Western blot on spike protein expression by MVA recombinants. Bacterially expressed and purified spike protein (deltaTM) (spike control) was used as a positive control and total lysate from MVA infected DF-1 cells were used as a negative control. The arrow indicates that the spike protein VLP moves higher than the soluble spike protein.
Figure 3:
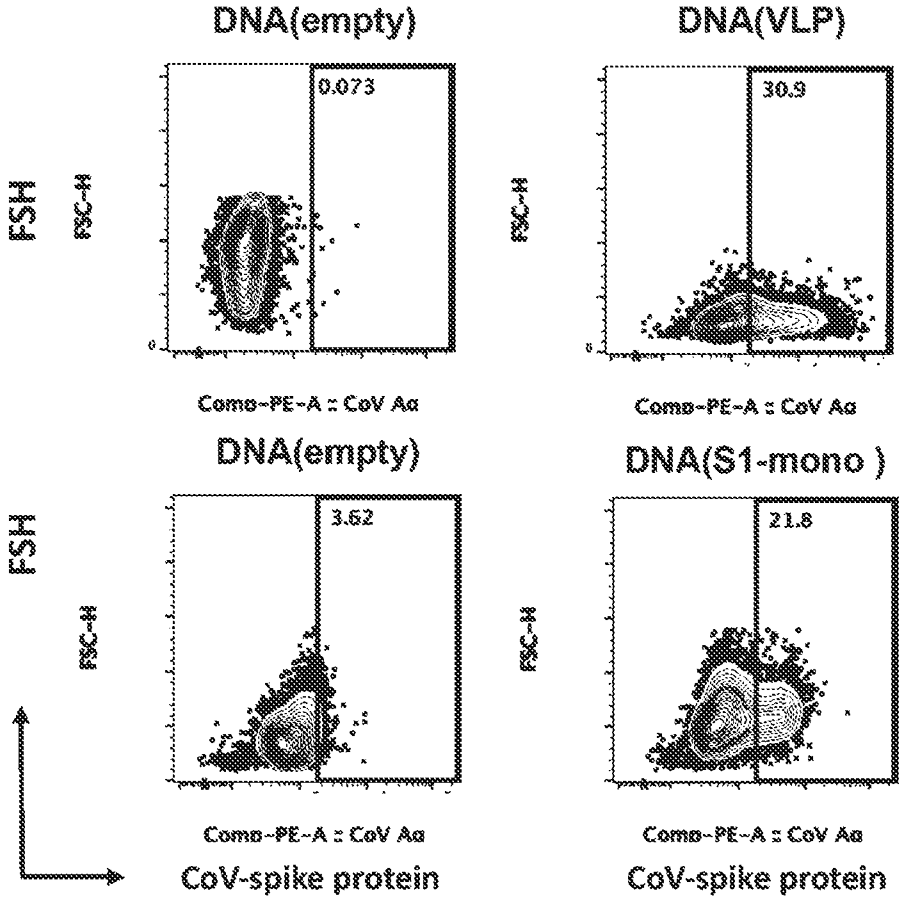
FIG. 3 shows flow cytometry data on spike protein expression by DNA recombinants where 293T cells were transfected with DNA/S-VLP or DNA/S1-Mono plasmids and the expression of spike protein was confirmed by a flow cytometry using rabbit polyclonal serum generated against SRAS-CoV.

Construction and Characterization of rMVAs:

Full-length consensus spike protein sequences of SARS-CoV-2 was modified recombinant methods. DNA sequences encoding the proteins were codon-optimized for vaccinia virus codon usage, synthesized, and subcloned in between Xma1 and BamH1 restriction sites of the plasmid transfer vector pLW-73 (see Patent EP2402451). Inserts are transfer in between two essential genes I8R and G1L of MVA, under the control of an independent early/late vaccinia virus promoter (modified H5 [mH5]) to generate stable MVAs. Recombinant MVAs are characterized for protein expression using Western blotting and flow cytometry, grown in large-scale in chicken embryo fibroblasts, purified, quality tested, and titrated. Expression data for two of the MVA recombinants MVA/S-Tri and MVA/S-VLP are shown in FIGS. 2A and 2B.

MVA Construct 1: MVA/S-VLP

| Name | Range | Description |
|---|---|---|
| Flank1 I8R | 1-537 | Essential gene region on MVA for recombination |
| P11 | 545-573 | promoter |
| GFP | 574-1293 | GFP |
| DR | 1294-1528 | Direct Repeats |
| mH5 | 1553-1619 | Promoter |
| Spike | 1634-5452 | Spike protein sequence |
| Aminoacid changed | 4589-4591 | K986P 4589AAA4591 changed to 4589CCA4591 |
| Aminoacid changed | 4592-4594 | V987P 4591GTT4594 changed to 4591CCT4594 |
| P2A | 5453-5518 | Porcine 2A sequence |
| Membrane | 5519-6184 | Membrane protein sequence |
| P2A | 6185-6250 | Porcine 2A sequence |
| Envelope | 6251-6475 | Envelope protein sequence |
| Flank 2 G1L | 6513-7214 | Essential gene region on MVA for recombination |
| Ampicillin resistance gene | 8500-9290 | Confers resistance to Ampicillin |

Plasmid Sequence (SEQ ID NO: 5) and Sequence encoding spike protein fusion (bold, SEQ ID NO: 6)

```
GAATTCCCTGGGACATACGTATATTTCTATGATCTGTCTTATATGAAGTCTATACAGC

GAATAGATTCAGAATTTCTACATAATTATATATTGTACGCTAATAAGTTTAATCTAA

CACTCCCCGAAGATTTGTTTATAATCCCTACAAATTTGGATATTCTATGGCGTACAA

AGGAATATATAGACTCGTTCGATATTAGTACAGAAACATGGAATAAATTATTATCCA

ATTATTATATGAAGATGATAGAGTATGCTAAACTTTATGTACTAAGTCCTATTCTCGC

TGAGGAGTTGGATAATTTTGAGAGGACGGGAGAATTAACTAGTATTGTACAAGAAG

CCATTTTATCTCTAAATTTACGAATTAAGATTTTAAATTTTAAACATAAAGATGATGA

TACGTATATACACTTTTGTAAAATATTATTCGGTGTCTATAACGGAACAAACGCTAC

TATATATTATCATAGACCTCTAACGGGATATATGAATATGATTTCAGATACTATATTT

GTTCCTGTAGATAATAACTAAGGCGCGCCTTTCATTTTGTTTTTTTCTATGCTATAAA

TGGTGAGCAAGGGCGAGGAGCTGTTCACCGGGGTGGTGCCCATCCTGGTCGAGCTG
```

-continued

GACGGCGACGTAAACGGCCACAAGTTCAGCGTGTCCGGCGAGGGCGAGGGCGATGC

CACCTACGGCAAGCTGACCCTGAAGTTCATCTGCACCACCGGCAAGCTGCCCGTGCC

CTGGCCCACCCTCGTGACCACCCTGACCTACGGCGTGCAGTGCTTCAGCCGCTACCC

CGACCACATGAAGCAGCACGACTTCTTCAAGTCCGCCATGCCCGAAGGCTACGTCC

AGGAGCGCACCATCTTCTTCAAGGACGACGGCAACTACAAGACCCGCGCCGAGGTG

AAGTTCGAGGGCGACACCCTGGTGAACCGCATCGAGCTGAAGGGCATCGACTTCAA

GGAGGACGGCAACATCCTGGGGCACAAGCTGGAGTACAACTACAACAGCCACAAC

GTCTATATCATGGCCGACAAGCAGAAGAACGGCATCAAGGTGAACTTCAAGATCCG

CCACAACATCGAGGACGGCAGCGTGCAGCTCGCCGACCACTACCAGCAGAACACCC

CCATCGGCGACGGCCCCGTGCTGCTGCCCGACAACCACTACCTGAGCACCCAGTCCG

CCCTGAGCAAAGACCCCAACGAGAAGCGCGATCACATGGTCCTGCTGGAGTTCGTG

ACCGCCGCCGGGATCACTCTCGGCATGCACGAGCTGTACAAGTAAGAGCTCGAGGA

CGGGAGAATTAACTAGTATTGTACAAGAAGCCATTTTATCTCTAAATTTACGAATTA

AGATTTTAAATTTTAAACATAAAGATGATGATACGTATATACACTTTTGTAAAATAT

TATTCGGTGTCTATAACGGAACAAACGCTACTATATATTATCATAGACCTCTAACGG

GATATATGAATATGATTTCAGATACTATATTTGTTCCTGTAGATAATAACTAACTCG

AGGCCGCTGGTACCCAACCTAAAAATTGAAAATAAATACAAAGGTTCTTGAGGGTT

GTGTTAAATTGAAAGCGAGAAATAATCATAAATAAGCCCGGGACCATGTTTGTTTT

TCTAGTTTTGCTACCGTTGGTTTCAAGTCAATGTGTAAATCTAACTACAAGAAC

TCAATTACCGCCTGCCTATACTAATTCTTTTACAAGAGGAGTATATTATCCTGA

TAAAGTTTTTAGATCTTCTGTATTACATTCTACACAAGATTTGTTTTTACCATTT

TTCTCTAATGTTACTTGGTTTCATGCAATACATGTATCTGGAACTAATGGAACA

AAAAGATTTGATAATCCAGTATTACCTTTTAATGATGGAGTTTATTTTGCTTCTA

CTGAAAAATCTAATATAATTAGAGGATGGATATTTGGAACTACATTAGATTCTA

AAACACAATCTCTACTAATTGTTAATAATGCAACTAATGTAGTTATAAAAGTAT

GTGAATTTCAATTTTGTAATGATCCATTTTTGGGAGTTTATTATCATAAAAATAA

TAAGTCTTGGATGGAATCTGAATTCAGAGTATATTCTTCTGCTAATAATTGTAC

ATTTGAATATGTATCTCAACCATTTTTGATGGATTTGGAAGGAAAACAAGGAAA

CTTTAAAAATTTGAGAGAATTTGTTTTTAAAAATATTGATGGATACTTTAAAATC

TATTCTAAACATACTCCAATTAATCTAGTAAGAGATTTGCCTCAAGGATTTTCT

GCTTTAGAACCACTAGTAGATTTGCCTATAGGAATTAATATTACTAGATTTCAA

ACATTATTAGCTTTACATAGATCTTATTTGACACCTGGAGATTCTTCTTCTGGAT

GGACTGCAGGAGCTGCAGCTTATTATGTTGGATATTTGCAACCAAGAACATTTT

TGTTAAAATATAATGAAAATGGAACTATAACAGATGCAGTTGATTGTGCTTTAG

ATCCTCTATCTGAAACTAAATGTACTTTAAAATCTTTTACTGTAGAAAAAGGAA

TCTATCAAACATCTAACTTTAGAGTACAACCAACTGAATCTATTGTTAGATTTCC

AAATATAACAAATCTATGTCCTTTTGGAGAAGTTTTTAATGCAACTAGATTTGC

TTCTGTATATGCATGGAATAGAAAAAGAATATCTAATTGCGTAGCTGATTATTC

TGTATTATATAATTCTGCATCTTTTTCTACTTTTAAATGTTATGGAGTATCTCCA

ACAAAATTGAATGATCTATGTTTTACTAATGTTTATGCAGATTCTTTTGTAATAA

GAGGAGATGAAGTTAGACAAATAGCTCCTGGACAAACAGGAAAAATAGCAGAT

-continued

TATAATTATAAATTACCAGATGATTTCACTGGATGCGTAATTGCTTGGAATTCT

AATAATTTGGATTCTAAAGTAGGAGGAAATTATAATTATTTGTATAGATTGTTT

AGAAAATCTAATTTGAAACCTTTTGAAAGAGATATTTCTACAGAAATCTATCAA

GCAGGATCTACTCCATGTAATGGAGTTGAAGGTTTTAATTGTTATTTTCCACTA

CAATCTTATGGATTTCAACCTACAAATGGAGTAGGATATCAACCATATAGAGTA

GTTGTATTATCTTTTGAATTATTACATGCACCAGCTACAGTATGTGGACCTAAA

AAATCTACTAATTTGGTTAAAAATAAGTGCGTAAACTTTAACTTTAATGGATTA

ACTGGAACAGGAGTTTTAACTGAATCTAATAAGAAATTTTTGCCTTTTCAACAA

TTTGGAAGAGATATTGCTGATACTACAGATGCAGTAAGAGATCCTCAAACTTTA

GAAATATTGGATATTACACCATGTTCTTTTGGAGGAGTTTCTGTAATAACACCA

GGAACTAATACATCTAATCAAGTTGCTGTATTATATCAAGATGTTAATTGTACT

GAAGTTCCTGTAGCAATTCATGCTGATCAATTAACTCCAACATGGAGAGTATAT

TCTACTGGATCTAATGTTTTTCAAACAAGAGCTGGATGTCTAATTGGAGCAGAA

CATGTAAATAATTCTTATGAATGTGATATTCCTATAGGAGCTGGAATATGTGCA

TCTTATCAAACTCAAACAAATTCTCCAAGAAGAGCTAGATCTGTTGCATCTCAA

TCTATAATTGCTTATACAATGTCTTTAGGAGCTGAAAATTCTGTAGCATATTCTA

ATAATTCTATTGCAATTCCTACTAACTTTACTATTTCTGTAACTACAGAAATATT

GCCAGTTTCTATGACTAAAACATCTGTAGATTGTACAATGTATATATGTGGAGA

TTCTACTGAATGTTCTAATTTGCTACTACAATATGGATCTTTTTGTACTCAATTG

AATAGAGCTTTAACAGGAATAGCAGTAGAACAAGATAAAAATACACAAGAAGT

TTTTGCTCAAGTAAAACAAATCTATAAAACTCCACCTATAAAAGATTTTGGAGG

TTTTAATTTTTCTCAAATATTGCCAGATCCTTCTAAACCTTCTAAAAGATCTTTT

ATTGAAGATTTGTTGTTTAATAAGGTTACATTAGCAGATGCTGGTTTTATAAAA

CAATATGGAGATTGTTTAGGAGATATTGCAGCTAGAGATTTGATTTGTGCTCAA

AAGTTTAATGGATTAACTGTATTACCACCTCTACTAACAGATGAAATGATAGCA

CAATATACATCTGCATTATTAGCTGGAACTATTACATCTGGATGGACTTTTGGA

GCTGGAGCAGCTTTACAAATACCATTTGCTATGCAAATGGCATATAGATTCAAT

GGAATTGGAGTTACTCAAAATGTATTATATGAAAATCAAAAACTAATTGCTAAT

CAATTCAATTCTGCAATTGGAAAAATTCAAGATTCTCTATCTTCTACAGCATCT

GCTTTAGGAAAACTACAAGATGTTGTAAATCAAAATGCACAAGCTTTAAATACT

CTAGTTAAACAACTATCTTCTAATTTTGGAGCTATTTCTTCTGTTTTAAATGATA

TATTGTCTAGACTAGATCCACCTGAAGCAGAAGTACAAATTGATAGACTAATTA

CAGGAAGATTACAATCTCTACAAACTTATGTAACACAACAACTAATTAGAGCAG

CTGAAATAAGAGCATCTGCTAATTTGGCAGCTACTAAAATGTCTGAATGCGTAT

TAGGACAATCTAAAAGAGTAGATTTTTGTGGAAAAGGATATCATTTGATGTCTT

TTCCACAATCTGCTCCTCATGGAGTAGTATTTTTGCATGTTACATATGTACCTG

CACAAGAAAAGAACTTTACTACAGCACCAGCTATATGTCATGATGGAAAAGCTC

ATTTTCCTAGAGAAGGAGTTTTTGTATCTAATGGAACTCATTGGTTTGTTACAC

AAAGAAACTTTTATGAACCACAAATTATAACTACAGATAATACATTTGTATCTG

GAAATTGTGATGTTGTAATTGGAATTGTTAATAATACTGTATATGATCCACTAC

-continued

AACCTGAACTAGATTCTTTTAAAGAAGAACTAGATAAATACTTTAAAAATCATA

CTTCTCCTGATGTTGATTTGGGAGATATATCTGGAATTAATGCTTCTGTTGTAA

ATATTCAAAAAGAAATAGATAGATTGAATGAAGTAGCAAAAAATTTGAATGAAT

CTCTAATTGATTTGCAAGAATTAGGAAAATATGAACAATATATCAAATGGCCAT

GGTATATTTGGCTAGGTTTTATAGCTGGATTAATAGCAATTGTTATGGTAACTA

TTATGTTATGTTGTATGACATCTTGTTGTTCTTGTCTAAAAGGATGTTGTTCTTG

TGGATCTTGTTGTAAATTTGATGAAGATGATTCTGAACCTGTTTTGAAAGGTGT

TAAACTACATTATACTGGATCTGGAGCAACTAATTTTTCTTTGTTAAAACAAGC

TGGAGATGTAGAAGAAAATCCAGGACCTATGGCTGATTCTAATGGAACTATAA

CAGTTGAAGAATTGAAAAAACTATTAGAACAATGGAATTTGGTAATAGGATTTT

TGTTTTTAACATGGATTTGTTTATTACAATTTGCATATGCTAATAGAAATAGATT

TTTGTATATCATAAAACTAATATTTTTGTGGTTATTATGGCCAGTTACTTTAGCA

TGTTTTGTTTTAGCAGCTGTATATAGAATTAATTGGATTACAGGAGGAATTGCA

ATAGCTATGGCATGTCTAGTAGGATTAATGTGGCTATCTTACTTTATAGCATCT

TTTAGACTATTTGCTAGAACTAGATCTATGTGGTCTTTTAATCCTGAAACAAAT

ATATTGTTAAATGTACCATTACATGGAACTATATTGACAAGACCTCTACTAGAA

TCTGAATTAGTTATTGGAGCAGTAATATTAAGAGGACATTTGAGAATTGCTGGA

CATCATTTGGGAAGATGTGATATCAAAGATTTGCCTAAAGAAATTACTGTTGCT

ACATCTAGAACTTTATCTTATTATAAACTAGGAGCATCTCAAAGAGTAGCTGGA

GATTCTGGATTTGCAGCTTATTCTAGATATAGAATTGGAAATTATAAATTGAAT

ACTGATCATTCTTCTTCTTCTGATAATATTGCATTATTAGTACAAGGATCTGGA

GCTACAAATTTTTCTTTGTTAAAACAGGCAGGAGATGTTGAAGAAAATCCAGGA

CCAATGTATTCTTTTGTATCTGAAGAAACTGGAACATTAATTGTTAATTCTGTAT

TATTGTTTTTAGCTTTTGTAGTATTTTTGCTAGTTACATTAGCAATATTGACTGC

TTTAAGATTATGTGCATATTGTTGTAATATTGTTAATGTATCTTTAGTAAAACCA

TCTTTTTATGTATATTCAAGAGTTAAAAATCTAAATTCATCAAGAGTTCCTGATC

TATTGGTATAATAATTTTTATGGATCCTCTAGAGTCGACCTGCAGTCAAACTCTAAT

GACCACATCTTTTTTTAGAGATGAAAAATTTTCCACATCTCCTTTTGTAGACACGACT

AAACATTTTGCAGAAAAAAGTTTATTAGTGTTTAGATAATCGTATACTTCATCAGTG

TAGATAGTAAATGTGAACAGATAAAAGGTATTCTTGCTCAATAGATTGGTAAATTCC

ATAGAATATATTAATCCTTTCTTCTTGAGATCCCACATCATTTCAACCAGAGACGTTT

TATCCAATGATTTACCTCGTACTATACCACATACAAAACTAGATTTTGCAGTGACGT

CGTATCTGGTATTCCTACCAAACAAAATTTTACTTTTAGTTCTTTTAGAAAATTCTAA

GGTAGAATCTCTATTTGCCAATATGTCATCTATGGAATTACCACTAGCAAAAAATGA

TAGAAATATATATTGATACATCGCAGCTGGTTTTGATCTACTATACTTTAAAAACGA

ATCAGATTCCATAATTGCCTGTATATCATCAGCTGAAAAACTATGTTTTACACGTATT

CCTTCGGCATTTCTTTTTAATGATATATCTTGTTTAGACAATGATAAAGTTATCATGT

CCATGAGAGACGCGTCTCCGTATCGTATAAATATTTCATTAGATGTTAGACGCTTCA

TTAGGGGTATACTTCTATAAGGTTTCTTAATCAGTCCATCATTGGTTGCGTCAAGAAC

AAGCTTGTCTCCCTATAGTGAGTCGTATTAGAGCTTGGCGTAATCATGGTCATAGCT

GTTTCCTGTGTGAAATTGTTATCCGCTCACAATTCCACACAACATACGAGCCGGAAG

-continued

CATAAAGTGTAAAGCCTGGGGTGCCTAATGAGTGAGCTAACTCACATTAATTGCGTT

GCGCTCACTGCCCGCTTTCGAGTCGGGAAACCTGTCGTGCCAGCTGCATTAATGAAT

CGGCCAACGCGCGGGGAGAGGCGGTTTGCGTATTGGGCGCTCTTCCGCTTCCTCGCT

CACTGACTCGCTGCGCTCGGTCGTTCGGCTGCGGCGAGCGGTATCAGCTCACTCAAA

GGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTC

GATAGGCTCCGCCCCCCTGACGAGCATCACAAAAATCGACGCTCAAGTCAGAGGTG

GCGAAACCCGACAGGACTATAAAGATACCAGGCGTTTCCCCCTGGAAGCTCCCTCG

TGCGCTCTCCTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCACT

GGCAGCAGCCACTGGTAACAGGATTAGCAGAGCGAGGTATGTAGGCGGTGCTACAG

AGTTCTTGAAGTGGTGGCCTAACTACGGCTACACTAGAAGGACAGTATTTGGTATCT

GCGCTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGCGCA

GAAAAAAAGGATCTCAAGAAGATCCTTTGATCTTTTCTACGGGGTCTGACGCTCAGT

GGAACGAAAACTCACGTTAAGGGATTTTGGTCATGAGATTATCAAAAAGGATCTTC

ACCTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGATC

TGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCA

CCGGCTCCAGATTTATCAGCAATAAACCAGCCAGCCGGAAGGGCCGAGCGCAGAAG

TGGTCCTGCAACTTTATCCGCCTCCATCCAGTCTATTAATTGTTGCCGGGAAGCTAGA

GTAAGTAGTTCGCCAGTTAATAGTTTGCGCAACGTTGTTGGCATTGCTACAGGCATC

GTGGTGTCACGCTCGTCGTTTGGTATGGCTTCATTCAGCTCCGGTTCCCAACGATCAA

GGCGAGTTACATGATCCCCCATGTTGTGCAAAAAAGCGGTTAGCTCCTTCGGTCCTC

CGATCGTTGTCAGAAGTAAGTTGGCCGCAGTGTTATCACTCATGGTTATGGCAGCAC

TGCATAATTCTCTTACTGTCATGCCATCCGTAAGATGCTTTTCTGTGACTGGTGAGTA

CTCAACCAAGTCATTCTGAGAATAGTGTATGCGGCGACCGAGTTGCTCTTGCCCGGC

GTCAATACGGGATAATACCGCGCCACATAGCAGAACTTTAAAAGTGCTCATCATTGG

AAAACGTTCTTCGGGGCGAAAACTCTCAAGGATCTTACCGCTGTTGAGATCCAGTTC

GATGTAACCCACTCGTGCACCCAACTGATCTTCAGCATCTTTTACTTTCACCAGCGTT

TCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCA

GGGTTATTGTCTCATGAGCGGATACATATTTGAATGTATTTAGAAAAATAAACAAAT

AGGGGTTCCGCGCACATTTCCCCGAAAAGTGCCACCTGACGTCTAAGAAACCATTAT

TATCATGACATTAACCTATAAAAATAGGCGTATCACGAGGCCCTTTCGTCTCGCGCG

TTTCGGTGATGACGGTGAAAACCTCTGACACATGCAGCTCCCGGAGACGGTCACAG

CTTGTCTGTAAGCGGATGCCGGGAGCAGACAAGCCCGTCAGGGCGCGTCAGCGGGT

-continued

GTTGGCGGGTGTCGGGGCTGGCTTAACTATGCGGCATCAGAGCAGATTGTACTGAG

AGTGCACCATATGCGGTGTGAAATACCGCACAGATGCGTAAGGAGAAAATACCGCA

TCAGGCGCCATTCGCCATTCAGGCTGCGCAACTGTTGGGAAGGGCGATCGGTGCGG

GCCTCTTCGCTATTACGCCAGCTGGCGAAAGGGGGATGTGCTGCAAGGCGATTAAGT

TGGGTAACGCCAGGGTTTTCCCAGTCACGACGTTGTAAAACGACGGCCAGTGAATTG

GATTTAGGTGACACTATA

MVA Construct 2: MVA/S-Tri

| Name | Range | Description |
|---|---|---|
| Flank1 I8R | 1-537 | Essential gene region on MVA for recombination |
| P11 | 545-573 | promoter |
| GFP | 574-1293 | GFP |
| DR | 1294-1528 | Direct Repeats |
| mHS | 1553-1619 | Promoter |
| Spike | 1634-5452 | Spike Protein sequence |
| Aminoacid changed | 4589-4591 | K986P 4589AAA4591 changed to 4589CCA4591 |
| Aminoacid changed | 4592-4594 | V987P 4591GTT4594 changed to 4591CCT4594 |
| Flank 2 G1L | 5490-6191 | Essential gene region on MVA for recombination |
| Ampicillin resistance gene | 7477-8267 | Confers resistance to Ampicillin |

Plasmid Sequence (SEQ ID NO: 7) and Sequence Encoding Spike Protein (Bold, SEQ ID NO: 8)

GAATTCCCTGGGACATACGTATATTTCTATGATCTGTCTTATATGAAGTCTATACAGC

GAATAGATTCAGAATTTCTACATAATTATATATTGTACGCTAATAAGTTTAATCTAA

CACTCCCCGAAGATTTGTTTATAATCCCTACAAATTTGGATATTCTATGGCGTACAA

AGGAATATATAGACTCGTTCGATATTAGTACAGAAACATGGAATAAATTATTATCCA

ATTATTATATGAAGATGATAGAGTATGCTAAACTTTATGTACTAAGTCCTATTCTCGC

TGAGGAGTTGGATAATTTTGAGAGGACGGGAGAATTAACTAGTATTGTACAAGAAG

CCATTTTATCTCTAAATTTACGAATTAAGATTTTAAATTTTAAACATAAAGATGATGA

TACGTATATACACTTTTGTAAAATATTATTCGGTGTCTATAACGGAACAAACGCTAC

TATATATTATCATAGACCTCTAACGGGATATATGAATATGATTTCAGATACTATATTT

GTTCCTGTAGATAATAACTAAGGCGCGCCTTTCATTTTGTTTTTTTCTATGCTATAAA

TGGTGAGCAAGGGCGAGGAGCTGTTCACCGGGGTGGTGCCCATCCTGGTCGAGCTG

GACGGCGACGTAAACGGCCACAAGTTCAGCGTGTCCGGCGAGGGCGAGGGCGATGC

CACCTACGGCAAGCTGACCCTGAAGTTCATCTGCACCACCGGCAAGCTGCCCGTGCC

CTGGCCCACCCTCGTGACCACCCTGACCTACGGCGTGCAGTGCTTCAGCCGCTACCC

CGACCACATGAAGCAGCACGACTTCTTCAAGTCCGCCATGCCCGAAGGCTACGTCC

AGGAGCGCACCATCTTCTTCAAGGACGACGGCAACTACAAGACCCGCGCCGAGGTG

AAGTTCGAGGGCGACACCCTGGTGAACCGCATCGAGCTGAAGGGCATCGACTTCAA

GGAGGACGGCAACATCCTGGGGCACAAGCTGGAGTACAACTACAACAGCCACAAC

GTCTATATCATGGCCGACAAGCAGAAGAACGGCATCAAGGTGAACTTCAAGATCCG

CCACAACATCGAGGACGGCAGCGTGCAGCTCGCCGACCACTACCAGCAGAACACCC

CCATCGGCGACGGCCCCGTGCTGCTGCCCGACAACCACTACCTGAGCACCCAGTCCG

CCCTGAGCAAAGACCCCAACGAGAAGCGCGATCACATGGTCCTGCTGGAGTTCGTG

ACCGCCGCCGGGATCACTCTCGGCATGCACGAGCTGTACAAGTAAGAGCTCGAGGA

CGGGAGAATTAACTAGTATTGTACAAGAAGCCATTTTATCTCTAAATTTACGAATTA

AGATTTTAAATTTTAAACATAAAGATGATGATACGTATATACACTTTTGTAAAATAT

-continued

TATTCGGTGTCTATAACGGAACAAACGCTACTATATATTATCATAGACCTCTAACGG

GATATATGAATATGATTTCAGATACTATATTTGTTCCTGTAGATAATAACTAACTCG

AGGCCGCTGGTACCCAACCTAAAAATTGAAAATAAATACAAAGGTTCTTGAGGGTT

GTGTTAAATTGAAAGCGAGAAATAATCATAAATAAGCCCGGGACCATGTTTGTTTT

TCTAGTTTTGCTACCGTTGGTTTCAAGTCAATGTGTAAATCTAACTACAAGAAC

TCAATTACCGCCTGCCTATACTAATTCTTTTACAAGAGGAGTATATTATCCTGA

TAAAGTTTTTAGATCTTCTGTATTACATTCTACACAAGATTTGTTTTTACCATTT

TTCTCTAATGTTACTTGGTTTCATGCAATACATGTATCTGGAACTAATGGAACA

AAAAGATTTGATAATCCAGTATTACCTTTTAATGATGGAGTTTATTTTGCTTCTA

CTGAAAAATCTAATATAATTAGAGGATGGATATTTGGAACTACATTAGATTCTA

AAACACAATCTCTACTAATTGTTAATAATGCAACTAATGTAGTTATAAAAGTAT

GTGAATTTCAATTTTGTAATGATCCATTTTTGGGAGTTTATTATCATAAAAATAA

TAAGTCTTGGATGGAATCTGAATTCAGAGTATATTCTTCTGCTAATAATTGTAC

ATTTGAATATGTATCTCAACCATTTTTGATGGATTTGGAAGGAAAACAAGGAAA

CTTTAAAAATTTGAGAGAATTTGTTTTTAAAAATATTGATGGATACTTTAAAATC

TATTCTAAACATACTCCAATTAATCTAGTAAGAGATTTGCCTCAAGGATTTTCT

GCTTTAGAACCACTAGTAGATTTGCCTATAGGAATTAATATTACTAGATTTCAA

ACATTATTAGCTTTACATAGATCTTATTTGACACCTGGAGATTCTTCTTCTGGAT

GGACTGCAGGAGCTGCAGCTTATTATGTTGGATATTTGCAACCAAGAACATTTT

TGTTAAAATATAATGAAAATGGAACTATAACAGATGCAGTTGATTGTGCTTTAG

ATCCTCTATCTGAAACTAAATGTACTTTAAAATCTTTTACTGTAGAAAAAGGAA

TCTATCAAACATCTAACTTTAGAGTACAACCAACTGAATCTATTGTTAGATTTCC

AAATATAACAAATCTATGTCCTTTTGGAGAAGTTTTTAATGCAACTAGATTTGC

TTCTGTATATGCATGGAATAGAAAAAGAATATCTAATTGCGTAGCTGATTATTC

TGTATTATATAATTCTGCATCTTTTTCTACTTTTAAATGTTATGGAGTATCTCCA

ACAAAATTGAATGATCTATGTTTTACTAATGTTTATGCAGATTCTTTTGTAATAA

GAGGAGATGAAGTTAGACAAATAGCTCCTGGACAAACAGGAAAAATAGCAGAT

TATAATTATAAATTACCAGATGATTTCACTGGATGCGTAATTGCTTGGAATTCT

AATAATTTGGATTCTAAAGTAGGAGGAAATTATAATTATTTGTATAGATTGTTT

AGAAAATCTAATTTGAAACCTTTTGAAAGAGATATTTCTACAGAAATCTATCAA

GCAGGATCTACTCCATGTAATGGAGTTGAAGGTTTTAATTGTTATTTTCCACTA

CAATCTTATGGATTTCAACCTACAAATGGAGTAGGATATCAACCATATAGAGTA

GTTGTATTATCTTTTGAATTATTACATGCACCAGCTACAGTATGTGGACCTAAA

AAATCTACTAATTTGGTTAAAAATAAGTGCGTAAACTTTAACTTTAATGGATTA

ACTGGAACAGGAGTTTTAACTGAATCTAATAAGAAATTTTTGCCTTTTCAACAA

TTTGGAAGAGATATTGCTGATACTACAGATGCAGTAAGAGATCCTCAAACTTTA

GAAATATTGGATATTACACCATGTTCTTTTGGAGGAGTTTCTGTAATAACACCA

GGAACTAATACATCTAATCAAGTTGCTGTATTATATCAAGATGTTAATTGTACT

GAAGTTCCTGTAGCAATTCATGCTGATCAATTAACTCCAACATGGAGAGTATAT

TCTACTGGATCTAATGTTTTTCAAACAAGAGCTGGATGTCTAATTGGAGCAGAA

CATGTAAATAATTCTTATGAATGTGATATTCCTATAGGAGCTGGAATATGTGCA

-continued

TCTTATCAAACTCAAACAAATTCTCCAAGAAGAGCTAGATCTGTTGCATCTCAA

TCTATAATTGCTTATACAATGTCTTTAGGAGCTGAAAATTCTGTAGCATATTCTA

ATAATTCTATTGCAATTCCTACTAACTTTACTATTTCTGTAACTACAGAAATATT

GCCAGTTTCTATGACTAAAACATCTGTAGATTGTACAATGTATATATGTGGAGA

TTCTACTGAATGTTCTAATTTGCTACTACAATATGGATCTTTTTGTACTCAATTG

AATAGAGCTTTAACAGGAATAGCAGTAGAACAAGATAAAAATACACAAGAAGT

TTTTGCTCAAGTAAAACAAATCTATAAAACTCCACCTATAAAAGATTTTGGAGG

TTTTAATTTTTCTCAAATATTGCCAGATCCTTCTAAACCTTCTAAAAGATCTTTT

ATTGAAGATTTGTTGTTTAATAAGGTTACATTAGCAGATGCTGGTTTTATAAAA

CAATATGGAGATTGTTTAGGAGATATTGCAGCTAGAGATTTGATTTGTGCTCAA

AAGTTTAATGGATTAACTGTATTACCACCTCTACTAACAGATGAAATGATAGCA

CAATATACATCTGCATTATTAGCTGGAACTATTACATCTGGATGGACTTTTGGA

GCTGGAGCAGCTTTACAAATACCATTTGCTATGCAAATGGCATATAGATTCAAT

GGAATTGGAGTTACTCAAAATGTATTATATGAAAATCAAAAACTAATTGCTAAT

CAATTCAATTCTGCAATTGGAAAAATTCAAGATTCTCTATCTTCTACAGCATCT

GCTTTAGGAAAACTACAAGATGTTGTAAATCAAAATGCACAAGCTTTAAATACT

CTAGTTAAACAACTATCTTCTAATTTTGGAGCTATTTCTTCTGTTTTAAATGATA

TATTGTCTAGACTAGATCCACCTGAAGCAGAAGTACAAATTGATAGACTAATTA

CAGGAAGATTACAATCTCTACAAACTTATGTAACACAACAACTAATTAGAGCAG

CTGAAATAAGAGCATCTGCTAATTTGGCAGCTACTAAAATGTCTGAATGCGTAT

TAGGACAATCTAAAAGAGTAGATTTTTGTGGAAAAGGATATCATTTGATGTCTT

TTCCACAATCTGCTCCTCATGGAGTAGTATTTTTGCATGTTACATATGTACCTG

CACAAGAAAAGAACTTTACTACAGCACCAGCTATATGTCATGATGGAAAAGCTC

ATTTTCCTAGAGAAGGAGTTTTTGTATCTAATGGAACTCATTGGTTTGTTACAC

AAAGAAACTTTTATGAACCACAAATTATAACTACAGATAATACATTTGTATCTG

GAAATTGTGATGTTGTAATTGGAATTGTTAATAATACTGTATATGATCCACTAC

AACCTGAACTAGATTCTTTTAAAGAAGAACTAGATAAATACTTTAAAAATCATA

CTTCTCCTGATGTTGATTTGGGAGATATATCTGGAATTAATGCTTCTGTTGTAA

ATATTCAAAAAGAAATAGATAGATTGAATGAAGTAGCAAAAAATTTGAATGAAT

CTCTAATTGATTTGCAAGAATTAGGAAAATATGAACAATATATCAAATGGCCAT

GGTATATTTGGCTAGGTTTTATAGCTGGATTAATAGCAATTGTTATGGTAACTA

TTATGTTATGTTGTATGACATCTTGTTGTTCTTGTCTAAAAGGATGTTGTTCTTG

TGGATCTTGTTGTAAATTTGATGAAGATGATTCTGAACCTGTTTTGAAAGGTGT

TAAACTACATTATACTTAATAATTTTTATGGATCCTCTAGAGTCGACCTGCAGTCAA

ACTCTAATGACCACATCTTTTTTTAGAGATGAAAAATTTTCCACATCTCCTTTTGTAG

ACACGACTAAACATTTTGCAGAAAAAAGTTTATTAGTGTTTAGATAATCGTATACTT

CATCAGTGTAGATAGTAAATGTGAACAGATAAAAGGTATTCTTGCTCAATAGATTGG

TAAATTCCATAGAATATATTAATCCTTTCTTCTTGAGATCCCACATCATTTCAACCAG

AGACGTTTTATCCAATGATTTACCTCGTACTATACCACATACAAAACTAGATTTTGC

AGTGACGTCGTATCTGGTATTCCTACCAAACAAAATTTACTTTTAGTTCTTTTAGAA

-continued

AATTCTAAGGTAGAATCTCTATTTGCCAATATGTCATCTATGGAATTACCACTAGCA

AAAAATGATAGAAATATATATTGATACATCGCAGCTGGTTTTGATCTACTATACTTT

AAAAACGAATCAGATTCCATAATTGCCTGTATATCATCAGCTGAAAAACTATGTTTT

ACACGTATTCCTTCGGCATTTCTTTTTAATGATATATCTTGTTTAGACAATGATAAAG

TTATCATGTCCATGAGAGACGCGTCTCCGTATCGTATAAATATTTCATTAGATGTTAG

ACGCTTCATTAGGGGTATACTTCTATAAGGTTTCTTAATCAGTCCATCATTGGTTGCG

TCAAGAACAAGCTTGTCTCCCTATAGTGAGTCGTATTAGAGCTTGGCGTAATCATGG

TCATAGCTGTTTCCTGTGTGAAATTGTTATCCGCTCACAATTCCACACAACATACGA

GCCGGAAGCATAAAGTGTAAAGCCTGGGGTGCCTAATGAGTGAGCTAACTCACATT

AATTGCGTTGCGCTCACTGCCCGCTTTCGAGTCGGGAAACCTGTCGTGCCAGCTGCA

TTAATGAATCGGCCAACGCGCGGGGAGAGGCGGTTTGCGTATTGGGCGCTCTTCCGC

TTCCTCGCTCACTGACTCGCTGCGCTCGGTCGTTCGGCTGCGGCGAGCGGTATCAGC

TCACTCAAAGGCGGTAATACGGTTATCCACAGAATCAGGGGATAACGCAGGAAAGA

ACATGTGAGCAAAAGGCCAGCAAAAGGCCAGGAACCGTAAAAAGGCCGCGTTGCT

GGCGTTTTTCGATAGGCTCCGCCCCCCTGACGAGCATCACAAAAATCGACGCTCAAG

TCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTT

TCTCCCTTCGGGAAGCGTGGCGCTTTCTCATAGCTCACGCTGTAGGTATCTCAGTTCG

GTGTAGGTCGTTCGCTCCAAGCTGGGCTGTGTGCACGAACCCCCCGTTCAGCCCGAC

CGCTGCGCCTTATCCGGTAACTATCGTCTTGAGTCCAACCCGGTAAGACACGACTTA

TCGCCACTGGCAGCAGCCACTGGTAACAGGATTAGCAGAGCGAGGTATGTAGGCGG

TGCTACAGAGTTCTTGAAGTGGTGGCCTAACTACGGCTACACTAGAAGGACAGTATT

TGGTATCTGCGCTCTGCTGAAGCCAGTTACCTTCGGAAAAAGAGTTGGTAGCTCTTG

ATCCGGCAAACAAACCACCGCTGGTAGCGGTGGTTTTTTTGTTTGCAAGCAGCAGAT

TACGCGCAGAAAAAAAGGATCTCAAGAAGATCCTTTGATCTTTTCTACGGGGTCTGA

CGCTCAGTGGAACGAAAACTCACGTTAAGGGATTTTGGTCATGAGATTATCAAAAA

GGATCTTCACCTAGATCCTTTTAAATTAAAAATGAAGTTTTAAATCAATCTAAAGTA

TATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAAC

TACGATACGGGAGGGCTTACCATCTGGCCCCAGTGCTGCAATGATACCGCGAGACC

CACGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCGG

GAAGCTAGAGTAAGTAGTTCGCCAGTTAATAGTTTGCGCAACGTTGTTGGCATTGCT

ACAGGCATCGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTTAGCTCCT

TCGGTCCTCCGATCGTTGTCAGAAGTAAGTTGGCCGCAGTGTTATCACTCATGGTTA

TGGCAGCACTGCATAATTCTCTTACTGTCATGCCATCCGTAAGATGCTTTTCTGTGAC

TGGTGAGTACTCAACCAAGTCATTCTGAGAATAGTGTATGCGGCGACCGAGTTGCTC

TTGCCCGGCGTCAATACGGGATAATACCGCGCCACATAGCAGAACTTTAAAAGTGCT

CATCATTGGAAAACGTTCTTCGGGGCGAAAACTCTCAAGGATCTTACCGCTGTTGAG

ATCCAGTTCGATGTAACCCACTCGTGCACCCAACTGATCTTCAGCATCTTTTACTTTC

-continued

ACCAGCGTTTCTGGGTGAGCAAAAACAGGAAGGCAAAATGCCGCAAAAAAGGGAA

TAAGGGCGACACGGAAATGTTGAATACTCATACTCTTCCTTTTTCAATATTATTGAA

GCATTTATCAGGGTTATTGTCTCATGAGCGGATACATATTTGAATGTATTTAGAAAA

ATAAACAAATAGGGGTTCCGCGCACATTTCCCCGAAAAGTGCCACCTGACGTCTAA

GAAACCATTATTATCATGACATTAACCTATAAAAATAGGCGTATCACGAGGCCCTTT

CGTCTCGCGCGTTTCGGTGATGACGGTGAAAACCTCTGACACATGCAGCTCCCGGAG

ACGGTCACAGCTTGTCTGTAAGCGGATGCCGGGAGCAGACAAGCCCGTCAGGGCGC

GTCAGCGGGTGTTGGCGGGTGTCGGGGCTGGCTTAACTATGCGGCATCAGAGCAGA

TTGTACTGAGAGTGCACCATATGCGGTGTGAAATACCGCACAGATGCGTAAGGAGA

AAATACCGCATCAGGCGCCATTCGCCATTCAGGCTGCGCAACTGTTGGGAAGGGCG

ATCGGTGCGGGCCTCTTCGCTATTACGCCAGCTGGCGAAAGGGGGATGTGCTGCAA

GGCGATTAAGTTGGGTAACGCCAGGGTTTTCCCAGTCACGACGTTGTAAAACGACG

GCCAGTGAATTGGATTTAGGTGACACTATA

MVA Construct 3: MVA/S-Tri-Sec

| Name | Range | Description |
|---|---|---|
| Flank1 I8R | 1-537 | Essential gene region on MVA for recombination |
| P11 | 545-573 | promoter |
| GFP | 574-1293 | GFP |
| DR | 1294-1528 | Direct Repeats |
| mH5 | 1553-1619 | Promoter |
| GmCSE signal peptide | 1634-1684 | Secretory signal sequence |
| Spike | 1685-5269 | Spike protein sequence and transmembrane domain deleted |
| Aminoacid changed | 4601-4603 | K986P 4601AAA4603 changed to 4601CCA4603 |
| Aminoacid changed | 4592-4594 | V987P 4604GTT4606 changed to 4604CCT4606 |
| Fold on sequence | 5270-5359 | Fold on sequence added |
| Flank 2 G1L | 5397-6098 | Essential gene region on MVA for recombination |
| Ampicillin resistance gene | 7384-8174 | Confers resistance to Ampicillin |

Plasmid Sequence (SEQ ID NO: 9) and Sequence Encoding Spike Protein (Bold, SEQ ID NO: 10)

GAATTCCCTGGGACATACGTATATTTCTATGATCTGTCTT

ATATGAAGTCTATACAGCGAATAGATTCAGAATTTCTACA

TAATTATATATTGTACGCTAATAAGTTTAATCTAACACTC

CCCGAAGATTTGTTTATAATCCCTACAAATTTGGATATTC

TATGGCGTACAAAGGAATATATAGACTCGTTCGATATTAG

TACAGAAACATGGAATAAATTATTATCCAATTATTATATG

AAGATGATAGAGTATGCTAAACTTTATGTACTAAGTCCTA

TTCTCGCTGAGGAGTTGGATAATTTTGAGAGGACGGGAGA

ATTAACTAGTATTGTACAAGAAGCCATTTTATCTCTAAAT

TTACGAATTAAGATTTTAAATTTTAAACATAAAGATGATG

ATACGTATATACACTTTTGTAAAATATTATTCGGTGTCTA

-continued

TAACGGAACAAACGCTACTATATATTATCATAGACCTCTA

ACGGGATATATGAATATGATTTCAGATACTATATTTGTTC

CTGTAGATAATAACTAAGGCGCGCCTTTCATTTTGTTTTT

TTCTATGCTATAAATGGTGAGCAAGGGCGAGGAGCTGTTC

ACCGGGGTGGTGCCCATCCTGGTCGAGCTGGACGGCGACG

TAAACGGCCACAAGTTCAGCGTGTCCGGCGAGGGCGAGGG

CGATGCCACCTACGGCAAGCTGACCCTGAAGTTCATCTGC

ACCACCGGCAAGCTGCCCGTGCCCTGGCCCACCCTCGTGA

CCACCCTGACCTACGGCGTGCAGTGCTTCAGCCGCTACCC

CGACCACATGAAGCAGCACGACTTCTTCAAGTCCGCCATG

CCCGAAGGCTACGTCCAGGAGCGCACCATCTTCTTCAAGG

ACGACGGCAACTACAAGACCCGCGCCGAGGTGAAGTTCGA

GGGCGACACCCTGGTGAACCGCATCGAGCTGAAGGGCATC

GACTTCAAGGAGGACGGCAACATCCTGGGGCACAAGCTGG

AGTACAACTACAACAGCCACAACGTCTATATCATGGCCGA

CAAGCAGAAGAACGGCATCAAGGTGAACTTCAAGATCCGC

CACAACATCGAGGACGGCAGCGTGCAGCTCGCCGACCACT

ACCAGCAGAACACCCCCATCGGCGACGGCCCCGTGCTGCT

GCCCGACAACCACTACCTGAGCACCCAGTCCGCCCTGAGC

AAAGACCCCAACGAGAAGCGCGATCACATGGTCCTGCTGG

AGTTCGTGACCGCCGCCGGGATCACTCTCGGCATGCACGA

GCTGTACAAGTAAGAGCTCGAGGACGGGAGAATTAACTAG

TATTGTACAAGAAGCCATTTTATCTCTAAATTTACGAATT

AAGATTTTAAATTTTAAACATAAAGATGATGATACGTATA

TACACTTTTGTAAAATATTATTCGGTGTCTATAACGGAAC

AAACGCTACTATATATTATCATAGACCTCTAACGGGATAT

-continued

ATGAATATGATTTCAGATACTATATTTGTTCCTGTAGATA
ATAACTAACTCGAGGCCGCTGGTACCCAACCTAAAAATTG
AAAATAAATACAAAGGTTCTTGAGGGTTGTGTTAAATTGA
AAGCGAGAAATAATCATAAATAAGCCCGGGACCATGTGGT
TACAAGGACTACTATTACTAGGTACTGTTGCCTGTTCAAT
TTCACAATGTGTAAATCTAACTACAAGAACTCAATTACCG
CCTGCCTATACTAATTCTTTTACAAGAGGAGTATATTATC
CTGATAAAGTTTTTAGATCTTCTGTATTACATTCTACACA
AGATTTGTTTTTACCATTTTTCTCTAATGTTACTTGGTTT
CATGCAATACATGTATCTGGAACTAATGGAACAAAAAGAT
TTGATAATCCAGTATTACCTTTTAATGATGGAGTTTATTT
TGCTTCTACTGAAAAATCTAATATAATTAGAGGATGGATA
TTTGGAACTACATTAGATTCTAAAACACAATCTCTACTAA
TTGTTAATAATGCAACTAATGTAGTTATAAAAGTATGTGA
ATTTCAATTTTGTAATGATCCATTTTTGGGAGTTTATTAT
CATAAAAATAATAAGTCTTGGATGGAATCTGAATTCAGAG
TATATTCTTCTGCTAATAATTGTACATTTGAATATGTATC
TCAACCATTTTTGATGGATTTGGAAGGAAAACAAGGAAAC
TTTAAAAATTTGAGAGAATTTGTTTTTAAAAATATTGATG
GATACTTTAAAATCTATTCTAAACATACTCCAATTAATCT
AGTAAGAGATTTGCCTCAAGGATTTTCTGCTTTAGAACCA
CTAGTAGATTTGCCTATAGGAATTAATATTACTAGATTTC
AAACATTATTAGCTTTACATAGATCTTATTTGACACCTGG
AGATTCTTCTTCTGGATGGACTGCAGGAGCTGCAGCTTAT
TATGTTGGATATTTGCAACCAAGAACATTTTTGTTAAAAT
ATAATGAAAATGGAACTATAACAGATGCAGTTGATTGTGC
TTTAGATCCTCTATCTGAAACTAAATGTACTTTAAAATCT
TTTACTGTAGAAAAAGGAATCTATCAAACATCTAACTTTA
GAGTACAACCAACTGAATCTATTGTTAGATTTCCAAATAT
AACAAATCTATGTCCTTTTGGAGAAGTTTTTAATGCAACT
AGATTTGCTTCTGTATATGCATGGAATAGAAAAAGAATAT
CTAATTGCGTAGCTGATTATTCTGTATTATATAATTCTGC
ATCTTTTTCTACTTTTAAATGTTATGGAGTATCTCCAACA
AAATTGAATGATCTATGTTTTACTAATGTTTATGCAGATT
CTTTTGTAATAAGAGGAGATGAAGTTAGACAAATAGCTCC
TGGACAAACAGGAAAAATAGCAGATTATAATTATAAATTA
CCAGATGATTTCACTGGATGCGTAATTGCTTGGAATTCTA
ATAATTTGGATTCTAAAGTAGGAGGAAATTATAATTATTT
GTATAGATTGTTTAGAAAATCTAATTTGAAACCTTTTGAA
AGAGATATTTCTACAGAAATCTATCAAGCAGGATCTACTC

-continued

CATGTAATGGAGTTGAAGGTTTTAATTGTTATTTTCCACT
ACAATCTTATGGATTTCAACCTACAAATGGAGTAGGATAT
CAACCATATAGAGTAGTTGTATTATCTTTTGAATTATTAC
ATGCACCAGCTACAGTATGTGGACCTAAAAAATCTACTAA
TTTGGTTAAAAATAAGTGCGTAAACTTTAACTTTAATGGA
TTAACTGGAACAGGAGTTTTAACTGAATCTAATAAGAAAT
TTTTGCCTTTTCAACAATTTGGAAGAGATATTGCTGATAC
TACAGATGCAGTAAGAGATCCTCAAACTTTAGAAATATTG
GATATTACACCATGTTCTTTTGGAGGAGTTTCTGTAATAA
CACCAGGAACTAATACATCTAATCAAGTTGCTGTATTATA
TCAAGATGTTAATTGTACTGAAGTTCCTGTAGCAATTCAT
GCTGATCAATTAACTCCAACATGGAGAGTATATTCTACTG
GATCTAATGTTTTTCAAACAAGAGCTGGATGTCTAATTGG
AGCAGAACATGTAAATAATTCTTATGAATGTGATATTCCT
ATAGGAGCTGGAATATGTGCATCTTATCAAACTCAAACAA
ATTCTCCAAGAAGAGCTAGATCTGTTGCATCTCAATCTAT
AATTGCTTATACAATGTCTTTAGGAGCTGAAAATTCTGTA
GCATATTCTAATAATTCTATTGCAATTCCTACTAACTTTA
CTATTTCTGTAACTACAGAAATATTGCCAGTTTCTATGAC
TAAAACATCTGTAGATTGTACAATGTATATATGTGGAGAT
TCTACTGAATGTTCTAATTTGCTACTACAATATGGATCTT
TTTGTACTCAATTGAATAGAGCTTTAACAGGAATAGCAGT
AGAACAAGATAAAAATACACAAGAAGTTTTTGCTCAAGTA
AAACAAATCTATAAAACTCCACCTATAAAAGATTTTGGAG
GTTTTAATTTTTCTCAAATATTGCCAGATCCTTCTAAACC
TTCTAAAAGATCTTTTATTGAAGATTTGTTGTTTAATAAG
GTTACATTAGCAGATGCTGGTTTTATAAAACAATATGGAG
ATTGTTTAGGAGATATTGCAGCTAGAGATTTGATTTGTGC
TCAAAAGTTTAATGGATTAACTGTATTACCACCTCTACTA
ACAGATGAAATGATAGCACAATATACATCTGCATTATTAG
CTGGAACTATTACATCTGGATGGACTTTTGGAGCTGGAGC
AGCTTTACAAATACCATTTGCTATGCAAATGGCATATAGA
TTCAATGGAATTGGAGTTACTCAAAATGTATTATATGAAA
ATCAAAAACTAATTGCTAATCAATTCAATTCTGCAATTGG
AAAAATTCAAGATTCTCTATCTTCTACAGCATCTGCTTTA
GGAAAACTACAAGATGTTGTAAATCAAAATGCACAAGCTT
TAAATACTCTAGTTAAACAACTATCTTCTAATTTTGGAGC
TATTTCTTCTGTTTTAAATGATATATTGTCTAGACTAGAT
CCACCTGAAGCAGAAGTACAAATTGATAGACTAATTACAG
GAAGATTACAATCTCTACAAACTTATGTAACACAACAACT
AATTAGAGCAGCTGAAATAAGAGCATCTGCTAATTTGGCA

-continued

GCTACTAAAATGTCTGAATGCGTATTAGGACAATCTAAAA

GAGTAGATTTTTGTGGAAAAGGATATCATTTGATGTCTTT

TCCACAATCTGCTCCTCATGGAGTAGTATTTTTGCATGTT

ACATATGTACCTGCACAAGAAAAGAACTTTACTACAGCAC

CAGCTATATGTCATGATGGAAAAGCTCATTTTCCTAGAGA

AGGAGTTTTTGTATCTAATGGAACTCATTGGTTTGTTACA

CAAAGAAACTTTTATGAACCACAAATTATAACTACAGATA

ATACATTTGTATCTGGAAATTGTGATGTTGTAATTGGAAT

TGTTAATAATACTGTATATGATCCACTACAACCTGAACTA

GATTCTTTTAAAGAAGAACTAGATAAATACTTTAAAAATC

ATACTTCTCCTGATGTTGATTTGGGAGATATATCTGGAAT

TAATGCTTCTGTTGTAAATATTCAAAAAGAAATAGATAGA

TTGAATGAAGTAGCAAAAAATTTGAATGAATCTCTAATTG

ATTTGCAAGAATTAGGAAAATATGAACAAGGATCTGCTGG

ATATATTCCAGAAGCACCTAGAGATGGACAAGCGTATGTT

AGAAAAGATGGTGAATGGGTATTATTGAGTACATTTTTGT

AATAATTTTTATGGATCCTCTAGAGTCGACCTGCAGTCAA

ACTCTAATGACCACATCTTTTTTTAGAGATGAAAAATTTT

CCACATCTCCTTTTGTAGACACGACTAAACATTTTGCAGA

AAAAAGTTTATTAGTGTTTAGATAATCGTATACTTCATCA

GTGTAGATAGTAAATGTGAACAGATAAAAGGTATTCTTGC

TCAATAGATTGGTAAATTCCATAGAATATATTAATCCTTT

CTTCTTGAGATCCCACATCATTTCAACCAGAGACGTTTTA

TCCAATGATTTACCTCGTACTATACCACATACAAAACTAG

ATTTTGCAGTGACGTCGTATCTGGTATTCCTACCAAACAA

AATTTTACTTTTAGTTCTTTTAGAAAATTCTAAGGTAGAA

TCTCTATTTGCCAATATGTCATCTATGGAATTACCACTAG

CAAAAAATGATAGAAATATATATTGATACATCGCAGCTGG

TTTTGATCTACTATACTTTAAAAACGAATCAGATTCCATA

ATTGCCTGTATATCATCAGCTGAAAAACTATGTTTTACAC

GTATTCCTTCGGCATTTCTTTTTAATGATATATCTTGTTT

AGACAATGATAAAGTTATCATGTCCATGAGAGACGCGTCT

CCGTATCGTATAAATATTTCATTAGATGTTAGACGCTTCA

TTAGGGGTATACTTCTATAAGGTTTCTTAATCAGTCCATC

ATTGGTTGCGTCAAGAACAAGCTTGTCTCCCTATAGTGAG

TCGTATTAGAGCTTGGCGTAATCATGGTCATAGCTGTTTC

CTGTGTGAAATTGTTATCCGCTCACAATTCCACACAACAT

ACGAGCCGGAAGCATAAAGTGTAAAGCCTGGGGTGCCTAA

TGAGTGAGCTAACTCACATTAATTGCGTTGCGCTCACTGC

CCGCTTTCGAGTCGGGAAACCTGTCGTGCCAGCTGCATTA

-continued

ATGAATCGGCCAACGCGCGGGGAGAGGCGGTTTGCGTATT

GGGCGCTCTTCCGCTTCCTCGCTCACTGACTCGCTGCGCT

CGGTCGTTCGGCTGCGGCGAGCGGTATCAGCTCACTCAAA

GGCGGTAATACGGTTATCCACAGAATCAGGGGATAACGCA

GGAAAGAACATGTGAGCAAAAGGCCAGCAAAAGGCCAGGA

ACCGTAAAAAGGCCGCGTTGCTGGCGTTTTTCGATAGGCT

CCGCCCCCCTGACGAGCATCACAAAAATCGACGCTCAAGT

CAGAGGTGGCGAAACCCGACAGGACTATAAAGATACCAGG

CGTTTCCCCCTGGAAGCTCCCTCGTGCGCTCTCCTGTTCC

GACCCTGCCGCTTACCGGATACCTGTCCGCCTTTCTCCCT

TCGGGAAGCGTGGCGCTTTCTCATAGCTCACGCTGTAGGT

ATCTCAGTTCGGTGTAGGTCGTTCGCTCCAAGCTGGGCTG

TGTGCACGAACCCCCCGTTCAGCCCGACCGCTGCGCCTTA

TCCGGTAACTATCGTCTTGAGTCCAACCCGGTAAGACACG

ACTTATCGCCACTGGCAGCAGCCACTGGTAACAGGATTAG

CAGAGCGAGGTATGTAGGCGGTGCTACAGAGTTCTTGAAG

TGGTGGCCTAACTACGGCTACACTAGAAGGACAGTATTTG

GTATCTGCGCTCTGCTGAAGCCAGTTACCTTCGGAAAAAG

AGTTGGTAGCTCTTGATCCGGCAAACAAACCACCGCTGGT

AGCGGTGGTTTTTTTGTTTGCAAGCAGCAGATTACGCGCA

GAAAAAAAGGATCTCAAGAAGATCCTTTGATCTTTTCTAC

GGGGTCTGACGCTCAGTGGAACGAAAACTCACGTTAAGGG

ATTTTGGTCATGAGATTATCAAAAAGGATCTTCACCTAGA

TCCTTTTAAATTAAAAATGAAGTTTTAAATCAATCTAAAG

TATATATGAGTAAACTTGGTCTGACAGTTACCAATGCTTA

ATCAGTGAGGCACCTATCTCAGCGATCTGTCTATTTCGTT

CATCCATAGTTGCCTGACTCCCCGTCGTGTAGATAACTAC

GATACGGGAGGGCTTACCATCTGGCCCCAGTGCTGCAATG

ATACCGCGAGACCCACGCTCACCGGCTCCAGATTTATCAG

CAATAAACCAGCCAGCCGGAAGGGCCGAGCGCAGAAGTGG

TCCTGCAACTTTATCCGCCTCCATCCAGTCTATTAATTGT

TGCCGGGAAGCTAGAGTAAGTAGTTCGCCAGTTAATAGTT

TGCGCAACGTTGTTGGCATTGCTACAGGCATCGTGGTGTC

ACGCTCGTCGTTTGGTATGGCTTCATTCAGCTCCGGTTCC

CAACGATCAAGGCGAGTTACATGATCCCCCATGTTGTGCA

AAAAAGCGGTTAGCTCCTTCGGTCCTCCGATCGTTGTCAG

AAGTAAGTTGGCCGCAGTGTTATCACTCATGGTTATGGCA

GCACTGCATAATTCTCTTACTGTCATGCCATCCGTAAGAT

GCTTTTCTGTGACTGGTGAGTACTCAACCAAGTCATTCTG

AGAATAGTGTATGCGGCGACCGAGTTGCTCTTGCCCGGCG

TCAATACGGGATAATACCGCGCCACATAGCAGAACTTTAA

AAGTGCTCATCATTGGAAAACGTTCTTCGGGGCGAAAACT

CTCAAGGATCTTACCGCTGTTGAGATCCAGTTCGATGTAA

CCCACTCGTGCACCCAACTGATCTTCAGCATCTTTTACTT

TCACCAGCGTTTCTGGGTGAGCAAAAACAGGAAGGCAAAA

TGCCGCAAAAAAGGGAATAAGGGCGACACGGAAATGTTGA

ATACTCATACTCTTCCTTTTTCAATATTATTGAAGCATTT

ATCAGGGTTATTGTCTCATGAGCGGATACATATTTGAATG

TATTTAGAAAAATAAACAAATAGGGGTTCCGCGCACATTT

CCCCGAAAAGTGCCACCTGACGTCTAAGAAACCATTATTA

TCATGACATTAACCTATAAAAATAGGCGTATCACGAGGCC

CTTTCGTCTCGCGCGTTTCGGTGATGACGGTGAAAACCTC

TGACACATGCAGCTCCCGGAGACGGTCACAGCTTGTCTGT

AAGCGGATGCCGGGAGCAGACAAGCCCGTCAGGGCGCGTC

AGCGGGTGTTGGCGGGTGTCGGGGCTGGCTTAACTATGCG

GCATCAGAGCAGATTGTACTGAGAGTGCACCATATGCGGT

GTGAAATACCGCACAGATGCGTAAGGAGAAAATACCGCAT

CAGGCGCCATTCGCCATTCAGGCTGCGCAACTGTTGGGAA

GGGCGATCGGTGCGGGCCTCTTCGCTATTACGCCAGCTGG

CGAAAGGGGGATGTGCTGCAAGGCGATTAAGTTGGGTAAC

GCCAGGGTTTTCCCAGTCACGACGTTGTAAAACGACGGCC

AGTGAATTGGATTTAGGTGACACTATA

MVA Construct 4: MVA/S1-Mono

| Name | Range | Description |
|---|---|---|
| Flank1 I8R | 1-537 | Essential gene region on MVA for recombination |
| P11 | 545-573 | promoter |
| GFP | 574-1293 | GFP |
| DR | 1294-1528 | Direct Repeats |
| mH5 | 1553 1619 | Promoter |
| GmCSF signal peptide | 1634-1684 | Secretory signal sequence |
| Spike | 1685-3985 | Secreted spike protein sequence |
| Flank 2 G1L | 4623-4724 | Essential gene region on MVA for recombination |
| Ampicillin resistance gene | 6010-6800 | Confers resistance to Ampicillin |

Plasmid Sequence (SEQ ID NO: 11) and Sequence Encoding Spike Protein (Bold, SEQ ID NO: 12)

GAATTCCCTGGGACATACGTATATTTCTATGATCTGTCTT

ATATGAAGTCTATACAGCGAATAGATTCAGAATTTCTACA

TAATTATATATTGTACGCTAATAAGTTTAATCTAACACTC

CCCGAAGATTTGTTTATAATCCCTACAAATTTGGATATTC

TATGGCGTACAAAGGAATATATAGACTCGTTCGATATTAG

TACAGAAACATGGAATAAATTATTATCCAATTATTATATG

AAGATGATAGAGTATGCTAAACTTTATGTACTAAGTCCTA

TTCTCGCTGAGGAGTTGGATAATTTTGAGAGGACGGGAGA

ATTAACTAGTATTGTACAAGAAGCCATTTTATCTCTAAAT

TTACGAATTAAGATTTTAAATTTTAAACATAAAGATGATG

ATACGTATATACACTTTTGTAAAATATTATTCGGTGTCTA

TAACGGAACAAACGCTACTATATATTATCATAGACCTCTA

ACGGGATATATGAATATGATTTCAGATACTATATTTGTTC

CTGTAGATAATAACTAAGGCGCGCCTTTCATTTTGTTTTT

TTCTATGCTATAAATGGTGAGCAAGGGCGAGGAGCTGTTC

ACCGGGGTGGTGCCCATCCTGGTCGAGCTGGACGGCGACG

TAAACGGCCACAAGTTCAGCGTGTCCGGCGAGGGCGAGGG

CGATGCCACCTACGGCAAGCTGACCCTGAAGTTCATCTGC

ACCACCGGCAAGCTGCCCGTGCCCTGGCCCACCCTCGTGA

CCACCCTGACCTACGGCGTGCAGTGCTTCAGCCGCTACCC

CGACCACATGAAGCAGCACGACTTCTTCAAGTCCGCCATG

CCCGAAGGCTACGTCCAGGAGCGCACCATCTTCTTCAAGG

ACGACGGCAACTACAAGACCCGCGCCGAGGTGAAGTTCGA

GGGCGACACCCTGGTGAACCGCATCGAGCTGAAGGGCATC

GACTTCAAGGAGGACGGCAACATCCTGGGGCACAAGCTGG

AGTACAACTACAACAGCCACAACGTCTATATCATGGCCGA

CAAGCAGAAGAACGGCATCAAGGTGAACTTCAAGATCCGC

CACAACATCGAGGACGGCAGCGTGCAGCTCGCCGACCACT

ACCAGCAGAACACCCCCATCGGCGACGGCCCCGTGCTGCT

GCCCGACAACCACTACCTGAGCACCCAGTCCGCCCTGAGC

AAAGACCCCAACGAGAAGCGCGATCACATGGTCCTGCTGG

AGTTCGTGACCGCCGCCGGGATCACTCTCGGCATGCACGA

GCTGTACAAGTAAGAGCTCGAGGACGGGAGAATTAACTAG

TATTGTACAAGAAGCCATTTTATCTCTAAATTTACGAATT

AAGATTTTAAATTTTAAACATAAAGATGATGATACGTATA

TACACTTTTGTAAAATATTATTCGGTGTCTATAACGGAAC

AAACGCTACTATATATTATCATAGACCTCTAACGGGATAT

ATGAATATGATTTCAGATACTATATTTGTTCCTGTAGATA

ATAACTAACTCGAGGCCGCTGGTACCCAACCTAAAAATTG

AAAATAAATACAAAGGTTCTTGAGGGTTGTGTTAAATTGA

AAGCGAGAAATAATCATAAATAAGCCCGGGACCATGTGGT

TACAAGGACTACTATTACTAGGTACTGTTGCCTGTTCAAT

TTCACAATGTGTAAATCTAACTACAAGAACTCAATTACCG

CCTGCCTATACTAATTCTTTTACAAGAGGAGTATATTATC

CTGATAAAGTTTTTAGATCTTCTGTATTACATTCTACACA

AGATTTGTTTTTACCATTTTTCTCTAATGTTACTTGGTTT

CATGCAATACATGTATCTGGAACTAATGGAACAAAAAGAT

TTGATAATCCAGTATTACCTTTTAATGATGGAGTTTATTT

-continued

TGCTTCTACTGAAAAATCTAATATAATTAGAGGATGGATA
TTTGGAACTACATTAGATTCTAAAACACAATCTCTACTAA
TTGTTAATAATGCAACTAATGTAGTTATAAAAGTATGTGA
ATTTCAATTTTGTAATGATCCATTTTTGGGAGTTTATTAT
CATAAAAATAATAAGTCTTGGATGGAATCTGAATTCAGAG
TATATTCTTCTGCTAATAATTGTACATTTGAATATGTATC
TCAACCATTTTTGATGGATTTGGAAGGAAAACAAGGAAAC
TTTAAAAATTTGAGAGAATTTGTTTTTAAAAATATTGATG
GATACTTTAAAATCTATTCTAAACATACTCCAATTAATCT
AGTAAGAGATTTGCCTCAAGGATTTTCTGCTTTAGAACCA
CTAGTAGATTTGCCTATAGGAATTAATATTACTAGATTTC
AAACATTATTAGCTTTACATAGATCTTATTTGACACCTGG
AGATTCTTCTTCTGGATGGACTGCAGGAGCTGCAGCTTAT
TATGTTGGATATTTGCAACCAAGAACATTTTTGTTAAAAT
ATAATGAAAATGGAACTATAACAGATGCAGTTGATTGTGC
TTTAGATCCTCTATCTGAAACTAAATGTACTTTAAAATCT
TTTACTGTAGAAAAAGGAATCTATCAAACATCTAACTTTA
GAGTACAACCAACTGAATCTATTGTTAGATTTCCAAATAT
AACAAATCTATGTCCTTTTGGAGAAGTTTTTAATGCAACT
AGATTTGCTTCTGTATATGCATGGAATAGAAAAAGAATAT
CTAATTGCGTAGCTGATTATTCTGTATTATATAATTCTGC
ATCTTTTTCTACTTTTAAATGTTATGGAGTATCTCCAACA
AAATTGAATGATCTATGTTTTACTAATGTTTATGCAGATT
CTTTTGTAATAAGAGGAGATGAAGTTAGACAAATAGCTCC
TGGACAAACAGGAAAAATAGCAGATTATAATTATAAATTA
CCAGATGATTTCACTGGATGCGTAATTGCTTGGAATTCTA
ATAATTTGGATTCTAAAGTAGGAGGAAATTATAATTATTT
GTATAGATTGTTTAGAAAATCTAATTTGAAACCTTTTGAA
AGAGATATTTCTACAGAAATCTATCAAGCAGGATCTACTC
CATGTAATGGAGTTGAAGGTTTTAATTGTTATTTTCCACT
ACAATCTTATGGATTTCAACCTACAAATGGAGTAGGATAT
CAACCATATAGAGTAGTTGTATTATCTTTTGAATTATTAC
ATGCACCAGCTACAGTATGTGGACCTAAAAAATCTACTAA
TTTGGTTAAAAATAAGTGCGTAAACTTTAACTTTAATGGA
TTAACTGGAACAGGAGTTTTAACTGAATCTAATAAGAAAT
TTTTGCCTTTTCAACAATTTGGAAGAGATATTGCTGATAC
TACAGATGCAGTAAGAGATCCTCAAACTTTAGAAATATTG
GATATTACACCATGTTCTTTTGGAGGAGTTTCTGTAATAA
CACCAGGAACTAATACATCTAATCAAGTTGCTGTATTATA
TCAAGATGTTAATTGTACTGAAGTTCCTGTAGCAATTCAT

-continued

GCTGATCAATTAACTCCAACATGGAGAGTATATTCTACTG
GATCTAATGTTTTTCAAACAAGAGCTGGATGTCTAATTGG
AGCAGAACATGTAAATAATTCTTATGAATGTGATATTCCT
ATAGGAGCTGGAATATGTGCATCTTATCAAACTCAAACAA
ATTCTCCAAGAAGAGCTAGATCTGTTGCATCTCAATCTAT
AATTGCTTATACAATGTCTTTAGGAGCTGAAAATTCTGTA
GCATATTCTAATAATTCTATTGCAATTCCTACTAACTTTA
CTATTTCTGTAACTACAGAAATATTGCCAGTTTCTATGAC
TAAAACATCTGTAGATTGTACAATGTATATATGTGGAGAT
TCTACTGAATGTTCTAATTTGCTACTACAATATGGATCTT
TTTGTACTCAATTGAATAGAGCTTTAACAGGAATAGCAGT
AGAACAAGATAAAAATACACAAGAATAATAATTTTTATGG
ATCCTCTAGAGTCGACCTGCAGTCAAACTCTAATGACCAC
ATCTTTTTTTAGAGATGAAAAATTTTCCACATCTCCTTTT
GTAGACACGACTAAACATTTTGCAGAAAAAAGTTTATTAG
TGTTTAGATAATCGTATACTTCATCAGTGTAGATAGTAAA
TGTGAACAGATAAAAGGTATTCTTGCTCAATAGATTGGTA
AATTCCATAGAATATATTAATCCTTTCTTCTTGAGATCCC
ACATCATTTCAACCAGAGACGTTTTATCCAATGATTTACC
TCGTACTATACCACATACAAAACTAGATTTTGCAGTGACG
TCGTATCTGGTATTCCTACCAAACAAAATTTTACTTTTAG
TTCTTTTAGAAAATTCTAAGGTAGAATCTCTATTTGCCAA
TATGTCATCTATGGAATTACCACTAGCAAAAAATGATAGA
AATATATATTGATACATCGCAGCTGGTTTTGATCTACTAT
ACTTTAAAAACGAATCAGATTCCATAATTGCCTGTATATC
ATCAGCTGAAAAACTATGTTTTACACGTATTCCTTCGGCA
TTTCTTTTTAATGATATATCTTGTTTAGACAATGATAAAG
TTATCATGTCCATGAGAGACGCGTCTCCGTATCGTATAAA
TATTTCATTAGATGTTAGACGCTTCATTAGGGGTATACTT
CTATAAGGTTTCTTAATCAGTCCATCATTGGTTGCGTCAA
GAACAAGCTTGTCTCCCTATAGTGAGTCGTATTAGAGCTT
GGCGTAATCATGGTCATAGCTGTTTCCTGTGTGAAATTGT
TATCCGCTCACAATTCCACACAACATACGAGCCGGAAGCA
TAAAGTGTAAAGCCTGGGGTGCCTAATGAGTGAGCTAACT
CACATTAATTGCGTTGCGCTCACTGCCCGCTTTCGAGTCG
GGAAACCTGTCGTGCCAGCTGCATTAATGAATCGGCCAAC
GCGCGGGGAGAGGCGGTTTGCGTATTGGGCGCTCTTCCGC
TTCCTCGCTCACTGACTCGCTGCGCTCGGTCGTTCGGCTG
CGGCGAGCGGTATCAGCTCACTCAAAGGCGGTAATACGGT
TATCCACAGAATCAGGGGATAACGCAGGAAAGAACATGTG
AGCAAAAGGCCAGCAAAAGGCCAGGAACCGTAAAAAGGCC

-continued

```
GCGTTGCTGGCGTTTTTCGATAGGCTCCGCCCCCCTGACG
AGCATCACAAAAATCGACGCTCAAGTCAGAGGTGGCGAAA
CCCGACAGGACTATAAAGATACCAGGCGTTTCCCCCTGGA
AGCTCCCTCGTGCGCTCTCCTGTTCCGACCCTGCCGCTTA
CCGGATACCTGTCCGCCTTTCTCCCTTCGGGAAGCGTGGC
GCTTTCTCATAGCTCACGCTGTAGGTATCTCAGTTCGGTG
TAGGTCGTTCGCTCCAAGCTGGGCTGTGTGCACGAACCCC
CCGTTCAGCCCGACCGCTGCGCCTTATCCGGTAACTATCG
TCTTGAGTCCAACCCGGTAAGACACGACTTATCGCCACTG
GCAGCAGCCACTGGTAACAGGATTAGCAGAGCGAGGTATG
TAGGCGGTGCTACAGAGTTCTTGAAGTGGTGGCCTAACTA
CGGCTACACTAGAAGGACAGTATTTGGTATCTGCGCTCTG
CTGAAGCCAGTTACCTTCGGAAAAAGAGTTGGTAGCTCTT
GATCCGGCAAACAAACCACCGCTGGTAGCGGTGGTTTTTT
TGTTTGCAAGCAGCAGATTACGCGCAGAAAAAAAGGATCT
CAAGAAGATCCTTTGATCTTTTCTACGGGGTCTGACGCTC
AGTGGAACGAAAACTCACGTTAAGGGATTTTGGTCATGAG
ATTATCAAAAAGGATCTTCACCTAGATCCTTTTAAATTAA
AAATGAAGTTTTAAATCAATCTAAAGTATATATGAGTAAA
CTTGGTCTGACAGTTACCAATGCTTAATCAGTGAGGCACC
TATCTCAGCGATCTGTCTATTTCGTTCATCCATAGTTGCC
TGACTCCCCGTCGTGTAGATAACTACGATACGGGAGGGCT
TACCATCTGGCCCCAGTGCTGCAATGATACCGCGAGACCC
ACGCTCACCGGCTCCAGATTTATCAGCAATAAACCAGCCA
GCCGGAAGGGCCGAGCGCAGAAGTGGTCCTGCAACTTTAT
CCGCCTCCATCCAGTCTATTAATTGTTGCCGGGAAGCTAG
AGTAAGTAGTTCGCCAGTTAATAGTTTGCGCAACGTTGTT
GGCATTGCTACAGGCATCGTGGTGTCACGCTCGTCGTTTG
GTATGGCTTCATTCAGCTCCGGTTCCCAACGATCAAGGCG
AGTTACATGATCCCCCATGTTGTGCAAAAAAGCGGTTAGC
TCCTTCGGTCCTCCGATCGTTGTCAGAAGTAAGTTGGCCG
CAGTGTTATCACTCATGGTTATGGCAGCACTGCATAATTC
TCTTACTGTCATGCCATCCGTAAGATGCTTTTCTGTGACT
GGTGAGTACTCAACCAAGTCATTCTGAGAATAGTGTATGC
GGCGACCGAGTTGCTCTTGCCCGGCGTCAATACGGGATAA
TACCGCGCCACATAGCAGAACTTTAAAAGTGCTCATCATT
GGAAAACGTTCTTCGGGGCGAAAACTCTCAAGGATCTTAC
CGCTGTTGAGATCCAGTTCGATGTAACCCACTCGTGCACC
CAACTGATCTTCAGCATCTTTTACTTTCACCAGCGTTTCT
GGGTGAGCAAAAACAGGAAGGCAAAATGCCGCAAAAAAGG
GAATAAGGGCGACACGGAAATGTTGAATACTCATACTCTT
CCTTTTTCAATATTATTGAAGCATTTATCAGGGTTATTGT
CTCATGAGCGGATACATATTTGAATGTATTTAGAAAAATA
AACAAATAGGGGTTCCGCGCACATTTCCCCGAAAAGTGCC
ACCTGACGTCTAAGAAACCATTATTATCATGACATTAACC
TATAAAAATAGGCGTATCACGAGGCCCTTTCGTCTCGCGC
GTTTCGGTGATGACGGTGAAAACCTCTGACACATGCAGCT
CCCGGAGACGGTCACAGCTTGTCTGTAAGCGGATGCCGGG
AGCAGACAAGCCCGTCAGGGCGCGTCAGCGGGTGTTGGCG
GGTGTCGGGGCTGGCTTAACTATGCGGCATCAGAGCAGAT
TGTACTGAGAGTGCACCATATGCGGTGTGAAATACCGCAC
AGATGCGTAAGGAGAAAATACCGCATCAGGCGCCATTCGC
CATTCAGGCTGCGCAACTGTTGGGAAGGGCGATCGGTGCG
GGCCTCTTCGCTATTACGCCAGCTGGCGAAAGGGGGATGT
GCTGCAAGGCGATTAAGTTGGGTAACGCCAGGGTTTTCCC
AGTCACGACGTTGTAAAACGACGGCCAGTGAATTGGATTT
AGGTGACACTATA
```

DNA Vaccines

Four DNA vaccines are made using the coronavirus spike protein as shown in FIG. 1A-D. The DNA inserts are codon-optimized for human codon usage and expressed under the human CMV promoter with intron A in pGA1 vector.

DNA Construct 1: DNA/S-VLP

| Name | Range | Description |
|---|---|---|
| CMV Promoter | 476 to 675 | Human cytomegalovirus (CMV) immediate early promoter |
| intron A | 702 to 1645 | Intron A positively regulate expression from the hCMV immediate-early enhancer/promoter |
| ORF | 1651 to 6495 | Insert nCoV VIP (Spike protein (1273 aa)-P2A (22 aa)-Matrix (222 aa)-P2A (22 aa)-Envelope (75 aa) |
| bGH poly(A) signal | 6535 to 6742 | Bovine growth hormone polyadenylation signal |
| Kanamycin resistance gene | 6775 to 756S | Confers resistance to neomycin, kanamycin, and G418 (Geneticin(R)) |
| Replication Origin | 7981 to 8570 | High-copy-number ColE1/pMB1/pBR322/pUC origin of replication |

pGA8-nCoV S-VLP Plasmid Sequences (SEQ ID NO: 13) and Sequence Encoding Spike Protein (Bold, SEQ ID NO: 14)

```
CGACAATATTGGCTATTGGCCATTGCATACGTTGTATCTATATCATAATATGTACATT
TATATTGGCTCATGTCCAATATGACCGCCATGTTGACATTGATTATTGACTAGTTATT
```

-continued

AATAGTAATCAATTACGGGTTCATTAGTTCATAGCCCATATATGGAGTTCCGCGTTA
CATAACTTACGGTAAATGGCCCGCCTGGCTGACCGCCCAACGACCCCCGCCCATTGA
CGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATA
TGCCAAGTCCGCCCCCTATTGACGTCAATGACGGTAAATGGCCCGCCTGGCATTATG
CCCAGTACATGACCTTACGGGACTTTCCTACTTGGCAGTACATCTACGGTATTAGTC
ATCGGCTATTACCATGGTGATGCGGTTTTGGCAGTACACCAATGGGCGTGGATAGCG
GTTTGACTCACGGGGATTTCCAAGTCTCCACCCCATTGACGTCAATGGGAGTTTGTTT
TGGCACCAAAATCAACGGGACTTTCCAAAATGTCGTAATAACCCCGCCCCGTTGACG
CAAATGGGCGGTAGGCGTGTACGGTGGGAGGTCTATATAAGCAGAGCTCGTTTAGT
GAACCGTCAGATCGCCTGGAGACGCCATCCACGCTGTTTTGACCTCCATAGAAGACA
CCGGGACCGATCCAGCCTCCGCGGCCGGGAACGGTGCATTGGAACGCGGATTCCCC
GTGCCAAGAGTGACGTAAGTACCGCCTATAGACTCTATAGGCACACCCCTTTGGCTC
TTATGCATGCTATACTGTTTTTGGCTTGGGGCCTATACACCCCCGCTTCCTTATGCTA
TAGGTGATGGTATAGCTTAGCCTATAGGTGTGGGTTATTGACCATTATTGACCACTC
CCCTATTGGTGACGATACTTTCCATTACTAATCCATAACATGGCTCTTTGCCACAACT
ATCTCTATTGGCTATATGCCAATACTCTGTCCTTCAGAGACTGACACGGACTCTGTAT
TTTTACAGGATGGGGTCCCATTTATTATTTACAAATTCACATATACAACAACGCCGT
CCCCCGTGCCCGCAGTTTTTATTAAACATAGCGTGGGATCTCCACGCGAATCTCGGG
TACCGTGTTCCGGACATGGGYTCTTCTCCGGTAGCGGCGGAGCTTCCACATCCGAGC
CCTGGTCCCATGCCTCCAGCGGCTCATGGTCGCTCGGCAGCTCCTTGCTCCTAACAG
TGGAGGCCAGACTTAGGCACAGCACAATGCCCACCACCACCAGTGTGCCGCACAAG
GCCGTGGCGGTAGGGTATGTGTCTGAAAATGAGCTCGGAGATTGGGCTCGCACCGC
TGACGCAGATGGAAGACTTAAGGCAGCGGCAGAAGAAGATGCAGGCAGCTGAGTT
GTTGTATTCTGATAAGAGTCAGAGGTAACTCCCGTTGCGGTGCTGTTAACGGTGGAG
GGCAGTGTAGTCTGAGCAGTACTCGTTGCTGCCGCGCGCGCCACCAGACATAATAG
CTGACAGACTAACAGACTGTTCCTTTCCATGGGTCTTTTCTGCAGTCACCATCGATAT
GTTTGTCTTCCTGGTCCTGCTGCCTCTGGTCTCCTCACAGTGCGTCAATCTGAC
TACCCGAACTCAGCTGCCCCCCGCCTACACCAACTCCTTCACCCGGGGCGTGT
ACTATCCAGACAAGGTGTTTAGAAGCTCCGTGCTGCACTCCACCCAGGATCTGT
TTCTGCCCTTCTTTTCTAATGTGACATGGTTCCACGCCATCCACGTGAGCGGCA
CCAACGGCACAAAGAGGTTCGACAACCCTGTGCTGCCATTCAATGATGGCGTG
TACTTTGCCTCCACCGAGAAGTCTAACATCATCCGCGGCTGGATCTTTGGCACC
ACACTGGACTCCAAGACCCAGTCCCTGCTGATCGTGAACAATGCCACAAACGT
GGTCATCAAGGTGTGCGAGTTCCAGTTTTGTAACGATCCTTTCCTGGGCGTGTA
CTATCACAAGAACAATAAGTCTTGGATGGAGAGCGAGTTTAGGGTGTATTCTA
GCGCCAACAATTGCACCTTCGAGTACGTGTCCCAGCCATTTCTGATGGACCTG
GAGGGCAAGCAGGGCAATTTCAAGAACCTGCGGGAGTTCGTGTTTAAGAACAT
CGACGGCTACTTCAAGATCTACTCCAAGCACACCCCCATCAACCTGGTGCGGG
ACCTGCCACAGGGCTTCTCTGCCCTGGAGCCTCTGGTGGATCTGCCAATCGGC

-continued

ATCAACATCACACGGTTTCAGACCCTGCTGGCCCTGCACAGAAGCTACCTGAC

CCCTGGCGACTCCTCTAGCGGATGGACAGCAGGAGCAGCAGCATACTATGTGG

GCTATCTGCAGCCACGGACCTTCCTGCTGAAGTACAACGAGAATGGCACCATC

ACAGACGCCGTGGATTGCGCCCTGGATCCACTGTCTGAGACAAAGTGTACACT

GAAGAGCTTTACAGTGGAGAAGGGCATCTATCAGACCAGCAACTTCAGGGTGC

AGCCCACAGAGTCCATCGTGCGCTTTCCAAATATCACCAACCTGTGCCCCTTCG

GCGAGGTGTTTAATGCCACAAGATTCGCCAGCGTGTACGCCTGGAACAGGAAG

CGCATCTCCAATTGCGTGGCCGACTATTCTGTGCTGTACAACTCTGCCAGCTTC

TCCACCTTTAAGTGCTATGGCGTGAGCCCCACCAAGCTGAACGACCTGTGCTTC

ACAAACGTGTACGCCGATTCCTTTGTGATCAGGGGCGACGAGGTGCGCCAGAT

CGCACCAGGACAGACCGGCAAGATCGCAGACTACAACTATAAGCTGCCCGACG

ATTTCACAGGCTGCGTGATCGCCTGGAATTCCAACAATCTGGATTCTAAAGTGG

GCGGCAACTACAATTATCTGTACAGGCTGTTCCGCAAGTCTAACCTGAAGCCTT

TTGAGCGGGACATCTCCACCGAGATCTACCAGGCCGGCTCTACACCATGCAAC

GGCGTGGAGGGCTTCAATTGTTATTTTCCCCTGCAGAGCTACGGCTTCCAGCCT

ACCAATGGCGTGGGCTATCAGCCATACAGAGTGGTGGTGCTGTCTTTTGAGCT

GCTGCACGCACCAGCAACCGTGTGCGGACCTAAGAAGAGCACAAATCTGGTGA

AGAACAAGTGCGTGAACTTCAACTTCAACGGCCTGACCGGAACAGGCGTGCTG

ACCGAGTCCAACAAGAAGTTCCTGCCCTTTCAGCAGTTCGGCAGGGACATCGC

AGATACCACAGACGCCGTGCGCGACCCCCAGACACTGGAGATCCTGGATATCA

CCCCTTGCAGCTTCGGCGGCGTGTCCGTGATCACCCCTGGAACCAATACAAGC

AACCAGGTGGCCGTGCTGTATCAGGACGTGAACTGTACAGAGGTGCCAGTGGC

CATCCACGCCGATCAGCTGACCCCCACATGGCGGGTGTACTCCACAGGCTCTA

ACGTGTTCCAGACCAGAGCAGGATGCCTGATCGGAGCAGAGCACGTGAACAAT

AGCTATGAGTGCGACATCCCCATCGGCGCCGGCATCTGTGCCTCCTACCAGAC

CCAGACAAACTCCCCTCGGAGAGCCAGGTCTGTGGCCTCTCAGAGCATCATCG

CCTATACCATGAGCCTGGGCGCCGAGAACTCCGTGGCCTACAGCAACAATTCC

ATCGCCATCCCCACCAATTTCACAATCTCCGTGACCACAGAGATCCTGCCCGTG

AGCATGACCAAGACAAGCGTGGACTGCACCATGTATATCTGTGGCGATTCCAC

AGAGTGCTCTAATCTGCTGCTGCAGTACGGCTCTTTTTGTACACAGCTGAACCG

CGCCCTGACCGGAATCGCAGTGGAGCAGGACAAGAATACCCAGGAGGTGTTCG

CCCAGGTGAAGCAGATCTACAAGACACCCCCTATCAAGGACTTTGGCGGCTTC

AACTTTAGCCAGATCCTGCCTGATCCATCTAAGCCTAGCAAGAGGTCCTTCATC

GAGGACCTGCTGTTTAATAAGGTGACCCTGGCCGATGCCGGCTTCATCAAGCA

GTATGGCGATTGCCTGGGCGACATCGCAGCACGCGACCTGATCTGTGCCCAGA

AGTTTAACGGCCTGACAGTGCTGCCACCCCTGCTGACCGATGAGATGATCGCA

CAGTACACCTCTGCCCTGCTGGCCGGAACCATCACAAGCGGATGGACATTCGG

CGCAGGAGCCGCCCTGCAGATCCCATTCGCCATGCAGATGGCCTATCGGTTTA

ATGGCATCGGCGTGACCCAGAACGTGCTGTACGAGAATCAGAAGCTGATCGCC

AATCAGTTTAACTCCGCCATCGGCAAGATCCAGGACTCTCTGTCCTCTACCGCC

AGCGCCCTGGGCAAGCTGCAGGATGTGGTGAATCAGAACGCCCAGGCCCTGAA

-continued

CACACTGGTGAAGCAGCTGAGCTCCAATTTCGGCGCCATCTCTAGCGTGCTGA

ACGATATCCTGAGCAGGCTGGACAAGGTGGAGGCCGAGGTGCAGATCGACCG

GCTGATCACCGGCAGACTGCAGTCCCTGCAGACCTACGTGACACAGCAGCTGA

TCAGGGCAGCAGAGATCAGGGCCTCTGCCAACCTGGCAGCAACAAAGATGAGC

GAGTGCGTGCTGGGACAGTCCAAGAGGGTGGACTTTTGTGGCAAGGGCTATCA

CCTGATGAGCTTCCCACAGTCCGCCCCACACGGAGTGGTGTTTCTGCACGTGA

CCTACGTGCCTGCCCAGGAGAAGAATTTCACCACAGCCCCAGCCATCTGCCAC

GATGGCAAGGCACACTTCCCAAGGGAGGGCGTGTTTGTGAGCAATGGCACACA

CTGGTTCGTGACCCAGAGAAACTTTTACGAGCCTCAGATCATCACCACAGACAA

CACCTTCGTGAGCGGCAATTGTGACGTGGTCATCGGCATCGTGAACAATACAG

TGTATGATCCCCTGCAGCCTGAGCTGGACTCTTTCAAGGAGGAGCTGGATAAG

TACTTTAAGAACCACACCAGCCCCGACGTGGATCTGGGCGACATCTCCGGCAT

CAACGCCTCTGTGGTGAATATCCAGAAGGAGATCGACAGACTGAATGAGGTGG

CCAAGAATCTGAACGAGAGCCTGATCGACCTGCAGGAGCTGGGCAAGTATGAG

CAGTACATCAAGTGGCCATGGTATATCTGGCTGGGCTTCATCGCCGGCCTGAT

CGCCATCGTGATGGTGACAATCATGCTGTGCTGTATGACCTCTTGCTGTAGCTG

CCTGAAGGGCTGCTGTTCCTGTGGCTCTTGCTGTAAGTTCGATGAGGACGATT

CCGAGCCCGTGCTGAAGGGCGTGAAGCTGCACTACACAGGCTCCGGCGCCACC

AACTTTTCTCTGCTGAAGCAGGCAGGCGACGTGGAGGAGAACCCAGGACCTAT

GGCCGATAGCAATGGCACCATCACAGTGGAGGAGCTGAAGAAGCTGCTGGAGC

AGTGGAACCTGGTCATCGGCTTCCTGTTTCTGACCTGGATCTGCCTGCTGCAGT

TCGCCTATGCCAATCGGAACAGATTTCTGTACATCATCAAGCTGATCTTCCTGT

GGCTGCTGTGGCCAGTGACCCTGGCCTGCTTCGTGCTGGCCGCCGTGTATCGG

ATCAACTGGATCACAGGCGGCATCGCCATCGCCATGGCCTGTCTGGTGGGCCT

GATGTGGCTGAGCTACTTCATCGCCTCCTTTAGACTGTTCGCCAGGACCCGCA

GCATGTGGTCCTTTAATCCCGAGACAAACATCCTGCTGAATGTGCCTCTGCACG

GCACCATCCTGACAAGGCCACTGCTGGAGTCCGAGCTGGTCATCGGAGCCGTG

ATCCTGAGGGGACACCTGAGAATCGCAGGACACCACCTGGGCCGCTGCGATAT

CAAGGACCTGCCTAAGGAGATCACCGTGGCCACATCTAGGACCCTGAGCTACT

ATAAGCTGGGAGCCAGCCAGAGGGTGGCAGGCGACAGCGGATTCGCAGCATA

TTCCCGGTACAGAATCGGCAACTACAAGCTGAATACCGATCACTCCTCTAGCTC

CGACAATATCGCCCTGCTGGTGCAGGGATCTGGAGCAACAAACTTCAGCCTGC

TGAAGCAGGCCGGCGATGTGGAAGAAAACCCAGGACCCATGTATTCTTTTGTG

AGCGAGGAGACAGGCACACTGATCGTGAATAGCGTGCTGCTGTTTCTGGCCTT

CGTGGTGTTTCTGCTGGTGACACTGGCCATCCTGACCGCCCTGAGACTGTGCG

CCTACTGCTGTAATATCGTGAACGTGTCTCTGGTGAAGCCCAGCTTTTACGTGT

ATAGTAGGGTGAAGAATCTGAACTCAAGTAGGGTGCCCGATCTGCTGGTCTAA

GCTAGCCCCGGGTGATAAACGGACCGCGCAATCCCTAGGCTGTGCCTTCTAGTTGCC

AGCCATCTGTTGTTTGCCCCTCCCCCGTGCCTTCCTTGACCCTGGAAGGTGCCACTCC

CACTGTCCTTTCCTAATAAAATGAGGAAATTGCATCGCATTGTCTGAGTAGGTGTCA

-continued

```
TTCTATTCTGGGGGGTGGGGTGGGGCAGGACAGCAAGGGGGAGGATTGGGAAGACA

ATAGCAGGCATGCTGGGGATGCGGTGGGCTCTATATAAAAAACGCCCGGCGGCAAC

CGAGCGTTCTGAACGCTAGAGTCGACAAATTCAGAAGAACTCGTCAAGAAGGCGAT

AGAAGGCGATGCGCTGCGAATCGGGAGCGGCGATACCGTAAAGCACGAGGAAGCG

GTCAGCCCATTCGCCGCCAAGCTCTTCAGCAATATCACGGGTAGCCAACGCTATGTC

CTGATAGCGGTCTGCCACACCCAGCCGGCCACAGTCGATGAATCCAGAAAAGCGGC

CATTTTCCACCATGATATTCGGCAAGCAGGCATCGCCATGGGTCACGACGAGATCCT

CGCCGTCGGGCATGCTCGCCTTGAGCCTGGCGAACAGTTCGGCTGGCGCGAGCCCCT

GATGCTCTTCGTCCAGATCATCCTGATCGACAAGACCGGCTTCCATCCGAGTACGTG

CTCGCTCGATGCGATGTTTCGCTTGGTGGTCGAATGGGCAGGTAGCCGGATCAAGCG

TATGCAGCCGCCGCATTGCATCAGCCATGATGGATACTTTCTCGGCAGGAGCAAGGT

GAGATGACAGGAGATCCTGCCCCGGCACTTCGCCCAATAGCAGCCAGTCCCTTCCCG

CTTCAGTGACAACGTCGAGCACAGCTGCGCAAGGAACGCCCGTCGTGGCCAGCCAC

GATAGCCGCGCTGCCTCGTCTTGCAGTTCATTCAGGGCACCGGACAGGTCGGTCTTG

ACAAAAAGAACCGGGCGCCCCTGCGCTGACAGCCGGAACACGGCGGCATCAGAGC

AGCCGATTGTCTGTTGTGCCCAGTCATAGCCGAATAGCCTCTCCACCCAAGCGGCCG

GAGAACCTGCGTGCAATCCATCTTGTTCAATCATGCGAAACGATCCTCATCCTGTCT

CTTGATCAGATCTTGATCCCCTGCGCCATCAGATCCTTGGCGGCAAGAAAGCCATCC

AGTTTACTTTGCAGGGCTTCCCAACCTTACCAGAGGGCGCCCCAGCTGGCAATTCCG

GTTCGCTTGCTGTCCATAAAACCGCCCAGTCTAGCTATCGCCATGTAAGCCCACTGC

AAGCTACCTGCTTTCTCTTTGCGCTTGCGTTTTCCCTTGTCCAGATAGCCCAGTAGCT

GACATTCATCCGGGGTCAGCACCGTTTCTGCGGACTGGCTTTCTACGTGAAAAGGAT

CTAGGTGAAGATCCTTTTTGATAATCTCATGACCAAAATCCCTTAACGTGAGTTTTCG

TTCCACTGAGCGTCAGACCCCGTAGAAAAGATCAAAGGATCTTCTTGAGATCCTTTT

TTTCTGCGCGTAATCTGCTGCTTGCAAACAAAAAAACCACCGCTACCAGCGGTGGTT

TGTTTGCCGGATCAAGAGCTACCAACTCTTTTTCCGAAGGTAACTGGCTTCAGCAGA

GCGCAGATACCAAATACTGTTCTTCTAGTGTAGCCGTAGTTAGGCCACCACTTCAAG

AACTCTGTAGCACCGCCTACATACCTCGCTCTGCTAATCCTGTTACCAGTGGCTGCT

GCCAGTGGCGATAAGTCGTGTCTTACCGGGTTGGACTCAAGACGATAGTTACCGGAT

AAGGCGCAGCGGTCGGGCTGAACGGGGGGTTCGTGCACACAGCCCAGCTTGGAGCG

AACGACCTACACCGAACTGAGATACCTACAGCGTGAGCTATGAGAAAGCGCCACG

CTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGCGG

AGCCTATGGAAAAACGCCAGCAACGCGGCCCTTTTACGGTTCCTGGCCTTTTGCTGG

CCTTTTGCTCACATGTTGT
```

DNA Construct 2: DNA/S-Tri

| Name | Range | Description |
|---|---|---|
| CMV Promoter | 476 to 675 | Human cytomegalovirus (CMV) immediate early promoter |

-continued

| Name | Range | Description |
|---|---|---|
| Intron A | 702 to 1645 | Intron A positively regulate expression from the hCMV immediate-early enhancer/promoter |

-continued

| Name | Range | Description |
|---|---|---|
| ORF | 1651 to 5472 | nCoV S-Tri Spike protein ss 14 to 1273 |
| bGH poly(A) signal | 5512 to 5719 | Bovine growth hormone polyadenylation signal |
| Kanamycin resistance gene | 5752 to 6546 | Confers resistance to neomycin, kanamycin, and G418 (Geneticin(R)) |

-continued

| Name | Range | Description |
|---|---|---|
| Replication Origin | 6958 to 7547 | High-copy-number ColE1/pMB1/PBR322/pUC origin of replication |

pGA8-nCoV-S-Tri Plasmid Sequences (SEQ ID NO: 15) and Sequence Encoding Spike Protein (Bold, SEQ ID NO: 16)

CGACAATATTGGCTATTGGCCATTGCATACGTTGTATCTATATCATAATATGTACATT

TATATTGGCTCATGTCCAATATGACCGCCATGTTGACATTGATTATTGACTAGTTATT

AATAGTAATCAATTACGGGTTCATTAGTTCATAGCCCATATATGGAGTTCCGCGTTA

CATAACTTACGGTAAATGGCCCGCCTGGCTGACCGCCCAACGACCCCCGCCCATTGA

CGTCAATAATGACGTATGTTCCCATAGTAACGCCAATAGGGACTTTCCATTGACGTC

AATGGGTGGAGTATTTACGGTAAACTGCCCACTTGGCAGTACATCAAGTGTATCATA

TGCCAAGTCCGCCCCCTATTGACGTCAATGACGGTAAATGGCCCGCCTGGCATTATG

CCCAGTACATGACCTTACGGGACTTTCCTACTTGGCAGTACATCTACGGTATTAGTC

ATCGGCTATTACCATGGTGATGCGGTTTTGGCAGTACACCAATGGGCGTGGATAGCG

GTTTGACTCACGGGGATTTCCAAGTCTCCACCCCATTGACGTCAATGGGAGTTTGTTT

TGGCACCAAAATCAACGGGACTTTCCAAAATGTCGTAATAACCCCGCCCCGTTGACG

CAAATGGGCGGTAGGCGTGTACGGTGGGAGGTCTATATAAGCAGAGCTCGTTTAGT

GAACCGTCAGATCGCCTGGAGACGCCATCCACGCTGTTTTGACCTCCATAGAAGACA

CCGGGACCGATCCAGCCTCCGCGGCCGGGAACGGTGCATTGGAACGCGGATTCCCC

GTGCCAAGAGTGACGTAAGTACCGCCTATAGACTCTATAGGCACACCCCTTTGGCTC

TTATGCATGCTATACTGTTTTTGGCTTGGGGCCTATACACCCCCGCTTCCTTATGCTA

TAGGTGATGGTATAGCTTAGCCTATAGGTGTGGGTTATTGACCATTATTGACCACTC

CCCTATTGGTGACGATACTTTCCATTACTAATCCATAACATGGCTCTTTGCCACAACT

ATCTCTATTGGCTATATGCCAATACTCTGTCCTTCAGAGACTGACACGGACTCTGTAT

TTTTACAGGATGGGGTCCCATTTATTATTTACAAATTCACATATACAACAACGCCGT

CCCCCGTGCCCGCAGTTTTTATTAAACATAGCGTGGGATCTCCACGCGAATCTCGGG

TACCGTGTTCCGGACATGGGYTCTTCTCCGGTAGCGGCGGAGCTTCCACATCCGAGC

CCTGGTCCCATGCCTCCAGCGGCTCATGGTCGCTCGGCAGCTCCTTGCTCCTAACAG

TGGAGGCCAGACTTAGGCACAGCACAATGCCCACCACCACCAGTGTGCCGCACAAG

GCCGTGGCGGTAGGGTATGTGTCTGAAAATGAGCTCGGAGATTGGGCTCGCACCGC

TGACGCAGATGGAAGACTTAAGGCAGCGGCAGAAGAAGATGCAGGCAGCTGAGTT

GTTGTATTCTGATAAGAGTCAGAGGTAACTCCCGTTGCGGTGCTGTTAACGGTGGAG

GGCAGTGTAGTCTGAGCAGTACTCGTTGCTGCCGCGCGCCACCAGACATAATAG

CTGACAGACTAACAGACTGTTCCTTTCCATGGGTCTTTTCTGCAGTCACCATCGATAT

GTTCGTGTTTCTGGTCTTGCTGCCCCTGGTGTCCAGCCAGTGCGTCAACCTGAC

AACCAGAACCCAACTGCCCCCAGCCTACACCAACTCCTTCACAAGAGGCGTGT

ATTACCCTGACAAGGTGTTTCGGAGCAGCGTGCTGCACTCCACCCAGGACTTG

TTTCTGCCTTTCTTCAGCAACGTGACCTGGTTCCACGCCATCCACGTGAGCGGC

ACCAATGGAACCAAGAGATTCGACAATCCTGTGCTCCCCTTCAACGACGGCGT

-continued

CTACTTCGCCAGCACCGAAAAGTCTAACATCATCAGGGGCTGGATCTTCGGCA

CAACACTGGACAGCAAGACCCAGTCCCTGCTGATTGTGAACAACGCCACAAAT

GTGGTGATCAAGGTGTGCGAATTCCAGTTTTGCAACGATCCCTTTTTGGGCGTG

TATTACCACAAGAACAACAAGAGCTGGATGGAAAGCGAATTCCGGGTGTACAG

CAGCGCCAACAACTGTACCTTCGAATACGTGAGCCAGCCTTTCCTGATGGACCT

GGAAGGCAAACAGGGCAACTTCAAGAACCTGCGGGAATTCGTGTTCAAGAACA

TCGACGGGTACTTCAAGATCTACTCTAAGCACACCCCTATCAACCTGGTCAGAG

ACCTGCCTCAAGGCTTTAGCGCCCTGGAACCTCTGGTGGACCTGCCGATCGGC

ATTAACATCACCAGATTCCAGACACTGCTGGCTCTGCACAGATCCTACCTGACC

CCTGGCGATAGCTCCAGCGGCTGGACCGCCGGAGCTGCTGCTTACTACGTGGG

CTACCTGCAACCAAGAACCTTTCTGCTGAAGTACAACGAAAACGGCACCATCAC

AGACGCCGTGGACTGCGCCCTGGATCCTCTCAGCGAGACAAAGTGTACCCTCA

AGTCGTTCACCGTGGAAAAGGGCATATACCAGACCTCTAACTTCAGAGTGCAG

CCTACAGAGAGCATCGTAAGATTCCCTAACATCACCAACCTCTGTCCCTTTGGC

GAGGTTTTCAACGCCACCAGATTCGCCAGCGTATACGCCTGGAACAGAAAGAG

AATCTCCAATTGCGTGGCCGACTACAGCGTGCTGTACAATTCTGCATCTTTTAG

CACATTCAAATGCTACGGCGTGTCCCCAACCAAGCTAAACGACCTGTGCTTCAC

CAACGTCTACGCCGACTCATTTGTGATTCGGGGCGACGAAGTGCGCCAGATCG

CCCCTGGCCAGACCGGCAAAATCGCCGATTACAACTACAAGCTGCCAGATGAC

TTCACCGGCTGTGTGATCGCCTGGAACAGCAATAATCTGGACAGCAAGGTTGG

AGGAAACTACAACTACCTGTATCGGCTGTTCAGAAAGAGCAACCTGAAGCCTTT

CGAGCGGGACATCAGTACAGAGATCTACCAGGCTGGCTCCACGCCATGCAATG

GCGTGGAGGGCTTCAACTGCTACTTCCCCCTGCAGAGCTATGGCTTCCAGCCC

ACAAACGGCGTGGGCTACCAGCCTTACAGAGTGGTGGTGCTGAGCTTCGAGCT

GCTTCATGCCCCTGCTACAGTCTGCGGCCCTAAGAAAAGCACCAATCTGGTGA

AAAATAAATGCGTGAACTTCAACTTTAACGGCCTGACCGGAACTGGAGTCCTTA

CCGAGAGCAACAAGAAGTTCCTGCCTTTTCAGCAGTTCGGAAGAGATATCGCC

GACACCACCGATGCCGTGCGGGATCCCCAGACCCTGGAGATCCTGGATATCAC

CCCCTGCAGCTTCGGCGGCGTGTCTGTGATCACGCCCGGCACCAACACCAGCA

ACCAGGTGGCCGTTCTGTACCAGGATGTGAATTGCACCGAGGTGCCTGTGGCC

ATCCACGCCGATCAGCTGACACCCACCTGGCGGGTGTATAGCACCGGATCTAA

TGTGTTCCAGACAAGAGCCGGATGTCTGATCGGAGCCGAACACGTGAACAATA

GCTACGAGTGTGACATCCCTATCGGCGCCGGAATCTGCGCCAGCTACCAAACA

CAGACTAACAGCCCTCGGAGAGCCAGAAGCGTGGCCTCTCAGTCAATCATCGC

CTACACCATGAGCCTGGGCGCCGAGAACAGCGTGGCCTACAGCAACAACAGCA

TCGCGATTCCTACCAACTTTACCATCAGCGTTACGACAGAGATCCTGCCTGTGA

GCATGACCAAAACCTCCGTGGACTGCACAATGTACATCTGCGGCGACAGCACC

GAGTGCAGCAACCTGCTGCTGCAATACGGAAGCTTCTGCACCCAGCTGAATCG

GGCCCTGACCGGCATCGCCGTTGAACAGGACAAGAACACTCAGGAGGTGTTTG

CCCAGGTCAAGCAGATATACAAGACCCCTCCTATCAAGGACTTCGGCGGATTT

-continued

AACTTTTCTCAGATCCTGCCTGACCCCAGCAAACCTTCCAAAAGAAGCTTCATC

GAAGACCTGCTGTTCAACAAGGTGACACTCGCCGACGCCGGATTTATCAAGCA

GTACGGCGATTGCCTGGGAGACATCGCCGCTAGAGATCTGATCTGCGCCCAAA

AATTCAACGGCCTGACAGTGCTGCCTCCACTGCTGACAGACGAGATGATCGCC

CAATACACCTCTGCCCTGCTGGCCGGAACCATCACAAGCGGCTGGACCTTCGG

CGCCGGCGCAGCCCTGCAAATCCCCTTCGCCATGCAGATGGCTTATAGATTCA

ATGGCATCGGCGTCACACAGAACGTGCTGTACGAGAATCAGAAGCTGATCGCC

AACCAGTTCAACTCTGCTATCGGCAAAATCCAGGATTCACTAAGCAGCACCGCC

TCAGCCCTGGGCAAACTGCAGGATGTGGTTAATCAGAATGCCCAGGCCCTGAA

CACACTGGTGAAGCAACTGTCCAGCAATTTCGGGGCTATTAGCAGTGTGCTGA

ACGATATCCTGAGTAGGCTGGATCCACCTGAGGCCGAAGTGCAGATCGACCGG

CTCATCACAGGGAGACTGCAGTCCCTGCAGACCTACGTGACCCAGCAGCTCAT

CAGAGCTGCTGAGATACGGGCCTCTGCTAATCTGGCCGCTACCAAAATGAGCG

AGTGCGTGCTGGGCCAGTCTAAGCGGGTAGATTTCTGCGGCAAGGGCTATCAC

CTGATGAGCTTCCCACAGAGCGCTCCGCACGGCGTAGTGTTCTTACATGTGAC

ATACGTCCCTGCCCAGGAGAAGAACTTCACCACAGCTCCTGCCATCTGTCACG

ATGGCAAGGCCCACTTCCCCAGAGAGGGCGTGTTCGTGTCCAACGGCACCCAC

TGGTTCGTGACGCAGCGGAACTTCTACGAGCCTCAGATTATCACAACAGACAA

CACCTTCGTGTCTGGAAATTGCGACGTTGTCATCGGCATCGTCAACAACACCGT

GTACGACCCACTGCAGCCTGAGCTGGACAGCTTCAAGGAAGAGCTGGACAAGT

ACTTCAAGAACCACACCAGCCCCGATGTGGACCTGGGCGACATCAGCGGAATC

AACGCCTCTGTGGTGAACATCCAGAAGGAAATCGACAGACTGAACGAGGTGGC

CAAGAACCTGAATGAGTCACTTATTGACCTGCAGGAACTGGGCAAATACGAAC

AGTACATCAAATGGCCCTGGTACATCTGGCTGGGATTCATCGCTGGCCTGATC

GCCATCGTGATGGTGACAATCATGCTGTGTTGCATGACATCTTGTTGTAGCTGC

CTGAAGGGCTGCTGTAGCTGTGGCTCTTGTTGCAAGTTCGACGAGGACGACAG

CGAGCCCGTGCTCAAGGGAGTGAAGCTGCACTATACCTAAACCATGATATTCGG

CAAGCAGGCATCGCCATGGGTCACGACGAGATCCTCGCCGTCGGGCATGCTCGCCTT

GAGCCTGGCGAACAGTTCGGCTGGCGCGAGCCCCTGATGCTCTTCGTCCAGATCATC

CTGATCGACAAGACCGGCTTCCATCCGAGTACGTGCTCGCTCGATGCGATGTTTCGC

TTGGTGGTCGAATGGGCAGGTAGCCGGATCAAGCGTATGCAGCCGCCGCATTGCAT

CAGCCATGATGGATACTTTCTCGGCAGGAGCAAGGTGAGATGACAGGAGATCCTGC

CCCGGCACTTCGCCCAATAGCAGCCAGTCCCTTCCCGCTTCAGTGACAACGTCGAGC

ACAGCTGCGCAAGGAACGCCCGTCGTGGCCAGCCACGATAGCCGCGCTGCCTCGTC

TTGCAGTTCATTCAGGGCACCGGACAGGTCGGTCTTGACAAAAAGAACCGGGCGCC

CCTGCGCTGACAGCCGGAACACGGCGGCATCAGAGCAGCCGATTGTCTGTTGTGCC

CAGTCATAGCCGAATAGCCTCTCCACCCAAGCGGCCGGAGAACCTGCGTGCAATCC

ATCTTGTTCAATCATGCGAAACGATCCTCATCCTGTCTCTTGATCAGATCTTGATCCC

CTGCGCCATCAGATCCTTGGCGGCAAGAAAGCCATCCAGTTTACTTTGCAGGGCTTC

CCAACCTTACCAGAGGGCGCCCCAGCTGGCAATTCCGGTTCGCTTGCTGTCCATAAA

ACCGCCCAGTCTAGCTATCGCCATGTAAGCCCACTGCAAGCTACCTGCTTTCTCTTTG

-continued

CGCTTGCGTTTTCCCTTGTCCAGATAGCCCAGTAGCTGACATTCATCCGGGGTCAGC

ACCGTTTCTGCGGACTGGCTTTCTACGTGAAAAGGATCTAGGTGAAGATCCTTTTTG

ATAATCTCATGACCAAAATCCCTTAACGTGAGTTTTCGTTCCACTGAGCGTCAGACC

CCGTAGAAAAGATCAAAGGATCTTCTTGAGATCCTTTTTTTCTGCGCGTAATCTGCTG

CTTGCAAACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAAATACTGT

TCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTG

TCTTACCGGGTTGGACTCAAGACGATAGTTACCGGATAAGGCGCAGCGGTCGGGCT

GAACGGGGGGTTCGTGCACACAGCCCAGCTTGGAGCGAACGACCTACACCGAACT

GAGATACCTACAGCGTGAGCTATGAGAAAGCGCCACGCTTCCCGAAGGGAGAAAGG

CGGACAGGTATCCGGTAAGCGGCAGGGTCGGAACAGGAGAGCGCACGAGGGAGCT

TCCAGGGGGAAACGCCTGGTATCTTTATAGTCCTGTCGGGTTTCGCCACCTCTGACTT

GAGCGTCGATTTTTGTGATGCTCGTCAGGGGGGCGGAGCCTATGGAAAAACGCCAG

CAACGCGGCCCTTTTACGGTTCCTGGCCTTTTGCTGGCCTTTTGCTCACATGTTGT

DNA Construct 3: DNA/S-Tri-Sec

| Name | Range | Description |
|---|---|---|
| CMV Promoter | 476 to 675 | Human cytomegalovirus (CMV) immediate early promoter |
| intron A | 702 to 1645 | Intron A positively regulate expression from the hCMV immediate-early enhancer/promoter |
| ORF | 1651 to 5379 | Insert nCoV S-Tri-Sec (GMCSF ss (17 aa)-Spike aa 14 to 1208 (1195 aa)-FOLD ON (30 aa)) |
| bGH poly(A) signal | 5419 to 5626 | Bovine growth hormone polyadenylation signal |
| Kanamycin resistance gene | 6775 to 7569 | Confers resistance to neomycin, kanamycin, and G418 (Geneticin(R)) |
| Replication Origin | 6865 to 7454 | High-copy-number ColE1/pMB1/pBR322/pUC origin of replication |

pGA8-nCoV S-Tri-Sec Plasmid Sequences (SEQ ID NO: 17) and Sequence Encoding Spike Protein (Bold, SEQ ID NO: 18)

CGACAATATTGGCTATTGGCCATTGCATACGTTGTATCTATATCATAATATGTACATT

TATATTGGCTCATGTCCAATATGACCGCCATGTTGACATTGATTATTGACTAGTTATT

AATAGTAATCAATTACGGGTCATTAGTTCATAGCCCATATATGGAGTTCCGCGTTA

CATAACTTACGGTAAATGGCCCGCCTGGCTGACCGCCCAACGACCCCCGCCCATTGA

CGTCAATAATGACGTATGTTCCCATAGTAACGCCAATAGGGACTTTCCATTGACGTC

AATGGGTGGAGTATTTACGGTAAACTGCCCACTTGGCAGTACATCAAGTGTATCATA

TGCCAAGTCCGCCCCCTATTGACGTCAATGACGGTAAATGGCCCGCCTGGCATTATG

CCCAGTACATGACCTTACGGGACTTTCCTACTTGGCAGTACATCTACGGTATTAGTC

ATCGGCTATTACCATGGTGATGCGGTTTTGGCAGTACACCAATGGGCGTGGATAGCG

GTTTGACTCACGGGGATTTCCAAGTCTCCACCCCATTGACGTCAATGGGAGTTTGTTT

TGGCACCAAAATCAACGGGACTTTCCAAAATGTCGTAATAACCCCGCCCCGTTGACG

CAAATGGGCGGTAGGCGTGTACGGTGGGAGGTCTATATAAGCAGAGCTCGTTTAGT

GAACCGTCAGATCGCCTGGAGACGCCATCCACGCTGTTTTGACCTCCATAGAAGACA

CCGGGACCGATCCAGCCTCCGCGGCCGGGAACGGTGCATTGGAACGCGGATTCCCC

GTGCCAAGAGTGACGTAAGTACCGCCTATAGACTCTATAGGCACACCCCTTTGGCTC

-continued

TTATGCATGCTATACTGTTTTTGGCTTGGGGCCTATACACCCCCGCTTCCTTATGCTA

TAGGTGATGGTATAGCTTAGCCTATAGGTGTGGGTTATTGACCATTATTGACCACTC

CCCTATTGGTGACGATACTTTCCATTACTAATCCATAACATGGCTCTTTGCCACAACT

ATCTCTATTGGCTATATGCCAATACTCTGTCCTTCAGAGACTGACACGGACTCTGTAT

TTTTACAGGATGGGGTCCCATTTATTATTTACAAATTCACATATACAACAACGCCGT

CCCCCGTGCCCGCAGTTTTTATTAAACATAGCGTGGGATCTCCACGCGAATCTCGGG

TACCGTGTTCCGGACATGGGYTCTTCTCCGGTAGCGGCGGAGCTTCCACATCCGAGC

CCTGGTCCCATGCCTCCAGCGGCTCATGGTCGCTCGGCAGCTCCTTGCTCCTAACAG

TGGAGGCCAGACTTAGGCACAGCACAATGCCCACCACCACCAGTGTGCCGCACAAG

GCCGTGGCGGTAGGGTATGTGTCTGAAAATGAGCTCGGAGATTGGGCTCGCACCGC

TGACGCAGATGGAAGACTTAAGGCAGCGGCAGAAGAAGATGCAGGCAGCTGAGTT

GTTGTATTCTGATAAGAGTCAGAGGTAACTCCCGTTGCGGTGCTGTTAACGGTGGAG

GGCAGTGTAGTCTGAGCAGTACTCGTTGCTGCCGCGCGCGCCACCAGACATAATAG

CTGACAGACTAACAGACTGTTCCTTTCCATGGGTCTTTTCTGCAGTCACCATCGATAT

GTGGCTGCAGGGCCTGCTGCTGCTGGGCACCGTGGCATGCAGTATCAGCCAAT

GTGTGAACCTGACCACCAGAACCCAACTGCCTCCTGCCTACACCAACTCTTTCA

CCAGAGGCGTGTACTACCCTGACAAGGTGTTCAGAAGCAGCGTGCTGCATTCT

ACCCAGGACCTGTTTCTGCCATTCTTCAGCAACGTCACCTGGTTCCACGCCATC

CACGTGTCTGGCACCAATGGCACTAAGAGATTCGACAACCCCGTGCTGCCTTT

CAACGACGGCGTGTACTTTGCCTCAACTGAGAAGAGCAACATCATCAGAGGAT

GGATCTTCGGCACCACACTTGACTCAAAGACACAGTCACTGCTGATCGTGAAC

AATGCTACCAATGTGGTGATCAAGGTGTGTGAATTCCAGTTTTGCAACGATCCT

TTCCTGGGTGTATACTACCACAAGAACAACAAGTCTTGGATGGAGAGCGAGTT

CCGGGTGTATAGTAGCGCCAACAACTGCACCTTCGAATACGTGAGCCAGCCTT

TCCTCATGGACCTGGAAGGCAAGCAAGGCAACTTCAAGAACCTGAGAGAGTTC

GTGTTTAAGAACATTGATGGCTACTTCAAGATCTACAGCAAGCACACCCCCATC

AACCTGGTGCGGGACCTCCCTCAGGGCTTCAGCGCCCTGGAACCCTTGGTTGA

TCTGCCAATTGGCATCAATATCACTCGGTTCCAAACCCTGCTGGCCCTGCACAG

AAGCTATCTGACACCTGGAGACAGCAGCAGCGGCTGGACCGCCGGAGCCGCC

GCCTACTACGTGGGCTACCTGCAGCCCCGGACCTTCCTGCTGAAGTACAACGA

GAACGGGACCATTACCGACGCCGTCGACTGCGCCCTGGATCCTCTGAGCGAAA

CCAAGTGCACACTTAAAAGCTTCACAGTGGAGAAGGGCATCTACCAAACCTCC

AATTTTCGGGTCCAGCCAACCGAGAGCATCGTTAGATTCCCCAACATCACCAAC

TTGTGCCCCTTCGGAGAAGTGTTCAACGCCACAAGATTCGCCAGCGTCTACGC

CTGGAACAGAAAGAGAATTTCCAATTGCGTCGCAGACTACTCTGTGCTGTACAA

CAGCGCCAGCTTTTCTACATTCAAGTGCTACGGCGTGAGCCCCACCAAGCTGA

ACGACCTATGCTTCACAAACGTGTACGCCGACAGCTTTGTGATCCGGGGCGAC

GAGGTGCGCCAGATCGCGCCAGGACAGACCGGTAAGATCGCCGATTACAATTA

CAAACTGCCTGACGACTTCACCGGCTGCGTCATCGCTTGGAACAGCAACAACC

TGGACTCTAAGGTGGGCGGAAACTACAACTACCTGTACCGGCTGTTTAGAAAG

AGCAACCTGAAGCCTTTTGAACGGGACATCTCTACAGAGATCTACCAGGCCGG

-continued

ATCTACCCCTTGTAATGGCGTGGAGGGCTTTAATTGCTACTTCCCCCTGCAATC

GTACGGCTTCCAGCCGACAAACGGCGTCGGCTACCAGCCTTACAGAGTGGTGG

TCCTGTCCTTCGAGCTGCTGCATGCCCCTGCTACAGTGTGCGGCCCTAAGAAA

AGCACCAACCTGGTGAAGAACAAGTGTGTGAACTTCAATTTCAATGGCCTGACT

GGCACCGGAGTGCTGACCGAATCCAACAAGAAGTTCCTGCCCTTCCAGCAGTT

CGGCAGAGACATCGCAGACACTACCGATGCTGTGCGGGATCCTCAGACACTGG

AGATCCTGGATATCACCCCCTGCAGCTTCGGAGGCGTGAGCGTGATCACACCT

GGCACAAACACATCCAACCAGGTGGCCGTGCTGTACCAGGATGTGAACTGCAC

AGAAGTGCCGGTTGCCATCCACGCCGATCAGCTCACACCTACTTGGCGGGTGT

ACTCCACAGGCAGCAACGTGTTCCAAACCAGAGCTGGCTGTCTGATCGGCGCT

GAACACGTGAACAATAGCTATGAGTGCGACATCCCAATCGGCGCCGGTATCTG

CGCCTCCTATCAGACGCAGACGAACAGCCCTAGGCGGGCTAGAAGCGTGGCCA

GCCAGAGCATCATCGCATATACAATGAGCCTGGGCGCCGAAAACTCTGTCGCC

TACAGCAACAACAGCATCGCTATCCCTACCAACTTCACCATAAGCGTAACAACC

GAGATCCTGCCTGTGTCCATGACAAAGACCAGCGTGGACTGTACAATGTACAT

CTGTGGCGACTCCACCGAGTGCAGCAACCTGCTCCTGCAATACGGCTCTTTCT

GCACCCAGCTGAATCGCGCCTTAACAGGCATTGCCGTGGAACAGGATAAGAAC

ACCCAGGAGGTGTTCGCCCAGGTGAAGCAGATCTATAAGACCCCACCCATCAA

GGACTTCGGCGGATTCAATTTCAGTCAAATCCTGCCCGATCCTAGCAAGCCCA

GTAAGAGATCTTTCATCGAGGACCTGCTTTTCAACAAAGTGACCCTGGCGGAC

GCCGGATTTATCAAACAGTACGGCGACTGTCTGGGCGACATCGCCGCTAGAGA

TCTGATCTGCGCCCAGAAATTCAACGGCCTGACGGTGCTGCCTCCTCTGCTGA

CAGATGAGATGATCGCCCAGTATACCAGCGCCCTGCTGGCTGGAACCATCACC

TCTGGCTGGACATTTGGCGCCGGTGCCGCTCTCCAGATCCCCTTTGCCATGCA

GATGGCCTACAGATTCAATGGAATCGGCGTGACCCAGAACGTGCTGTACGAGA

ACCAGAAGCTGATCGCTAATCAGTTCAACTCTGCCATTGGCAAAATCCAGGACA

GCCTGTCTTCCACCGCCAGCGCCCTGGGCAAACTGCAAGACGTGGTGAATCAA

AACGCCCAGGCCCTGAACACTCTGGTGAAGCAGCTGTCCAGCAACTTCGGAGC

CATCAGCAGCGTGCTGAACGACATACTGAGCAGACTGGACCCTCCGGAGGCCG

AGGTGCAGATCGACAGGCTGATCACAGGCAGACTGCAGAGCCTGCAGACCTAC

GTCACACAGCAGCTGATCAGAGCCGCTGAGATCCGAGCTTCTGCCAATCTCGC

CGCGACAAAGATGTCTGAGTGCGTGCTCGGCCAGAGCAAAAGAGTGGATTTCT

GCGGAAAAGGCTATCACCTGATGAGCTTCCCTCAGTCTGCCCCACACGGCGTC

GTGTTCCTGCACGTGACCTACGTGCCTGCCCAGGAAAAAAACTTTACCACCGC

CCCGGCCATCTGCCACGACGGCAAGGCCCACTTCCCTAGAGAAGGCGTGTTCG

TGAGCAATGGCACCCACTGGTTCGTGACACAAAGAAACTTCTACGAGCCTCAA

ATCATCACAACAGATAACACCTTCGTGTCAGGCAACTGTGACGTGGTCATCGG

AATCGTGAATAATACCGTGTACGACCCCCTGCAGCCTGAACTGGACAGCTTTAA

GGAGGAACTGGACAAGTACTTCAAAAACCACACATCTCCTGATGTGGACCTGG

GGGATATCAGCGGCATCAACGCTTCTGTGGTGAACATCCAGAAGGAAATCGAC

-continued

AGACTGAACGAGGTGGCCAAGAATCTCAACGAAAGCCTCATTGACCTTCAGGA

GCTGGGGAAGTACGAGCAGGGCTCTGCCGGCTACATCCCTGAGGCTCCTAGGG

ACGGCCAGGCCTACGTGCGGAAGGACGGGGAGTGGGTGCTGCTGAGCACATT

CCTGTAAACCATGATATTCGGCAAGCAGGCATCGCCATGGGTCACGACGAGATCCT

CGCCGTCGGGCATGCTCGCCTTGAGCCTGGCGAACAGTTCGGCTGGCGCGAGCCCCT

GATGCTCTTCGTCCAGATCATCCTGATCGACAAGACCGGCTTCCATCCGAGTACGTG

CTCGCTCGATGCGATGTTTCGCTTGGTGGTCGAATGGGCAGGTAGCCGGATCAAGCG

TATGCAGCCGCCGCATTGCATCAGCCATGATGGATACTTTCTCGGCAGGAGCAAGGT

GAGATGACAGGAGATCCTGCCCCGGCACTTCGCCCAATAGCAGCCAGTCCCTTCCCG

CTTCAGTGACAACGTCGAGCACAGCTGCGCAAGGAACGCCCGTCGTGGCCAGCCAC

GATAGCCGCGCTGCCTCGTCTTGCAGTTCATTCAGGGCACCGGACAGGTCGGTCTTG

ACAAAAAGAACCGGGCGCCCCTGCGCTGACAGCCGGAACACGGCGGCATCAGAGC

AGCCGATTGTCTGTTGTGCCCAGTCATAGCCGAATAGCCTCTCCACCCAAGCGGCCG

GAGAACCTGCGTGCAATCCATCTTGTTCAATCATGCGAAACGATCCTCATCCTGTCT

CTTGATCAGATCTTGATCCCCTGCGCCATCAGATCCTTGGCGGCAAGAAAGCCATCC

AGTTTACTTTGCAGGGCTTCCCAACCTTACCAGAGGGCGCCCCAGCTGGCAATTCCG

GTTCGCTTGCTGTCCATAAAACCGCCCAGTCTAGCTATCGCCATGTAAGCCCACTGC

AAGCTACCTGCTTTCTCTTTGCGCTTGCGTTTTCCCTTGTCCAGATAGCCCAGTAGCT

GACATTCATCCGGGGTCAGCACCGTTTCTGCGGACTGGCTTTCTACGTGAAAAGGAT

CTAGGTGAAGATCCTTTTTGATAATCTCATGACCAAAATCCCTTAACGTGAGTTTTCG

TTCCACTGAGCGTCAGACCCCGTAGAAAAGATCAAAGGATCTTCTTGAGATCCTTTT

TTTCTGCGCGTAATCTGCTGCTTGCAAACAAAAAAACCACCGCTACCAGCGGTGGTT

TGTTTGCCGGATCAAGAGCTACCAACTCTTTTTCCGAAGGTAACTGGCTTCAGCAGA

GCGCAGATACCAAATACTGTTCTTCTAGTGTAGCCGTAGTTAGGCCACCACTTCAAG

AACTCTGTAGCACCGCCTACATACCTCGCTCTGCTAATCCTGTTACCAGTGGCTGCT

GCCAGTGGCGATAAGTCGTGTCTTACCGGGTTGGACTCAAGACGATAGTTACCGGAT

AAGGCGCAGCGGTCGGGCTGAACGGGGGGTTCGTGCACACAGCCCAGCTTGGAGCG

AACGACCTACACCCGAACTGAGATACCTACAGCGTGAGCTATGAGAAAGCGCCACG

CTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGCGG

AGCCTATGGAAAAACGCCAGCAACGCGGCCCTTTTTACGGTTCCTGGCCTTTTGCTGG

CCTTTTGCTCACATGTTGT

DNA Construct 4: DNA/S1-Mono

| Name | Range | Description |
|---|---|---|
| CMV Promoter | 476 to 675 | Human cytomegalovirus (CMV) immediate early promoter |
| Intron A | 702 to 1645 | Intron A positively regulate expression from the hCMV immediate-early enhancer/promoter |
| GM-CSF signal sequences | 1651 to 1761 | Secreted, signal peptide |
| ORF | 1651 to 4005 | Insert nCoV GM-CSF S1 soluble |

-continued

| Name | Range | Description |
|---|---|---|
| bGH poly(A) signal | 4045 to 4252 | Bovine growth hormone polyadenylation signal |
| Kanamycin resistance gene | 4285 to 5079 | Confers resistance to neomycin, kanamycin, and G418 (Geneticin(R)) |
| Replication Origin | 5491 to 6080 | High-copy-number ColE1/pMB1/pBR322/pUC origin of replication |

pGA8-nCoV GMCSF-S1 Plasmid Sequences (SEQ ID NO: 19) and Sequence Encoding Spike Protein (Bold, SEQ ID NO: 20)

CGACAATATTGGCTATTGGCCATTGCATACGTTGT
ATCTATATCATAATATGTACATTTATATTGGCTCA
TGTCCAATATGACCGCCATGTTGACATTGATTATT
GACTAGTTATTAATAGTAATCAATTACGGGTCAT
TAGTTCATAGCCCATATATGGAGTTCCGCGTTACA
TAACTTACGGTAAATGGCCCGCCTGGCTGACCGCC
CAACGACCCCCGCCCATTGACGTCAATAATGACGT
ATGTTCCCATAGTAACGCCAATAGGGACTTTCCAT
TGACGTCAATGGGTGGAGTATTTACGGTAAACTGC
CCACTTGGCAGTACATCAAGTGTATCATATGCCAA
GTCCGCCCCCTATTGACGTCAATGACGGTAAATGG
CCCGCCTGGCATTATGCCCAGTACATGACCTTACG
GGACTTTCCTACTTGGCAGTACATCTACGGTATTA
GTCATCGGCTATTACCATGGTGATGCGGTTTTGGC
AGTACACCAATGGGCGTGGATAGCGGTTTGACTCA
CGGGGATTTCCAAGTCTCCACCCCATTGACGTCAA
TGGGAGTTTGTTTTGGCACCAAAATCAACGGGACT
TTCCAAAATGTCGTAATAACCCCGCCCCGTTGACG
CAAATGGGCGGTAGGCGTGTACGGTGGGAGGTCTA
TATAAGCAGAGCTCGTTTAGTGAACCGTCAGATCG
CCTGGAGACGCCATCCACGCTGTTTTGACCTCCAT
AGAAGACACCGGGACCGATCCAGCCTCCGCGGCCG
GGAACGGTGCATTGGAACGCGGATTCCCCGTGCCA
AGAGTGACGTAAGTACCGCCTATAGACTCTATAGG
CACACCCCTTTGGCTCTTATGCATGCTATACTGTT
TTTGGCTTGGGGCCTATACACCCCCGCTTCCTTAT
GCTATAGGTGATGGTATAGCTTAGCCTATAGGTGT
GGGTTATTGACCATTATTGACCACTCCCCTATTGG
TGACGATACTTTCCATTACTAATCCATAACATGGC
TCTTTGCCACAACTATCTCTATTGGCTATATGCCA
ATACTCTGTCCTTCAGAGACTGACACGGACTCTGT
ATTTTTACAGGATGGGGTCCCATTTATTATTTACA
AATTCACATATACAACAACGCCGTCCCCCGTGCCC
GCAGTTTTTATTAAACATAGCGTGGGATCTCCACG
CGAATCTCGGGTACCGTGTTCCGGACATGGGYTCT
TCTCCGGTAGCGGCGGAGCTTCCACATCCGAGCCC
TGGTCCCATGCCTCCAGCGGCTCATGGTCGCTCGG
CAGCTCCTTGCTCCTAACAGTGGAGGCCAGACTTA

-continued

GGCACAGCACAATGCCCACCACCACCAGTGTGCCG
CACAAGGCCGTGGCGGTAGGGTATGTGTCTGAAAA
TGAGCTCGGAGATTGGGCTCGCACCGCTGACGCAG
ATGGAAGACTTAAGGCAGCGGCAGAAGAAGATGCA
GGCAGCTGAGTTGTTGTATTCTGATAAGAGTCAGA
GGTAACTCCCGTTGCGGTGCTGTTAACGGTGGAGG
GCAGTGTAGTCTGAGCAGTACTCGTTGCTGCCGCG
CGCGCCACCAGACATAATAGCTGACAGACTAACAG
ACTGTTCCTTTCCATGGGTCTTTTCTGCAGTCACC
ATCGATATGTGGCTGCAGGGGCTGCTGCTGCTGGG
AACCGTGGCTTGCTCCATTTCTCAGTGCGTCAATC
TGACTACCCGAACTCAGCTGCCCCCCGCCTACACC
AACTCCTTCACCCGGGGCGTGTACTATCCAGACAA
GGTGTTTAGAAGCTCCGTGCTGCACTCCACCCAGG
ATCTGTTTCTGCCCTTCTTTTCTAATGTGACATGG
TTCCACGCCATCCACGTGAGCGGCACCAACGGCAC
AAAGAGGTTCGACAACCCTGTGCTGCCATTCAATG
ATGGCGTGTACTTTGCCTCCACCGAGAAGTCTAAC
ATCATCCGCGGCTGGATCTTTGGCACCACACTGGA
CTCCAAGACCCAGTCCCTGCTGATCGTGAACAATG
CCACAAACGTGGTCATCAAGGTGTGCGAGTTCCAG
TTTTGTAACGATCCTTTCCTGGGCGTGTACTATCA
CAAGAACAATAAGTCTTGGATGGAGAGCGAGTTTA
GGGTGTATTCTAGCGCCAACAATTGCACCTTCGAG
TACGTGTCCCAGCCATTTCTGATGGACCTGGAGGG
CAAGCAGGGCAATTTCAAGAACCTGCGGGAGTTCG
TGTTTAAGAACATCGACGGCTACTTCAAGATCTAC
TCCAAGCACACCCCCATCAACCTGGTGCGGGACCT
GCCACAGGGCTTCTCTGCCCTGGAGCCTCTGGTGG
ATCTGCCAATCGGCATCAACATCACACGGTTTCAG
ACCCTGCTGGCCCTGCACAGAAGCTACCTGACCCC
TGGCGACTCCTCTAGCGGATGGACAGCAGGAGCAG
CAGCATACTATGTGGGCTATCTGCAGCCACGGACC
TTCCTGCTGAAGTACAACGAGAATGGCACCATCAC
AGACGCCGTGGATTGCGCCCTGGATCCACTGTCTG
AGACAAAGTGTACACTGAAGAGCTTTACAGTGGAG
AAGGGCATCTATCAGACCAGCAACTTCAGGGTGCA
GCCCACAGAGTCCATCGTGCGCTTTCCAAATATCA
CCAACCTGTGCCCCTTCGGCGAGGTGTTTAATGCC
ACAAGATTCGCCAGCGTGTACGCCTGGAACAGGAA
GCGCATCTCCAATTGCGTGGCCGACTATTCTGTGC

-continued

TGTACAACTCTGCCAGCTTCTCCACCTTTAAGTGC
TATGGCGTGAGCCCCACCAAGCTGAACGACCTGTG
CTTCACAAACGTGTACGCCGATTCCTTTGTGATCA
GGGGCGACGAGGTGCGCCAGATCGCACCAGGACAG
ACCGGCAAGATCGCAGACTACAACTATAAGCTGCC
CGACGATTTCACAGGCTGCGTGATCGCCTGGAATT
CCAACAATCTGGATTCTAAAGTGGGCGGCAACTAC
AATTATCTGTACAGGCTGTTCCGCAAGTCTAACCT
GAAGCCTTTTGAGCGGGACATCTCCACCGAGATCT
ACCAGGCCGGCTCTACACCATGCAACGGCGTGGAG
GGCTTCAATTGTTATTTTCCCCTGCAGAGCTACGG
CTTCCAGCCTACCAATGGCGTGGGCTATCAGCCAT
ACAGAGTGGTGGTGCTGTCTTTTGAGCTGCTGCAC
GCACCAGCAACCGTGTGCGGACCTAAGAAGAGCAC
AAATCTGGTGAAGAACAAGTGCGTGAACTTCAACT
TCAACGGCCTGACCGGAACAGGCGTGCTGACCGAG
TCCAACAAGAAGTTCCTGCCCTTTCAGCAGTTCGG
CAGGGACATCGCAGATACCACAGACGCCGTGCGCG
ACCCCCAGACACTGGAGATCCTGGATATCACCCCT
TGCAGCTTCGGCGGCGTGTCCGTGATCACCCCTGG
AACCAATACAAGCAACCAGGTGGCCGTGCTGTATC
AGGACGTGAACTGTACAGAGGTGCCAGTGGCCATC
CACGCCGATCAGCTGACCCCCACATGGCGGGTGTA
CTCCACAGGCTCTAACGTGTTCCAGACCAGAGCAG
GATGCCTGATCGGAGCAGAGCACGTGAACAATAGC
TATGAGTGCGACATCCCCATCGGCGCCGGCATCTG
TGCCTCCTACCAGACCCAGACAAACTCCCCTCGGA
GAGCCAGGTCTGTGGCCTCTCAGAGCATCATCGCC
TATACCATGAGCCTGGGCGCCGAGAACTCCGTGGC
CTACAGCAACAATTCCATCGCCATCCCCACCAATT
TCACAATCTCCGTGACCACAGAGATCCTGCCCGTG
AGCATGACCAAGACAAGCGTGGACTGCACCATGTA
TATCTGTGGCGATTCCACAGAGTGCTCTAATCTGC
TGCTGCAGTACGGCTCTTTTTGTACACAGCTGAAC
CGCGCCCTGACCGGAATCGCAGTGGAGCAGGACAA
GAATACCCAGGAGTAAACCATGATATTCGGCAAGC
AGGCATCGCCATGGGTCACGACGAGATCCTCGCCG
TCGGGCATGCTCGCCTTGAGCCTGGCGAACAGTTC
GGCTGGCGCGAGCCCCTGATGCTCTTCGTCCAGAT
CATCCTGATCGACAAGACCGGCTTCCATCCGAGTA

-continued

CGTGCTCGCTCGATGCGATGTTTCGCTTGGTGGTC
GAATGGGCAGGTAGCCGGATCAAGCGTATGCAGCC
GCCGCATTGCATCAGCCATGATGGATACTTTCTCG
GCAGGAGCAAGGTGAGATGACAGGAGATCCTGCCC
CGGCACTTCGCCCAATAGCAGCCAGTCCCTTCCCG
CTTCAGTGACAACGTCGAGCACAGCTGCGCAAGGA
ACGCCCGTCGTGGCCAGCCACGATAGCCGCGCTGC
CTCGTCTTGCAGTTCATTCAGGGCACCGGACAGGT
CGGTCTTGACAAAAAGAACCGGGCGCCCCTGCGCT
GACAGCCGGAACACGGCGGCATCAGAGCAGCCGAT
TGTCTGTTGTGCCCAGTCATAGCCGAATAGCCTCT
CCACCCAAGCGGCCGGAGAACCTGCGTGCAATCCA
TCTTGTTCAATCATGCGAAACGATCCTCATCCTGT
CTCTTGATCAGATCTTGATCCCCTGCGCCATCAGA
TCCTTGGCGGCAAGAAAGCCATCCAGTTTACTTTG
CAGGGCTTCCCAACCTTACCAGAGGGCGCCCCAGC
TGGCAATTCCGGTTCGCTTGCTGTCCATAAAACCG
CCCAGTCTAGCTATCGCCATGTAAGCCCACTGCAA
GCTACCTGCTTTCTCTTTGCGCTTGCGTTTTCCCT
TGTCCAGATAGCCCAGTAGCTGACATTCATCCGGG
GTCAGCACCGTTTCTGCGGACTGGCTTTCTACGTG
AAAAGGATCTAGGTGAAGATCCTTTTTGATAATCT
CATGACCAAAATCCCTTAACGTGAGTTTTCGTTCC
ACTGAGCGTCAGACCCCGTAGAAAAGATCAAAGGA
TCTTCTTGAGATCCTTTTTTTCTGCGCGTAATCTG
CTGCTTGCAAACAAAAAAACCACCGCTACCAGCGG
TGGTTTGTTTGCCGGATCAAGAGCTACCAACTCTT
TTTCCGAAGGTAACTGGCTTCAGCAGAGCGCAGAT
ACCAAATACTGTTCTTCTAGTGTAGCCGTAGTTAG
GCCACCACTTCAAGAACTCTGTAGCACCGCCTACA
TACCTCGCTCTGCTAATCCTGTTACCAGTGGCTGC
TGCCAGTGGCGATAAGTCGTGTCTTACCGGGTTGG
ACTCAAGACGATAGTTACCGGATAAGGCGCAGCGG
TCGGGCTGAACGGGGGGTTCGTGCACACAGCCCAG
CTTGGAGCGAACGACCTACACCCGAACTGAGATAC
CTACAGCGTGAGCTATGAGAAAGCGCCACGCTTCC
CGAAGGGAGAAAGGCGGACAGGTATCCGGTAAGCG
GCAGGGTCGGAACAGGAGAGCGCACGAGGGAGCTT
CCAGGGGGAAACGCCTGGTATCTTTATAGTCCTGT
CGGGTTTCGCCACCTCTGACTTGAGCGTCGATTTT
TGTGATGCTCGTCAGGGGGGCGGAGCCTATGGAAA

-continued

AACGCCAGCAACGCGGCCCTTTTACGGTTCCTGGC

CTTTTGCTGGCCTTTTGCTCACATGTTGT

Chimera T Cell Immunogens and Vaccination Approach to Generate Broadly Cross-Reactive T Cells DNA based T cell chimera antigens we have designed encoding proteins derived from 6 genes of SARS-CoV-2 i.e., Spike, N, M, NSP3, NSP4 and NSP6. These proteins have been chosen because: 1) they show strong conservation between multiple human betacoronaviruses; and 2) they account for greater than 90% of the CoV2 specific T cell response observed in SARS-CoV-2 infected individuals. Chimera 1 carry immunodominant T cell epitopes of spike glycoprotein (S), nucleocapsid (N) and membrane (M) proteins. The other construct has regions derived from non-structural regions, expressed during virus active replication and translation. This includes non-structural protein 3 (NSP3), NSP4, and NSP6. about 66% of the N terminal region of the NSP3 protein was deleted since this region contains peptide sequences and functional domains which can disrupt the process of epitope processing and presentation. These regions include nucleic acid binding domains, viral proteinase activity domains and autophagy modulating domains. However, the remaining C-terminal region contains three immunodominant CD8 T cell epitopes that are conserved in SARS-CoV and CoV2. Versions of each construct lacking transmembrane (TM) regions were developed providing the four chimera constructs (d/delta is deleted): Chimera 1 (SdRBD-N-M) and 3 (NSP3-4-6), and the chimeras lacking TM, Chimera 2 (SdRBD-N-M_dTM) and 4 (NSP3-4-6_dTM), respectively.

The RBD region (major target of neutralization) was deleted from the S protein to avoid antibody response to this region induced by improperly folded chimeric protein which could interfere with the neutralizing antibody responses induced by properly folded RBD protein immunogen. Two versions for each construct are provided, one with and the other without the transmembrane regions from S, M, Nsp3, Nsp4 and Nsp6 proteins in order to compare their ability to induce T cell responses. The chimeric proteins without transmembrane regions are expected to be localized to the cytoplasm and will be susceptible to degradation by proteasomes. This could potentially promote class I HLA epitope presentation to generate CD8 T cell response. In addition, these chimeric proteins expressed as fusion proteins and do not have secretory signals facilitating the priming of T cell response as opposed to antibody response with the idea that the expressed chimeric proteins may not retain the proper conformation to generate a neutralizing antibody response. These chimeric immunogens that are designed to induce a broad CD4 and CD8 T cell response with cross-reactivity to other coronaviruses by use in combination with the other DNA prime/MVA boost strategies reported herein providing an improved T cell response.

Chimera 1: SdRBD-N-M (SEQ ID NO: 24)

MCVNLTTRTQLPPAYTNSFTRGVYYPDKVFRSSVLHSTQD

LFLPFFSNVTWFHAIHVSGTNGTKRFDNPVLPFNDGVYFA

STEKSNIIRGWIFGTTLDSKTQSLLIVNNATNVVIKVCEF

QFCNDPFLGVYYHKNNKSWMESEFRVYSSANNCTFEYVSQ

-continued

PFLMDLEGKQGNFKNLREFVFKNIDGYFKIYSKHTPINLV

RDLPQGFSALEPLVDLPIGINITRFQTLLALHRSYLTPGD

SSSGWTAGAAAYYVGYLQPRTFLLKYNENGTITDAVDCAL

DPLSETKCTLKSFTVEKGIYQTSNFRVQPTESIVRFATVC

GPKKSTNLVKNKCVNFNFNGLTGTGVLTESNKKFLPFQQF

GRDIADTTDAVRDPQTLEILDITPCSFGGVSVITPGTNTS

NQVAVLYQDVNCTEVPVAIHADQLTPTWRVYSTGSNVFQT

RAGCLIGAEHVNNSYECDIPIGAGICASYQTQTNSPSRAG

SVASQSIIAYTMSLGAENSVAYSNNSIAIPTNFTISVTTE

ILPVSMTKTSVDCTMYICGDSTECSNLLLQYGSFCTQLNR

ALTGIAVEQDKNTQEVFAQVKQIYKTPPIKDFGGFNFSQI

LPDPSKPSKRSFIEDLLFNKVTLADAGFIKQYGDCLGDIA

ARDLICAQKFNGLTVLPPLLTDEMIAQYTSALLAGTITSG

WTFGAGAALQIPFAMQMAYRFNGIGVTQNVLYENQKLIAN

QFNSAIGKIQDSLSSTASALGKLQDVVNQNAQALNTLVKQ

LSSNFGAISSVLNDILSRLDPPEAEVQIDRLITGRLQSLQ

TYVTQQLIRAAEIRASANLAATKMSECVLGQSKRVDFCGK

GYHLMSFPQSAPHGVVFLHVTYVPAQEKNFTTAPAICHDG

KAHFPREGVFVSNGTHWFVTQRNFYEPQIITTDNTFVSGN

CDVVIGIVNNTVYDPLQPELDSFKEELDKYFKNHTSPDVD

LGDISGINASVVNIQKEIDRLNEVAKNLNESLIDLQELGK

YEQSDNGPQNQRNAPRITFGGPSDSTGSNQNGERSGARSK

QRRPQGLPNNTASWFTALTQHGKEDLKFPRGQGVPINTNS

SPDDQIGYYRRATRRIRGGDGKMKDLSPRWYFYYLGTGPE

AGLPYGANKDGIIWVATEGALNTPKDHIGTRNPANNAAIV

LQLPQGTTLPKGFYAEGSRGGSQASSRSSSRSRNSSRNST

PGSSRGTSPARMAGNGGDAALALLLLDRLNQLESKMSGKG

QQQQGQTVTKKSAAEASKKPRQKRTATKAYNVTQAFGRRG

PEQTQGNFGDQELIRQGTDYKHWPQIAQFAPSASAFFGMS

RIGMEVTPSGTWLTYTGAIKLDDKDPNFKDQVILLNKHID

AYKTFPPTEPKKDKKKKADETQALPQRQKKQQTVTLLPAA

DLDDFSKQLQQSMSSADSTQAADSNGTITVEELKKLLEQW

NLVIGFLFLTWICLLQFAYANRNRFLYIIKLIFLWLLWPV

TLACFVLAAVYRINWITGGIAIAMACLVGLMWLSYFIASF

RLFARTRSMWSFNPETNILLNVPLHGTILTRPLLESELVI

GAVILRGHLRIAGHHLGRCDIKDLPKEITVATSRTLSYYK

LGASQRVAGDSGFAAYSRYRIGNYKLNTDHSSSSDNIALL

VQ

Chimera 2: SdRBD-N-M_dTM (SEQ ID NO: 25)

MCVNLTTRTQLPPAYTNSFTRGVYYPDKVFRSSVLHSTQD
LFLPFFSNVTWFHAIHVSGTNGTKRFDNPVLPFNDGVYFA
STEKSNIIRGWIFGTTLDSKTQSLLIVNNATNVVIKVCEF
QFCNDPFLGVYYHKNNKSWMESEFRVYSSANNCTFEYVSQ
PFLMDLEGKQGNFKNLREFVFKNIDGYFKIYSKHTPINLV
RDLPQGFSALEPLVDLPIGINITRFQTLLALHRSYLTPGD
SSSGWTAGAAAYYVGYLQPRTFLLKYNENGTITDAVDCAL
DPLSETKCTLKSFTVEKGIYQTSNFRVQPTESIVRFATVC
GPKKSTNLVKNKCVNFNFNGLTGTGVLTESNKKFLPFQQF
GRDIADTTDAVRDPQTLEILDITPCSFGGVSVITPGTNTS
NQVAVLYQDVNCTEVPVAIHADQLTPTWRVYSTGSNVFQT
RAGCLIGAEHVNNSYECDIPIGAGICASYQTQTNSPSRAG
SVASQSIIAYTMSLGAENSVAYSNNSIAIPTNFTISVTTE
ILPVSMTKTSVDCTMYICGDSTECSNLLLQYGSFCTQLNR
ALTGIAVEQDKNTQEVFAQVKQIYKTPPIKDFGGFNFSQI
LPDPSKPSKRSFIEDLLFNKVTLADAGFIKQYGDCLGDIA
ARDLICAQKFNGLTVLPPLLTDEMIAQYTSALLAGTITSG
WTFGAGAALQIPFAMQMAYRFNGIGVTQNVLYENQKLIAN
QFNSAIGKIQDSLSSTASALGKLQDVVNQNAQALNTLVKQ
LSSNFGAISSVLNDILSRLDPPEAEVQIDRLITGRLQSLQ
TYVTQQLIRAAEIRASANLAATKMSECVLGQSKRVDFCGK
GYHLMSFPQSAPHGVVFLHVTYVPAQEKNFTTAPAICHDG
KAHFPREGVFVSNGTHWFVTQRNFYEPQIITTDNTFVSGN
CDVVIGIVNNTVYDPLQPELDSFKEELDKYFKNHTSPDVD
LGDISGINASVVNIQKEIDRLNEVAKNLNESLIDLQELGK
YEQSDNGPQNQRNAPRITFGGPSDSTGSNQNGERSGARSK
QRRPQGLPNNTASWFTALTQHGKEDLKFPRGQGVPINTNS
SPDDQIGYYRRATRRIRGGDGKMKDLSPRWYFYYLGTGPE
AGLPYGANKDGIIWVATEGALNTPKDHIGTRNPANNAAIV
LQLPQGTTLPKGFYAEGSRGGSQASSRSSSRSRNSSRNST
PGSSRGTSPARMAGNGGDAALALLLLDRLNQLESKMSGKG
QQQQGQTVTKKSAAEASKKPRQKRTATKAYNVTQAFGRRG
PEQTQGNFGDQELIRQGTDYKHWPQIAQFAPSASAFFGMS
RIGMEVTPSGTWLTYTGAIKLDDKDPNFKDQVILLNKHID
AYKTFPPTEPKKDKKKKADETQALPQRQKKQQTVTLLPAA
DLDDFSKQLQQSMSSADSTQAADSNGTITVEELKKLLEQN
RNRFLYIIKLTLACFVLAAVNWITGGLMWLSYFIARTRSM
WSFNPETNILLNVPLHGTILTRPLLESELVIGAVILRGHL

-continued

RIAGHHLGRCDIKDLPKEITVATSRTLSYYKLGASQRVAG

DSGFAAYSRYRIGNYKLNTDHSSSSDNIALLVQ

Chimera 3: NSP3-4-6

(SEQ ID NO: 26)

MTNSRIKASMPTTIAKNTVKSVGKFCLEASFNYLKSPNFS
KLINIIIWFLLLSVCLGSLIYSTAALGVLMSNLGMPSYCT
GYREGYLNSTNVTIATYCTGSIPCSVCLSGLDSLDTYPSL
ETIQITISSFKWDLTAFGLVAEWFLAYILFTRFFYVLGLA
AIMQLFFSYFAVHFISNSWLMWLIINLVQMAPISAMVRMY
IFFASFYYVWKSYVHVVDGCNSSTCMMCYKRNRATRVECT
TIVNGVRRSFYVYANGGKGFCKLHNWNCVNCDTFCAGSTF
ISDEVARDLSLQFKRPINPTDQSSYIVDSVTVKNGSIHLY
FDKAGQKTYERHSLSHFVNLDNLRANNTKGSLPINVIVFD
GKSKCEESSAKSASVYYSQLMCQPILLLDQALVSDVGDSA
EVAVKMFDAYVNTFSSTFNVPMEKLKTLVATAEAELAKNV
SLDNVLSTFISAARQGFVDSDVETKDVVECLKLSHQSDIE
VTGDSCNNYMLTYNKVENMTPRDLGACIDCSARHINAQVA
KSHNIALIWNVKDFMSLSEQLRKQIRSAAKKNNLPFKLTC
ATTRQVVNVVTTKIALKGGKIVNNWLKQLIKVTLVFLFVA
AIFYLITPVHVMSKHTDFSSEIIGYKAIDGGVTRDIASTD
TCFANKHADFDTWFSQRGGSYTNDKACPLIAAVITREVGF
VVPGLPGTILRTTNGDFLHFLPRVFSAVGNICYTPSKLIE
YTDFATSACVLAAECTIFKDASGKPVPYCYDTNVLEGSVA
YESLRPDTRYVLMDGSIIQFPNTYLEGSVRVVTTFDSEYC
RHGTCERSEAGVCVSTSGRWVLNNDYYRSLPGVFCGVDAV
NLLTNMFTPLIQPIGALDISASIVAGGIVAIVVTCLAYYF
MRFRRAFGEYSHVVAFNTLLFLMSFTVLCLTPVYSFLPGV
YSVIYLYLTFYLTNDVSFLAHIQWMVMFTPLVPFWITIAY
IICISTKHFYWFFSNYLKRRVVFNGVSFSTFEEAALCTFL
LNKEMYLKLRSDVLLPLTQYNRYLALYNKYKYFSGAMDTT
SYREAACCHLAKALNDFSNSGSDVLYQPPQTSITSAVLQS
AVKRTIKGTHHWLLLTILTSLLVLVQSTQWSLFFFLYENA
FLPFAMGIIAMSAFAMMFVKHKHAFLCLFLLPSLATVAYF
NMVYMPASWVMRIMTWLDMVDTSLSGFKLKDCVMYASAVV
LLILMTARTVYDDGARRVWTLMNVLTLVYKVYYGNALDQA
ISMWALIISVTSNYSGVVTTVMFLARGIVFMCVEYCPIFF
ITGNTLQCIMLVYCFLGYFCTCYFGLFCLLNRYFRLTLGV
YDYLVSTQEFRYMNSQGLLPPKNSIDAFKLNIKLLGVGGK
PCIKVATVQ

Chimera 4: NSP3-4-6_dTM (SEQ ID NO: 27)

```
MTNSRIKASMPTTIAKNTVKSVGKFCLEASFNYLKSPNFS

KLINLMSNLGMPSYCTGYREGYLNSTNVTIATYCTGSIPC

SVCLSGLDSLDTYPSLETIQITISSFKWDLTAFGLVAEWS

YFAVHFISNSWLMWLIINLKSYVHVVDGCNSSTCMMCYKR

NRATRVECTTIVNGVRRSFYVYANGGKGFCKLHNWNCVNC

DTFCAGSTFISDEVARDLSLQFKRPINPTDQSSYIVDSVT

VKNGSIHLYFDKAGQKTYERHSLSHFVNLDNLRANNTKGS

LPINVIVFDGKSKCEESSAKSASVYYSQLMCQPILLLDQA

LVSDVGDSAEVAVKMFDAYVNTFSSTFNVPMEKLKTLVAT

AEAELAKNVSLDNVLSTFISAARQGFVDSDVETKDVVECL

KLSHQSDIEVTGDSCNNYMLTYNKVENMTPRDLGACIDCS

ARHINAQVAKSHNIALIWNVKDFMSLSEQLRKQIRSAAKK

NNLPFKLTCATTRQVVNVVTTKIALKGGKIVNNWSKHTDF

SSEIIGYKAIDGGVTRDIASTDTCFANKHADFDTWFSQRG

GSYTNDKACPLIAAVITREVGFVVPGLPGTILRTTNGDFL

HFLPRVFSAVGNICYTPSKLIEYTDFATSACVLAAECTIF

KDASGKPVPYCYDTNVLEGSVAYESLRPDTRYVLMDGSII

QFPNTYLEGSVRVVTTFDSEYCRHGTCERSEAGVCVSTSG

RWVLNNDYYRSLPGVFCGVPLIQPIGALDRFRRAFGEYSH

SFLPGHIQWMVMFTPLWFFSNYLKRRVNKEMYLKLRSDVL

LPLTQYNRYLALYNKYKYFSGAMDTTSYREAACCHLAKAL

NDFSNSGSDVLYQPPQTSITSAVLQSAVKRTIKGTHLYEN

AKHKHAFSWVMRIMTWLDMVDTSLSGFKLKDCDDGARRVW

TLMNVLTLVALDQAISMWALIISVRGIVFMCVEYCCTCYF

GLFCLLNRYFRLTLGVYDYLVSTQEFRYMNSQGLLPPKNS

IDAFKLNIKLLGVGGKPCIKVATVQ
```

Figure 4A:
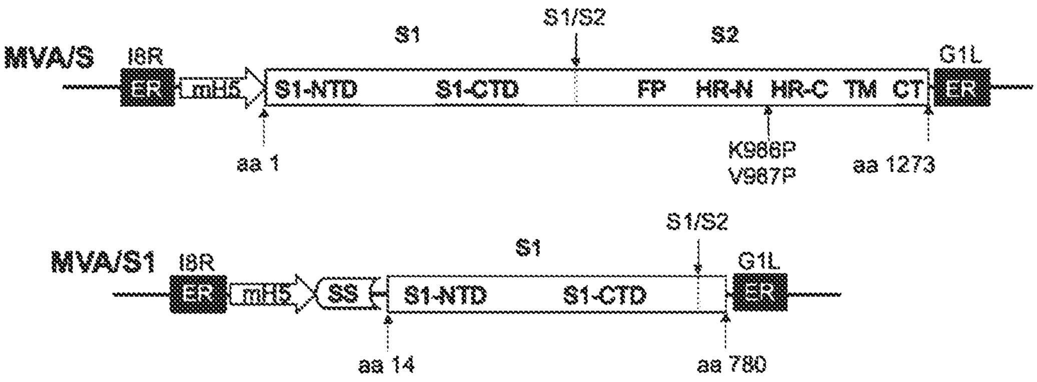
FIG. 4A illustrates two MVA recombinants one expressing full length Spike with stabilizing mutations and the other expressing only the S1 region of Spike. Both constructs expressed the proteins at the correlated size. MVA/S and MVA/S1, spike protein inserts of SARS-CoV-2 were cloned in between essential regions in plasmid pLW72 (18R and G1L), under mH5 promoter.
Figure 4B:
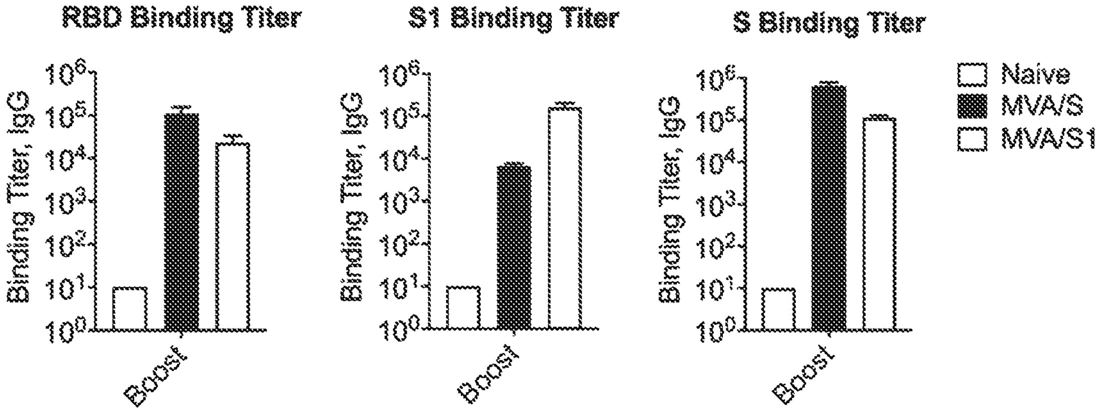
FIG. 4B shows data when mice were immunized with two doses of the vaccines described in FIG. 4A. Both vaccines induced comparable binding antibody responses to RBD and S proteins. The MVA/S1 mice induced a stronger binding antibody response to S1 protein. Antibody responses were induced by MVA/S or MVA/S1 vaccinated Balb/c mice. BALB/c mice were immunized on week 0 and 3 with recombinant MVA expressing either S (MVA/S) (n=5) or S1 (MVA/S1) (n=5) in a prime-boost strategy through intramuscular (i.m.) route. Unvaccinated (naïve) animals served as controls (n=5). Endpoint IgG titers against SARS-CoV-2 RBD, S1 and S measured at week 2 after immunization. Titers are presented as the reciprocal of the serum dilution and plotted as log 10.

Modified Vaccinia Ankara Based SARS-CoV-2 Vaccine Expressing Full Spike but not S1 Induces Strong Neutralizing Antibody Response Modified vaccinia Ankara (MVA) based vaccines were developed one expressing the full-length spike protein (MVA/S) that is designed to be stabilized in prefusion state and anchored on the membrane of MVA infected cells, and the other expressing the S1 region of the spike (MVA/S1) that forms trimers and is secreted (FIG. 4A). Both immunogens contained the receptor binding domain (RBD) that is the primary target for neutralization. Following immunization of mice, both recombinants induced strong binding antibody to S protein but differed in their specificity. The MVA/S induced strong antibody to RBD, S1 and S2, whereas the MVA/S1 induced strong antibody to S1 but regions other than RBD. Both vaccines induced antibody response in the lung and that was associated with induction of bronchus-associated lymphoid tissue. Sera from MVA/S mice but not MVA/S1 mice showed a strong neutralizing activity against SARS-CoV-2 virus that correlated with RBD binding titer. Binding to ACE-2 revealed that S1 presents RBD in the proper confirmation but this interaction is less stable at room temperature with time. These results demonstrate MVA/S is a potential vaccine candidate against SARS-CoV-2 infection.

Modified vaccinia Ankara (MVA) is a highly attenuated strain of vaccinia virus. There are several advantages to MVA based vaccines. MVA can accommodate large inserts (>10 kb) that will allow expression of multiple antigens in a single vector. MVA recombinants are quite stable and can be produced at high titer that makes vaccine manufacture feasible. MVA vaccines also induce strong CD4 and CD8 T cell responses that will be important for protection against viral infections. MVA vaccination can provide protection against multiple virus infections including SARS-CoV, MERS, Zika and Ebola viruses.

MVA recombinants, one expressing the full-length spike protein (MVA/S) that is anchored on the membrane of MVA infected cells and the other expressing the S1 portion of the spike (MVA/S1) that is secreted were developed. Both constructs contained the RBD that is the prime target for neutralizing antibody response. The MVA/S also incorporated two mutations that have been shown to keep spike in a prefusion confirmation. These two recombinants were tested in mice for their ability to generate neutralizing antibody response.

MVA vaccines expressing either the full length prefusion stabilized spike or secreted S1 demonstrated that while both immunogens induce strong binding antibody response to spike only the former induces a strong neutralizing antibody response against the SARS-CoV-2. The failure of MVA/S1 immunogen to induce neutralizing activity was associated with its failure to induce antibody to RBD. This was surprising given the fact that RBD is part of S1. Binding to ACE-2 revealed that S1 presents RBD in the proper confirmation at cold temperature however the stability of RBD confirmation seems to change markedly at the room temperature. This instability of S1 protein seems to contribute to induction of strong binding antibody to other regions in S1 other than RBD following immunization. Systemic MVA vaccination also induced T cell and antibody responses in the lung that will be critical for protection against respiratory infections such as SARS-CoV-2. A dose of about $10^8$ pfu (between $10^7$ and $10^9$) is contemplated for human vaccination. Collectively these results demonstrate that MVA/S is a promising vaccine for SARS-CoV-2.

Recombinant MVA Vaccines

The full-length spike protein sequences of the SARS-CoV-2 strain was obtained from GenBank (Accession number QHD43416.1) and generated various forms of antigens for the improved immunization responses in our vaccination studies. These antigens were expressed using Modified Vaccinia Ankara (MVA) vectors. SARS-CoV-2 full-length spike (S) (aa 1 to 1273) has site-specific mutations introduced at K986P, and V987P for better stabilization and whereas, S1-mono, aa 14 to 780 of spike protein were fused at N-terminus with 16 aa long granulocyte-macrophage colony-stimulating factor (GM-CSF) signal sequences for better secretions. Inserts of rMVA were subcloned in between XmaI and BamHI restriction sites of the pLW-73 transfer vectors, to transfer the inserts into deletion III site. These inserts express under the control of an independent early/late vaccinia virus promoter (modified H5 [mH5]).

For MVA/S, the 3821-nt ORF (GenBank accession #MN996527.1_30-Dec-2019 China: Wuhan) encoding the SARS-nCoV Spike gene was codon optimized for vaccinia virus expression, and cloned into pLW-73 using the XmaI and BamH1 sites under the control of the vaccinia virus modified H5 early late promoter and adjacent to the gene encoding enhanced GFP regulated by the vaccinia virus P11 late promoter. Similarly, to develop MVA/S1, spike secreted monomeric form, GMCSF signal sequence followed with Spike DNA sequence of 14-780 AA was synthesized and cloned between XmaI and BamH1 sites of pLW-73 vector as described above. These plasmid DNAs were subsequently used to generate recombinant MVAs by transfecting transfer plasmids into DF-1 cells that were infected with 0.05 plaque forming units (pfu) of MVA per cell into the essential region of MVA 1974 strain between genes I8R and G1L. Recombinant MVA (rMVA) was isolated using standard methods, but sorting was used during the first round of selection using green fluorescent protein (GFP). Each round GFP plaque picked were characterized for the expression using anti SARS-CoV-2 spike antibody to detect cell surface spike protein expression of MVA/S. For MVA/S1, anti SARS-CoV-2 RBD antibody was used to stain intracellularly. Plaques were picked after 7 rounds to obtain GFP-negative rMVA/S, rMVA/S1 and spike DNA sequences were confirmed. The recombinants were characterized for spike expression by flow cytometry and Western blotting. Viral stocks were purified from lysates of infected DF1 cells using a 36% sucrose cushion and titrated using DF-1 cells by counting pfu/ml. Absence of wildtype MVA was confirmed by PCR using recombinant specific primers of flanking sequences with rMVA/S and rMVA/S1 infected cellular DNA isolated from DF-1 cells. Absence of 542 bp (essential region) band indicates there is no wild type reverted MVAs in the preps.

The MVA Vaccines Express High Levels of Full-Length Stabilized Spike and Trimeric Soluble S1 Proteins To develop the MVA recombinants the full-length spike gene (amino acids 1-1273) was synthesized with stabilizing mutations (K986P, V987P) or just the S1 region with a small portion of S2 region (amino acids 14 to 780). To promote active secretion of the S1, the first 14 amino acids of the spike sequence were replaced with the signal sequence from GM-CSF (FIG. 4A). Both sequences were optimized for MVA codon usage, corrected for poxvirus transcription termination sequences and cloned into pLW73 vector that will allow us to insert the recombinant sequences under mH5 promoter in the essential region of MVA. The recombinants were selected and characterized for protein expression by flow cytometry and Western blotting. The MVA/S expressed high levels of spike on the cell surface and the expressed protein had a molecular moss of about 180 kDa. Similarly, the MVA/S1 expressed at high levels intracellularly, a protein with a molecular moss of about 100 kDA that was also secreted into the supernatants of the MVA infected cells. The spike protein expressed by MVA/S on the surface seemed folded correctly based on strong binding to ACE2. Interestingly, the S1 protein was found to form trimers based on gel filtration profile and native-PAGE analysis.

Both MVA/S and MVA/S1 Vaccines Induce a Strong Binding Antibody Response but with Different Specificities Balb/c mice were immunized with MVA/S or MVA/S1 on weeks 0 and 4, and measured binding antibody responses to total and different parts of spike i.e. RBD, S1, and S (S) using ELISA at 2 weeks post prime and boost. While both vaccines induced a strong binding antibody response to S, they differentially targeted binding to RBD and S1. The MVA/S sera showed strong binding to RBD whereas MVA/S1 sera showed strong binding to S1. This was interesting considering that S1 protein includes complete RBD and suggested that binding activity in MVA/S1 sera may be targeting regions other than RBD in S1. Luminex assay were performed using sera obtained from 3 weeks post boost to measure binding to different parts of S including S2, and to determine the antibody subclass and their ability to bind different soluble FcgRs. These analyses revealed that antibody responses in MVA/S group binding equally to RBD, S1 and S2 whereas in MVA/S1 group the antibody bound primarily to S1 but not to RBD and S2. While the lack of binding to S2 is expected, poor binding to RBD was not expected. Analysis of IgG subclass and FcgR binding of RBD-specific antibody showed strong IgG2a response (Th1 biased) and binding to all three FcRs tested with strongest binding to FcR2 and FcR4 in the MVA/S group. In contrast, poor binding of RBD-specific antibody was observed in general with MVA/S1 sera. However, the S1-specific antibody showed similar results in both groups. These results demonstrated differential targeting of spike specific antibody with Th1 profile induced by MVA/S and MVA/S1 vaccines.

Figure 4C:
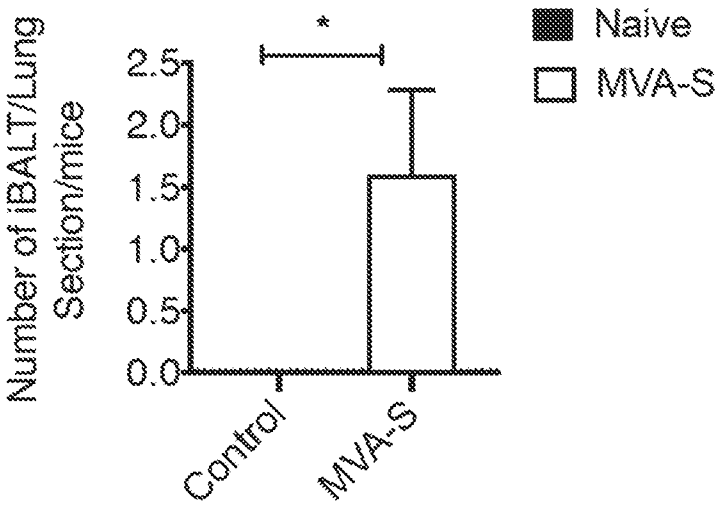
FIG. 4C shows data indicating inducible bronchus associated lymphoid tissues (iBALT) formation upon MVA/S vaccination. Frozen lung sections from vaccinated mice were either stained for H&E to analyze tissue structure and formation of iBALT aggregates, or immunofluorescence stained to visualize B cell and T cell (B) forming B cell follicle like structure (iBALT) induced by MVA/S vaccination given via i.m. route and compared with unvaccinated control mice. Total number of iBALT like structures visualized in each section per mice was quantified and compared between the groups.

MVA Vaccination Induces Strong Bronchus-Associated Lymphoid Tissue and Antibody Responses in the Lung Experiments were performed to determine if vaccination induced immune responses in the lung, a primary site of SARS-CoV-2 virus exposure. The formation of bronchus-associated lymphoid tissue (BALT) was measure using the immunohistochemistry at 3 weeks after the MVA boost by staining for B and T cells. The naïve mice showed very little or no BALT, however, the MVA vaccinated mice showed significant induction of BALT indicating the generation of local lymphoid tissue (FIG. 4C). While we do not know the longevity of persistence of these BALT, they are hoped to help with rapid expansion of immunity in the lung following exposure to SARS-CoV-2 infection. Consistent with BALT, the induction of spike specific IgG and IgA responses in the BAL was observed. These results demonstrate strong induction of antibody responses in the lung following MVA vaccination.

MVA/S but not MVA/S1 Induces Strong Neutralizing Antibody Response

Figure 4D:
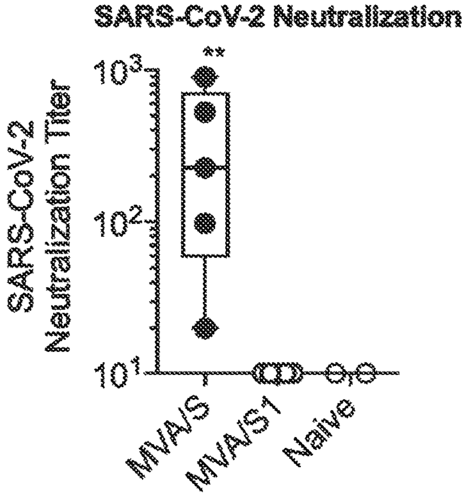
FIG. 4D shows data on neutralizing antibody responses. Six to 8-week-old Balb/c mice were immunized via i.m. twice on week 0 and 3 with different SARS-CoV-2 MVA-based vaccines candidates MVA/S or MVA/S1. Serum was collected two weeks post-boost and performed SARS-CoV-2 virus (expressing GFP-mNG50) neutralization assay in Vero cells in serial dilutions. Serum collected from the naïve animals used as negative controls. The SARS-COV-2 FRNT-mNG50 titers in naïve, MVA/S and MVA/S1 immunized animals were quantified.
Figure 4E:
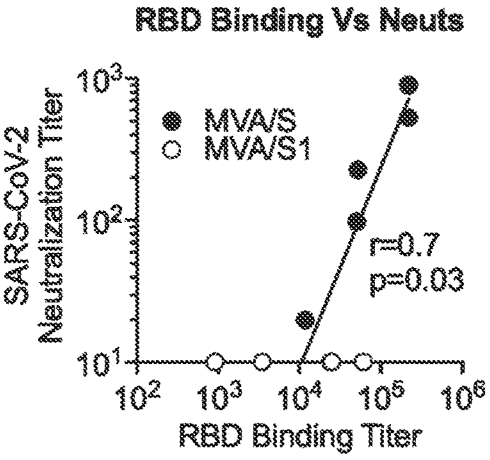
FIG. 4E shows data which compares binding and neutralizing data indicating MVA/S vaccine is highly immunogenic and can induce strong neutralizing antibody responses. Correlations analysis was performed to compare the relation between SARS-CoV-2 proteins (RBD, S1 and S)-binding IgG antibody endpoint titers analyzed by ELISA assay with neutralization titers induced by MVA/S and MVA/S1, respectively. Strong neutralizing antibody response was observed only in mice immunized with MVA/S but not in MVA/S1. This difference was unexpected considering the binding antibodies are comparable or higher in the MVA/S1 group. This data suggests that the MVA/S vaccine has high potential to protect against SARS-CoV-2 infection.
Figure 5A:
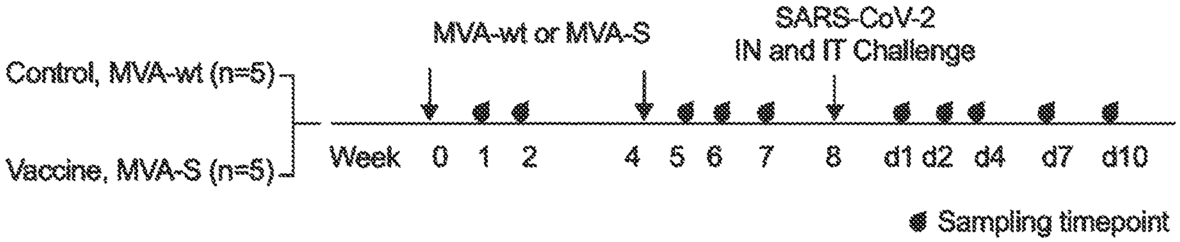
FIG. 5A illustrates experimental timeline for evaluation of immunogenicity and protective efficacy of MVA-SARS-2 Spike (prefusion stabilized).
Figure 5B:
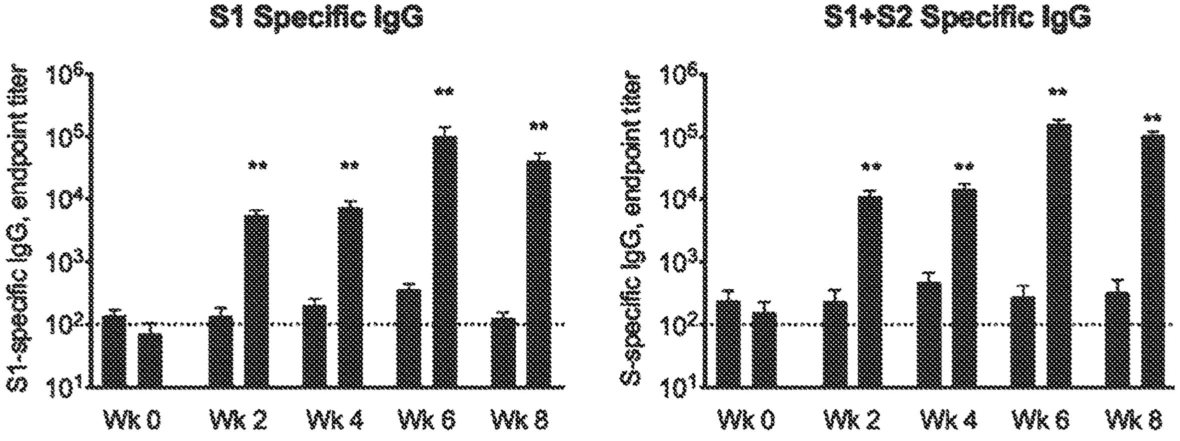
FIG. 5B shows data indicating strong binding antibody response against SARS-2 S1 and S1+S2 in MVA/S vaccinated Rhesus Macaques, performed by ELISA.
Figure 5C:
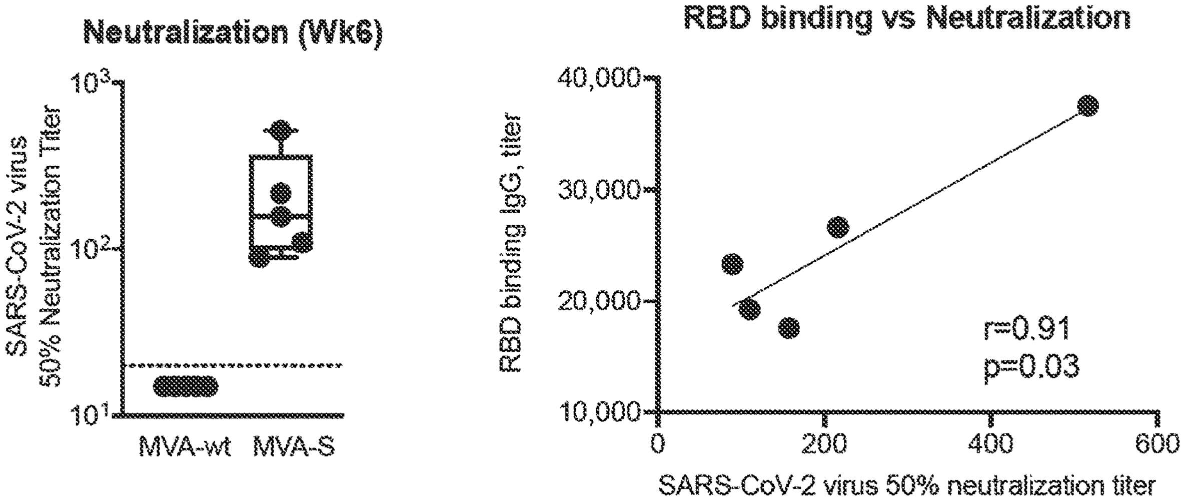
FIG. 5C shows data indicating neutralization and correlation between binding ab response and functional neutralization titer.
Figure 5D:
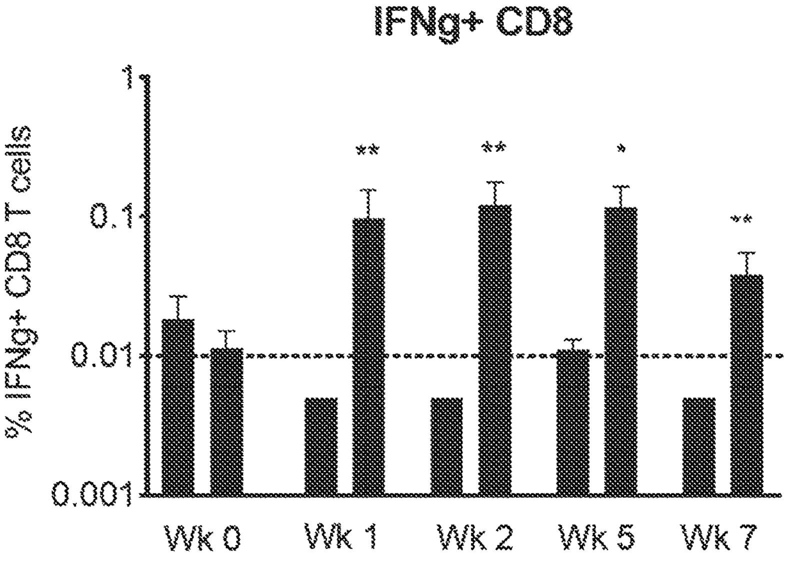
FIG. 5D shows data indicating intracellular cytokine stimulation (ICS), IFNg+ CD8 response against S1 peptide pool of SARS-2 spike.
Figure 5E:
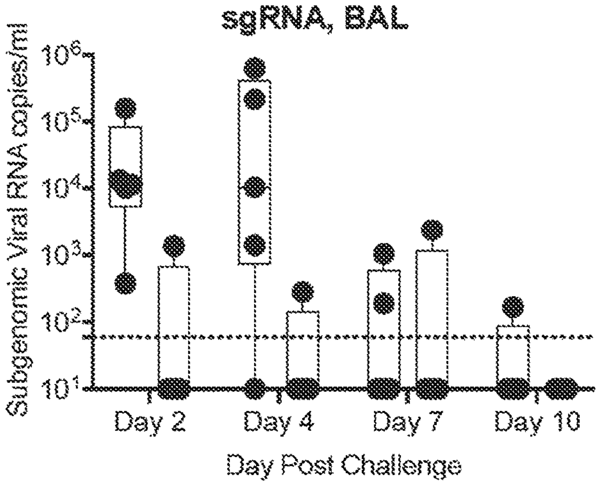
FIG. 5E shows data indicating Efficacy of MVA-S against upper and lower respiratory viral replication, estimated sub genomic viral RNA copies by quantitative real time PCR.

Neutralization against the SARS-CoV-2 virus was tested using the FRNT-GFP assay using sera from 2 weeks post boost. Impressively, a strong neutralizing activity was observed with sera from mice vaccinated with MVA/S that ranged from 20-900 with a median of 200 (FIG. 4D). In contrast, detectable neutralization was not observed in sera from mice immunized with MVA/S1. This was despite the fact that MVA/S1 mice showed comparable or higher binding antibody response to RBD, S1 and S proteins. There was an indication of higher infection at lower dilutions of MVA/S1 sera. The neutralization titer correlated directly with the RBD binding titer (FIG. 4E) whereas correlated inversely with S1 binding titer. These results demonstrated that MVA/S immunogen can induce a strong neutralizing antibody response against SARS-CoV-2 and could serve as a potential vaccine for SARS-CoV-2. Importantly, they also reveal that MVA/S1 is not a good vaccine as it fails to induce antibody with neutralizing activity.

SARS-CoV-2 S1 Exhibits Lower Affinity to ACE2 than RBD, which Further Weakens upon Incubation at 25° C.

To further understand the failure of MVA/S1 vaccine to induce strong RBD binding antibody and neutralizing antibody, we purified the S1 trimer protein expressed by MVA/S1 vaccine and determined its ability to bind to human ACE-2 using biolayer interferometry (BLI). Purified RBD protein was used as a benchmark. SARS-CoV-2 S1 bound to hu-ACE2 quite strongly but at 2-fold lower affinity than RBD (KD=70.1 nM and 36 nM respectively). S1 exhibited 10-fold lower association rate than RBD ($k_{on}$(1/Ms) 1.1E+04 and 1.3E+05 respectively). However, the affinity of S1-ACE2 further decreased by 5-fold when the protein was incubated at 25° C. for 60 min. In contrary, RBD was stable and retained its affinity (KD=24 nM). The data indicated the receptor binding domain of S1 to be unstable, thereby loosing association with ACE2 protein upon prolonged incubation at room temperature, unlike RBD. A 10-fold reduction in the association rate for S1-ACE2 was observed, compared to RBD which was meagerly affected.

RBD-Binding IgG Antibody Titers for Assaying Modified Vaccinia Ankara Based SARS-CoV-2 Vaccine Candidate having a Mutant Furin Cleavage Site (MVA/S-Tri-dFCS) in BALB/c Mice.

A mutation of the furin cleavage site was introduced in order to stabilize the expressed proteins of the MVA vaccines, i.e., sequence encoding RRAR was altered to produce FCS mutation—SRAG. MVA/S-tri and MVA/S-tri-dFCS recombinants were expressed as membrane anchored spike protein variants (MVA/S-tri and MVA/S-tri-dFCS) on the surface which was confirmed by flow cytometry and western blot analysis bind studies of hACE2 to MVA/S-tri and MVA/S-tri-dFCS expressing infected cells.

Figure 6A:
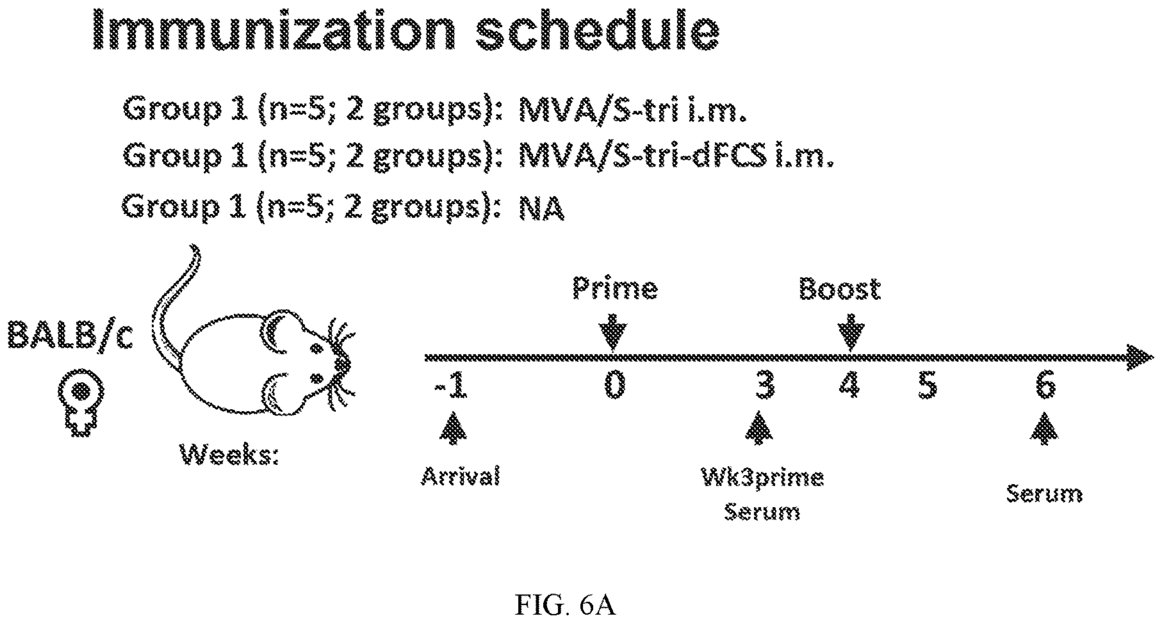
FIG. 6A illustrates an experimental schedule for assaying Modified Vaccinia Ankara Based SARS-CoV-2 Vaccine candidates' (MVA/S-tri and MVA/S-tri-dFCS) in BALB/c mice. Female mice were brought to the experimental room and adapted for 1 week prior to study initiation. Approximately, 6-8-week-old female BALB/c mice intramuscularly (i.m.), immunized on wk0 and wk4 with either MVA/S-tri (107 PFU) or MVA/S-tri-dFCS ($10^7$ PFU). Control group received no treatment served as controls.
Figure 6B:
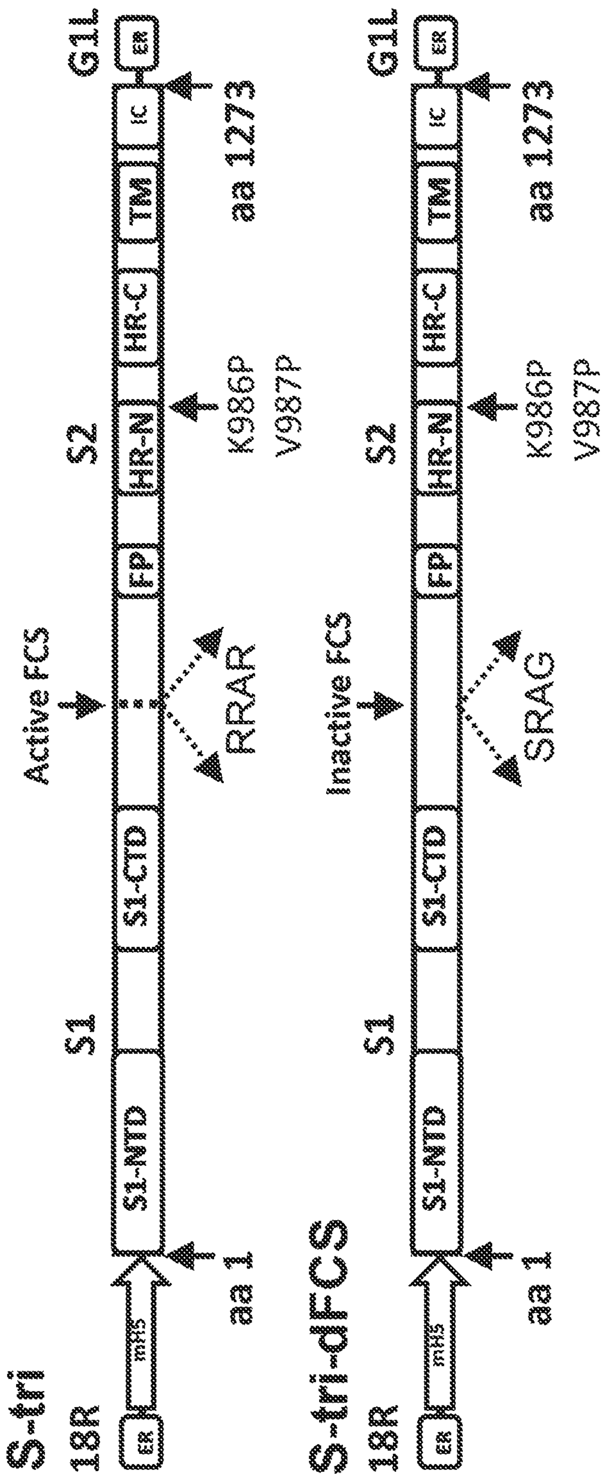
FIG. 6B illustrates of Modified Vaccinia Ankara Based SARS-CoV-2 Vaccine candidates (MVA-S-tri and MVA-S-tri-dFCS). Recombinant inserts were cloned in the essential region in between 18R and G1L under mH5 promoter. Spike protein (S) based vaccines. NTD—N terminal domain; CTD—C terminal domain; FP—Fusion peptide; HR-N—Heptad repeat N; HR-C—Heptad repeat C; TM—Transmembrane anchor; IC—intracellular tail; Active FCS (FCS—Furin cleavage site—RRAR (SEQ ID NO: 21)); Inactive FCS (FCS mutation—SRAG (SEQ ID NO: 22)). Arrows represents amino acid number and protease cleavage sites.
Figure 6C:
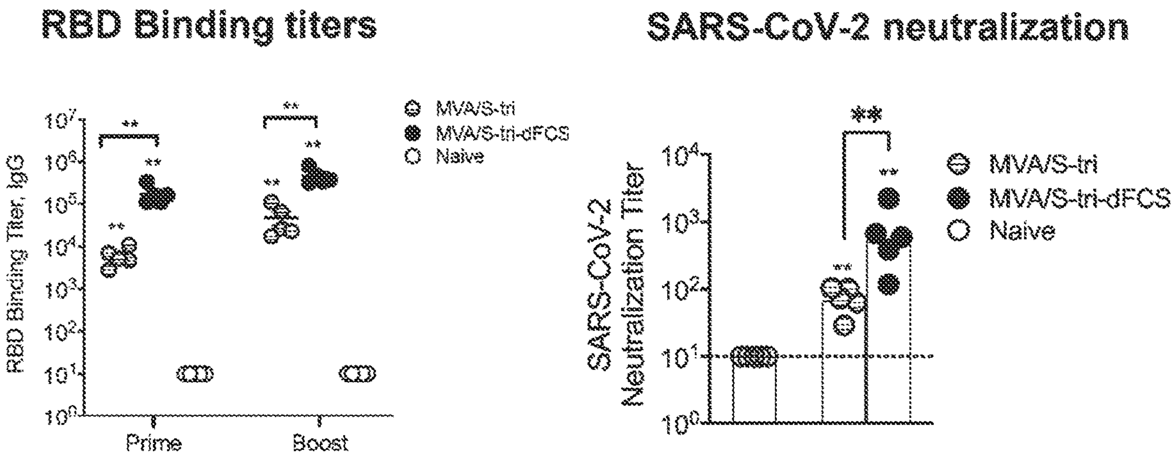
FIG. 6C shows data of experiments. Right shows data on measured RBD binding IgG antibody using ELISA and presented Endpoint IgG titers of serum from 3-weeks post-prime and 2-weeks post-boost immunization. Left shows data on neutralization titer against live mNeonGreen SARS-CoV-2 virus in serum collected at week 2 post-boost immunizations.
Figure 7:
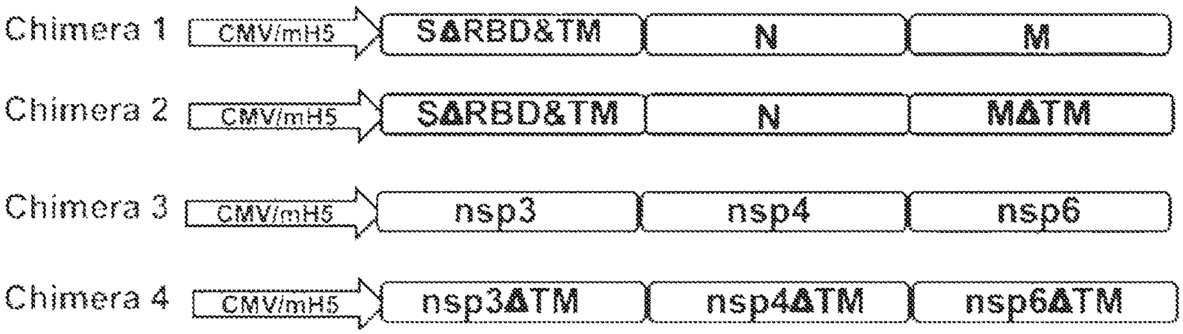
FIG. 7 illustrates chimeric constructs wherein CMV mH5 is is the promoter in DNA, S(delta)RBD is the spike protein of SARS-CoV-2 with the RBD deleted, N is the SARS-CoV-2 Nucleocapsid, M is the SARS-CoV-2 Membrane protein, NSPs are SARS-CoV-2 Non-structural proteins (e.g., nsp3, nsp4, and nsp6). Chimeric antigens with and without transmembrane regions (TM) are used for inducing T cells to DNA and MVA immunogens.
Figure 8:
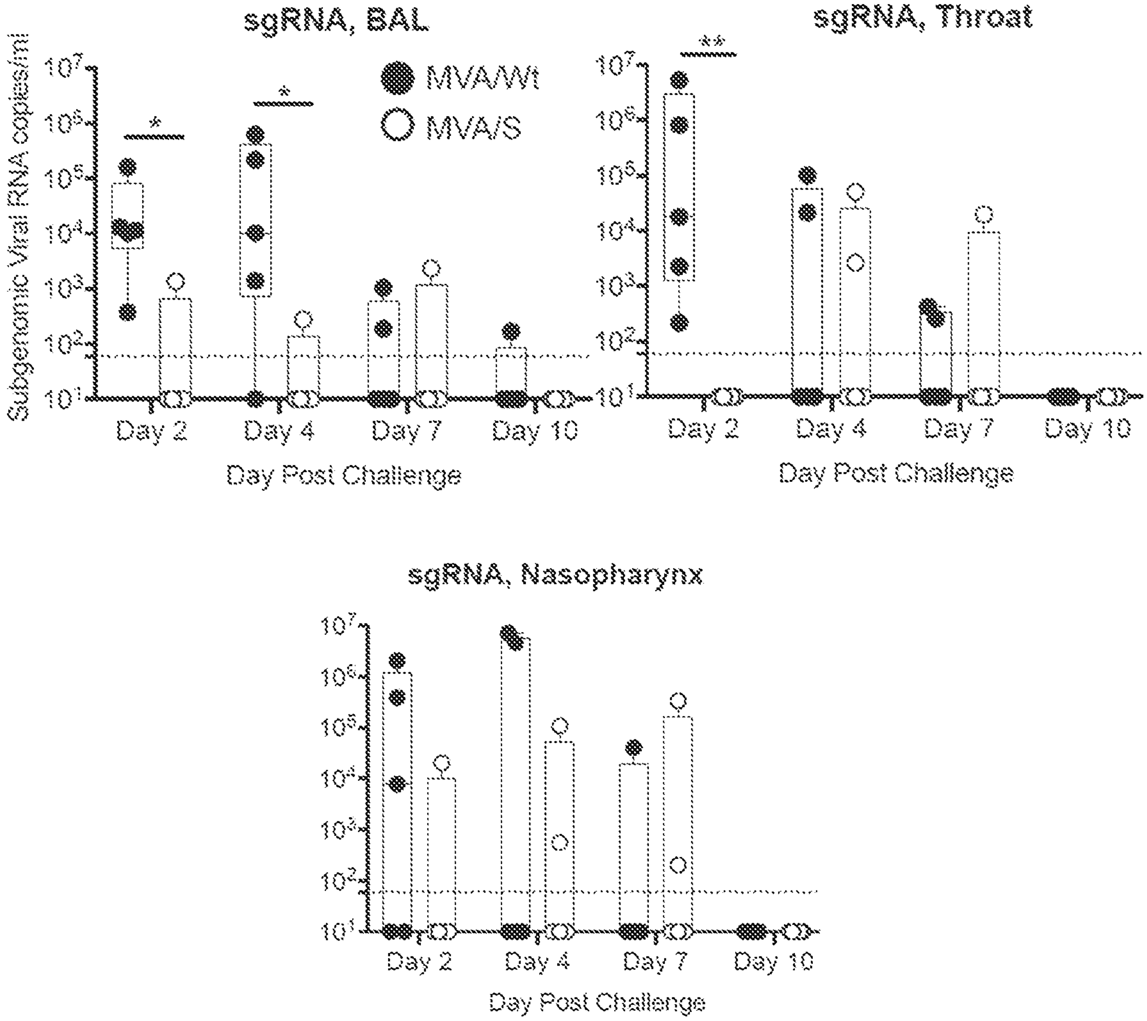
FIG. 8 shows data indicating MVA/S vaccine protects from SARS-CoV-2 infection in rhesus macaques.

Female BALB/c mice were intramuscularly (i.m.) immunized on wk0 and wk4 with either MVA/S-tri (107 PFU) or MVA/S-tri-dFCS (107 PFU) (FIG. 6A-B). Control group received no treatment served as controls. Serum from 3-weeks post-prime and 2-weeks post-boost immunization was used to measure RBD binding IgG antibody using ELISA and presented Endpoint IgG titers. Neutralization titer against live mNeonGreen SARS-CoV-2 virus was performed in serum collected at week 2 post-boost immunizations (FIG. 6C).

Vaccination of Rhesus Macaques

Two MVA based vaccines which express either a membrane anchored full-length spike protein (MVA/S) stabilized in a prefusion state or the soluble secreted trimeric S1 of the spike (MVA/S1). Both immunogens contained the receptor-binding domain (RBD) which is a known target of antibody-mediated neutralization in SARS-CoV-2 infected individuals. The MVA/S also incorporated two mutations that maintain the spike protein in a prefusion confirmation.

MVA/S-Tri-dFCS

| Name | Range | Length (bp) | Description |
|---|---|---|---|
| Flank1 I8R | 1-537 | 537 | Essential gene region on MVA for recombination |
| P11 | 545-573 | 29 | promoter |
| GFP | 574-1293 | 720 | GFP |
| DR | 1294-1528 | 235 | Direct Repeats |
| mH5 | 1553-1619 | 67 | Promoter |
| Spike | 1634-5452 | 3819 | Spike Protein sequence |
| Furin cleavage site change | 3677-3679 | 3 | R682S AGA changed to TCT |
| Furin cleavage site change | 3686-3688 | 3 | R685G AGA changed to GGA |
| Proline mutation 1 | 4589-4591 | 3 | K986P AAA changed to CCA |
| Proline mutation 2 | 4592-4594 | 3 | V987P GTT changed to CCT |
| Flank 2 G1L | 5490-6191 | 702 | Essential gene region on MVA for recombination |
| Ampicillin resistance gene | 7477-8267 | 791 | Confers resistance to Ampicillin |

Vaccination of rhesus macaques followed by SARS-CoV-2 challenge demonstrated MVA/S vaccine induces neutralizing antibodies and CD8 T cells and protects from SARS-CoV-2 infection and replication in the lung.

The MVA recombinants expressing the full-length spike (amino acids 1-1273) carrying the prefusion-stabilized mutations (MVA/S) or only S1 portion of spike (amino acids 14-780)(MVA-S1) were generated and confirmed by standard methods. SARS-CoV-2 (MN996527.1; Wuhan strain) S ORF was codon optimized for vaccinia virus expression, synthesized, and cloned into pLW-73 between the XmaI and BamHI sites under the control of the vaccinia virus modified H5 (mH5) early late promoter and adjacent to the gene encoding enhanced GFP (green fluorescent protein). To promote active secretion of the S1, amino acids 1-14 of the spike sequence were replaced with the signal sequence from GMCSF, SEQ ID NO: 31 (WLQGLLLLGTVACSIS). Plaques were picked for 7 rounds to obtain GFP-negative recombinants and DNA sequenced to confirm lack of any mutations. Viral stocks were purified from lysates of infected DF-1 cells using a 36% sucrose cushion and titrated using DF-1 cells by counting pfu/ml. Absence of the wild-type MVA was confirmed by PCR using recombinant specific primers, flanking the inserts.

Ten adult male rhesus macaques (Macaca mulatta), 4-5 years old, were randomly allocated into two groups; one group (n=5) received MVA empty vector (MVA-wt) and the second group (n=5) received MVA-expressing prefusion stabilized (with proline mutations) SARS-CoV-2 full-length spike protein (MVA-S). Animals received $1\times10^8$ pfu in 1 ml vaccines at week 0 and week 4 by the intramuscular (IM) route.

In addition to the neutralizing activity, the vaccine induced sera showed strong antibody dependent complement deposition (ADCD) activity and low antibody-dependent cellular phagocytosis (ADCP) and antibody-dependent neutrophil phagocytosis (ADNP) activities. The MVA/S vaccine also generated a strong spike-specific IFNγ+CD8 T cell response that was evident as early as one week post priming immunization. The frequency of CD8 T cell response was not further boosted following the 2nd MVA/S immunization. The vaccine-induced CD8 T cells were also positive for TNFα and IL-2 and negative for IL-17. The MVA/S vaccine induced very low frequencies of IFNγ+CD4 T cells. These data demonstrated that MVA/S vaccinations induced a poly-functional CD8 T cell response capable of producing IFNγ, IL-2 and TNFα in macaques.

Following vaccination, all macaques were challenged with SARS-CoV-2 at week 8 by intratracheal (IT) and intranasal (IN) route. MVA/S vaccinated animals rapidly controlled SARS-CoV-2 replication in the lung at Day 2 ($p<0.05$) and Day 4 ($p<0.05$) compared to controls with 4 of the 5 vaccinated animals being negative in BAL. However, in the throat, all vaccinated animals tested negative at Day 2 ($p<0.01$) but low titer of virus replication was evident in one or two vaccinated animals on Days 4 and 7. Similarly, in nasopharynx one or two animals showed virus replication on Days 2, 4 and 7 and the virus replication was not significantly different between controls and vaccinated animals at all time points. By Day 10 all control and vaccinated animals were negative in all compartments. These results demonstrated that MVA/S vaccination provides protection from SARS-CoV2 infection or replication in the lower respiratory tract. Virus replication, lung pathology, binding and neutralizing antibody titer and T cell responses were measured. Data indicates MVA/S vaccine protects from SARS-CoV-2 infection and replication and reduces lung pathology in rhesus macaques.

In order to define protection offered by MVA vaccine expressing Spike and nucleocapsid (NC) against SARS-CoV-2 South African variant (B.1.351) one can immunize rhesus macaques with a double recombinant MVA/S-tri-dFCS-NC on weeks 0 and 4, and challenge with B.1.351. One can assess the protective immune responses generated by the vaccine by measuring antibody and T cell responses in blood and mucosal secretions following vaccination. Animals can be challenged with SARS-CoV-2 virus intranasally and intratracheally to determine vaccine protection. One can collect blood, bone marrow, LN biopsies, BAL, rectal biopsies, rectal swabs, nasal and salivary/oral swabs at multiple times during vaccination and challenge.

Evaluation of MVA Based Vaccination Induced Neutralizing Antibody Responses Against SARS-CoV-2 Variants of Concern in Macaques and Mouse Models.

Vaccines were injected via intramuscular (IM) route at weeks 0 and 4. Serum collected at week 6 (peak) were used to assess neutralizing antibody titers against live Washington SARS-CoV-2, and variants of concern—UK variants, 501Y.V1, VOC 202012/01 (B.1.1.7) and South African variants (B.1.351), and Fold-Change in neutralization titers between WA virus to the variants of concern are presented. Each sample was analyzed in duplicates and repeated twice and repeated twice and GMT values for each vaccination groups were presented in table.

| Vaccine Type | SARS-CoV-2 Wuhan Wild-type strain | UK variants, 501Y.V1, VOC 202012/01 (B.1.1.7) | South African variants (B.1.351) | WA/UK Fold-Change | WA/RSA Fold-Change |
|---|---|---|---|---|---|
| MVA/Stri (macaque) | 63.8 | 51.3 | 18.0 | 1.2 | 3.6 |
| MVA-Stri-dFCS (mouse) | 489.1 | NT | 134.0 | NT | 3.7 |

MVA/S study, n=5 rhesus macaques were immunized with 10ˆ8 pfu/macaques MVA/S-tri vaccine. MVA/S-tri-dFCS study, n=5 BALB/c mice were immunized with 10ˆ7 pfu/mice MVA/S-tri-dFCS vaccine. NT, not tested Heterologous Vector (DNA/MVA)-Based Vaccine Induce Greater Magnitude of CD8 T Cells Compared to MVA-Only Vaccination in Mice.

BALB/c mice were primed with DNA (50 ug/mice) and boosted with 10ˆ7 pfu/mice with spike expressing vaccine. All the vaccines were injected via intramuscular (IM) route at weeks 0 and 4. Blood collected at week 5 (peak) was used to assess % spike-specific tetramer positive CD8 T cells analyzed using flow cytometry.

| Vaccine Type (Prime/Boost) | S (539-541)-specific tetramer positive CD8 T cells (%) |
|---|---|
| DNA-SdFCS/MVA-SdFCS | 21 |
| MVA-SdFCS/MVA-SdFCS | 3 |

The invention claimed is:

1. A protein comprising the amino acid of SEQ ID NO: 1.

2. The protein of claim 1 further comprising a heterologous N-terminal signal sequence.

3. The protein of claim 1 comprising the amino acid sequence of SEQ ID NO: 2.

4. The protein of claim 1 comprising a coronavirus M protein sequence downstream from the C-terminal end of the protein sequence, and wherein the M protein sequence and SEQ ID NO: 1 are separated by a self-cleaving sequence.

5. The protein of claim 4 comprising a coronavirus E protein sequence downstream from the C-terminal end of the M protein sequence, and wherein the coronavirus E protein sequence and the coronavirus M protein sequence are separated by a self-cleaving sequence.

6. The protein of claim 1 comprising amino acid sequence SEQ ID NO: 3 (SEQ ID NO: 3).

7. A virus-like particle comprising a protein of claim 1.

8. A nucleic acid comprising a sequence encoding a protein of claim 1 in operable combination with a heterologous promotor.

9. The nucleic acid of claim 8 wherein the sequence encoding a protein comprises (SEQ ID NO: 4).

10. A vector comprising a nucleic acid of claim 8.

11. The vector of claim 10 further comprising a vaccinia virus Ankara gene.

* * * * *

SEQUENCE LISTING

```
<160> NUMBER OF SEQ ID NOS: 35

<210> SEQ ID NO 1
<211> LENGTH: 987
<212> TYPE: PRT
<213> ORGANISM: Artificial
<220> FEATURE:
<223> OTHER INFORMATION: Synthetic construct

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110
```

```
Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525
```

-continued

```
Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
```

945 950 955 960

Thr Leu Val Lys Gln Leu Ser Ser Asn Phe Gly Ala Ile Ser Ser Val
965 970 975

Leu Asn Asp Ile Leu Ser Arg Leu Asp Pro Pro
980 985

<210> SEQ ID NO 2
<211> LENGTH: 1273
<212> TYPE: PRT
<213> ORGANISM: Artificial
<220> FEATURE:
<223> OTHER INFORMATION: Synthetic construct

<400> SEQUENCE: 2

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys

-continued

```
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750
```

```
Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155
```

His Thr Ser Pro Asp Val Asp Leu Gly Asp Ile Ser Gly Ile Asn
1160 1165 1170

Ala Ser Val Val Asn Ile Gln Lys Glu Ile Asp Arg Leu Asn Glu
1175 1180 1185

Val Ala Lys Asn Leu Asn Glu Ser Leu Ile Asp Leu Gln Glu Leu
1190 1195 1200

Gly Lys Tyr Glu Gln Tyr Ile Lys Trp Pro Trp Tyr Ile Trp Leu
1205 1210 1215

Gly Phe Ile Ala Gly Leu Ile Ala Ile Val Met Val Thr Ile Met
1220 1225 1230

Leu Cys Cys Met Thr Ser Cys Cys Ser Cys Leu Lys Gly Cys Cys
1235 1240 1245

Ser Cys Gly Ser Cys Cys Lys Phe Asp Glu Asp Asp Ser Glu Pro
1250 1255 1260

Val Leu Lys Gly Val Lys Leu His Tyr Thr
1265 1270

<210> SEQ ID NO 3
<211> LENGTH: 1614
<212> TYPE: PRT
<213> ORGANISM: Artificial
<220> FEATURE:
<223> OTHER INFORMATION: Synthetic construct

<400> SEQUENCE: 3

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

```
Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
```

```
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080
```

```
Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr Gly Ser  Gly Ala Thr
    1265                 1270                 1275

Asn Phe  Ser Leu Leu Lys Gln  Ala Gly Asp Val Glu  Glu Asn Pro
    1280                 1285                 1290

Gly Pro  Met Ala Asp Ser Asn  Gly Thr Ile Thr Val  Glu Glu Leu
    1295                 1300                 1305

Lys Lys  Leu Leu Glu Gln Trp  Asn Leu Val Ile Gly  Phe Leu Phe
    1310                 1315                 1320

Leu Thr  Trp Ile Cys Leu Leu  Gln Phe Ala Tyr Ala  Asn Arg Asn
    1325                 1330                 1335

Arg Phe  Leu Tyr Ile Ile Lys  Leu Ile Phe Leu Trp  Leu Leu Trp
    1340                 1345                 1350

Pro Val  Thr Leu Ala Cys Phe  Val Leu Ala Ala Val  Tyr Arg Ile
    1355                 1360                 1365

Asn Trp  Ile Thr Gly Gly Ile  Ala Ile Ala Met Ala  Cys Leu Val
    1370                 1375                 1380

Gly Leu  Met Trp Leu Ser Tyr  Phe Ile Ala Ser Phe  Arg Leu Phe
    1385                 1390                 1395

Ala Arg  Thr Arg Ser Met Trp  Ser Phe Asn Pro Glu  Thr Asn Ile
    1400                 1405                 1410

Leu Leu  Asn Val Pro Leu His  Gly Thr Ile Leu Thr  Arg Pro Leu
    1415                 1420                 1425

Leu Glu  Ser Glu Leu Val Ile  Gly Ala Val Ile Leu  Arg Gly His
    1430                 1435                 1440

Leu Arg  Ile Ala Gly His His  Leu Gly Arg Cys Asp  Ile Lys Asp
    1445                 1450                 1455

Leu Pro  Lys Glu Ile Thr Val  Ala Thr Ser Arg Thr  Leu Ser Tyr
    1460                 1465                 1470
```

```
Tyr Lys  Leu Gly Ala Ser Gln  Arg Val Ala Gly Asp  Ser Gly Phe
    1475                 1480                 1485

Ala Ala  Tyr Ser Arg Tyr Arg  Ile Gly Asn Tyr Lys  Leu Asn Thr
    1490                 1495                 1500

Asp His  Ser Ser Ser Ser Asp  Asn Ile Ala Leu Leu  Val Gln Gly
    1505                 1510                 1515

Ser Gly  Ala Thr Asn Phe Ser  Leu Leu Lys Gln Ala  Gly Asp Val
    1520                 1525                 1530

Glu Glu  Asn Pro Gly Pro Met  Tyr Ser Phe Val Ser  Glu Glu Thr
    1535                 1540                 1545

Gly Thr  Leu Ile Val Asn Ser  Val Leu Leu Phe Leu  Ala Phe Val
    1550                 1555                 1560

Val Phe  Leu Leu Val Thr Leu  Ala Ile Leu Thr Ala  Leu Arg Leu
    1565                 1570                 1575

Cys Ala  Tyr Cys Cys Asn Ile  Val Asn Val Ser Leu  Val Lys Pro
    1580                 1585                 1590

Ser Phe  Tyr Val Tyr Ser Arg  Val Lys Asn Leu Asn  Ser Ser Arg
    1595                 1600                 1605

Val Pro  Asp Leu Leu Val
    1610
```

<210> SEQ ID NO 4
<211> LENGTH: 2973
<212> TYPE: DNA
<213> ORGANISM: Artificial
<220> FEATURE:
<223> OTHER INFORMATION: Synthetic construct

<400> SEQUENCE: 4

```
atgtggttac aaggactact attactaggt actgttgcct gttcaatttc acaatgtgta     60

aatctaacta caagaactca attaccgcct gcctatacta attcttttac aagaggagta    120

tattatcctg ataaagtttt tagatcttct gtattacatt ctacacaaga tttgttttta    180

ccatttttct ctaatgttac ttggtttcat gcaatacatg tatctggaac taatggaaca    240

aaaagatttg ataatccagt attacctttt aatgatggag tttattttgc ttctactgaa    300

aaatctaata taattagagg atggatattt ggaactacat tagattctaa aacacaatct    360

ctactaattg ttaataatgc aactaatgta gttataaaag tatgtgaatt tcaattttgt    420

aatgatccat ttttgggagt ttattatcat aaaaataata agtcttggat ggaatctgaa    480

ttcagagtat attcttctgc taataattgt acatttgaat atgtatctca accatttttg    540

atggatttgg aaggaaaaca aggaaacttt aaaaatttga gagaatttgt ttttaaaaat    600

attgatggat actttaaaat ctattctaaa catactccaa ttaatctagt aagagatttg    660

cctcaaggat tttctgcttt agaaccacta gtagatttgc ctataggaat taatattact    720

agatttcaaa cattattagc tttacataga tcttatttga cacctggaga ttcttcttct    780

ggatggactg caggagctgc agcttattat gttggatatt tgcaaccaag aacatttttg    840

ttaaaatata atgaaaatgg aactataaca gatgcagttg attgtgcttt agatcctcta    900

tctgaaacta aatgtacttt aaaatctttt actgtagaaa aaggaatcta tcaaacatct    960

aactttagag tacaaccaac tgaatctatt gttagatttc caaatataac aaatctatgt   1020

ccttttggag aagtttttaa tgcaactaga tttgcttctg tatatgcatg gaatagaaaa   1080

agaatatcta attgcgtagc tgattattct gtattatata attctgcatc tttttctact   1140

tttaaatgtt atggagtatc tccaacaaaa ttgaatgatc tatgttttac taatgtttat   1200
```

gcagattctt ttgtaataag aggagatgaa gttagacaaa tagctcctgg acaaacagga 1260
aaaatagcag attataatta taaattacca gatgatttca ctggatgcgt aattgcttgg 1320
aattctaata atttggattc taaagtagga ggaaattata attatttgta tagattgttt 1380
agaaaatcta atttgaaacc ttttgaaaga gatatttcta cagaaatcta tcaagcagga 1440
tctactccat gtaatggagt tgaaggtttt aattgttatt ttccactaca atcttatgga 1500
tttcaaccta caaatggagt aggatatcaa ccatatagag tagttgtatt atcttttgaa 1560
ttattacatg caccagctac agtatgtgga cctaaaaaat ctactaattt ggttaaaaat 1620
aagtgcgtaa actttaactt taatggatta actggaacag gagttttaac tgaatctaat 1680
aagaaatttt tgccttttca acaatttgga agagatattg ctgatactac agatgcagta 1740
agagatcctc aaactttaga aatattggat attacaccat gttcttttgg aggagtttct 1800
gtaataacac caggaactaa tacatctaat caagttgctg tattatatca agatgttaat 1860
tgtactgaag ttcctgtagc aattcatgct gatcaattaa ctccaacatg gagagtatat 1920
tctactggat ctaatgtttt tcaaacaaga gctggatgtc taattggagc agaacatgta 1980
aataattctt atgaatgtga tattcctata ggagctggaa tatgtgcatc ttatcaaact 2040
caaacaaatt ctccaagaag agctagatct gttgcatctc aatctataat tgcttataca 2100
atgtctttag gagctgaaaa ttctgtagca tattctaata attctattgc aattcctact 2160
aactttacta tttctgtaac tacagaaata ttgccagttt ctatgactaa aacatctgta 2220
gattgtacaa tgtatatatg tggagattct actgaatgtt ctaatttgct actacaatat 2280
ggatcttttt gtactcaatt gaatagagct ttaacaggaa tagcagtaga acaagataaa 2340
aatacacaag aagtttttgc tcaagtaaaa caaatctata aaactccacc tataaaagat 2400
tttggaggtt ttaatttttc tcaaatattg ccagatcctt ctaaaccttc taaaagatct 2460
tttattgaag atttgttgtt taataaggtt acattagcag atgctggttt tataaaacaa 2520
tatggagatt gtttaggaga tattgcagct agagatttga tttgtgctca aaagtttaat 2580
ggattaactg tattaccacc tctactaaca gatgaaatga tagcacaata tacatctgca 2640
ttattagctg gaactattac atctggatgg acttttggag ctggagcagc tttacaaata 2700
ccatttgcta tgcaaatggc atatagattc aatggaattg gagttactca aaatgtatta 2760
tatgaaaatc aaaaactaat tgctaatcaa ttcaattctg caattggaaa aattcaagat 2820
tctctatctt ctacagcatc tgctttagga aaactacaag atgttgtaaa tcaaaatgca 2880
caagctttaa atactctagt taaacaacta tcttctaatt ttggagctat ttcttctgtt 2940
ttaaatgata tattgtctag actagatcca cct 2973

<210> SEQ ID NO 5
<211> LENGTH: 9903
<212> TYPE: DNA
<213> ORGANISM: Artificial
<220> FEATURE:
<223> OTHER INFORMATION: Synthetic construct

<400> SEQUENCE: 5
gaattccctg ggacatacgt atatttctat gatctgtctt atatgaagtc tatacagcga 60
atagattcag aatttctaca taattatata ttgtacgcta ataagtttaa tctaacactc 120
cccgaagatt tgtttataat ccctacaaat ttggatattc tatggcgtac aaaggaatat 180
atagactcgt tcgatattag tacagaaaca tggaataaat tattatccaa ttattatatg 240

```
aagatgatag agtatgctaa actttatgta ctaagtccta ttctcgctga ggagttggat    300
aattttgaga ggacgggaga attaactagt attgtacaag aagccatttt atctctaaat    360
ttacgaatta agattttaaa ttttaaacat aaagatgatg atacgtatat acacttttgt    420
aaaatattat tcggtgtcta taacggaaca aacgctacta tatattatca tagacctcta    480
acgggatata tgaatatgat ttcagatact atatttgttc ctgtagataa taactaaggc    540
gcgcctttca ttttgttttt ttctatgcta taaatggtga gcaagggcga ggagctgttc    600
accggggtgg tgcccatcct ggtcgagctg gacggcgacg taaacggcca caagttcagc    660
gtgtccggcg agggcgaggg cgatgccacc tacggcaagc tgaccctgaa gttcatctgc    720
accaccggca agctgcccgt gccctggccc accctcgtga ccaccctgac ctacggcgtg    780
cagtgcttca gccgctaccc cgaccacatg aagcagcacg acttcttcaa gtccgccatg    840
cccgaaggct acgtccagga gcgcaccatc ttcttcaagg acgacggcaa ctacaagacc    900
cgcgccgagg tgaagttcga gggcgacacc ctggtgaacc gcatcgagct gaagggcatc    960
gacttcaagg aggacggcaa catcctgggg cacaagctgg agtacaacta caacagccac   1020
aacgtctata tcatggccga caagcagaag aacggcatca aggtgaactt caagatccgc   1080
cacaacatcg aggacggcag cgtgcagctc gccgaccact accagcagaa cacccccatc   1140
ggcgacggcc ccgtgctgct gcccgacaac cactacctga gcacccagtc cgccctgagc   1200
aaagacccca acgagaagcg cgatcacatg gtcctgctgg agttcgtgac cgccgccggg   1260
atcactctcg gcatgcacga gctgtacaag taagagctcg aggacgggag aattaactag   1320
tattgtacaa gaagccattt tatctctaaa tttacgaatt aagattttaa attttaaaca   1380
taaagatgat gatacgtata tacacttttg taaaatatta ttcggtgtct ataacggaac   1440
aaacgctact atatattatc atagacctct aacgggatat atgaatatga tttcagatac   1500
tatatttgtt cctgtagata ataactaact cgaggccgct ggtacccaac ctaaaaattg   1560
aaaataaata caaaggttct tgagggttgt gttaaattga aagcgagaaa taatcataaa   1620
taagcccggg accatgtttg tttttctagt tttgctaccg ttggtttcaa gtcaatgtgt   1680
aaatctaact acaagaactc aattaccgcc tgcctatact aattctttta caagaggagt   1740
atattatcct gataaagttt ttagatcttc tgtattacat tctacacaag atttgttttt   1800
accatttttc tctaatgtta cttggtttca tgcaatacat gtatctggaa ctaatggaac   1860
aaaaagattt gataatccag tattaccttt taatgatgga gtttattttg cttctactga   1920
aaaatctaat ataattagag gatggatatt tggaactaca ttagattcta aaacacaatc   1980
tctactaatt gttaataatg caactaatgt agttataaaa gtatgtgaat ttcaattttg   2040
taatgatcca tttttgggag tttattatca taaaaataat aagtcttgga tggaatctga   2100
attcagagta tattcttctg ctaataattg tacatttgaa tatgtatctc aaccattttt   2160
gatggatttg gaaggaaaac aaggaaactt taaaaatttg agagaatttg tttttaaaaa   2220
tattgatgga tactttaaaa tctattctaa acatactcca attaatctag taagagattt   2280
gcctcaagga ttttctgctt tagaaccact agtagatttg cctataggaa ttaatattac   2340
tagatttcaa acattattag ctttacatag atcttatttg acacctggag attcttcttc   2400
tggatggact gcaggagctg cagcttatta tgttggatat ttgcaaccaa gaacattttt   2460
gttaaaatat aatgaaaatg gaactataac agatgcagtt gattgtgctt tagatcctct   2520
atctgaaact aaatgtactt taaaatcttt tactgtagaa aaaggaatct atcaaacatc   2580
taactttaga gtacaaccaa ctgaatctat tgttagattt ccaaatataa caaatctatg   2640
```

```
tccttttgga gaagttttta atgcaactag atttgcttct gtatatgcat ggaatagaaa   2700
aagaatatct aattgcgtag ctgattattc tgtattatat aattctgcat ctttttctac   2760
ttttaaatgt tatggagtat ctccaacaaa attgaatgat ctatgtttta ctaatgttta   2820
tgcagattct tttgtaataa gaggagatga agttagacaa atagctcctg gacaaacagg   2880
aaaaatagca gattataatt ataaattacc agatgatttc actggatgcg taattgcttg   2940
gaattctaat aatttggatt ctaaagtagg aggaaattat aattatttgt atagattgtt   3000
tagaaaatct aatttgaaac cttttgaaag agatatttct acagaaatct atcaagcagg   3060
atctactcca tgtaatggag ttgaaggttt taattgttat tttccactac aatcttatgg   3120
atttcaacct acaaatggag taggatatca accatataga gtagttgtat tatcttttga   3180
attattacat gcaccagcta cagtatgtgg acctaaaaaa tctactaatt tggttaaaaa   3240
taagtgcgta aactttaact ttaatggatt aactggaaca ggagttttaa ctgaatctaa   3300
taagaaattt ttgccttttc aacaatttgg aagagatatt gctgatacta cagatgcagt   3360
aagagatcct caaactttag aaatattgga tattacacca tgttcttttg gaggagtttc   3420
tgtaataaca ccaggaacta atacatctaa tcaagttgct gtattatatc aagatgttaa   3480
ttgtactgaa gttcctgtag caattcatgc tgatcaatta actccaacat ggagagtata   3540
ttctactgga tctaatgttt ttcaaacaag agctggatgt ctaattggag cagaacatgt   3600
aaataattct tatgaatgtg atattcctat aggagctgga atatgtgcat cttatcaaac   3660
tcaaacaaat tctccaagaa gagctagatc tgttgcatct caatctataa ttgcttatac   3720
aatgtcttta ggagctgaaa attctgtagc atattctaat aattctattg caattcctac   3780
taactttact atttctgtaa ctacagaaat attgccagtt tctatgacta aaacatctgt   3840
agattgtaca atgtatatat gtggagattc tactgaatgt tctaatttgc tactacaata   3900
tggatctttt tgtactcaat tgaatagagc tttaacagga atagcagtag aacaagataa   3960
aaatacacaa gaagtttttg ctcaagtaaa acaaatctat aaaactccac ctataaaaga   4020
ttttggaggt tttaattttt ctcaaatatt gccagatcct tctaaacctt ctaaaagatc   4080
ttttattgaa gatttgttgt ttaataaggt tacattagca gatgctggtt ttataaaaca   4140
atatggagat tgtttaggag atattgcagc tagagatttg atttgtgctc aaaagtttaa   4200
tggattaact gtattaccac ctctactaac agatgaaatg atagcacaat atacatctgc   4260
attattagct ggaactatta catctggatg gacttttgga gctggagcag ctttacaaat   4320
accatttgct atgcaaatgg catatagatt caatggaatt ggagttactc aaaatgtatt   4380
atatgaaaat caaaaactaa ttgctaatca attcaattct gcaattggaa aaattcaaga   4440
ttctctatct tctacagcat ctgctttagg aaaactacaa gatgttgtaa atcaaaatgc   4500
acaagcttta aatactctag ttaaacaact atcttctaat tttggagcta tttcttctgt   4560
tttaaatgat atattgtcta gactagatcc acctgaagca gaagtacaaa ttgatagact   4620
aattacagga agattacaat ctctacaaac ttatgtaaca caacaactaa ttagagcagc   4680
tgaaataaga gcatctgcta atttggcagc tactaaaatg tctgaatgcg tattaggaca   4740
atctaaaaga gtagattttt gtggaaaagg atatcatttg atgtcttttc cacaatctgc   4800
tcctcatgga gtagtatttt tgcatgttac atatgtacct gcacaagaaa agaactttac   4860
tacagcacca gctatatgtc atgatggaaa agctcatttt cctagagaag gagtttttgt   4920
atctaatgga actcattggt ttgttacaca aagaaacttt tatgaaccac aaattataac   4980
```

-continued

```
tacagataat acatttgtat ctggaaattg tgatgttgta attggaattg ttaataatac   5040
tgtatatgat ccactacaac ctgaactaga ttcttttaaa gaagaactag ataaatactt   5100
taaaaatcat acttctcctg atgttgattt gggagatata tctggaatta atgcttctgt   5160
tgtaaatatt caaaaagaaa tagatagatt gaatgaagta gcaaaaaatt tgaatgaatc   5220
tctaattgat ttgcaagaat taggaaaata tgaacaatat atcaaatggc catggtatat   5280
ttggctaggt tttatagctg gattaatagc aattgttatg gtaactatta tgttatgttg   5340
tatgacatct tgttgttctt gtctaaaagg atgttgttct tgtggatctt gttgtaaatt   5400
tgatgaagat gattctgaac ctgttttgaa aggtgttaaa ctacattata ctggatctgg   5460
agcaactaat ttttctttgt taaaacaagc tggagatgta gaagaaaatc caggacctat   5520
ggctgattct aatggaacta taacagttga agaattgaaa aaactattag aacaatggaa   5580
tttggtaata ggatttttgt ttttaacatg gatttgttta ttacaatttg catatgctaa   5640
tagaaataga tttttgtata tcataaaact aatatttttg tggttattat ggccagttac   5700
tttagcatgt tttgttttag cagctgtata tagaattaat tggattacag gaggaattgc   5760
aatagctatg gcatgtctag taggattaat gtggctatct tactttatag catcttttag   5820
actatttgct agaactagat ctatgtggtc ttttaatcct gaaacaaata tattgttaaa   5880
tgtaccatta catggaacta tattgacaag acctctacta gaatctgaat tagttattgg   5940
agcagtaata ttaagaggac atttgagaat tgctggacat catttgggaa gatgtgatat   6000
caaagatttg cctaaagaaa ttactgttgc tacatctaga actttatctt attataaact   6060
aggagcatct caaagagtag ctggagattc tggatttgca gcttattcta gatatagaat   6120
tggaaattat aaattgaata ctgatcattc ttcttcttct gataatattg cattattagt   6180
acaaggatct ggagctacaa atttttcttt gttaaaacag gcaggagatg ttgaagaaaa   6240
tccaggacca atgtattctt ttgtatctga agaaactgga acattaattg ttaattctgt   6300
attattgttt ttagcttttg tagtattttt gctagttaca ttagcaatat tgactgcttt   6360
aagattatgt gcatattgtt gtaatattgt taatgtatct ttagtaaaac catcttttta   6420
tgtatattca agagttaaaa atctaaattc atcaagagtt cctgatctat tggtataata   6480
atttttatgg atcctctaga gtcgacctgc agtcaaactc taatgaccac atcttttttt   6540
agagatgaaa aatttttccac atctcctttt gtagacacga ctaaacattt tgcagaaaaa   6600
agtttattag tgtttagata atcgtatact tcatcagtgt agatagtaaa tgtgaacaga   6660
taaaaggtat tcttgctcaa tagattggta aattccatag aatatattaa tcctttcttc   6720
ttgagatccc acatcatttc aaccagagac gttttatcca atgatttacc tcgtactata   6780
ccacatacaa aactagattt tgcagtgacg tcgtatctgg tattcctacc aaacaaaatt   6840
ttacttttag ttcttttaga aaattctaag gtagaatctc tatttgccaa tatgtcatct   6900
atggaattac cactagcaaa aaatgataga aatatatatt gatacatcgc agctggtttt   6960
gatctactat actttaaaaa cgaatcagat tccataattg cctgtatatc atcagctgaa   7020
aaactatgtt ttacacgtat tccttcggca tttcttttta atgatatatc ttgtttagac   7080
aatgataaag ttatcatgtc catgagagac gcgtctccgt atcgtataaa tatttcatta   7140
gatgttagac gcttcattag ggtatactt ctataaggtt tcttaatcag tccatcattg   7200
gttgcgtcaa gaacaagctt gtctccctat agtgagtcgt attagagctt ggcgtaatca   7260
tggtcatagc tgtttcctgt gtgaaattgt tatccgctca caattccaca caacatacga   7320
gccggaagca taaagtgtaa agcctggggt gcctaatgag tgagctaact cacattaatt   7380
```

```
gcgttgcgct cactgcccgc tttcgagtcg ggaaacctgt cgtgccagct gcattaatga   7440
atcggccaac gcgcggggag aggcggtttg cgtattgggc gctcttccgc ttcctcgctc   7500
actgactcgc tgcgctcggt cgttcggctg cggcgagcgg tatcagctca ctcaaaggcg   7560
gtaatacggt tatccacaga atcaggggat aacgcaggaa agaacatgtg agcaaaaggc   7620
cagcaaaagg ccaggaaccg taaaaaggcc gcgttgctgg cgtttttcga taggctccgc   7680
cccccctgacg agcatcacaa aaatcgacgc tcaagtcaga ggtggcgaaa cccgacagga   7740
ctataaagat accaggcgtt tccccctgga agctccctcg tgcgctctcc tgttccgacc   7800
ctgccgctta ccggatacct gtccgccttt ctcccttcgg gaagcgtggc gctttctcat   7860
agctcacgct gtaggtatct cagttcggtg taggtcgttc gctccaagct gggctgtgtg   7920
cacgaacccc ccgttcagcc cgaccgctgc gccttatccg gtaactatcg tcttgagtcc   7980
aacccggtaa gacacgactt atcgccactg gcagcagcca ctggtaacag gattagcaga   8040
gcgaggtatg taggcggtgc tacagagttc ttgaagtggt ggcctaacta cggctacact   8100
agaaggacag tatttggtat ctgcgctctg ctgaagccag ttaccttcgg aaaaagagtt   8160
ggtagctctt gatccggcaa acaaaccacc gctggtagcg gtggtttttt tgtttgcaag   8220
cagcagatta cgcgcagaaa aaaaggatct caagaagatc ctttgatctt ttctacgggg   8280
tctgacgctc agtggaacga aaactcacgt taagggattt tggtcatgag attatcaaaa   8340
aggatcttca cctagatcct tttaaattaa aaatgaagtt ttaaatcaat ctaaagtata   8400
tatgagtaaa cttggtctga cagttaccaa tgcttaatca gtgaggcacc tatctcagcg   8460
atctgtctat ttcgttcatc catagttgcc tgactccccg tcgtgtagat aactacgata   8520
cgggagggct taccatctgg ccccagtgct gcaatgatac cgcgagaccc acgctcaccg   8580
gctccagatt tatcagcaat aaaccagcca gccggaaggg ccgagcgcag aagtggtcct   8640
gcaactttat ccgcctccat ccagtctatt aattgttgcc gggaagctag agtaagtagt   8700
tcgccagtta atagtttgcg caacgttgtt ggcattgcta caggcatcgt ggtgtcacgc   8760
tcgtcgtttg gtatggcttc attcagctcc ggttcccaac gatcaaggcg agttacatga   8820
tcccccatgt tgtgcaaaaa agcggttagc tccttcggtc ctccgatcgt tgtcagaagt   8880
aagttggccg cagtgttatc actcatggtt atggcagcac tgcataattc tcttactgtc   8940
atgccatccg taagatgctt ttctgtgact ggtgagtact caaccaagtc attctgagaa   9000
tagtgtatgc ggcgaccgag ttgctcttgc ccggcgtcaa tacgggataa taccgcgcca   9060
catagcagaa ctttaaaagt gctcatcatt ggaaaacgtt cttcggggcg aaaactctca   9120
aggatcttac cgctgttgag atccagttcg atgtaaccca ctcgtgcacc caactgatct   9180
tcagcatctt ttactttcac cagcgtttct gggtgagcaa aaacaggaag gcaaaatgcc   9240
gcaaaaaagg gaataagggc gacacggaaa tgttgaatac tcatactctt cctttttcaa   9300
tattattgaa gcatttatca gggttattgt ctcatgagcg gatacatatt tgaatgtatt   9360
tagaaaaata aacaaatagg ggttccgcgc acatttcccc gaaaagtgcc acctgacgtc   9420
taagaaacca ttattatcat gacattaacc tataaaaata ggcgtatcac gaggcccttt   9480
cgtctcgcgc gtttcggtga tgacggtgaa aacctctgac acatgcagct cccggagacg   9540
gtcacagctt gtctgtaagc ggatgccggg agcagacaag cccgtcaggg cgcgtcagcg   9600
ggtgttggcg ggtgtcgggg ctggcttaac tatgcggcat cagagcagat tgtactgaga   9660
gtgcaccata tgcggtgtga aataccgcac agatgcgtaa ggagaaaata ccgcatcagg   9720
```

cgccattcgc cattcaggct gcgcaactgt tgggaagggc gatcggtgcg ggcctcttcg 9780
ctattacgcc agctggcgaa agggggatgt gctgcaaggc gattaagttg ggtaacgcca 9840
gggttttccc agtcacgacg ttgtaaaacg acggccagtg aattggattt aggtgacact 9900
ata 9903

<210> SEQ ID NO 6
<211> LENGTH: 4848
<212> TYPE: DNA
<213> ORGANISM: Artificial
<220> FEATURE:
<223> OTHER INFORMATION: Synthetic construct

<400> SEQUENCE: 6
atgtttgttt ttctagtttt gctaccgttg gtttcaagtc aatgtgtaaa tctaactaca 60
agaactcaat taccgcctgc ctatactaat tcttttacaa gaggagtata ttatcctgat 120
aaagttttta gatcttctgt attacattct acacaagatt tgtttttacc atttttctct 180
aatgttactt ggtttcatgc aatacatgta tctggaacta atggaacaaa aagatttgat 240
aatccagtat taccttttaa tgatggagtt tattttgctt ctactgaaaa atctaatata 300
attagaggat ggatatttgg aactacatta gattctaaaa cacaatctct actaattgtt 360
aataatgcaa ctaatgtagt tataaaagta tgtgaatttc aattttgtaa tgatccattt 420
ttgggagttt attatcataa aaataataag tcttggatgg aatctgaatt cagagtatat 480
tcttctgcta ataattgtac atttgaatat gtatctcaac catttttgat ggatttggaa 540
ggaaaacaag gaaactttaa aaatttgaga gaatttgttt ttaaaaatat tgatggatac 600
tttaaaatct attctaaaca tactccaatt aatctagtaa gagatttgcc tcaaggattt 660
tctgctttag aaccactagt agatttgcct ataggaatta atattactag atttcaaaca 720
ttattagctt tacatagatc ttatttgaca cctggagatt cttcttctgg atggactgca 780
ggagctgcag cttattatgt tggatatttg caaccaagaa catttttgtt aaaatataat 840
gaaaatggaa ctataacaga tgcagttgat tgtgctttag atcctctatc tgaaactaaa 900
tgtactttaa aatcttttac tgtagaaaaa ggaatctatc aaacatctaa ctttagagta 960
caaccaactg aatctattgt tagatttcca aatataacaa atctatgtcc ttttggagaa 1020
gtttttaatg caactagatt tgcttctgta tatgcatgga atagaaaaag aatatctaat 1080
tgcgtagctg attattctgt attatataat tctgcatctt tttctacttt taaatgttat 1140
ggagtatctc caacaaaatt gaatgatcta tgttttacta atgtttatgc agattctttt 1200
gtaataagag gagatgaagt tagacaaata gctcctggac aaacaggaaa aatagcagat 1260
tataattata aattaccaga tgatttcact ggatgcgtaa ttgcttggaa ttctaataat 1320
ttggattcta aagtaggagg aaattataat tatttgtata gattgtttag aaaatctaat 1380
ttgaaacctt ttgaaagaga tatttctaca gaaatctatc aagcaggatc tactccatgt 1440
aatggagttg aaggttttaa ttgttatttt ccactacaat cttatggatt tcaacctaca 1500
aatggagtag gatatcaacc atatagagta gttgtattat cttttgaatt attacatgca 1560
ccagctacag tatgtggacc taaaaaatct actaatttgg ttaaaaataa gtgcgtaaac 1620
tttaacttta atggattaac tggaacagga gttttaactg aatctaataa gaaatttttg 1680
ccttttcaac aatttggaag agatattgct gatactacag atgcagtaag agatcctcaa 1740
actttagaaa tattggatat tacaccatgt tcttttggag gagtttctgt aataacacca 1800
ggaactaata catctaatca agttgctgta ttatatcaag atgttaattg tactgaagtt 1860

```
cctgtagcaa ttcatgctga tcaattaact ccaacatgga gagtatattc tactggatct   1920
aatgtttttc aaacaagagc tggatgtcta attggagcag aacatgtaaa taattcttat   1980
gaatgtgata ttcctatagg agctggaata tgtgcatctt atcaaactca aacaaattct   2040
ccaagaagag ctagatctgt tgcatctcaa tctataattg cttatacaat gtctttagga   2100
gctgaaaatt ctgtagcata ttctaataat tctattgcaa ttcctactaa ctttactatt   2160
tctgtaacta cagaaatatt gccagtttct atgactaaaa catctgtaga ttgtacaatg   2220
tatatatgtg gagattctac tgaatgttct aatttgctac tacaatatgg atctttttgt   2280
actcaattga atagagcttt aacaggaata gcagtagaac aagataaaaa tacacaagaa   2340
gtttttgctc aagtaaaaca aatctataaa actccaccta taaaagattt tggaggtttt   2400
aatttttctc aaatattgcc agatccttct aaaccttcta aaagatcttt tattgaagat   2460
ttgttgttta ataaggttac attagcagat gctggtttta taaaacaata tggagattgt   2520
ttaggagata ttgcagctag agatttgatt tgtgctcaaa agtttaatgg attaactgta   2580
ttaccacctc tactaacaga tgaaatgata gcacaatata catctgcatt attagctgga   2640
actattacat ctggatggac ttttggagct ggagcagctt tacaaatacc atttgctatg   2700
caaatggcat atagattcaa tggaattgga gttactcaaa atgtattata tgaaaatcaa   2760
aaactaattg ctaatcaatt caattctgca attggaaaaa ttcaagattc tctatcttct   2820
acagcatctg ctttaggaaa actacaagat gttgtaaatc aaaatgcaca agctttaaat   2880
actctagtta aacaactatc ttctaatttt ggagctattt cttctgtttt aaatgatata   2940
ttgtctagac tagatccacc tgaagcagaa gtacaaattg atagactaat tacaggaaga   3000
ttacaatctc tacaaactta tgtaacacaa caactaatta gagcagctga aataagagca   3060
tctgctaatt tggcagctac taaaatgtct gaatgcgtat taggacaatc taaaagagta   3120
gatttttgtg gaaaaggata tcatttgatg tcttttccac aatctgctcc tcatggagta   3180
gtatttttgc atgttacata tgtacctgca caagaaaaga actttactac agcaccagct   3240
atatgtcatg atggaaaagc tcattttcct agagaaggag tttttgtatc taatggaact   3300
cattggtttg ttacacaaag aaacttttat gaaccacaaa ttataactac agataataca   3360
tttgtatctg gaaattgtga tgttgtaatt ggaattgtta ataatactgt atatgatcca   3420
ctacaacctg aactagattc ttttaaagaa gaactagata aatactttaa aaatcatact   3480
tctcctgatg ttgatttggg agatatatct ggaattaatg cttctgttgt aaatattcaa   3540
aaagaaatag atagattgaa tgaagtagca aaaaatttga atgaatctct aattgatttg   3600
caagaattag gaaaatatga acaatatatc aaatggccat ggtatatttg gctaggtttt   3660
atagctggat taatagcaat tgttatggta actattatgt tatgttgtat gacatcttgt   3720
tgttcttgtc taaaaggatg ttgttcttgt ggatcttgtt gtaaatttga tgaagatgat   3780
tctgaacctg ttttgaaagg tgttaaacta cattatactg gatctggagc aactaatttt   3840
tctttgttaa aacaagctgg agatgtagaa gaaaatccag gacctatggc tgattctaat   3900
ggaactataa cagttgaaga attgaaaaaa ctattagaac aatggaattt ggtaatagga   3960
tttttgtttt taacatggat ttgtttatta caatttgcat atgctaatag aaatagattt   4020
ttgtatatca taaaactaat atttttgtgg ttattatggc cagttacttt agcatgtttt   4080
gttttagcag ctgtatatag aattaattgg attacaggag gaattgcaat agctatggca   4140
tgtctagtag gattaatgtg gctatcttac tttatagcat cttttagact atttgctaga   4200
```

actagatcta tgtggtcttt taatcctgaa acaaatatat tgttaaatgt accattacat 4260
ggaactatat tgacaagacc tctactagaa tctgaattag ttattggagc agtaatatta 4320
agaggacatt tgagaattgc tggacatcat ttgggaagat gtgatatcaa agatttgcct 4380
aaagaaatta ctgttgctac atctagaact ttatcttatt ataaactagg agcatctcaa 4440
agagtagctg gagattctgg atttgcagct tattctagat atagaattgg aaattataaa 4500
ttgaatactg atcattcttc ttcttctgat aatattgcat tattagtaca aggatctgga 4560
gctacaaatt tttctttgtt aaaacaggca ggagatgttg aagaaaatcc aggaccaatg 4620
tattcttttg tatctgaaga aactggaaca ttaattgtta attctgtatt attgttttta 4680
gcttttgtag tatttttgct agttacatta gcaatattga ctgctttaag attatgtgca 4740
tattgttgta atattgttaa tgtatcttta gtaaaaccat ctttttatgt atattcaaga 4800
gttaaaaatc taaattcatc aagagttcct gatctattgg tataataa 4848

<210> SEQ ID NO 7
<211> LENGTH: 8880
<212> TYPE: DNA
<213> ORGANISM: Artificial
<220> FEATURE:
<223> OTHER INFORMATION: Synthetic construct

<400> SEQUENCE: 7
gaattccctg ggacatacgt atatttctat gatctgtctt atatgaagtc tatacagcga 60
atagattcag aatttctaca taattatata ttgtacgcta ataagtttaa tctaacactc 120
cccgaagatt tgtttataat ccctacaaat ttggatattc tatggcgtac aaaggaatat 180
atagactcgt tcgatattag tacagaaaca tggaataaat tattatccaa ttattatatg 240
aagatgatag agtatgctaa actttatgta ctaagtccta ttctcgctga ggagttggat 300
aattttgaga ggacgggaga attaactagt attgtacaag aagccatttt atctctaaat 360
ttacgaatta agattttaaa ttttaaacat aaagatgatg atacgtatat acacttttgt 420
aaaatattat tcggtgtcta taacggaaca aacgctacta tatattatca tagacctcta 480
acgggatata tgaatatgat ttcagatact atatttgttc ctgtagataa taactaaggc 540
gcgcctttca ttttgttttt ttctatgcta taaatggtga gcaagggcga ggagctgttc 600
accggggtgg tgcccatcct ggtcgagctg gacggcgacg taaacggcca caagttcagc 660
gtgtccggcg agggcgaggg cgatgccacc tacggcaagc tgaccctgaa gttcatctgc 720
accaccggca agctgcccgt gccctggccc accctcgtga ccaccctgac ctacggcgtg 780
cagtgcttca gccgctaccc cgaccacatg aagcagcacg acttcttcaa gtccgccatg 840
cccgaaggct acgtccagga gcgcaccatc ttcttcaagg acgacggcaa ctacaagacc 900
cgcgccgagg tgaagttcga gggcgacacc ctggtgaacc gcatcgagct gaagggcatc 960
gacttcaagg aggacggcaa catcctgggg cacaagctgg agtacaacta caacagccac 1020
aacgtctata tcatggccga caagcagaag aacggcatca aggtgaactt caagatccgc 1080
cacaacatcg aggacggcag cgtgcagctc gccgaccact accagcagaa cacccccatc 1140
ggcgacggcc ccgtgctgct gcccgacaac cactacctga gcacccagtc cgccctgagc 1200
aaagacccca acgagaagcg cgatcacatg gtcctgctgg agttcgtgac cgccgccggg 1260
atcactctcg gcatgcacga gctgtacaag taagagctcg aggacgggag aattaactag 1320
tattgtacaa gaagccattt tatctctaaa tttacgaatt aagattttaa attttaaaca 1380
taaagatgat gatacgtata tacacttttg taaaatatta ttcggtgtct ataacggaac 1440
aaacgctact atatattatc atagacctct aacgggatat atgaatatga tttcagatac 1500
tatatttgtt cctgtagata ataactaact cgaggccgct ggtacccaac ctaaaaattg 1560
aaaataaata caaaggttct tgagggttgt gttaaattga aagcgagaaa taatcataaa 1620
taagcccggg accatgtttg tttttctagt tttgctaccg ttggtttcaa gtcaatgtgt 1680
aaatctaact acaagaactc aattaccgcc tgcctatact aattctttta caagaggagt 1740
atattatcct gataaagttt ttagatcttc tgtattacat tctacacaag atttgttttt 1800
accatttttc tctaatgtta cttggtttca tgcaatacat gtatctggaa ctaatggaac 1860
aaaaagattt gataatccag tattaccttt taatgatgga gtttattttg cttctactga 1920
aaaatctaat ataattagag gatggatatt tggaactaca ttagattcta aaacacaatc 1980
tctactaatt gttaataatg caactaatgt agttataaaa gtatgtgaat ttcaattttg 2040
taatgatcca tttttgggag tttattatca taaaaataat aagtcttgga tggaatctga 2100
attcagagta tattcttctg ctaataattg tacatttgaa tatgtatctc aaccattttt 2160
gatggatttg gaaggaaaac aaggaaactt taaaaatttg agagaatttg tttttaaaaa 2220
tattgatgga tactttaaaa tctattctaa acatactcca attaatctag taagagattt 2280
gcctcaagga ttttctgctt tagaaccact agtagatttg cctataggaa ttaatattac 2340
tagatttcaa acattattag ctttacatag atcttatttg acacctggag attcttcttc 2400
tggatggact gcaggagctg cagcttatta tgttggatat ttgcaaccaa gaacattttt 2460
gttaaaatat aatgaaaatg gaactataac agatgcagtt gattgtgctt tagatcctct 2520
atctgaaact aaatgtactt taaaatcttt tactgtagaa aaaggaatct atcaaacatc 2580
taactttaga gtacaaccaa ctgaatctat tgttagattt ccaaatataa caaatctatg 2640
tccttttgga gaagttttta atgcaactag atttgcttct gtatatgcat ggaatagaaa 2700
aagaatatct aattgcgtag ctgattattc tgtattatat aattctgcat ctttttctac 2760
ttttaaatgt tatggagtat ctccaacaaa attgaatgat ctatgtttta ctaatgttta 2820
tgcagattct tttgtaataa gaggagatga agttagacaa atagctcctg gacaaacagg 2880
aaaaatagca gattataatt ataaattacc agatgatttc actggatgcg taattgcttg 2940
gaattctaat aatttggatt ctaaagtagg aggaaattat aattatttgt atagattgtt 3000
tagaaaatct aatttgaaac cttttgaaag agatatttct acagaaatct atcaagcagg 3060
atctactcca tgtaatggag ttgaaggttt taattgttat tttccactac aatcttatgg 3120
atttcaacct acaaatggag taggatatca accatataga gtagttgtat tatcttttga 3180
attattacat gcaccagcta cagtatgtgg acctaaaaaa tctactaatt tggttaaaaa 3240
taagtgcgta aactttaact ttaatggatt aactggaaca ggagttttaa ctgaatctaa 3300
taagaaattt ttgccttttc aacaatttgg aagagatatt gctgatacta cagatgcagt 3360
aagagatcct caaactttag aaatattgga tattacacca tgttcttttg gaggagtttc 3420
tgtaataaca ccaggaacta atacatctaa tcaagttgct gtattatatc aagatgttaa 3480
ttgtactgaa gttcctgtag caattcatgc tgatcaatta actccaacat ggagagtata 3540
ttctactgga tctaatgttt ttcaaacaag agctggatgt ctaattggag cagaacatgt 3600
aaataattct tatgaatgtg atattcctat aggagctgga atatgtgcat cttatcaaac 3660
tcaaacaaat tctccaagaa gagctagatc tgttgcatct caatctataa ttgcttatac 3720
aatgtcttta ggagctgaaa attctgtagc atattctaat aattctattg caattcctac 3780

```
taactttact atttctgtaa ctacagaaat attgccagtt tctatgacta aaacatctgt   3840
agattgtaca atgtatatat gtggagattc tactgaatgt tctaatttgc tactacaata   3900
tggatctttt tgtactcaat tgaatagagc tttaacagga atagcagtag aacaagataa   3960
aaatacacaa gaagtttttg ctcaagtaaa acaaatctat aaaactccac ctataaaaga   4020
ttttggaggt tttaattttt ctcaaatatt gccagatcct tctaaacctt ctaaaagatc   4080
ttttattgaa gatttgttgt ttaataaggt tacattagca gatgctggtt ttataaaaca   4140
atatggagat tgtttaggag atattgcagc tagagatttg atttgtgctc aaaagtttaa   4200
tggattaact gtattaccac ctctactaac agatgaaatg atagcacaat atacatctgc   4260
attattagct ggaactatta catctggatg gacttttgga gctggagcag ctttacaaat   4320
accatttgct atgcaaatgg catatagatt caatggaatt ggagttactc aaaatgtatt   4380
atatgaaaat caaaaactaa ttgctaatca attcaattct gcaattggaa aaattcaaga   4440
ttctctatct tctacagcat ctgctttagg aaaactacaa gatgttgtaa atcaaaatgc   4500
acaagcttta aatactctag ttaaacaact atcttctaat tttggagcta tttcttctgt   4560
tttaaatgat atattgtcta gactagatcc acctgaagca gaagtacaaa ttgatagact   4620
aattacagga agattacaat ctctacaaac ttatgtaaca caacaactaa ttagagcagc   4680
tgaaataaga gcatctgcta atttggcagc tactaaaatg tctgaatgcg tattaggaca   4740
atctaaaaga gtagattttt gtggaaaagg atatcatttg atgtcttttc cacaatctgc   4800
tcctcatgga gtagtatttt tgcatgttac atatgtacct gcacaagaaa agaactttac   4860
tacagcacca gctatatgtc atgatggaaa agctcatttt cctagagaag gagtttttgt   4920
atctaatgga actcattggt ttgttacaca aagaaacttt tatgaaccac aaattataac   4980
tacagataat acatttgtat ctggaaattg tgatgttgta attggaattg ttaataatac   5040
tgtatatgat ccactacaac ctgaactaga ttcttttaaa gaagaactag ataaatactt   5100
taaaaatcat acttctcctg atgttgattt gggagatata tctggaatta atgcttctgt   5160
tgtaaatatt caaaaagaaa tagatagatt gaatgaagta gcaaaaaatt tgaatgaatc   5220
tctaattgat ttgcaagaat taggaaaata tgaacaatat atcaaatggc catggtatat   5280
ttggctaggt tttatagctg gattaatagc aattgttatg gtaactatta tgttatgttg   5340
tatgacatct tgttgttctt gtctaaaagg atgttgttct tgtggatctt gttgtaaatt   5400
tgatgaagat gattctgaac ctgttttgaa aggtgttaaa ctacattata cttaataatt   5460
tttatggatc ctctagagtc gacctgcagt caaactctaa tgaccacatc ttttttttaga   5520
gatgaaaaat tttccacatc tccttttgta gacacgacta aacattttgc agaaaaaagt   5580
ttattagtgt ttagataatc gtatacttca tcagtgtaga tagtaaatgt gaacagataa   5640
aaggtattct tgctcaatag attggtaaat tccatagaat atattaatcc tttcttcttg   5700
agatcccaca tcatttcaac cagagacgtt ttatccaatg atttacctcg tactatacca   5760
catacaaaac tagattttgc agtgacgtcg tatctggtat tcctaccaaa caaaatttta   5820
cttttagttc ttttagaaaa ttctaaggta gaatctctat ttgccaatat gtcatctatg   5880
gaattaccac tagcaaaaaa tgatagaaat atatattgat acatcgcagc tggttttgat   5940
ctactatact ttaaaaacga atcagattcc ataattgcct gtatatcatc agctgaaaaa   6000
ctatgtttta cacgtattcc ttcggcattt ctttttaatg atatatcttg tttagacaat   6060
gataaagtta tcatgtccat gagagacgcg tctccgtatc gtataaatat ttcattagat   6120
gttagacgct tcattagggg tatacttcta taaggtttct taatcagtcc atcattggtt   6180
```

gcgtcaagaa caagcttgtc tccctatagt gagtcgtatt agagcttggc gtaatcatgg 6240
tcatagctgt ttcctgtgtg aaattgttat ccgctcacaa ttccacacaa catacgagcc 6300
ggaagcataa agtgtaaagc ctggggtgcc taatgagtga gctaactcac attaattgcg 6360
ttgcgctcac tgcccgcttt cgagtcggga aacctgtcgt gccagctgca ttaatgaatc 6420
ggccaacgcg cggggagagg cggtttgcgt attgggcgct cttccgcttc ctcgctcact 6480
gactcgctgc gctcggtcgt tcggctgcgg cgagcggtat cagctcactc aaaggcggta 6540
atacggttat ccacagaatc aggggataac gcaggaaaga acatgtgagc aaaaggccag 6600
caaaaggcca ggaaccgtaa aaaggccgcg ttgctggcgt ttttcgatag gctccgcccc 6660
cctgacgagc atcacaaaaa tcgacgctca agtcagaggt ggcgaaaccc gacaggacta 6720
taaagatacc aggcgtttcc ccctggaagc tccctcgtgc gctctcctgt tccgaccctg 6780
ccgcttaccg gatacctgtc cgcctttctc ccttcgggaa gcgtggcgct ttctcatagc 6840
tcacgctgta ggtatctcag ttcggtgtag gtcgttcgct ccaagctggg ctgtgtgcac 6900
gaaccccccg ttcagcccga ccgctgcgcc ttatccggta actatcgtct tgagtccaac 6960
ccggtaagac acgacttatc gccactggca gcagccactg gtaacaggat tagcagagcg 7020
aggtatgtag gcggtgctac agagttcttg aagtggtggc ctaactacgg ctacactaga 7080
aggacagtat ttggtatctg cgctctgctg aagccagtta ccttcggaaa aagagttggt 7140
agctcttgat ccggcaaaca aaccaccgct ggtagcggtg gtttttttgt ttgcaagcag 7200
cagattacgc gcagaaaaaa aggatctcaa gaagatcctt tgatcttttc tacggggtct 7260
gacgctcagt ggaacgaaaa ctcacgttaa gggattttgg tcatgagatt atcaaaaagg 7320
atcttcacct agatcctttt aaattaaaaa tgaagtttta aatcaatcta aagtatatat 7380
gagtaaactt ggtctgacag ttaccaatgc ttaatcagtg aggcacctat ctcagcgatc 7440
tgtctatttc gttcatccat agttgcctga ctccccgtcg tgtagataac tacgatacgg 7500
gagggcttac catctggccc cagtgctgca atgataccgc gagacccacg ctcaccggct 7560
ccagatttat cagcaataaa ccagccagcc ggaagggccg agcgcagaag tggtcctgca 7620
actttatccg cctccatcca gtctattaat tgttgccggg aagctagagt aagtagttcg 7680
ccagttaata gtttgcgcaa cgttgttggc attgctacag gcatcgtggt gtcacgctcg 7740
tcgtttggta tggcttcatt cagctccggt tcccaacgat caaggcgagt tacatgatcc 7800
cccatgttgt gcaaaaaagc ggttagctcc ttcggtcctc cgatcgttgt cagaagtaag 7860
ttggccgcag tgttatcact catggttatg gcagcactgc ataattctct tactgtcatg 7920
ccatccgtaa gatgcttttc tgtgactggt gagtactcaa ccaagtcatt ctgagaatag 7980
tgtatgcggc gaccgagttg ctcttgcccg gcgtcaatac gggataatac cgcgccacat 8040
agcagaactt taaaagtgct catcattgga aaacgttctt cggggcgaaa actctcaagg 8100
atcttaccgc tgttgagatc cagttcgatg taacccactc gtgcacccaa ctgatcttca 8160
gcatctttta ctttcaccag cgtttctggg tgagcaaaaa caggaaggca aaatgccgca 8220
aaaaagggaa taagggcgac acggaaatgt tgaatactca tactcttcct ttttcaatat 8280
tattgaagca tttatcaggg ttattgtctc atgagcggat acatatttga atgtatttag 8340
aaaaataaac aaataggggt tccgcgcaca tttccccgaa aagtgccacc tgacgtctaa 8400
gaaaccatta ttatcatgac attaacctat aaaaataggc gtatcacgag gccctttcgt 8460
ctcgcgcgtt tcggtgatga cggtgaaaac ctctgacaca tgcagctccc ggagacggtc 8520
acagcttgtc tgtaagcgga tgccgggagc agacaagccc gtcagggcgc gtcagcgggt 8580
gttggcgggt gtcggggctg gcttaactat gcggcatcag agcagattgt actgagagtg 8640
caccatatgc ggtgtgaaat accgcacaga tgcgtaagga gaaaataccg catcaggcgc 8700
cattcgccat tcaggctgcg caactgttgg gaagggcgat cggtgcgggc ctcttcgcta 8760
ttacgccagc tggcgaaagg gggatgtgct gcaaggcgat taagttgggt aacgccaggg 8820
ttttcccagt cacgacgttg taaaacgacg gccagtgaat tggatttagg tgacactata 8880

<210> SEQ ID NO 8
<211> LENGTH: 3825
<212> TYPE: DNA
<213> ORGANISM: Artificial
<220> FEATURE:
<223> OTHER INFORMATION: Synthetic construct

<400> SEQUENCE: 8
atgtttgttt ttctagtttt gctaccgttg gtttcaagtc aatgtgtaaa tctaactaca 60
agaactcaat taccgcctgc ctatactaat tcttttacaa gaggagtata ttatcctgat 120 aaagtttttta gatcttctgt attacattct acacaagatt tgtttttacc atttttctct 180
aatgttactt ggtttcatgc aatacatgta tctggaacta atggaacaaa aagatttgat 240
aatccagtat taccttttaa tgatggagtt tattttgctt ctactgaaaa atctaatata 300
attagaggat ggatatttgg aactacatta gattctaaaa cacaatctct actaattgtt 360
aataatgcaa ctaatgtagt tataaaagta tgtgaatttc aattttgtaa tgatccattt 420
ttgggagttt attatcataa aaataataag tcttggatgg aatctgaatt cagagtatat 480
tcttctgcta ataattgtac atttgaatat gtatctcaac catttttgat ggatttggaa 540
ggaaaacaag gaaactttaa aaatttgaga gaatttgttt ttaaaaatat tgatggatac 600
tttaaaatct attctaaaca tactccaatt aatctagtaa gagatttgcc tcaaggattt 660
tctgctttag aaccactagt agatttgcct ataggaatta atattactag atttcaaaca 720
ttattagctt tacatagatc ttatttgaca cctggagatt cttcttctgg atggactgca 780
ggagctgcag cttattatgt tggatatttg caaccaagaa catttttgtt aaaatataat 840
gaaaatggaa ctataacaga tgcagttgat tgtgctttag atcctctatc tgaaactaaa 900
tgtactttaa aatcttttac tgtagaaaaa ggaatctatc aaacatctaa ctttagagta 960
caaccaactg aatctattgt tagatttcca aatataacaa atctatgtcc ttttggagaa 1020
gtttttaatg caactagatt tgcttctgta tatgcatgga atagaaaaag aatatctaat 1080
tgcgtagctg attattctgt attatataat tctgcatctt tttctacttt taaatgttat 1140
ggagtatctc caacaaaatt gaatgatcta tgttttacta atgtttatgc agattctttt 1200
gtaataagag gagatgaagt tagacaaata gctcctggac aaacaggaaa aatagcagat 1260
tataattata aattaccaga tgatttcact ggatgcgtaa ttgcttggaa ttctaataat 1320
ttggattcta aagtaggagg aaattataat tatttgtata gattgtttag aaaatctaat 1380
ttgaaacctt ttgaaagaga tatttctaca gaaatctatc aagcaggatc tactccatgt 1440
aatggagttg aaggttttaa ttgttatttt ccactacaat cttatggatt tcaacctaca 1500
aatggagtag gatatcaacc atatagagta gttgtattat cttttgaatt attacatgca 1560
ccagctacag tatgtggacc taaaaaatct actaatttgg ttaaaaataa gtgcgtaaac 1620
tttaacttta atggattaac tggaacagga gttttaactg aatctaataa gaaatttttg 1680
ccttttcaac aatttggaag agatattgct gatactacag atgcagtaag agatcctcaa 1740

```
actttagaaa tattggatat tacaccatgt tcttttggag gagtttctgt aataacacca   1800
ggaactaata catctaatca agttgctgta ttatatcaag atgttaattg tactgaagtt   1860
cctgtagcaa ttcatgctga tcaattaact ccaacatgga gagtatattc tactggatct   1920
aatgtttttc aaacaagagc tggatgtcta attggagcag aacatgtaaa taattcttat   1980
gaatgtgata ttcctatagg agctggaata tgtgcatctt atcaaactca aacaaattct   2040
ccaagaagag ctagatctgt tgcatctcaa tctataattg cttatacaat gtctttagga   2100
gctgaaaatt ctgtagcata ttctaataat tctattgcaa ttcctactaa ctttactatt   2160
tctgtaacta cagaaatatt gccagtttct atgactaaaa catctgtaga ttgtacaatg   2220
tatatatgtg gagattctac tgaatgttct aatttgctac tacaatatgg atctttttgt   2280
actcaattga atagagcttt aacaggaata gcagtagaac aagataaaaa tacacaagaa   2340
gtttttgctc aagtaaaaca aatctataaa actccaccta taaaagattt tggaggtttt   2400
aatttttctc aaatattgcc agatccttct aaaccttcta aaagatcttt tattgaagat   2460
ttgttgttta ataaggttac attagcagat gctggtttta taaaacaata tggagattgt   2520
ttaggagata ttgcagctag agatttgatt tgtgctcaaa agtttaatgg attaactgta   2580
ttaccacctc tactaacaga tgaaatgata gcacaatata catctgcatt attagctgga   2640
actattacat ctggatggac ttttggagct ggagcagctt tacaaatacc atttgctatg   2700
caaatggcat atagattcaa tggaattgga gttactcaaa atgtattata tgaaaatcaa   2760
aaactaattg ctaatcaatt caattctgca attggaaaaa ttcaagattc tctatcttct   2820
acagcatctg ctttaggaaa actacaagat gttgtaaatc aaaatgcaca agctttaaat   2880
actctagtta aacaactatc ttctaatttt ggagctattt cttctgtttt aaatgatata   2940
ttgtctagac tagatccacc tgaagcagaa gtacaaattg atagactaat tacaggaaga   3000
ttacaatctc tacaaactta tgtaacacaa caactaatta gagcagctga aataagagca   3060
tctgctaatt tggcagctac taaaatgtct gaatgcgtat taggacaatc taaaagagta   3120
gatttttgtg gaaaaggata tcatttgatg tcttttccac aatctgctcc tcatggagta   3180
gtatttttgc atgttacata tgtacctgca caagaaaaga actttactac agcaccagct   3240
atatgtcatg atggaaaagc tcattttcct agagaaggag tttttgtatc taatggaact   3300
cattggtttg ttacacaaag aaacttttat gaaccacaaa ttataactac agataataca   3360
tttgtatctg gaaattgtga tgttgtaatt ggaattgtta ataatactgt atatgatcca   3420
ctacaacctg aactagattc ttttaaagaa gaactagata aatactttaa aaatcatact   3480
tctcctgatg ttgatttggg agatatatct ggaattaatg cttctgttgt aaatattcaa   3540
aaagaaatag atagattgaa tgaagtagca aaaaatttga atgaatctct aattgatttg   3600
caagaattag gaaaatatga acaatatatc aaatggccat ggtatatttg gctaggtttt   3660
atagctggat taatagcaat tgttatggta actattatgt tatgttgtat gacatcttgt   3720
tgttcttgtc taaaaggatg ttgttcttgt ggatcttgtt gtaaatttga tgaagatgat   3780
tctgaacctg ttttgaaagg tgttaaacta cattatactt aataa                   3825
```

<210> SEQ ID NO 9
<211> LENGTH: 8787
<212> TYPE: DNA
<213> ORGANISM: Artificial
<220> FEATURE:
<223> OTHER INFORMATION: Synthetic construct

<400> SEQUENCE: 9

```
gaattccctg ggacatacgt atatttctat gatctgtctt atatgaagtc tatacagcga     60
atagattcag aatttctaca taattatata ttgtacgcta ataagtttaa tctaacactc    120
cccgaagatt tgtttataat ccctacaaat ttggatattc tatggcgtac aaaggaatat    180
atagactcgt tcgatattag tacagaaaca tggaataaat tattatccaa ttattatatg    240
aagatgatag agtatgctaa actttatgta ctaagtccta ttctcgctga ggagttggat    300
aattttgaga ggacgggaga attaactagt attgtacaag aagccatttt atctctaaat    360
ttacgaatta agattttaaa ttttaaacat aaagatgatg atacgtatat acacttttgt    420
aaaatattat tcggtgtcta taacggaaca aacgctacta tatattatca tagacctcta    480
acgggatata tgaatatgat ttcagatact atatttgttc ctgtagataa taactaaggc    540
gcgcctttca ttttgttttt ttctatgcta taaatggtga gcaagggcga ggagctgttc    600
accggggtgg tgcccatcct ggtcgagctg gacggcgacg taaacggcca caagttcagc    660
gtgtccggcg agggcgaggg cgatgccacc tacggcaagc tgaccctgaa gttcatctgc    720
accaccggca agctgcccgt gccctggccc accctcgtga ccaccctgac ctacggcgtg    780
cagtgcttca gccgctaccc cgaccacatg aagcagcacg acttcttcaa gtccgccatg    840
cccgaaggct acgtccagga gcgcaccatc ttcttcaagg acgacggcaa ctacaagacc    900
cgcgccgagg tgaagttcga gggcgacacc ctggtgaacc gcatcgagct gaagggcatc    960
gacttcaagg aggacggcaa catcctgggg cacaagctgg agtacaacta caacagccac   1020
aacgtctata tcatggccga caagcagaag aacggcatca aggtgaactt caagatccgc   1080
cacaacatcg aggacggcag cgtgcagctc gccgaccact accagcagaa cacccccatc   1140
ggcgacggcc ccgtgctgct gcccgacaac cactacctga gcacccagtc cgccctgagc   1200
aaagacccca acgagaagcg cgatcacatg gtcctgctgg agttcgtgac cgccgccggg   1260
atcactctcg gcatgcacga gctgtacaag taagagctcg aggacgggag aattaactag   1320
tattgtacaa gaagccattt tatctctaaa tttacgaatt aagattttaa attttaaaca   1380
taaagatgat gatacgtata tacacttttg taaaatatta ttcggtgtct ataacggaac   1440
aaacgctact atatattatc atagacctct aacgggatat atgaatatga tttcagatac   1500
tatatttgtt cctgtagata ataactaact cgaggccgct ggtacccaac ctaaaaattg   1560
aaaataaata caaaggttct tgagggttgt gttaaattga aagcgagaaa taatcataaa   1620
taagcccggg accatgtggt tacaaggact actattacta ggtactgttg cctgttcaat   1680
ttcacaatgt gtaaatctaa ctacaagaac tcaattaccg cctgcctata ctaattcttt   1740
tacaagagga gtatattatc ctgataaagt ttttagatct tctgtattac attctacaca   1800
agatttgttt ttaccatttt tctctaatgt tacttggttt catgcaatac atgtatctgg   1860
aactaatgga acaaaaagat ttgataatcc agtattacct tttaatgatg gagtttattt   1920
tgcttctact gaaaaatcta atataattag aggatggata tttggaacta cattagattc   1980
taaaacacaa tctctactaa ttgttaataa tgcaactaat gtagttataa aagtatgtga   2040
atttcaattt tgtaatgatc catttttggg agtttattat cataaaaata ataagtcttg   2100
gatggaatct gaattcagag tatattcttc tgctaataat tgtacatttg aatatgtatc   2160
tcaaccattt ttgatggatt tggaaggaaa acaaggaaac tttaaaaatt tgagagaatt   2220
tgtttttaaa aatattgatg gatactttaa aatctattct aaacatactc caattaatct   2280
agtaagagat ttgcctcaag gattttctgc tttagaacca ctagtagatt tgcctatagg   2340
```

```
aattaatatt actagatttc aaacattatt agctttacat agatcttatt tgacacctgg   2400
agattcttct tctggatgga ctgcaggagc tgcagcttat tatgttggat atttgcaacc   2460
aagaacattt ttgttaaaat ataatgaaaa tggaactata acagatgcag ttgattgtgc   2520
tttagatcct ctatctgaaa ctaaatgtac tttaaaatct tttactgtag aaaaaggaat   2580
ctatcaaaca tctaacttta gagtacaacc aactgaatct attgttagat ttccaaatat   2640
aacaaatcta tgtccttttg gagaagtttt taatgcaact agatttgctt ctgtatatgc   2700
atggaataga aaaagaatat ctaattgcgt agctgattat tctgtattat ataattctgc   2760
atctttttct acttttaaat gttatggagt atctccaaca aaattgaatg atctatgttt   2820
tactaatgtt tatgcagatt cttttgtaat aagaggagat gaagttagac aaatagctcc   2880
tggacaaaca ggaaaaatag cagattataa ttataaatta ccagatgatt tcactggatg   2940
cgtaattgct tggaattcta ataatttgga ttctaaagta ggaggaaatt ataattattt   3000
gtatagattg tttagaaaat ctaatttgaa accttttgaa agagatattt ctacagaaat   3060
ctatcaagca ggatctactc catgtaatgg agttgaaggt tttaattgtt attttccact   3120
acaatcttat ggatttcaac ctacaaatgg agtaggatat caaccatata gagtagttgt   3180
attatctttt gaattattac atgcaccagc tacagtatgt ggacctaaaa aatctactaa   3240
tttggttaaa aataagtgcg taaactttaa ctttaatgga ttaactggaa caggagtttt   3300
aactgaatct aataagaaat ttttgccttt tcaacaattt ggaagagata ttgctgatac   3360
tacagatgca gtaagagatc ctcaaacttt agaaatattg gatattacac catgttcttt   3420
tggaggagtt tctgtaataa caccaggaac taatacatct aatcaagttg ctgtattata   3480
tcaagatgtt aattgtactg aagttcctgt agcaattcat gctgatcaat taactccaac   3540
atggagagta tattctactg gatctaatgt ttttcaaaca agagctggat gtctaattgg   3600
agcagaacat gtaaataatt cttatgaatg tgatattcct ataggagctg gaatatgtgc   3660
atcttatcaa actcaaacaa attctccaag aagagctaga tctgttgcat ctcaatctat   3720
aattgcttat acaatgtctt taggagctga aaattctgta gcatattcta ataattctat   3780
tgcaattcct actaacttta ctatttctgt aactacagaa atattgccag tttctatgac   3840
taaaacatct gtagattgta caatgtatat atgtggagat tctactgaat gttctaattt   3900
gctactacaa tatggatctt tttgtactca attgaataga gctttaacag gaatagcagt   3960
agaacaagat aaaaatacac aagaagtttt tgctcaagta aaacaaatct ataaaactcc   4020
acctataaaa gattttggag gttttaattt ttctcaaata ttgccagatc cttctaaacc   4080
ttctaaaaga tcttttattg aagatttgtt gtttaataag gttacattag cagatgctgg   4140
ttttataaaa caatatggag attgtttagg agatattgca gctagagatt tgatttgtgc   4200
tcaaaagttt aatggattaa ctgtattacc acctctacta acagatgaaa tgatagcaca   4260
atatacatct gcattattag ctggaactat tacatctgga tggacttttg gagctggagc   4320
agctttacaa ataccatttg ctatgcaaat ggcatataga ttcaatggaa ttggagttac   4380
tcaaaatgta ttatatgaaa atcaaaaact aattgctaat caattcaatt ctgcaattgg   4440
aaaaattcaa gattctctat cttctacagc atctgcttta ggaaaactac aagatgttgt   4500
aaatcaaaat gcacaagctt taaatactct agttaaacaa ctatcttcta attttggagc   4560
tatttcttct gttttaaatg atatattgtc tagactagat ccacctgaag cagaagtaca   4620
aattgataga ctaattacag gaagattaca atctctacaa acttatgtaa cacaacaact   4680
```

aattagagca gctgaaataa gagcatctgc taatttggca gctactaaaa tgtctgaatg 4740
cgtattagga caatctaaaa gagtagattt ttgtggaaaa ggatatcatt tgatgtcttt 4800
tccacaatct gctcctcatg gagtagtatt tttgcatgtt acatatgtac ctgcacaaga 4860
aaagaacttt actacagcac cagctatatg tcatgatgga aaagctcatt ttcctagaga 4920
aggagttttt gtatctaatg gaactcattg gtttgttaca caaagaaact tttatgaacc 4980
acaaattata actacagata atacatttgt atctggaaat tgtgatgttg taattggaat 5040
tgttaataat actgtatatg atccactaca acctgaacta gattctttta aagaagaact 5100
agataaatac tttaaaaatc atacttctcc tgatgttgat ttgggagata tatctggaat 5160
taatgcttct gttgtaaata ttcaaaaaga aatagataga ttgaatgaag tagcaaaaaa 5220
tttgaatgaa tctctaattg atttgcaaga attaggaaaa tatgaacaag gatctgctgg 5280
atatattcca gaagcaccta gagatggaca agcgtatgtt agaaaagatg gtgaatgggt 5340
attattgagt acatttttgt aataattttt atggatcctc tagagtcgac ctgcagtcaa 5400
actctaatga ccacatcttt ttttagagat gaaaaatttt ccacatctcc ttttgtagac 5460
acgactaaac attttgcaga aaaaagttta ttagtgttta gataatcgta tacttcatca 5520
gtgtagatag taaatgtgaa cagataaaag gtattcttgc tcaatagatt ggtaaattcc 5580
atagaatata ttaatccttt cttcttgaga tcccacatca tttcaaccag agacgtttta 5640
tccaatgatt tacctcgtac tataccacat acaaaactag attttgcagt gacgtcgtat 5700
ctggtattcc taccaaacaa aattttactt ttagttcttt tagaaaattc taaggtagaa 5760
tctctatttg ccaatatgtc atctatggaa ttaccactag caaaaaatga tagaaatata 5820
tattgataca tcgcagctgg ttttgatcta ctatacttta aaaacgaatc agattccata 5880
attgcctgta tatcatcagc tgaaaaacta tgttttacac gtattccttc ggcatttctt 5940
tttaatgata tatcttgttt agacaatgat aaagttatca tgtccatgag agacgcgtct 6000
ccgtatcgta taaatatttc attagatgtt agacgcttca ttaggggtat acttctataa 6060
ggtttcttaa tcagtccatc attggttgcg tcaagaacaa gcttgtctcc ctatagtgag 6120
tcgtattaga gcttggcgta atcatggtca tagctgtttc ctgtgtgaaa ttgttatccg 6180
ctcacaattc cacacaacat acgagccgga agcataaagt gtaaagcctg gggtgcctaa 6240
tgagtgagct aactcacatt aattgcgttg cgctcactgc ccgctttcga gtcgggaaac 6300
ctgtcgtgcc agctgcatta atgaatcggc caacgcgcgg ggagaggcgg tttgcgtatt 6360
gggcgctctt ccgcttcctc gctcactgac tcgctgcgct cggtcgttcg gctgcggcga 6420
gcggtatcag ctcactcaaa ggcggtaata cggttatcca cagaatcagg ggataacgca 6480
ggaaagaaca tgtgagcaaa aggccagcaa aaggccagga accgtaaaaa ggccgcgttg 6540
ctggcgtttt tcgataggct ccgcccccct gacgagcatc acaaaaatcg acgctcaagt 6600
cagaggtggc gaaacccgac aggactataa agataccagg cgtttccccc tggaagctcc 6660
ctcgtgcgct ctcctgttcc gaccctgccg cttaccggat acctgtccgc ctttctccct 6720
tcgggaagcg tggcgctttc tcatagctca cgctgtaggt atctcagttc ggtgtaggtc 6780
gttcgctcca agctgggctg tgtgcacgaa ccccccgttc agcccgaccg ctgcgcctta 6840
tccggtaact atcgtcttga gtccaacccg gtaagacacg acttatcgcc actggcagca 6900
gccactggta acaggattag cagagcgagg tatgtaggcg gtgctacaga gttcttgaag 6960
tggtggccta actacggcta cactagaagg acagtatttg gtatctgcgc tctgctgaag 7020
ccagttacct tcggaaaaag agttggtagc tcttgatccg gcaaacaaac caccgctggt 7080

```
agcggtggtt tttttgtttg caagcagcag attacgcgca gaaaaaaagg atctcaagaa   7140
gatcctttga tcttttctac ggggtctgac gctcagtgga acgaaaactc acgttaaggg   7200
attttggtca tgagattatc aaaaaggatc ttcacctaga tccttttaaa ttaaaaatga   7260
agttttaaat caatctaaag tatatatgag taaacttggt ctgacagtta ccaatgctta   7320
atcagtgagg cacctatctc agcgatctgt ctatttcgtt catccatagt tgcctgactc   7380
cccgtcgtgt agataactac gatacgggag ggcttaccat ctggccccag tgctgcaatg   7440
ataccgcgag acccacgctc accggctcca gatttatcag caataaacca gccagccgga   7500
agggccgagc gcagaagtgg tcctgcaact ttatccgcct ccatccagtc tattaattgt   7560
tgccgggaag ctagagtaag tagttcgcca gttaatagtt tgcgcaacgt tgttggcatt   7620
gctacaggca tcgtggtgtc acgctcgtcg tttggtatgg cttcattcag ctccggttcc   7680
caacgatcaa ggcgagttac atgatccccc atgttgtgca aaaaagcggt tagctccttc   7740
ggtcctccga tcgttgtcag aagtaagttg gccgcagtgt tatcactcat ggttatggca   7800
gcactgcata attctcttac tgtcatgcca tccgtaagat gcttttctgt gactggtgag   7860
tactcaacca agtcattctg agaatagtgt atgcggcgac cgagttgctc ttgcccggcg   7920
tcaatacggg ataataccgc gccacatagc agaactttaa aagtgctcat cattggaaaa   7980
cgttcttcgg ggcgaaaact ctcaaggatc ttaccgctgt tgagatccag ttcgatgtaa   8040
cccactcgtg cacccaactg atcttcagca tcttttactt tcaccagcgt ttctgggtga   8100
gcaaaaacag gaaggcaaaa tgccgcaaaa aagggaataa gggcgacacg gaaatgttga   8160
atactcatac tcttcctttt tcaatattat tgaagcattt atcagggtta ttgtctcatg   8220
agcggataca tatttgaatg tatttagaaa aataaacaaa taggggttcc gcgcacattt   8280
ccccgaaaag tgccacctga cgtctaagaa accattatta tcatgacatt aacctataaa   8340
aataggcgta tcacgaggcc ctttcgtctc gcgcgtttcg gtgatgacgg tgaaaacctc   8400
tgacacatgc agctcccgga gacggtcaca gcttgtctgt aagcggatgc cgggagcaga   8460
caagcccgtc agggcgcgtc agcgggtgtt ggcgggtgtc ggggctggct taactatgcg   8520
gcatcagagc agattgtact gagagtgcac catatgcggt gtgaaatacc gcacagatgc   8580
gtaaggagaa aataccgcat caggcgccat tcgccattca ggctgcgcaa ctgttgggaa   8640
gggcgatcgg tgcgggcctc ttcgctatta cgccagctgg cgaaaggggg atgtgctgca   8700
aggcgattaa gttgggtaac gccagggttt tcccagtcac gacgttgtaa aacgacggcc   8760
agtgaattgg atttaggtga cactata                                       8787
```

<210> SEQ ID NO 10
<211> LENGTH: 3732
<212> TYPE: DNA
<213> ORGANISM: Artificial
<220> FEATURE:
<223> OTHER INFORMATION: Synthetic construct

<400> SEQUENCE: 10

```
atgtggttac aaggactact attactaggt actgttgcct gttcaatttc acaatgtgta     60
aatctaacta caagaactca attaccgcct gcctatacta attcttttac aagaggagta    120
tattatcctg ataaagtttt tagatcttct gtattacatt ctacacaaga tttgttttta    180
ccatttttct ctaatgttac ttggtttcat gcaatacatg tatctggaac taatggaaca    240
aaaagatttg ataatccagt attacctttt aatgatggag tttattttgc ttctactgaa    300
```

```
aaatctaata taattagagg atggatattt ggaactacat tagattctaa aacacaatct    360
ctactaattg ttaataatgc aactaatgta gttataaaag tatgtgaatt tcaattttgt    420
aatgatccat ttttgggagt ttattatcat aaaaataata agtcttggat ggaatctgaa    480
ttcagagtat attcttctgc taataattgt acatttgaat atgtatctca accatttttg    540
atggatttgg aaggaaaaca aggaaacttt aaaaatttga gagaatttgt ttttaaaaat    600
attgatggat actttaaaat ctattctaaa catactccaa ttaatctagt aagagatttg    660
cctcaaggat tttctgcttt agaaccacta gtagatttgc ctataggaat taatattact    720
agatttcaaa cattattagc tttacataga tcttatttga cacctggaga ttcttcttct    780
ggatggactg caggagctgc agcttattat gttggatatt tgcaaccaag aacatttttg    840
ttaaaatata atgaaaatgg aactataaca gatgcagttg attgtgcttt agatcctcta    900
tctgaaacta aatgtacttt aaaatctttt actgtagaaa aaggaatcta tcaaacatct    960
aactttagag tacaaccaac tgaatctatt gttagatttc caaatataac aaatctatgt   1020
ccttttggag aagtttttaa tgcaactaga tttgcttctg tatatgcatg gaatagaaaa   1080
agaatatcta attgcgtagc tgattattct gtattatata attctgcatc tttttctact   1140
tttaaatgtt atggagtatc tccaacaaaa ttgaatgatc tatgttttac taatgtttat   1200
gcagattctt ttgtaataag aggagatgaa gttagacaaa tagctcctgg acaaacagga   1260
aaaatagcag attataatta taaattacca gatgatttca ctggatgcgt aattgcttgg   1320
aattctaata atttggattc taaagtagga ggaaattata attatttgta tagattgttt   1380
agaaaatcta atttgaaacc ttttgaaaga gatatttcta cagaaatcta tcaagcagga   1440
tctactccat gtaatggagt tgaaggtttt aattgttatt ttccactaca atcttatgga   1500
tttcaaccta caaatggagt aggatatcaa ccatatagag tagttgtatt atcttttgaa   1560
ttattacatg caccagctac agtatgtgga cctaaaaaat ctactaattt ggttaaaaat   1620
aagtgcgtaa actttaactt taatggatta actggaacag gagttttaac tgaatctaat   1680
aagaaatttt tgccttttca acaatttgga agagatattg ctgatactac agatgcagta   1740
agagatcctc aaactttaga aatattggat attacaccat gttcttttgg aggagtttct   1800
gtaataacac caggaactaa tacatctaat caagttgctg tattatatca agatgttaat   1860
tgtactgaag ttcctgtagc aattcatgct gatcaattaa ctccaacatg gagagtatat   1920
tctactggat ctaatgtttt tcaaacaaga gctggatgtc taattggagc agaacatgta   1980
aataattctt atgaatgtga tattcctata ggagctggaa tatgtgcatc ttatcaaact   2040
caaacaaatt ctccaagaag agctagatct gttgcatctc aatctataat tgcttataca   2100
atgtctttag gagctgaaaa ttctgtagca tattctaata attctattgc aattcctact   2160
aactttacta tttctgtaac tacagaaata ttgccagttt ctatgactaa aacatctgta   2220
gattgtacaa tgtatatatg tggagattct actgaatgtt ctaatttgct actacaatat   2280
ggatcttttt gtactcaatt gaatagagct ttaacaggaa tagcagtaga acaagataaa   2340
aatacacaag aagtttttgc tcaagtaaaa caaatctata aaactccacc tataaaagat   2400
tttggaggtt ttaatttttc tcaaatattg ccagatcctt ctaaaccttc taaaagatct   2460
tttattgaag atttgttgtt taataaggtt acattagcag atgctggttt tataaaacaa   2520
tatggagatt gtttaggaga tattgcagct agagatttga tttgtgctca aaagtttaat   2580
ggattaactg tattaccacc tctactaaca gatgaaatga tagcacaata tacatctgca   2640
ttattagctg gaactattac atctggatgg acttttggag ctggagcagc tttacaaata   2700
```

ccatttgcta tgcaaatggc atatagattc aatggaattg gagttactca aaatgtatta 2760
tatgaaaatc aaaaactaat tgctaatcaa ttcaattctg caattggaaa aattcaagat 2820
tctctatctt ctacagcatc tgctttagga aaactacaag atgttgtaaa tcaaaatgca 2880
caagctttaa atactctagt taaacaacta tcttctaatt ttggagctat ttcttctgtt 2940
ttaaatgata tattgtctag actagatcca cctgaagcag aagtacaaat tgatagacta 3000
attacaggaa gattacaatc tctacaaact tatgtaacac aacaactaat tagagcagct 3060
gaaataagag catctgctaa tttggcagct actaaaatgt ctgaatgcgt attaggacaa 3120
tctaaaagag tagatttttg tggaaaagga tatcatttga tgtcttttcc acaatctgct 3180
cctcatggag tagtattttt gcatgttaca tatgtacctg cacaagaaaa gaactttact 3240
acagcaccag ctatatgtca tgatggaaaa gctcattttc ctagagaagg agtttttgta 3300
tctaatggaa ctcattggtt tgttacacaa agaaactttt atgaaccaca aattataact 3360
acagataata catttgtatc tggaaattgt gatgttgtaa ttggaattgt taataatact 3420
gtatatgatc cactacaacc tgaactagat tcttttaaag aagaactaga taaatacttt 3480
aaaaatcata cttctcctga tgttgatttg ggagatatat ctggaattaa tgcttctgtt 3540
gtaaatattc aaaaagaaat agatagattg aatgaagtag caaaaaattt gaatgaatct 3600
ctaattgatt tgcaagaatt aggaaaatat gaacaaggat ctgctggata tattccagaa 3660
gcacctagag atggacaagc gtatgttaga aaagatggtg aatgggtatt attgagtaca 3720
tttttgtaat aa 3732

<210> SEQ ID NO 11
<211> LENGTH: 7413
<212> TYPE: DNA
<213> ORGANISM: Artificial
<220> FEATURE:
<223> OTHER INFORMATION: Synthetic construct

<400> SEQUENCE: 11
gaattccctg ggacatacgt atatttctat gatctgtctt atatgaagtc tatacagcga 60
atagattcag aatttctaca taattatata ttgtacgcta ataagtttaa tctaacactc 120
cccgaagatt tgtttataat ccctacaaat ttggatattc tatggcgtac aaaggaatat 180
atagactcgt tcgatattag tacagaaaca tggaataaat tattatccaa ttattatatg 240
aagatgatag agtatgctaa actttatgta ctaagtccta ttctcgctga ggagttggat 300
aattttgaga ggacgggaga attaactagt attgtacaag aagccatttt atctctaaat 360
ttacgaatta agattttaaa ttttaaacat aaagatgatg atacgtatat acacttttgt 420
aaaatattat tcggtgtcta taacggaaca aacgctacta tatattatca tagacctcta 480
acgggatata tgaatatgat ttcagatact atatttgttc ctgtagataa taactaaggc 540
gcgcctttca ttttgttttt ttctatgcta taaatggtga gcaagggcga ggagctgttc 600
accggggtgg tgcccatcct ggtcgagctg gacggcgacg taaacggcca caagttcagc 660
gtgtccggcg agggcgaggg cgatgccacc tacggcaagc tgaccctgaa gttcatctgc 720
accaccggca agctgcccgt gccctggccc accctcgtga ccaccctgac ctacggcgtg 780
cagtgcttca gccgctaccc cgaccacatg aagcagcacg acttcttcaa gtccgccatg 840
cccgaaggct acgtccagga gcgcaccatc ttcttcaagg acgacggcaa ctacaagacc 900
cgcgccgagg tgaagttcga gggcgacacc ctggtgaacc gcatcgagct gaagggcatc 960

```
gacttcaagg aggacggcaa catcctgggg cacaagctgg agtacaacta caacagccac   1020
aacgtctata tcatggccga caagcagaag aacggcatca aggtgaactt caagatccgc   1080
cacaacatcg aggacggcag cgtgcagctc gccgaccact accagcagaa cacccccatc   1140
ggcgacggcc ccgtgctgct gcccgacaac cactacctga gcacccagtc cgccctgagc   1200
aaagacccca acgagaagcg cgatcacatg gtcctgctgg agttcgtgac cgccgccggg   1260
atcactctcg gcatgcacga gctgtacaag taagagctcg aggacgggag aattaactag   1320
tattgtacaa gaagccattt tatctctaaa tttacgaatt aagattttaa attttaaaca   1380
taaagatgat gatacgtata tacacttttg taaaatatta ttcggtgtct ataacggaac   1440
aaacgctact atatattatc atagacctct aacgggatat atgaatatga tttcagatac   1500
tatatttgtt cctgtagata ataactaact cgaggccgct ggtacccaac ctaaaaattg   1560
aaaataaata caaaggttct tgagggttgt gttaaattga aagcgagaaa taatcataaa   1620
taagcccggg accatgtggt tacaaggact actattacta ggtactgttg cctgttcaat   1680
ttcacaatgt gtaaatctaa ctacaagaac tcaattaccg cctgcctata ctaattcttt   1740
tacaagagga gtatattatc ctgataaagt ttttagatct tctgtattac attctacaca   1800
agatttgttt ttaccatttt tctctaatgt tacttggttt catgcaatac atgtatctgg   1860
aactaatgga acaaaaagat ttgataatcc agtattacct tttaatgatg gagtttattt   1920
tgcttctact gaaaaatcta atataattag aggatggata tttggaacta cattagattc   1980
taaaacacaa tctctactaa ttgttaataa tgcaactaat gtagttataa aagtatgtga   2040
atttcaattt tgtaatgatc catttttggg agtttattat cataaaaata ataagtcttg   2100
gatggaatct gaattcagag tatattcttc tgctaataat tgtacatttg aatatgtatc   2160
tcaaccattt ttgatggatt tggaaggaaa acaaggaaac tttaaaaatt tgagagaatt   2220
tgtttttaaa aatattgatg gatactttaa aatctattct aaacatactc caattaatct   2280
agtaagagat ttgcctcaag gattttctgc tttagaacca ctagtagatt tgcctatagg   2340
aattaatatt actagatttc aaacattatt agctttacat agatcttatt tgacacctgg   2400
agattcttct tctggatgga ctgcaggagc tgcagcttat tatgttggat atttgcaacc   2460
aagaacattt ttgttaaaat ataatgaaaa tggaactata acagatgcag ttgattgtgc   2520
tttagatcct ctatctgaaa ctaaatgtac tttaaaatct tttactgtag aaaaaggaat   2580
ctatcaaaca tctaacttta gagtacaacc aactgaatct attgttagat ttccaaatat   2640
aacaaatcta tgtccttttg gagaagtttt taatgcaact agatttgctt ctgtatatgc   2700
atggaataga aaaagaatat ctaattgcgt agctgattat tctgtattat ataattctgc   2760
atctttttct acttttaaat gttatggagt atctccaaca aaattgaatg atctatgttt   2820
tactaatgtt tatgcagatt cttttgtaat aagaggagat gaagttagac aaatagctcc   2880
tggacaaaca ggaaaaatag cagattataa ttataaatta ccagatgatt tcactggatg   2940
cgtaattgct tggaattcta ataatttgga ttctaaagta ggaggaaatt ataattattt   3000
gtatagattg tttagaaaat ctaatttgaa accttttgaa agagatattt ctacagaaat   3060
ctatcaagca ggatctactc catgtaatgg agttgaaggt tttaattgtt attttccact   3120
acaatcttat ggatttcaac ctacaaatgg agtaggatat caaccatata gagtagttgt   3180
attatctttt gaattattac atgcaccagc tacagtatgt ggacctaaaa aatctactaa   3240
tttggttaaa aataagtgcg taaactttaa ctttaatgga ttaactggaa caggagtttt   3300
aactgaatct aataagaaat tttgcctttt tcaacaattt ggaagagata ttgctgatac   3360
```

```
tacagatgca gtaagagatc ctcaaacttt agaaatattg gatattacac catgttcttt   3420
tggaggagtt tctgtaataa caccaggaac taatacatct aatcaagttg ctgtattata   3480
tcaagatgtt aattgtactg aagttcctgt agcaattcat gctgatcaat taactccaac   3540
atggagagta tattctactg gatctaatgt ttttcaaaca agagctggat gtctaattgg   3600
agcagaacat gtaaataatt cttatgaatg tgatattcct ataggagctg gaatatgtgc   3660
atcttatcaa actcaaacaa attctccaag aagagctaga tctgttgcat ctcaatctat   3720
aattgcttat acaatgtctt taggagctga aaattctgta gcatattcta ataattctat   3780
tgcaattcct actaacttta ctatttctgt aactacagaa atattgccag tttctatgac   3840
taaaacatct gtagattgta caatgtatat atgtggagat tctactgaat gttctaattt   3900
gctactacaa tatggatctt tttgtactca attgaataga gctttaacag gaatagcagt   3960
agaacaagat aaaaatacac aagaataata atttttatgg atcctctaga gtcgacctgc   4020
agtcaaactc taatgaccac atcttttttt agagatgaaa aattttccac atctcctttt   4080
gtagacacga ctaaacattt tgcagaaaaa agtttattag tgtttagata atcgtatact   4140
tcatcagtgt agatagtaaa tgtgaacaga taaaaggtat tcttgctcaa tagattggta   4200
aattccatag aatatattaa tcctttcttc ttgagatccc acatcatttc aaccagagac   4260
gttttatcca atgatttacc tcgtactata ccacatacaa aactagattt tgcagtgacg   4320
tcgtatctgg tattcctacc aaacaaaatt ttacttttag ttcttttaga aaattctaag   4380
gtagaatctc tatttgccaa tatgtcatct atggaattac cactagcaaa aaatgataga   4440
aatatatatt gatacatcgc agctggtttt gatctactat actttaaaaa cgaatcagat   4500
tccataattg cctgtatatc atcagctgaa aaactatgtt ttacacgtat tccttcggca   4560
tttctttttta atgatatatc ttgtttagac aatgataaag ttatcatgtc catgagagac   4620
gcgtctccgt atcgtataaa tatttcatta gatgttagac gcttcattag ggtatactt    4680
ctataaggtt tcttaatcag tccatcattg gttgcgtcaa gaacaagctt gtctccctat   4740
agtgagtcgt attagagctt ggcgtaatca tggtcatagc tgtttcctgt gtgaaattgt   4800
tatccgctca caattccaca caacatacga gccggaagca taaagtgtaa agcctggggt   4860
gcctaatgag tgagctaact cacattaatt gcgttgcgct cactgcccgc tttcgagtcg   4920
ggaaacctgt cgtgccagct gcattaatga atcggccaac gcgcggggag aggcggtttg   4980
cgtattgggc gctcttccgc ttcctcgctc actgactcgc tgcgctcggt cgttcggctg   5040
cggcgagcgg tatcagctca ctcaaaggcg gtaatacggt tatccacaga atcaggggat   5100
aacgcaggaa agaacatgtg agcaaaaggc cagcaaaagg ccaggaaccg taaaaaggcc   5160
gcgttgctgg cgtttttcga taggctccgc ccccctgacg agcatcacaa aaatcgacgc   5220
tcaagtcaga ggtggcgaaa cccgacagga ctataaagat accaggcgtt tccccctgga   5280
agctccctcg tgcgctctcc tgttccgacc ctgccgctta ccggatacct gtccgccttt   5340
ctcccttcgg gaagcgtggc gctttctcat agctcacgct gtaggtatct cagttcggtg   5400
taggtcgttc gctccaagct gggctgtgtg cacgaacccc ccgttcagcc cgaccgctgc   5460
gccttatccg gtaactatcg tcttgagtcc aacccggtaa gacacgactt atcgccactg   5520
gcagcagcca ctggtaacag gattagcaga gcgaggtatg taggcggtgc tacagagttc   5580
ttgaagtggt ggcctaacta cggctacact agaaggacag tatttggtat ctgcgctctg   5640
ctgaagccag ttaccttcgg aaaaagagtt ggtagctctt gatccggcaa acaaaccacc   5700
```

```
gctggtagcg gtggtttttt tgtttgcaag cagcagatta cgcgcagaaa aaaaggatct   5760

caagaagatc ctttgatctt ttctacgggg tctgacgctc agtggaacga aaactcacgt   5820

taagggattt tggtcatgag attatcaaaa aggatcttca cctagatcct tttaaattaa   5880

aaatgaagtt ttaaatcaat ctaaagtata tatgagtaaa cttggtctga cagttaccaa   5940

tgcttaatca gtgaggcacc tatctcagcg atctgtctat ttcgttcatc catagttgcc   6000

tgactccccg tcgtgtagat aactacgata cgggagggct taccatctgg ccccagtgct   6060

gcaatgatac cgcgagaccc acgctcaccg gctccagatt tatcagcaat aaaccagcca   6120

gccggaaggg ccgagcgcag aagtggtcct gcaactttat ccgcctccat ccagtctatt   6180

aattgttgcc gggaagctag agtaagtagt tcgccagtta atagtttgcg caacgttgtt   6240

ggcattgcta caggcatcgt ggtgtcacgc tcgtcgtttg gtatggcttc attcagctcc   6300

ggttcccaac gatcaaggcg agttacatga tcccccatgt tgtgcaaaaa agcggttagc   6360

tccttcggtc ctccgatcgt tgtcagaagt aagttggccg cagtgttatc actcatggtt   6420

atggcagcac tgcataattc tcttactgtc atgccatccg taagatgctt ttctgtgact   6480

ggtgagtact caaccaagtc attctgagaa tagtgtatgc ggcgaccgag ttgctcttgc   6540

ccggcgtcaa tacgggataa taccgcgcca catagcagaa ctttaaaagt gctcatcatt   6600

ggaaaacgtt cttcggggcg aaaactctca aggatcttac cgctgttgag atccagttcg   6660

atgtaaccca ctcgtgcacc caactgatct tcagcatctt ttactttcac cagcgtttct   6720

gggtgagcaa aaacaggaag gcaaaatgcc gcaaaaaagg gaataagggc gacacggaaa   6780

tgttgaatac tcatactctt cctttttcaa tattattgaa gcatttatca gggttattgt   6840

ctcatgagcg gatacatatt tgaatgtatt tagaaaaata aacaaatagg ggttccgcgc   6900

acatttcccc gaaaagtgcc acctgacgtc taagaaacca ttattatcat gacattaacc   6960

tataaaaata ggcgtatcac gaggcccttt cgtctcgcgc gtttcggtga tgacggtgaa   7020

aacctctgac acatgcagct cccggagacg gtcacagctt gtctgtaagc ggatgccggg   7080

agcagacaag cccgtcaggg cgcgtcagcg ggtgttggcg ggtgtcgggg ctggcttaac   7140

tatgcggcat cagagcagat tgtactgaga gtgcaccata tgcggtgtga aataccgcac   7200

agatgcgtaa ggagaaaata ccgcatcagg cgccattcgc cattcaggct gcgcaactgt   7260

tgggaagggc gatcggtgcg ggcctcttcg ctattacgcc agctggcgaa agggggatgt   7320

gctgcaaggc gattaagttg ggtaacgcca gggttttccc agtcacgacg ttgtaaaacg   7380

acggccagtg aattggattt aggtgacact ata                                7413
```

<210> SEQ ID NO 12
<211> LENGTH: 2358
<212> TYPE: DNA
<213> ORGANISM: Artificial
<220> FEATURE:
<223> OTHER INFORMATION: Synthetic construct

<400> SEQUENCE: 12

```
atgtggttac aaggactact attactaggt actgttgcct gttcaatttc acaatgtgta     60

aatctaacta caagaactca attaccgcct gcctatacta attcttttac aagaggagta    120

tattatcctg ataaagtttt tagatcttct gtattacatt ctacacaaga tttgttttta    180

ccatttttct ctaatgttac ttggtttcat gcaatacatg tatctggaac taatggaaca    240

aaaagatttg ataatccagt attacctttt aatgatggag tttattttgc ttctactgaa    300

aaatctaata taattagagg atggatattt ggaactacat tagattctaa aacacaatct    360
```

```
ctactaattg ttaataatgc aactaatgta gttataaaag tatgtgaatt tcaattttgt    420
aatgatccat ttttgggagt ttattatcat aaaaataata agtcttggat ggaatctgaa    480
ttcagagtat attcttctgc taataattgt acatttgaat atgtatctca accatttttg    540
atggatttgg aaggaaaaca aggaaacttt aaaaatttga gagaatttgt ttttaaaaat    600
attgatggat actttaaaat ctattctaaa catactccaa ttaatctagt aagagatttg    660
cctcaaggat tttctgcttt agaaccacta gtagatttgc ctataggaat taatattact    720
agatttcaaa cattattagc tttacataga tcttatttga cacctggaga ttcttcttct    780
ggatggactg caggagctgc agcttattat gttggatatt tgcaaccaag aacatttttg    840
ttaaaatata atgaaaatgg aactataaca gatgcagttg attgtgcttt agatcctcta    900
tctgaaacta aatgtacttt aaaatctttt actgtagaaa aaggaatcta tcaaacatct    960
aactttagag tacaaccaac tgaatctatt gttagatttc caaatataac aaatctatgt   1020
ccttttggag aagtttttaa tgcaactaga tttgcttctg tatatgcatg gaatagaaaa   1080
agaatatcta attgcgtagc tgattattct gtattatata attctgcatc tttttctact   1140
tttaaatgtt atggagtatc tccaacaaaa ttgaatgatc tatgttttac taatgtttat   1200
gcagattctt ttgtaataag aggagatgaa gttagacaaa tagctcctgg acaaacagga   1260
aaaatagcag attataatta taaattacca gatgatttca ctggatgcgt aattgcttgg   1320
aattctaata atttggattc taaagtagga ggaaattata attatttgta tagattgttt   1380
agaaaatcta atttgaaacc ttttgaaaga gatatttcta cagaaatcta tcaagcagga   1440
tctactccat gtaatggagt tgaaggtttt aattgttatt ttccactaca atcttatgga   1500
tttcaaccta caaatggagt aggatatcaa ccatatagag tagttgtatt atcttttgaa   1560
ttattacatg caccagctac agtatgtgga cctaaaaaat ctactaattt ggttaaaaat   1620
aagtgcgtaa actttaactt taatggatta actggaacag gagttttaac tgaatctaat   1680
aagaaatttt tgccttttca acaatttgga agagatattg ctgatactac agatgcagta   1740
agagatcctc aaactttaga aatattggat attacaccat gttcttttgg aggagtttct   1800
gtaataacac caggaactaa tacatctaat caagttgctg tattatatca agatgttaat   1860
tgtactgaag ttcctgtagc aattcatgct gatcaattaa ctccaacatg gagagtatat   1920
tctactggat ctaatgtttt tcaaacaaga gctggatgtc taattggagc agaacatgta   1980
aataattctt atgaatgtga tattcctata ggagctggaa tatgtgcatc ttatcaaact   2040
caaacaaatt ctccaagaag agctagatct gttgcatctc aatctataat tgcttataca   2100
atgtctttag gagctgaaaa ttctgtagca tattctaata attctattgc aattcctact   2160
aactttacta tttctgtaac tacagaaata ttgccagttt ctatgactaa aacatctgta   2220
gattgtacaa tgtatatatg tggagattct actgaatgtt ctaatttgct actacaatat   2280
ggatcttttt gtactcaatt gaatagagct ttaacaggaa tagcagtaga acaagataaa   2340
aatacacaag aataataa                                                 2358
```

<210> SEQ ID NO 13
<211> LENGTH: 8670
<212> TYPE: DNA
<213> ORGANISM: Artificial
<220> FEATURE:
<223> OTHER INFORMATION: Synthetic construct

<400> SEQUENCE: 13

-continued

```
cgacaatatt ggctattggc cattgcatac gttgtatcta tatcataata tgtacattta     60
tattggctca tgtccaatat gaccgccatg ttgacattga ttattgacta gttattaata    120
gtaatcaatt acgggttcat tagttcatag cccatatatg gagttccgcg ttacataact    180
tacggtaaat ggcccgcctg gctgaccgcc caacgacccc cgcccattga cgtcaataat    240
gacgtatgtt cccatagtaa cgccaatagg gactttccat tgacgtcaat gggtggagta    300
tttacggtaa actgcccact tggcagtaca tcaagtgtat catatgccaa gtccgccccc    360
tattgacgtc aatgacggta aatggcccgc ctggcattat gcccagtaca tgaccttacg    420
ggactttcct acttggcagt acatctacgg tattagtcat cggctattac catggtgatg    480
cggttttggc agtacaccaa tgggcgtgga tagcggtttg actcacgggg atttccaagt    540
ctccacccca ttgacgtcaa tgggagtttg ttttggcacc aaaatcaacg ggactttcca    600
aaatgtcgta ataaccccgc cccgttgacg caaatgggcg gtaggcgtgt acggtgggag    660
gtctatataa gcagagctcg tttagtgaac cgtcagatcg cctggagacg ccatccacgc    720
tgttttgacc tccatagaag acaccgggac cgatccagcc tccgcggccg ggaacggtgc    780
attggaacgc ggattccccg tgccaagagt gacgtaagta ccgcctatag actctatagg    840
cacacccctt tggctcttat gcatgctata ctgtttttgg cttggggcct atacaccccc    900
gcttccttat gctataggtg atggtatagc ttagcctata ggtgtgggtt attgaccatt    960
attgaccact cccctattgg tgacgatact ttccattact aatccataac atggctcttt   1020
gccacaacta tctctattgg ctatatgcca atactctgtc cttcagagac tgacacggac   1080
tctgtatttt tacaggatgg ggtcccattt attatttaca aattcacata tacaacaacg   1140
ccgtcccccg tgcccgcagt ttttattaaa catagcgtgg gatctccacg cgaatctcgg   1200
gtaccgtgtt ccggacatgg gytcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtg tgccgcacaa ggccgtggcg   1380
gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620
tccatgggtc ttttctgcag tcaccatcga tatgtttgtc ttcctggtcc tgctgcctct   1680
ggtctcctca cagtgcgtca atctgactac ccgaactcag ctgccccccg cctacaccaa   1740
ctccttcacc cggggcgtgt actatccaga caaggtgttt agaagctccg tgctgcactc   1800
cacccaggat ctgtttctgc ccttcttttc taatgtgaca tggttccacg ccatccacgt   1860
gagcggcacc aacggcacaa agaggttcga caaccctgtg ctgccattca atgatggcgt   1920
gtactttgcc tccaccgaga agtctaacat catccgcggc tggatctttg gcaccacact   1980
ggactccaag acccagtccc tgctgatcgt gaacaatgcc acaaacgtgg tcatcaaggt   2040
gtgcgagttc cagttttgta acgatccttt cctgggcgtg tactatcaca agaacaataa   2100
gtcttggatg gagagcgagt ttagggtgta ttctagcgcc aacaattgca ccttcgagta   2160
cgtgtcccag ccatttctga tggacctgga gggcaagcag ggcaatttca agaacctgcg   2220
ggagttcgtg tttaagaaca tcgacggcta cttcaagatc tactccaagc acaccccccat   2280
caacctggtg cgggacctgc cacagggctt ctctgccctg gagcctctgg tggatctgcc   2340
aatcggcatc aacatcacac ggtttcagac cctgctggcc ctgcacagaa gctacctgac   2400
```

```
ccctggcgac tcctctagcg gatggacagc aggagcagca gcatactatg tgggctatct   2460
gcagccacgg accttcctgc tgaagtacaa cgagaatggc accatcacag acgccgtgga   2520
ttgcgccctg gatccactgt ctgagacaaa gtgtacactg aagagcttta cagtggagaa   2580
gggcatctat cagaccagca acttcagggt gcagcccaca gagtccatcg tgcgctttcc   2640
aaatatcacc aacctgtgcc ccttcggcga ggtgtttaat gccacaagat tcgccagcgt   2700
gtacgcctgg aacaggaagc gcatctccaa ttgcgtggcc gactattctg tgctgtacaa   2760
ctctgccagc ttctccacct ttaagtgcta tggcgtgagc ccaccaagc tgaacgacct   2820
gtgcttcaca aacgtgtacg ccgattcctt tgtgatcagg ggcgacgagg tgcgccagat   2880
cgcaccagga cagaccggca agatcgcaga ctacaactat aagctgcccg acgatttcac   2940
aggctgcgtg atcgcctgga attccaacaa tctggattct aaagtgggcg gcaactacaa   3000
ttatctgtac aggctgttcc gcaagtctaa cctgaagcct tttgagcggg acatctccac   3060
cgagatctac caggccggct ctacaccatg caacggcgtg gagggcttca attgttattt   3120
tcccctgcag agctacggct tccagcctac caatggcgtg ggctatcagc catacagagt   3180
ggtggtgctg tcttttgagc tgctgcacgc accagcaacc gtgtgcggac ctaagaagag   3240
cacaaatctg gtgaagaaca agtgcgtgaa cttcaacttc aacggcctga ccggaacagg   3300
cgtgctgacc gagtccaaca agaagttcct gccctttcag cagttcggca gggacatcgc   3360
agataccaca gacgccgtgc gcgaccccca gacactggag atcctggata tcacccccttg   3420
cagcttcggc ggcgtgtccg tgatcacccc tggaaccaat acaagcaacc aggtggccgt   3480
gctgtatcag gacgtgaact gtacagaggt gccagtggcc atccacgccg atcagctgac   3540
cccacatgg cgggtgtact ccacaggctc taacgtgttc cagaccagag caggatgcct   3600
gatcggagca gagcacgtga acaatagcta tgagtgcgac atccccatcg gcgccggcat   3660
ctgtgcctcc taccagaccc agacaaactc ccctcggaga gccaggtctg tggcctctca   3720
gagcatcatc gcctatacca tgagcctggg cgccgagaac tccgtggcct acagcaacaa   3780
ttccatcgcc atccccacca atttcacaat ctccgtgacc acagagatcc tgcccgtgag   3840
catgaccaag acaagcgtgg actgcaccat gtatatctgt ggcgattcca cagagtgctc   3900
taatctgctg ctgcagtacg gctctttttg tacacagctg aaccgcgccc tgaccggaat   3960
cgcagtggag caggacaaga atacccagga ggtgttcgcc caggtgaagc agatctacaa   4020
gacacccccct atcaaggact ttggcggctt caactttagc cagatcctgc ctgatccatc   4080
taagcctagc aagaggtcct tcatcgagga cctgctgttt aataaggtga ccctggccga   4140
tgccggcttc atcaagcagt atggcgattg cctgggcgac atcgcagcac gcgacctgat   4200
ctgtgcccag aagtttaacg gcctgacagt gctgccaccc ctgctgaccg atgagatgat   4260
cgcacagtac acctctgccc tgctggccgg aaccatcaca agcggatgga cattcggcgc   4320
aggagccgcc ctgcagatcc cattcgccat gcagatggcc tatcggttta atggcatcgg   4380
cgtgacccag aacgtgctgt acgagaatca gaagctgatc gccaatcagt ttaactccgc   4440
catcggcaag atccaggact ctctgtcctc taccgccagc gccctgggca agctgcagga   4500
tgtggtgaat cagaacgccc aggccctgaa cacactggtg aagcagctga gctccaattt   4560
cggcgccatc tctagcgtgc tgaacgatat cctgagcagg ctggacaagg tggaggccga   4620
ggtgcagatc gaccggctga tcaccggcag actgcagtcc ctgcagacct acgtgacaca   4680
gcagctgatc agggcagcag agatcagggc ctctgccaac ctggcagcaa caaagatgag   4740
```

```
cgagtgcgtg ctgggacagt ccaagagggt ggacttttgt ggcaagggct atcacctgat   4800
gagcttccca cagtccgccc cacacggagt ggtgtttctg cacgtgacct acgtgcctgc   4860
ccaggagaag aatttcacca cagccccagc catctgccac gatggcaagg cacacttccc   4920
aagggagggc gtgtttgtga gcaatggcac acactggttc gtgacccaga gaaactttta   4980
cgagcctcag atcatcacca cagacaacac cttcgtgagc ggcaattgtg acgtggtcat   5040
cggcatcgtg aacaatacag tgtatgatcc cctgcagcct gagctggact ctttcaagga   5100
ggagctggat aagtacttta agaaccacac cagccccgac gtggatctgg gcgacatctc   5160
cggcatcaac gcctctgtgg tgaatatcca gaaggagatc gacagactga atgaggtggc   5220
caagaatctg aacgagagcc tgatcgacct gcaggagctg ggcaagtatg agcagtacat   5280
caagtggcca tggtatatct ggctgggctt catcgccggc ctgatcgcca tcgtgatggt   5340
gacaatcatg ctgtgctgta tgacctcttg ctgtagctgc ctgaagggct gctgttcctg   5400
tggctcttgc tgtaagttcg atgaggacga ttccgagccc gtgctgaagg gcgtgaagct   5460
gcactacaca ggctccggcg ccaccaactt ttctctgctg aagcaggcag gcgacgtgga   5520
ggagaaccca ggacctatgg ccgatagcaa tggcaccatc acagtggagg agctgaagaa   5580
gctgctggag cagtggaacc tggtcatcgg cttcctgttt ctgacctgga tctgcctgct   5640
gcagttcgcc tatgccaatc ggaacagatt tctgtacatc atcaagctga tcttcctgtg   5700
gctgctgtgg ccagtgaccc tggcctgctt cgtgctggcc gccgtgtatc ggatcaactg   5760
gatcacaggc ggcatcgcca tcgccatggc ctgtctggtg ggcctgatgt ggctgagcta   5820
cttcatcgcc tcctttagac tgttcgccag gacccgcagc atgtggtcct ttaatcccga   5880
gacaaacatc ctgctgaatg tgcctctgca cggcaccatc ctgacaaggc cactgctgga   5940
gtccgagctg gtcatcggag ccgtgatcct gaggggacac ctgagaatcg caggacacca   6000
cctgggccgc tgcgatatca aggacctgcc taaggagatc accgtggcca catctaggac   6060
cctgagctac tataagctgg gagccagcca gagggtggca ggcgacagcg gattcgcagc   6120
atattcccgg tacagaatcg gcaactacaa gctgaatacc gatcactcct ctagctccga   6180
caatatcgcc ctgctggtgc agggatctgg agcaacaaac ttcagcctgc tgaagcaggc   6240
cggcgatgtg gaagaaaacc caggacccat gtattctttt gtgagcgagg agacaggcac   6300
actgatcgtg aatagcgtgc tgctgtttct ggccttcgtg gtgtttctgc tggtgacact   6360
ggccatcctg accgccctga gactgtgcgc ctactgctgt aatatcgtga acgtgtctct   6420
ggtgaagccc agcttttacg tgtatagtag ggtgaagaat ctgaactcaa gtagggtgcc   6480
cgatctgctg gtctaagcta gccccgggtg ataaacggac cgcgcaatcc ctaggctgtg   6540
ccttctagtt gccagccatc tgttgtttgc ccctcccccg tgccttcctt gaccctggaa   6600
ggtgccactc ccactgtcct ttcctaataa aatgaggaaa ttgcatcgca ttgtctgagt   6660
aggtgtcatt ctattctggg gggtggggtg gggcaggaca gcaaggggga ggattgggaa   6720
gacaatagca ggcatgctgg ggatgcggtg ggctctatat aaaaaacgcc cggcggcaac   6780
cgagcgttct gaacgctaga gtcgacaaat tcagaagaac tcgtcaagaa ggcgatagaa   6840
ggcgatgcgc tgcgaatcgg gagcggcgat accgtaaagc acgaggaagc ggtcagccca   6900
ttcgccgcca agctcttcag caatatcacg ggtagccaac gctatgtcct gatagcggtc   6960
tgccacaccc agccggccac agtcgatgaa tccagaaaag cggccatttt ccaccatgat   7020
attcggcaag caggcatcgc catgggtcac gacgagatcc tcgccgtcgg gcatgctcgc   7080
cttgagcctg gcgaacagtt cggctggcgc gagcccctga tgctcttcgt ccagatcatc   7140
```

ctgatcgaca agaccggctt ccatccgagt acgtgctcgc tcgatgcgat gtttcgcttg 7200
gtggtcgaat gggcaggtag ccggatcaag cgtatgcagc cgccgcattg catcagccat 7260
gatggatact ttctcggcag gagcaaggtg agatgacagg agatcctgcc ccggcacttc 7320
gcccaatagc agccagtccc ttcccgcttc agtgacaacg tcgagcacag ctgcgcaagg 7380
aacgcccgtc gtggccagcc acgatagccg cgctgcctcg tcttgcagtt cattcagggc 7440
accggacagg tcggtcttga caaaaagaac cgggcgcccc tgcgctgaca gccggaacac 7500
ggcggcatca gagcagccga ttgtctgttg tgcccagtca tagccgaata gcctctccac 7560
ccaagcggcc ggagaacctg cgtgcaatcc atcttgttca atcatgcgaa acgatcctca 7620
tcctgtctct tgatcagatc ttgatcccct gcgccatcag atccttggcg gcaagaaagc 7680
catccagttt actttgcagg gcttcccaac cttaccagag ggcgccccag ctggcaattc 7740
cggttcgctt gctgtccata aaaccgccca gtctagctat cgccatgtaa gcccactgca 7800
agctacctgc tttctctttg cgcttgcgtt ttcccttgtc cagatagccc agtagctgac 7860
attcatccgg ggtcagcacc gtttctgcgg actggctttc tacgtgaaaa ggatctaggt 7920
gaagatcctt tttgataatc tcatgaccaa aatcccttaa cgtgagtttt cgttccactg 7980
agcgtcagac cccgtagaaa agatcaaagg atcttcttga gatccttttt ttctgcgcgt 8040
aatctgctgc ttgcaaacaa aaaaaccacc gctaccagcg gtggtttgtt tgccggatca 8100
agagctacca actctttttc cgaaggtaac tggcttcagc agagcgcaga taccaaatac 8160
tgttcttcta gtgtagccgt agttaggcca ccacttcaag aactctgtag caccgcctac 8220
atacctcgct ctgctaatcc tgttaccagt ggctgctgcc agtggcgata agtcgtgtct 8280
taccgggttg gactcaagac gatagttacc ggataaggcg cagcggtcgg gctgaacggg 8340
gggttcgtgc acacagccca gcttggagcg aacgacctac acccgaactg agatacctac 8400
agcgtgagct atgagaaagc gccacgcttc ccgaagggag aaaggcggac aggtatccgg 8460
taagcggcag ggtcggaaca ggagagcgca cgagggagct tccaggggga aacgcctggt 8520
atctttatag tcctgtcggg tttcgccacc tctgacttga gcgtcgattt ttgtgatgct 8580
cgtcaggggg gcggagccta tggaaaaacg ccagcaacgc ggccttttta cggttcctgg 8640
ccttttgctg gccttttgct cacatgttgt 8670

<210> SEQ ID NO 14
<211> LENGTH: 4845
<212> TYPE: DNA
<213> ORGANISM: Artificial
<220> FEATURE:
<223> OTHER INFORMATION: Synthetic construct

<400> SEQUENCE: 14
atgtttgtct tcctggtcct gctgcctctg gtctcctcac agtgcgtcaa tctgactacc 60
cgaactcagc tgcccccCgc ctacaccaac tccttcaccc ggggcgtgta ctatccagac 120
aaggtgttta gaagctccgt gctgcactcc acccaggatc tgtttctgcc cttcttttct 180
aatgtgacat ggttccacgc catccacgtg agcggcacca acggcacaaa gaggttcgac 240
aaccctgtgc tgccattcaa tgatggcgtg tactttgcct ccaccgagaa gtctaacatc 300
atccgcggct ggatctttgg caccacactg gactccaaga cccagtccct gctgatcgtg 360
aacaatgcca caaacgtggt catcaaggtg tgcgagttcc agttttgtaa cgatcctttc 420
ctgggcgtgt actatcacaa gaacaataag tcttggatgg agagcgagtt tagggtgtat 480

```
tctagcgcca acaattgcac cttcgagtac gtgtcccagc catttctgat ggacctggag    540
ggcaagcagg gcaatttcaa gaacctgcgg gagttcgtgt ttaagaacat cgacggctac    600
ttcaagatct actccaagca cacccccatc aacctggtgc gggacctgcc acagggcttc    660
tctgccctgg agcctctggt ggatctgcca atcggcatca acatcacacg gtttcagacc    720
ctgctggccc tgcacagaag ctacctgacc cctggcgact cctctagcgg atggacagca    780
ggagcagcag catactatgt gggctatctg cagccacgga ccttcctgct gaagtacaac    840
gagaatggca ccatcacaga cgccgtggat tgcgccctgg atccactgtc tgagacaaag    900
tgtacactga agagctttac agtggagaag ggcatctatc agaccagcaa cttcagggtg    960
cagcccacag agtccatcgt gcgctttcca aatatcacca acctgtgccc cttcggcgag   1020
gtgtttaatg ccacaagatt cgccagcgtg tacgcctgga acaggaagcg catctccaat   1080
tgcgtggccg actattctgt gctgtacaac tctgccagct tctccacctt taagtgctat   1140
ggcgtgagcc ccaccaagct gaacgacctg tgcttcacaa acgtgtacgc cgattccttt   1200
gtgatcaggg gcgacgaggt gcgccagatc gcaccaggac agaccggcaa gatcgcagac   1260
tacaactata agctgcccga cgatttcaca ggctgcgtga tcgcctggaa ttccaacaat   1320
ctggattcta aagtgggcgg caactacaat tatctgtaca ggctgttccg caagtctaac   1380
ctgaagcctt ttgagcggga catctccacc gagatctacc aggccggctc tacaccatgc   1440
aacggcgtgg agggcttcaa ttgttatttt cccctgcaga gctacggctt ccagcctacc   1500
aatggcgtgg gctatcagcc atacagagtg gtggtgctgt cttttgagct gctgcacgca   1560
ccagcaaccg tgtgcggacc taagaagagc acaaatctgg tgaagaacaa gtgcgtgaac   1620
ttcaacttca acggcctgac cggaacaggc gtgctgaccg agtccaacaa gaagttcctg   1680
ccctttcagc agttcggcag ggacatcgca gataccacag acgccgtgcg cgacccccag   1740
acactggaga tcctggatat caccccttgc agcttcggcg gcgtgtccgt gatcacccct   1800
ggaaccaata caagcaacca ggtggccgtg ctgtatcagg acgtgaactg tacagaggtg   1860
ccagtggcca tccacgccga tcagctgacc cccacatggc gggtgtactc cacaggctct   1920
aacgtgttcc agaccagagc aggatgcctg atcggagcag agcacgtgaa caatagctat   1980
gagtgcgaca tccccatcgg cgccggcatc tgtgcctcct accagaccca gacaaactcc   2040
cctcggagag ccaggtctgt ggcctctcag agcatcatcg cctataccat gagcctgggc   2100
gccgagaact ccgtggccta cagcaacaat tccatcgcca tccccaccaa tttcacaatc   2160
tccgtgacca cagagatcct gcccgtgagc atgaccaaga caagcgtgga ctgcaccatg   2220
tatatctgtg gcgattccac agagtgctct aatctgctgc tgcagtacgg ctctttttgt   2280
acacagctga accgcgccct gaccggaatc gcagtggagc aggacaagaa tacccaggag   2340
gtgttcgccc aggtgaagca gatctacaag acaccccccta tcaaggactt tggcggcttc   2400
aactttagcc agatcctgcc tgatccatct aagcctagca agaggtcctt catcgaggac   2460
ctgctgttta ataaggtgac cctggccgat gccggcttca tcaagcagta tggcgattgc   2520
ctgggcgaca tcgcagcacg cgacctgatc tgtgcccaga agtttaacgg cctgacagtg   2580
ctgccacccc tgctgaccga tgagatgatc gcacagtaca cctctgccct gctggccgga   2640
accatcacaa gcggatggac attcggcgca ggagccgccc tgcagatccc attcgccatg   2700
cagatggcct atcggtttaa tggcatcggc gtgacccaga acgtgctgta cgagaatcag   2760
aagctgatcg ccaatcagtt taactccgcc atcggcaaga tccaggactc tctgtcctct   2820
accgccagcg ccctgggcaa gctgcaggat gtggtgaatc agaacgccca ggccctgaac   2880
```

```
acactggtga agcagctgag ctccaatttc ggcgccatct ctagcgtgct gaacgatatc   2940

ctgagcaggc tggacaaggt ggaggccgag gtgcagatcg accggctgat caccggcaga   3000

ctgcagtccc tgcagaccta cgtgacacag cagctgatca gggcagcaga gatcagggcc   3060

tctgccaacc tggcagcaac aaagatgagc gagtgcgtgc tgggacagtc caagagggtg   3120

gacttttgtg gcaagggcta tcacctgatg agcttcccac agtccgcccc acacggagtg   3180

gtgtttctgc acgtgaccta cgtgcctgcc caggagaaga atttcaccac agccccagcc   3240

atctgccacg atggcaaggc acacttccca agggagggcg tgtttgtgag caatggcaca   3300

cactggttcg tgacccagag aaacttttac gagcctcaga tcatcaccac agacaacacc   3360

ttcgtgagcg gcaattgtga cgtggtcatc ggcatcgtga acaatacagt gtatgatccc   3420

ctgcagcctg agctggactc tttcaaggag gagctggata agtactttaa gaaccacacc   3480

agccccgacg tggatctggg cgacatctcc ggcatcaacg cctctgtggt gaatatccag   3540

aaggagatcg acagactgaa tgaggtggcc aagaatctga acgagagcct gatcgacctg   3600

caggagctgg gcaagtatga gcagtacatc aagtggccat ggtatatctg gctgggcttc   3660

atcgccggcc tgatcgccat cgtgatggtg acaatcatgc tgtgctgtat gacctcttgc   3720

tgtagctgcc tgaagggctg ctgttcctgt ggctcttgct gtaagttcga tgaggacgat   3780

tccgagcccg tgctgaaggg cgtgaagctg cactacacag gctccggcgc caccaacttt   3840

tctctgctga agcaggcagg cgacgtggag gagaacccag gacctatggc cgatagcaat   3900

ggcaccatca cagtggagga gctgaagaag ctgctggagc agtggaacct ggtcatcggc   3960

ttcctgtttc tgacctggat ctgcctgctg cagttcgcct atgccaatcg gaacagattt   4020

ctgtacatca tcaagctgat cttcctgtgg ctgctgtggc cagtgaccct ggcctgcttc   4080

gtgctggccg ccgtgtatcg gatcaactgg atcacaggcg gcatcgccat cgccatggcc   4140

tgtctggtgg gcctgatgtg gctgagctac ttcatcgcct cctttagact gttcgccagg   4200

acccgcagca tgtggtcctt taatcccgag acaaacatcc tgctgaatgt gcctctgcac   4260

ggcaccatcc tgacaaggcc actgctggag tccgagctgg tcatcggagc cgtgatcctg   4320

aggggacacc tgagaatcgc aggacaccac ctgggccgct gcgatatcaa ggacctgcct   4380

aaggagatca ccgtggccac atctaggacc ctgagctact ataagctggg agccagccag   4440

agggtggcag gcgacagcgg attcgcagca tattcccggt acagaatcgg caactacaag   4500

ctgaataccg atcactcctc tagctccgac aatatcgccc tgctggtgca gggatctgga   4560

gcaacaaact tcagcctgct gaagcaggcc ggcgatgtgg aagaaaaccc aggacccatg   4620

tattcttttg tgagcgagga gacaggcaca ctgatcgtga atagcgtgct gctgtttctg   4680

gccttcgtgg tgtttctgct ggtgacactg gccatcctga ccgccctgag actgtgcgcc   4740

tactgctgta atatcgtgaa cgtgtctctg gtgaagccca gcttttacgt gtatagtagg   4800

gtgaagaatc tgaactcaag tagggtgccc gatctgctgg tctaa                 4845
```

<210> SEQ ID NO 15
<211> LENGTH: 7131
<212> TYPE: DNA
<213> ORGANISM: Artificial
<220> FEATURE:
<223> OTHER INFORMATION: Synthetic construct

<400> SEQUENCE: 15

```
cgacaatatt ggctattggc cattgcatac gttgtatcta tatcataata tgtacattta     60
```

-continued

```
tattggctca tgtccaatat gaccgccatg ttgacattga ttattgacta gttattaata    120
gtaatcaatt acgggttcat tagttcatag cccatatatg gagttccgcg ttacataact    180
tacggtaaat ggcccgcctg gctgaccgcc caacgacccc cgcccattga cgtcaataat    240
gacgtatgtt cccatagtaa cgccaatagg gactttccat tgacgtcaat gggtggagta    300
tttacggtaa actgcccact tggcagtaca tcaagtgtat catatgccaa gtccgccccc    360
tattgacgtc aatgacggta aatggcccgc ctggcattat gcccagtaca tgaccttacg    420
ggactttcct acttggcagt acatctacgg tattagtcat cggctattac catggtgatg    480
cggttttggc agtacaccaa tgggcgtgga tagcggtttg actcacgggg atttccaagt    540
ctccacccca ttgacgtcaa tgggagtttg ttttggcacc aaaatcaacg ggactttcca    600
aaatgtcgta ataaccccgc cccgttgacg caaatgggcg gtaggcgtgt acggtgggag    660
gtctatataa gcagagctcg tttagtgaac cgtcagatcg cctggagacg ccatccacgc    720
tgttttgacc tccatagaag acaccgggac cgatccagcc tccgcggccg ggaacggtgc    780
attggaacgc ggattccccg tgccaagagt gacgtaagta ccgcctatag actctatagg    840
cacacccctt tggctcttat gcatgctata ctgtttttgg cttggggcct atacaccccc    900
gcttccttat gctataggtg atggtatagc ttagcctata ggtgtgggtt attgaccatt    960
attgaccact cccctattgg tgacgatact ttccattact aatccataac atggctcttt   1020
gccacaacta tctctattgg ctatatgcca atactctgtc cttcagagac tgacacggac   1080
tctgtatttt tacaggatgg ggtcccattt attatttaca aattcacata tacaacaacg   1140
ccgtcccccg tgcccgcagt ttttattaaa catagcgtgg gatctccacg cgaatctcgg   1200
gtaccgtgtt ccggacatgg gytcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtg tgccgcacaa ggccgtggcg   1380
gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620
tccatgggtc ttttctgcag tcaccatcga tatgttcgtg tttctggtct tgctgcccct   1680
ggtgtccagc cagtgcgtca acctgacaac cagaacccaa ctgcccccag cctacaccaa   1740
ctccttcaca agaggcgtgt attaccctga caaggtgttt cggagcagcg tgctgcactc   1800
cacccaggac ttgtttctgc ctttcttcag caacgtgacc tggttccacg ccatccacgt   1860
gagcggcacc aatggaacca agagattcga caatcctgtg ctccccttca acgacggcgt   1920
ctacttcgcc agcaccgaaa agtctaacat catcaggggc tggatcttcg gcacaacact   1980
ggacagcaag acccagtccc tgctgattgt gaacaacgcc acaaatgtgg tgatcaaggt   2040
gtgcgaattc cagttttgca acgatccctt tttgggcgtg tattaccaca agaacaacaa   2100
gagctggatg gaaagcgaat tccgggtgta cagcagcgcc aacaactgta ccttcgaata   2160
cgtgagccag cctttcctga tggacctgga aggcaaacag ggcaacttca agaacctgcg   2220
ggaattcgtg ttcaagaaca tcgacgggta cttcaagatc tactctaagc acacccctat   2280
caacctggtc agagacctgc ctcaaggctt tagcgccctg gaacctctgg tggacctgcc   2340
gatcggcatt aacatcacca gattccagac actgctggct ctgcacagat cctacctgac   2400
ccctggcgat agctccagcg gctggaccgc cggagctgct gcttactacg tgggctacct   2460
```

```
gcaaccaaga acctttctgc tgaagtacaa cgaaaacggc accatcacag acgccgtgga   2520
ctgcgccctg gatcctctca gcgagacaaa gtgtaccctc aagtcgttca ccgtggaaaa   2580
gggcatatac cagacctcta acttcagagt gcagcctaca gagagcatcg taagattccc   2640
taacatcacc aacctctgtc cctttggcga ggttttcaac gccaccagat tcgccagcgt   2700
atacgcctgg aacagaaaga gaatctccaa ttgcgtggcc gactacagcg tgctgtacaa   2760
ttctgcatct tttagcacat tcaaatgcta cggcgtgtcc ccaaccaagc taaacgacct   2820
gtgcttcacc aacgtctacg ccgactcatt tgtgattcgg ggcgacgaag tgcgccagat   2880
cgcccctggc cagaccggca aaatcgccga ttacaactac aagctgccag atgacttcac   2940
cggctgtgtg atcgcctgga acagcaataa tctggacagc aaggttggag gaaactacaa   3000
ctacctgtat cggctgttca gaaagagcaa cctgaagcct ttcgagcggg acatcagtac   3060
agagatctac caggctggct ccacgccatg caatggcgtg gagggcttca actgctactt   3120
ccccctgcag agctatggct tccagcccac aaacggcgtg ggctaccagc cttacagagt   3180
ggtggtgctg agcttcgagc tgcttcatgc ccctgctaca gtctgcggcc ctaagaaaag   3240
caccaatctg gtgaaaaata aatgcgtgaa cttcaacttt aacggcctga ccggaactgg   3300
agtccttacc gagagcaaca agaagttcct gccttttcag cagttcggaa gagatatcgc   3360
cgacaccacc gatgccgtgc gggatcccca gaccctggag atcctggata tcacccccctg   3420
cagcttcggc ggcgtgtctg tgatcacgcc cggcaccaac accagcaacc aggtggccgt   3480
tctgtaccag gatgtgaatt gcaccgaggt gcctgtggcc atccacgccg atcagctgac   3540
acccacctgg cgggtgtata gcaccggatc taatgtgttc cagacaagag ccggatgtct   3600
gatcggagcc gaacacgtga acaatagcta cgagtgtgac atccctatcg gcgccggaat   3660
ctgcgccagc taccaaacac agactaacag ccctcggaga gccagaagcg tggcctctca   3720
gtcaatcatc gcctacacca tgagcctggg cgccgagaac agcgtggcct acagcaacaa   3780
cagcatcgcg attcctacca actttaccat cagcgttacg acagagatcc tgcctgtgag   3840
catgaccaaa acctccgtgg actgcacaat gtacatctgc ggcgacagca ccgagtgcag   3900
caacctgctg ctgcaatacg gaagcttctg cacccagctg aatcgggccc tgaccggcat   3960
cgccgttgaa caggacaaga acactcagga ggtgtttgcc caggtcaagc agatatacaa   4020
gacccctcct atcaaggact tcggcggatt taacttttct cagatcctgc ctgaccccag   4080
caaaccttcc aaaagaagct tcatcgaaga cctgctgttc aacaaggtga cactcgccga   4140
cgccggattt atcaagcagt acggcgattg cctgggagac atcgccgcta gagatctgat   4200
ctgcgcccaa aaattcaacg gcctgacagt gctgcctcca ctgctgacag acgagatgat   4260
cgcccaatac acctctgccc tgctggccgg aaccatcaca agcggctgga ccttcggcgc   4320
cggcgcagcc ctgcaaatcc ccttcgccat gcagatggct tatagattca atggcatcgg   4380
cgtcacacag aacgtgctgt acgagaatca gaagctgatc gccaaccagt tcaactctgc   4440
tatcggcaaa atccaggatt cactaagcag caccgcctca gccctgggca aactgcagga   4500
tgtggttaat cagaatgccc aggccctgaa cacactggtg aagcaactgt ccagcaattt   4560
cggggctatt agcagtgtgc tgaacgatat cctgagtagg ctggatccac ctgaggccga   4620
agtgcagatc gaccggctca tcacagggag actgcagtcc ctgcagacct acgtgaccca   4680
gcagctcatc agagctgctg agatacgggc ctctgctaat ctggccgcta ccaaaatgag   4740
cgagtgcgtg ctgggccagt ctaagcgggt agatttctgc ggcaagggct atcacctgat   4800
```

-continued

```
gagcttccca cagagcgctc cgcacggcgt agtgttctta catgtgacat acgtccctgc   4860
ccaggagaag aacttcacca cagctcctgc catctgtcac gatggcaagg cccacttccc   4920
cagagagggc gtgttcgtgt ccaacggcac ccactggttc gtgacgcagc ggaacttcta   4980
cgagcctcag attatcacaa cagacaacac cttcgtgtct ggaaattgcg acgttgtcat   5040
cggcatcgtc aacaacaccg tgtacgaccc actgcagcct gagctggaca gcttcaagga   5100
agagctggac aagtacttca agaaccacac cagccccgat gtggacctgg gcgacatcag   5160
cggaatcaac gcctctgtgg tgaacatcca gaaggaaatc gacagactga acgaggtggc   5220
caagaacctg aatgagtcac ttattgacct gcaggaactg ggcaaatacg aacagtacat   5280
caaatggccc tggtacatct ggctgggatt catcgctggc ctgatcgcca tcgtgatggt   5340
gacaatcatg ctgtgttgca tgacatcttg ttgtagctgc ctgaagggct gctgtagctg   5400
tggctcttgt tgcaagttcg acgaggacga cagcgagccc gtgctcaagg gagtgaagct   5460
gcactatacc taaaccatga tattcggcaa gcaggcatcg ccatgggtca cgacgagatc   5520
ctcgccgtcg ggcatgctcg ccttgagcct ggcgaacagt tcggctggcg cgagcccctg   5580
atgctcttcg tccagatcat cctgatcgac aagaccggct tccatccgag tacgtgctcg   5640
ctcgatgcga tgtttcgctt ggtggtcgaa tgggcaggta gccggatcaa gcgtatgcag   5700
ccgccgcatt gcatcagcca tgatggatac tttctcggca ggagcaaggt gagatgacag   5760
gagatcctgc cccggcactt cgcccaatag cagccagtcc cttcccgctt cagtgacaac   5820
gtcgagcaca gctgcgcaag gaacgcccgt cgtggccagc cacgatagcc gcgctgcctc   5880
gtcttgcagt tcattcaggg caccggacag gtcggtcttg acaaaaagaa ccgggcgccc   5940
ctgcgctgac agccggaaca cggcggcatc agagcagccg attgtctgtt gtgcccagtc   6000
atagccgaat agcctctcca cccaagcggc cggagaacct gcgtgcaatc catcttgttc   6060
aatcatgcga aacgatcctc atcctgtctc ttgatcagat cttgatcccc tgcgccatca   6120
gatccttggc ggcaagaaag ccatccagtt tactttgcag ggcttcccaa ccttaccaga   6180
gggcgcccca gctggcaatt ccggttcgct tgctgtccat aaaaccgccc agtctagcta   6240
tcgccatgta agcccactgc aagctacctg ctttctcttt gcgcttgcgt tttcccttgt   6300
ccagatagcc cagtagctga cattcatccg gggtcagcac cgtttctgcg gactggcttt   6360
ctacgtgaaa aggatctagg tgaagatcct ttttgataat ctcatgacca aaatccctta   6420
acgtgagttt tcgttccact gagcgtcaga ccccgtagaa aagatcaaag gatcttcttg   6480
agatcctttt tttctgcgcg taatctgctg cttgcaaaca aaaaaaccac cgctaccagc   6540
ggtggtttgt ttgccggatc aagagctacc aactcttttt ccgaaggtaa ctggcttcag   6600
cagagcgcag ataccaaata ctgttcttct agtgtagccg tagttaggcc accacttcaa   6660
gaactctgta gcaccgccta catacctcgc tctgctaatc ctgttaccag tggctgctgc   6720
cagtggcgat aagtcgtgtc ttaccgggtt ggactcaaga cgatagttac cggataaggc   6780
gcagcggtcg ggctgaacgg ggggttcgtg cacacagccc agcttggagc gaacgaccta   6840
cacccgaact gagataccta cagcgtgagc tatgagaaag cgccacgctt cccgaaggga   6900
gaaaggcgga caggtatccg gtaagcggca gggtcggaac aggagagcgc acgagggagc   6960
ttccaggggg aaacgcctgg tatctttata gtcctgtcgg gtttcgccac ctctgacttg   7020
agcgtcgatt tttgtgatgc tcgtcagggg ggcggagcct atggaaaaac gccagcaacg   7080
cggccctttt acggttcctg gccttttgct ggccttttgc tcacatgttg t             7131
```

<210> SEQ ID NO 16
<211> LENGTH: 3822
<212> TYPE: DNA
<213> ORGANISM: Artificial
<220> FEATURE:
<223> OTHER INFORMATION: Synthetic construct

<400> SEQUENCE: 16
atgttcgtgt ttctggtctt gctgcccctg gtgtccagcc agtgcgtcaa cctgacaacc 60
agaacccaac tgcccccagc ctacaccaac tccttcacaa gaggcgtgta ttaccctgac 120
aaggtgtttc ggagcagcgt gctgcactcc acccaggact tgtttctgcc tttcttcagc 180
aacgtgacct ggttccacgc catccacgtg agcggcacca atggaaccaa gagattcgac 240
aatcctgtgc tccccttcaa cgacggcgtc tacttcgcca gcaccgaaaa gtctaacatc 300
atcaggggct ggatcttcgg cacaacactg gacagcaaga cccagtccct gctgattgtg 360
aacaacgcca caaatgtggt gatcaaggtg tgcgaattcc agttttgcaa cgatcccttt 420
ttgggcgtgt attaccacaa gaacaacaag agctggatgg aaagcgaatt ccgggtgtac 480
agcagcgcca acaactgtac cttcgaatac gtgagccagc ctttcctgat ggacctggaa 540
ggcaaacagg gcaacttcaa gaacctgcgg gaattcgtgt tcaagaacat cgacgggtac 600
ttcaagatct actctaagca cacccctatc aacctggtca gagacctgcc tcaaggcttt 660
agcgccctgg aacctctggt ggacctgccg atcggcatta acatcaccag attccagaca 720
ctgctggctc tgcacagatc ctacctgacc cctggcgata gctccagcgg ctggaccgcc 780
ggagctgctg cttactacgt gggctacctg caaccaagaa cctttctgct gaagtacaac 840
gaaaacggca ccatcacaga cgccgtggac tgcgccctgg atcctctcag cgagacaaag 900
tgtaccctca agtcgttcac cgtggaaaag ggcatatacc agacctctaa cttcagagtg 960
cagcctacag agagcatcgt aagattccct aacatcacca acctctgtcc ctttggcgag 1020
gttttcaacg ccaccagatt cgccagcgta tacgcctgga acagaaagag aatctccaat 1080
tgcgtggccg actacagcgt gctgtacaat tctgcatctt ttagcacatt caaatgctac 1140
ggcgtgtccc caaccaagct aaacgacctg tgcttcacca acgtctacgc cgactcattt 1200
gtgattcggg gcgacgaagt gcgccagatc gcccctggcc agaccggcaa aatcgccgat 1260
tacaactaca agctgccaga tgacttcacc ggctgtgtga tcgcctggaa cagcaataat 1320
ctggacagca aggttggagg aaactacaac tacctgtatc ggctgttcag aaagagcaac 1380
ctgaagcctt tcgagcggga catcagtaca gagatctacc aggctggctc cacgccatgc 1440
aatggcgtgg agggcttcaa ctgctacttc cccctgcaga gctatggctt ccagcccaca 1500
aacggcgtgg gctaccagcc ttacagagtg gtggtgctga gcttcgagct gcttcatgcc 1560
cctgctacag tctgcggccc taagaaaagc accaatctgg tgaaaaataa atgcgtgaac 1620
ttcaacttta acggcctgac cggaactgga gtccttaccg agagcaacaa gaagttcctg 1680
ccttttcagc agttcggaag agatatcgcc gacaccaccg atgccgtgcg ggatccccag 1740
accctggaga tcctggatat caccccctgc agcttcggcg gcgtgtctgt gatcacgccc 1800
ggcaccaaca ccagcaacca ggtggccgtt ctgtaccagg atgtgaattg caccgaggtg 1860
cctgtggcca tccacgccga tcagctgaca cccacctggc gggtgtatag caccggatct 1920
aatgtgttcc agacaagagc cggatgtctg atcggagccg aacacgtgaa caatagctac 1980
gagtgtgaca tccctatcgg cgccggaatc tgcgccagct accaaacaca gactaacagc 2040
cctcggagag ccagaagcgt ggcctctcag tcaatcatcg cctacaccat gagcctgggc 2100

```
gccgagaaca gcgtggccta cagcaacaac agcatcgcga ttcctaccaa ctttaccatc   2160

agcgttacga cagagatcct gcctgtgagc atgaccaaaa cctccgtgga ctgcacaatg   2220

tacatctgcg gcgacagcac cgagtgcagc aacctgctgc tgcaatacgg aagcttctgc   2280

acccagctga atcgggccct gaccggcatc gccgttgaac aggacaagaa cactcaggag   2340

gtgtttgccc aggtcaagca gatatacaag acccctccta tcaaggactt cggcggattt   2400

aacttttctc agatcctgcc tgaccccagc aaaccttcca aaagaagctt catcgaagac   2460

ctgctgttca acaaggtgac actcgccgac gccggattta tcaagcagta cggcgattgc   2520

ctgggagaca tcgccgctag agatctgatc tgcgcccaaa aattcaacgg cctgacagtg   2580

ctgcctccac tgctgacaga cgagatgatc gcccaataca cctctgccct gctggccgga   2640

accatcacaa gcggctggac cttcggcgcc ggcgcagccc tgcaaatccc cttcgccatg   2700

cagatggctt atagattcaa tggcatcggc gtcacacaga acgtgctgta cgagaatcag   2760

aagctgatcg ccaaccagtt caactctgct atcggcaaaa tccaggattc actaagcagc   2820

accgcctcag ccctgggcaa actgcaggat gtggttaatc agaatgccca ggccctgaac   2880

acactggtga agcaactgtc cagcaatttc ggggctatta gcagtgtgct gaacgatatc   2940

ctgagtaggc tggatccacc tgaggccgaa gtgcagatcg accggctcat cacagggaga   3000

ctgcagtccc tgcagaccta cgtgacccag cagctcatca gagctgctga gatacgggcc   3060

tctgctaatc tggccgctac caaaatgagc gagtgcgtgc tgggccagtc taagcgggta   3120

gatttctgcg gcaagggcta tcacctgatg agcttcccac agagcgctcc gcacggcgta   3180

gtgttcttac atgtgacata cgtccctgcc caggagaaga acttcaccac agctcctgcc   3240

atctgtcacg atggcaaggc ccacttcccc agagagggcg tgttcgtgtc caacggcacc   3300

cactggttcg tgacgcagcg gaacttctac gagcctcaga ttatcacaac agacaacacc   3360

ttcgtgtctg gaaattgcga cgttgtcatc ggcatcgtca acaacaccgt gtacgaccca   3420

ctgcagcctg agctggacag cttcaaggaa gagctggaca agtacttcaa gaaccacacc   3480

agccccgatg tggacctggg cgacatcagc ggaatcaacg cctctgtggt gaacatccag   3540

aaggaaatcg acagactgaa cgaggtggcc aagaacctga atgagtcact tattgacctg   3600

caggaactgg gcaaatacga acagtacatc aaatggccct ggtacatctg gctgggattc   3660

atcgctggcc tgatcgccat cgtgatggtg acaatcatgc tgtgttgcat gacatcttgt   3720

tgtagctgcc tgaagggctg ctgtagctgt ggctcttgtt gcaagttcga cgaggacgac   3780

agcgagcccg tgctcaaggg agtgaagctg cactatacct aa                      3822
```

<210> SEQ ID NO 17
<211> LENGTH: 7038
<212> TYPE: DNA
<213> ORGANISM: Artificial
<220> FEATURE:
<223> OTHER INFORMATION: Synthetic construct

<400> SEQUENCE: 17

```
cgacaatatt ggctattggc cattgcatac gttgtatcta tatcataata tgtacattta     60

tattggctca tgtccaatat gaccgccatg ttgacattga ttattgacta gttattaata    120

gtaatcaatt acgggttcat tagttcatag cccatatatg gagttccgcg ttacataact    180

tacggtaaat ggcccgcctg gctgaccgcc caacgacccc cgcccattga cgtcaataat    240

gacgtatgtt cccatagtaa cgccaatagg gactttccat tgacgtcaat gggtggagta    300

tttacggtaa actgcccact tggcagtaca tcaagtgtat catatgccaa gtccgccccc    360
```

```
tattgacgtc aatgacggta aatggcccgc ctggcattat gcccagtaca tgaccttacg    420
ggactttcct acttggcagt acatctacgg tattagtcat cggctattac catggtgatg    480
cggttttggc agtacaccaa tgggcgtgga tagcggtttg actcacgggg atttccaagt    540
ctccacccca ttgacgtcaa tgggagtttg ttttggcacc aaaatcaacg ggactttcca    600
aaatgtcgta ataaccccgc cccgttgacg caaatgggcg gtaggcgtgt acggtgggag    660
gtctatataa gcagagctcg tttagtgaac cgtcagatcg cctggagacg ccatccacgc    720
tgttttgacc tccatagaag acaccgggac cgatccagcc tccgcggccg ggaacggtgc    780
attggaacgc ggattccccg tgccaagagt gacgtaagta ccgcctatag actctatagg    840
cacacccctt tggctcttat gcatgctata ctgtttttgg cttggggcct atacaccccc    900
gcttccttat gctataggtg atggtatagc ttagcctata ggtgtgggtt attgaccatt    960
attgaccact cccctattgg tgacgatact ttccattact aatccataac atggctcttt   1020
gccacaacta tctctattgg ctatatgcca atactctgtc cttcagagac tgacacggac   1080
tctgtatttt tacaggatgg ggtcccattt attatttaca aattcacata tacaacaacg   1140
ccgtcccccg tgcccgcagt ttttattaaa catagcgtgg gatctccacg cgaatctcgg   1200
gtaccgtgtt ccggacatgg gytcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtg tgccgcacaa ggccgtggcg   1380
gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620
tccatgggtc ttttctgcag tcaccatcga tatgtggctg cagggcctgc tgctgctggg   1680
caccgtggca tgcagtatca gccaatgtgt gaacctgacc accagaaccc aactgcctcc   1740
tgcctacacc aactctttca ccagaggcgt gtactaccct gacaaggtgt tcagaagcag   1800
cgtgctgcat tctacccagg acctgtttct gccattcttc agcaacgtca cctggttcca   1860
cgccatccac gtgtctggca ccaatggcac taagagattc gacaaccccg tgctgccttt   1920
caacgacggc gtgtactttg cctcaactga gaagagcaac atcatcagag gatggatctt   1980
cggcaccaca cttgactcaa agacacagtc actgctgatc gtgaacaatg ctaccaatgt   2040
ggtgatcaag gtgtgtgaat tccagttttg caacgatcct ttcctgggtg tatactacca   2100
caagaacaac aagtcttgga tggagagcga gttccgggtg tatagtagcg ccaacaactg   2160
caccttcgaa tacgtgagcc agcctttcct catggacctg gaaggcaagc aaggcaactt   2220
caagaacctg agagagttcg tgtttaagaa cattgatggc tacttcaaga tctacagcaa   2280
gcacaccccc atcaacctgg tgcgggacct ccctcagggc ttcagcgccc tggaaccctt   2340
ggttgatctg ccaattggca tcaatatcac tcggttccaa accctgctgg ccctgcacag   2400
aagctatctg acacctggag acagcagcag cggctggacc gccggagccg ccgcctacta   2460
cgtgggctac ctgcagcccc ggaccttcct gctgaagtac aacgagaacg ggaccattac   2520
cgacgccgtc gactgcgccc tggatcctct gagcgaaacc aagtgcacac ttaaaagctt   2580
cacagtggag aagggcatct accaaacctc caattttcgg gtccagccaa ccgagagcat   2640
cgttagattc cccaacatca ccaacttgtg ccccttcgga gaagtgttca acgccacaag   2700
```

-continued

```
attcgccagc gtctacgcct ggaacagaaa gagaatttcc aattgcgtcg cagactactc   2760
tgtgctgtac aacagcgcca gcttttctac attcaagtgc tacggcgtga gccccaccaa   2820
gctgaacgac ctatgcttca caaacgtgta cgccgacagc tttgtgatcc ggggcgacga   2880
ggtgcgccag atcgcgccag gacagaccgg taagatcgcc gattacaatt acaaactgcc   2940
tgacgacttc accggctgcg tcatcgcttg gaacagcaac aacctggact ctaaggtggg   3000
cggaaactac aactacctgt accggctgtt tagaaagagc aacctgaagc cttttgaacg   3060
ggacatctct acagagatct accaggccgg atctacccct tgtaatggcg tggagggctt   3120
taattgctac ttcccccctgc aatcgtacgg cttccagccg acaaacggcg tcggctacca   3180
gccttacaga gtggtggtcc tgtccttcga gctgctgcat gcccctgcta cagtgtgcgg   3240
ccctaagaaa agcaccaacc tggtgaagaa caagtgtgtg aacttcaatt tcaatggcct   3300
gactggcacc ggagtgctga ccgaatccaa caagaagttc ctgcccttcc agcagttcgg   3360
cagagacatc gcagacacta ccgatgctgt gcgggatcct cagacactgg agatcctgga   3420
tatcaccccc tgcagcttcg gaggcgtgag cgtgatcaca cctggcacaa acacatccaa   3480
ccaggtggcc gtgctgtacc aggatgtgaa ctgcacagaa gtgccggttg ccatccacgc   3540
cgatcagctc acacctactt ggcgggtgta ctccacaggc agcaacgtgt tccaaaccag   3600
agctggctgt ctgatcggcg ctgaacacgt gaacaatagc tatgagtgcg acatcccaat   3660
cggcgccggt atctgcgcct cctatcagac gcagacgaac agccctaggc gggctagaag   3720
cgtggccagc cagagcatca tcgcatatac aatgagcctg ggcgccgaaa actctgtcgc   3780
ctacagcaac aacagcatcg ctatccctac caacttcacc ataagcgtaa caaccgagat   3840
cctgcctgtg tccatgacaa agaccagcgt ggactgtaca atgtacatct gtggcgactc   3900
caccgagtgc agcaacctgc tcctgcaata cggctctttc tgcacccagc tgaatcgcgc   3960
cttaacaggc attgccgtgg aacaggataa gaacacccag gaggtgttcg cccaggtgaa   4020
gcagatctat aagaccccac ccatcaagga cttcggcgga ttcaatttca gtcaaatcct   4080
gcccgatcct agcaagccca gtaagagatc tttcatcgag gacctgcttt tcaacaaagt   4140
gaccctggcg gacgccggat ttatcaaaca gtacggcgac tgtctgggcg acatcgccgc   4200
tagagatctg atctgcgccc agaaattcaa cggcctgacg gtgctgcctc ctctgctgac   4260
agatgagatg atcgcccagt ataccagcgc cctgctggct ggaaccatca cctctggctg   4320
gacatttggc gccggtgccg ctctccagat ccccttttgcc atgcagatgg cctacagatt   4380
caatggaatc ggcgtgaccc agaacgtgct gtacgagaac cagaagctga tcgctaatca   4440
gttcaactct gccattggca aaatccagga cagcctgtct tccaccgcca gcgccctggg   4500
caaactgcaa gacgtggtga atcaaaacgc ccaggccctg aacactctgg tgaagcagct   4560
gtccagcaac ttcggagcca tcagcagcgt gctgaacgac atactgagca gactggaccc   4620
tccggaggcc gaggtgcaga tcgacaggct gatcacaggc agactgcaga gcctgcagac   4680
ctacgtcaca cagcagctga tcagagccgc tgagatccga gcttctgcca atctcgccgc   4740
gacaaagatg tctgagtgcg tgctcggcca gagcaaaaga gtggatttct gcggaaaagg   4800
ctatcacctg atgagcttcc ctcagtctgc ccccacacggc gtcgtgttcc tgcacgtgac   4860
ctacgtgcct gcccaggaaa aaaactttac caccgccccg gccatctgcc acgacggcaa   4920
ggcccacttc cctagagaag gcgtgttcgt gagcaatggc acccactggt tcgtgacaca   4980
aagaaacttc tacgagcctc aaatcatcac aacagataac accttcgtgt caggcaactg   5040
tgacgtggtc atcggaatcg tgaataatac cgtgtacgac cccctgcagc ctgaactgga   5100
```

cagctttaag gaggaactgg acaagtactt caaaaaccac acatctcctg atgtggacct 5160
gggggatatc agcggcatca acgcttctgt ggtgaacatc cagaaggaaa tcgacagact 5220
gaacgaggtg gccaagaatc tcaacgaaag cctcattgac cttcaggagc tggggaagta 5280
cgagcagggc tctgccggct acatccctga ggctcctagg gacggccagg cctacgtgcg 5340
gaaggacggg gagtgggtgc tgctgagcac attcctgtaa accatgatat tcggcaagca 5400
ggcatcgcca tgggtcacga cgagatcctc gccgtcgggc atgctcgcct tgagcctggc 5460
gaacagttcg gctggcgcga gcccctgatg ctcttcgtcc agatcatcct gatcgacaag 5520
accggcttcc atccgagtac gtgctcgctc gatgcgatgt ttcgcttggt ggtcgaatgg 5580
gcaggtagcc ggatcaagcg tatgcagccg ccgcattgca tcagccatga tggatacttt 5640
ctcggcagga gcaaggtgag atgacaggag atcctgcccc ggcacttcgc ccaatagcag 5700
ccagtccctt cccgcttcag tgacaacgtc gagcacagct gcgcaaggaa cgcccgtcgt 5760
ggccagccac gatagccgcg ctgcctcgtc ttgcagttca ttcagggcac cggacaggtc 5820
ggtcttgaca aaaagaaccg ggcgcccctg cgctgacagc cggaacacgg cggcatcaga 5880
gcagccgatt gtctgttgtg cccagtcata gccgaatagc ctctccaccc aagcggccgg 5940
agaacctgcg tgcaatccat cttgttcaat catgcgaaac gatcctcatc ctgtctcttg 6000
atcagatctt gatcccctgc gccatcagat ccttggcggc aagaaagcca tccagtttac 6060
tttgcagggc ttcccaacct taccagaggg cgccccagct ggcaattccg gttcgcttgc 6120
tgtccataaa accgcccagt ctagctatcg ccatgtaagc ccactgcaag ctacctgctt 6180
tctctttgcg cttgcgtttt cccttgtcca gatagcccag tagctgacat tcatccgggg 6240
tcagcaccgt ttctgcggac tggctttcta cgtgaaaagg atctaggtga agatcctttt 6300
tgataatctc atgaccaaaa tcccttaacg tgagttttcg ttccactgag cgtcagaccc 6360
cgtagaaaag atcaaaggat cttcttgaga tccttttttt ctgcgcgtaa tctgctgctt 6420
gcaaacaaaa aaaccaccgc taccagcggt ggtttgtttg ccggatcaag agctaccaac 6480
tctttttccg aaggtaactg gcttcagcag agcgcagata ccaaatactg ttcttctagt 6540
gtagccgtag ttaggccacc acttcaagaa ctctgtagca ccgcctacat acctcgctct 6600
gctaatcctg ttaccagtgg ctgctgccag tggcgataag tcgtgtctta ccgggttgga 6660
ctcaagacga tagttaccgg ataaggcgca gcggtcgggc tgaacggggg gttcgtgcac 6720
acagcccagc ttggagcgaa cgacctacac ccgaactgag atacctacag cgtgagctat 6780
gagaaagcgc cacgcttccc gaagggagaa aggcggacag gtatccggta agcggcaggg 6840
tcggaacagg agagcgcacg agggagcttc caggggggaaa cgcctggtat ctttatagtc 6900
ctgtcgggtt tcgccacctc tgacttgagc gtcgattttt gtgatgctcg tcaggggggc 6960
ggagcctatg gaaaaacgcc agcaacgcgg cctttttacg gttcctggcc ttttgctggc 7020
cttttgctca catgttgt 7038

<210> SEQ ID NO 18
<211> LENGTH: 3722
<212> TYPE: DNA
<213> ORGANISM: Artificial
<220> FEATURE:
<223> OTHER INFORMATION: Synthetic construct

<400> SEQUENCE: 18
atgtggctgc agggcctgct gctgctgggc accgtggcat gcagtatcag ccaatgtgtg 60

-continued

```
aacctgacca ccagaaccca actgcctcct gcctacacca actctttcac cagaggcgtg    120
tactaccctg acaaggtgtt cagaagcagc gtgctgcatt ctacccagga cctgtttctg    180
ccattcttca gcaacgtcac ctggttccac gccatccacg tgtctggcac caatggcact    240
aagagattcg acaaccccgt gctgcctttc aacgacggcg tgtactttgc ctcaactgag    300
aagagcaaca tcatcagagg atggatcttc ggcaccacac ttgactcaaa gacacagtca    360
ctgctgatcg tgaacaatgc taccaatgtg gtgatcaagg tgtgtgaatt ccagttttgc    420
aacgatcctt tcctgggtgt atactaccac aagaacaaca agtcttggat ggagagcgag    480
ttccgggtgt atagtagcgc caacaactgc accttcgaat acgtgagcca gcctttcctc    540
atggacctgg aaggcaagca aggcaacttc aagaacctga gagagttcgt gtttaagaac    600
attgatggct acttcaagat ctacagcaag cacaccccca tcaacctggt gcgggacctc    660
cctcagggct tcagcgccct ggaacccttg gttgatctgc caattggcat caatatcact    720
cggttccaaa ccctgctggc cctgcacaga agctatctga cacctggaga cagcagcagc    780
ggctggaccg ccggagccgc cgcctactac gtgggctacc tgcagccccg gaccttcctg    840
ctgaagtaca acgagaacgg gaccattacc gacgccgtcg actgcgccct ggatcctctg    900
agcgaaacca agtgcacact taaaagcttc acagtggaga agggcatcta ccaaacctcc    960
aattttcggg tccagccaac cgagagcatc gttagattcc ccaacatcac caacttgtgc   1020
cccttcggag aagtgttcaa cgccacaaga ttcgccagcg tctacgcctg gaacagaaag   1080
agaatttcca attgcgtcgc agactactct gtgctgtaca acagcgccag cttttctaca   1140
ttcaagtgct acggcgtgag ccccaccaag ctgaacgacc tatgcttcac aaacgtgtac   1200
gccgacagct ttgtgatccg gggcgacgag gtgcgccaga tcgcgccagg acagaccggt   1260
aagatcgccg attacaatta caaactgcct gacgacttca ccggctgcgt catcgcttgg   1320
aacagcaaca acctggactc taaggtgggc ggaaactaca actacctgta ccggctgttt   1380
agaaagagca acctgaagcc ttttgaacgg gacatctcta cagagatcta ccaggccgga   1440
tctacccctt gtaatggcgt ggagggcttt aattgctact tcccccctgca atcgtacggc  1500
ttccagccga caaacggcgt cggctaccag ccttacagag tggtggtcct gtccttcgag   1560
ctgctgcatg cccctgctac agtgtgcggc cctaagaaaa gcaccaacct ggtgaagaac   1620
aagtgtgtga acttcaattt caatggcctg actggcaccg gagtgctgac cgaatccaac   1680
aagaagttcc tgcccttcca gcagttcggc agagacatcg cagacactac cgatgctgtg   1740
cgggatcctc agacactgga gatcctggat atcacccccct gcagcttcgg aggcgtgagc  1800
gtgatcacac ctggcacaaa cacatccaac caggtggccg tgctgtacca ggatgtgaac   1860
tgcacagaag tgccggttgc catccacgcc gatcagctca cacctacttg gcgggtgtac   1920
tccacaggca gcaacgtgtt ccaaaccaga gctggctgtc tgatcggcgc tgaacacgtg   1980
aacaatagct atgagtgcga catcccaatc ggcgccggta tctgcgcctc ctatcagacg   2040
cagacgaaca gccctaggcg ggctagaagc gtggccagcc agagcatcat cgcatataca   2100
atgagcctgg gcgccgaaaa ctctgtcgcc tacagcaaca acagcatcgc tatccctacc   2160
aacttcacca taagcgtaac aaccgagatc ctgcctgtgt ccatgacaaa gaccagcgtg   2220
gactgtacaa tgtacatctg tggcgactcc accgagtgca gcaacctgct cctgcaatac   2280
ggctctttct gcacccagct gaatcgcgcc ttaacaggca ttgccgtgga acaggataag   2340
aacacccagg aggtgttcgc ccaggtgaag cagatctata agaccccacc catcaaggac   2400
ttcggcggat tcaatttcag tcaaatcctg cccgatccta gcaagcccag taagagatct   2460
```

ttcatcgagg acctgctttt caacaaagtg accctggcgg acgccggatt tatcaaacag 2520
tacggcgact gtctgggcga catcgccgct agagatctga tctgcgccca gaaattcaac 2580
ggcctgacgg tgctgcctcc tctgctgaca gatgagatga tcgcccagta taccagcgcc 2640
ctgctggctg gaaccatcac ctctggctgg acatttggcg ccggtgccgc tctccagatc 2700
ccctttgcca tgcagatggc ctacagattc aatggaatcg gcgtgaccca gaacgtgctg 2760
tacgagaacc agaagctgat cgctaatcag ttcaactctg ccattggcaa aatccaggac 2820
agcctgtctt ccaccgccag cgccctgggc aaactgcaag acgtggtgaa tcaaaacgcc 2880
caggccctga acactctggt gaagcagctg tccagcaact tcggagccat cagcagcgtg 2940
ctgaacgaca tactgagcag actggaccct ccggaggccg aggtgcagat cgacaggctg 3000
atcacaggca gactgcagag cctgcagacc tacgtcacac agcagctgat cagagccgct 3060
gagatccgag cttctgccaa tctcgccgcg acaaagatgt ctgagtgcgt gctcggccag 3120
agcaaaagag tggatttctg cggaaaaggc tatcacctga tgagcttccc tcagtctgcc 3180
ccacacggcg tcgtgttcct gcacgtgacc tacgtgcctg cccaggaaaa aaactttacc 3240
accgccccgg ccatctgcca cgacggcaag gcccacttcc ctagagaagg cgtgttcgtg 3300
agcaatggca cccactggtt cgtgacacaa agaaacttct acgagcctca aatcatcaca 3360
acagataaca ccttcgtgtc aggcaactgt gacgtggtca tcggaatcgt gaataatacc 3420
gtgtacgacc ccctgcagcc tgaactggac agctttaagg aggaactgga caagtacttc 3480
aaaaaccaca catctcctga tgtggacctg gggatatca gcggcatcaa cgcttctgtg 3540
gtgaacatcc agaaggaaat cgacagactg aacgaggtgg ccaagaatct caacgaaagc 3600
ctcattgacc ttcaggagct ggggaagtac gagcagggct ctgccggcta catccctgag 3660
gctcctaggg acggccaggc ctacgtgcgg aaggacgggg agtgggtgct gctgagcaca 3720
tt 3722

<210> SEQ ID NO 19
<211> LENGTH: 5664
<212> TYPE: DNA
<213> ORGANISM: Artificial
<220> FEATURE:
<223> OTHER INFORMATION: Synthetic construct

<400> SEQUENCE: 19
cgacaatatt ggctattggc cattgcatac gttgtatcta tatcataata tgtacattta 60
tattggctca tgtccaatat gaccgccatg ttgacattga ttattgacta gttattaata 120
gtaatcaatt acgggtcat tagttcatag cccatatatg gagttccgcg ttacataact 180
tacggtaaat ggcccgcctg gctgaccgcc caacgacccc cgcccattga cgtcaataat 240
gacgtatgtt cccatagtaa cgccaatagg gactttccat tgacgtcaat gggtggagta 300
tttacggtaa actgcccact tggcagtaca tcaagtgtat catatgccaa gtccgccccc 360
tattgacgtc aatgacggta aatggcccgc ctggcattat gcccagtaca tgaccttacg 420
ggactttcct acttggcagt acatctacgg tattagtcat cggctattac catggtgatg 480
cggttttggc agtacaccaa tgggcgtgga tagcggtttg actcacgggg atttccaagt 540
ctccacccca ttgacgtcaa tgggagtttg ttttggcacc aaaatcaacg ggactttcca 600
aaatgtcgta ataaccccgc cccgttgacg caaatgggcg gtaggcgtgt acggtgggag 660
gtctatataa gcagagctcg tttagtgaac cgtcagatcg cctggagacg ccatccacgc 720

```
tgttttgacc tccatagaag acaccgggac cgatccagcc tccgcggccg ggaacggtgc    780
attggaacgc ggattccccg tgccaagagt gacgtaagta ccgcctatag actctatagg    840
cacacccctt tggctcttat gcatgctata ctgtttttgg cttggggcct atacaccccc    900
gcttccttat gctataggtg atggtatagc ttagcctata ggtgtgggtt attgaccatt    960
attgaccact cccctattgg tgacgatact ttccattact aatccataac atggctcttt   1020
gccacaacta tctctattgg ctatatgcca atactctgtc cttcagagac tgacacggac   1080
tctgtatttt tacaggatgg ggtcccattt attatttaca aattcacata tacaacaacg   1140
ccgtcccccg tgcccgcagt ttttattaaa catagcgtgg gatctccacg cgaatctcgg   1200
gtaccgtgtt ccggacatgg gytcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtg tgccgcacaa ggccgtggcg   1380
gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620
tccatgggtc ttttctgcag tcaccatcga tatgtggctg caggggctgc tgctgctggg   1680
aaccgtggct tgctccattt ctcagtgcgt caatctgact acccgaactc agctgccccc   1740
cgcctacacc aactccttca cccggggcgt gtactatcca gacaaggtgt ttagaagctc   1800
cgtgctgcac tccacccagg atctgtttct gcccttcttt tctaatgtga catggttcca   1860
cgccatccac gtgagcggca ccaacggcac aaagaggttc gacaaccctg tgctgccatt   1920
caatgatggc gtgtactttg cctccaccga gaagtctaac atcatccgcg gctggatctt   1980
tggcaccaca ctggactcca agacccagtc cctgctgatc gtgaacaatg ccacaaacgt   2040
ggtcatcaag gtgtgcgagt tccagttttg taacgatcct ttcctgggcg tgtactatca   2100
caagaacaat aagtcttgga tggagagcga gtttagggtg tattctagcg ccaacaattg   2160
caccttcgag tacgtgtccc agccatttct gatggacctg gagggcaagc agggcaattt   2220
caagaacctg cgggagttcg tgtttaagaa catcgacggc tacttcaaga tctactccaa   2280
gcacaccccc atcaacctgg tgcgggacct gccacagggc ttctctgccc tggagcctct   2340
ggtggatctg ccaatcggca tcaacatcac acggtttcag accctgctgg ccctgcacag   2400
aagctacctg acccctggcg actcctctag cggatggaca gcaggagcag cagcatacta   2460
tgtgggctat ctgcagccac ggaccttcct gctgaagtac aacgagaatg gcaccatcac   2520
agacgccgtg gattgcgccc tggatccact gtctgagaca aagtgtacac tgaagagctt   2580
tacagtggag aagggcatct atcagaccag caacttcagg gtgcagccca cagagtccat   2640
cgtgcgcttt ccaaatatca ccaacctgtg ccccttcggc gaggtgttta atgccacaag   2700
attcgccagc gtgtacgcct ggaacaggaa gcgcatctcc aattgcgtgg ccgactattc   2760
tgtgctgtac aactctgcca gcttctccac ctttaagtgc tatggcgtga gccccaccaa   2820
gctgaacgac ctgtgcttca caaacgtgta cgccgattcc tttgtgatca ggggcgacga   2880
ggtgcgccag atcgcaccag gacagaccgg caagatcgca gactacaact ataagctgcc   2940
cgacgatttc acaggctgcg tgatcgcctg gaattccaac aatctggatt ctaaagtggg   3000
cggcaactac aattatctgt acaggctgtt ccgcaagtct aacctgaagc cttttgagcg   3060
ggacatctcc accgagatct accaggccgg ctctacacca tgcaacggcg tggagggctt   3120
```

caattgttat tttcccctgc agagctacgg cttccagcct accaatggcg tgggctatca 3180
gccatacaga gtggtggtgc tgtcttttga gctgctgcac gcaccagcaa ccgtgtgcgg 3240
acctaagaag agcacaaatc tggtgaagaa caagtgcgtg aacttcaact tcaacggcct 3300
gaccggaaca ggcgtgctga ccgagtccaa caagaagttc ctgccctttc agcagttcgg 3360
cagggacatc gcagatacca cagacgccgt gcgcgacccc cagacactgg agatcctgga 3420
tatcacccct tgcagcttcg gcggcgtgtc cgtgatcacc cctggaacca atacaagcaa 3480
ccaggtggcc gtgctgtatc aggacgtgaa ctgtacagag gtgccagtgg ccatccacgc 3540
cgatcagctg acccccacat ggcgggtgta ctccacaggc tctaacgtgt tccagaccag 3600
agcaggatgc ctgatcggag cagagcacgt gaacaatagc tatgagtgcg acatccccat 3660
cggcgccggc atctgtgcct cctaccagac ccagacaaac tcccctcgga gagccaggtc 3720
tgtggcctct cagagcatca tcgcctatac catgagcctg ggcgccgaga actccgtggc 3780
ctacagcaac aattccatcg ccatccccac caatttcaca atctccgtga ccacagagat 3840
cctgcccgtg agcatgacca agacaagcgt ggactgcacc atgtatatct gtggcgattc 3900
cacagagtgc tctaatctgc tgctgcagta cggctctttt tgtacacagc tgaaccgcgc 3960
cctgaccgga atcgcagtgg agcaggacaa gaatacccag gagtaaacca tgatattcgg 4020
caagcaggca tcgccatggg tcacgacgag atcctcgccg tcgggcatgc tcgccttgag 4080
cctggcgaac agttcggctg gcgcgagccc ctgatgctct tcgtccagat catcctgatc 4140
gacaagaccg gcttccatcc gagtacgtgc tcgctcgatg cgatgtttcg cttggtggtc 4200
gaatgggcag gtagccggat caagcgtatg cagccgccgc attgcatcag ccatgatgga 4260
tactttctcg gcaggagcaa ggtgagatga caggagatcc tgccccggca cttcgcccaa 4320
tagcagccag tcccttcccg cttcagtgac aacgtcgagc acagctgcgc aaggaacgcc 4380
cgtcgtggcc agccacgata gccgcgctgc ctcgtcttgc agttcattca gggcaccgga 4440
caggtcggtc ttgacaaaaa gaaccgggcg cccctgcgct gacagccgga acacggcggc 4500
atcagagcag ccgattgtct gttgtgccca gtcatagccg aatagcctct ccacccaagc 4560
ggccggagaa cctgcgtgca atccatcttg ttcaatcatg cgaaacgatc ctcatcctgt 4620
ctcttgatca gatcttgatc ccctgcgcca tcagatcctt ggcggcaaga aagccatcca 4680
gtttactttg cagggcttcc caaccttacc agagggcgcc ccagctggca attccggttc 4740
gcttgctgtc cataaaaccg cccagtctag ctatcgccat gtaagcccac tgcaagctac 4800
ctgctttctc tttgcgcttg cgttttccct tgtccagata gcccagtagc tgacattcat 4860
ccggggtcag caccgtttct gcggactggc tttctacgtg aaaaggatct aggtgaagat 4920
cctttttgat aatctcatga ccaaaatccc ttaacgtgag ttttcgttcc actgagcgtc 4980
agaccccgta gaaaagatca aaggatcttc ttgagatcct ttttttctgc gcgtaatctg 5040
ctgcttgcaa acaaaaaaac caccgctacc agcggtggtt tgtttgccgg atcaagagct 5100
accaactctt tttccgaagg taactggctt cagcagagcg cagataccaa atactgttct 5160
tctagtgtag ccgtagttag gccaccactt caagaactct gtagcaccgc ctacatacct 5220
cgctctgcta atcctgttac cagtggctgc tgccagtggc gataagtcgt gtcttaccgg 5280
gttggactca agacgatagt taccggataa ggcgcagcgg tcgggctgaa cggggggttc 5340
gtgcacacag cccagcttgg agcgaacgac ctacacccga actgagatac ctacagcgtg 5400
agctatgaga aagcgccacg cttcccgaag ggagaaaggc ggacaggtat ccggtaagcg 5460
gcagggtcgg aacaggagag cgcacgaggg agcttccagg gggaaacgcc tggtatcttt 5520
atagtcctgt cgggtttcgc cacctctgac ttgagcgtcg atttttgtga tgctcgtcag 5580
gggggcggag cctatggaaa aacgccagca acgcggccct tttacggttc ctggcctttt 5640
gctggccttt tgctcacatg ttgt 5664

<210> SEQ ID NO 20
<211> LENGTH: 2355
<212> TYPE: DNA
<213> ORGANISM: Artificial
<220> FEATURE:
<223> OTHER INFORMATION: Synthetic construct

<400> SEQUENCE: 20
atgtggctgc aggggctgct gctgctggga accgtggctt gctccatttc tcagtgcgtc 60
aatctgacta cccgaactca gctgcccccc gcctacacca actccttcac ccggggcgtg 120
tactatccag acaaggtgtt tagaagctcc gtgctgcact ccacccagga tctgtttctg 180
cccttctttt ctaatgtgac atggttccac gccatccacg tgagcggcac caacggcaca 240
aagaggttcg acaaccctgt gctgccattc aatgatggcg tgtactttgc ctccaccgag 300
aagtctaaca tcatccgcgg ctggatcttt ggcaccacac tggactccaa gacccagtcc 360
ctgctgatcg tgaacaatgc cacaaacgtg gtcatcaagg tgtgcgagtt ccagttttgt 420
aacgatcctt tcctgggcgt gtactatcac aagaacaata agtcttggat ggagagcgag 480
tttagggtgt attctagcgc caacaattgc accttcgagt acgtgtccca gccatttctg 540
atggacctgg agggcaagca gggcaatttc aagaacctgc gggagttcgt gtttaagaac 600
atcgacggct acttcaagat ctactccaag cacacccccca tcaacctggt gcgggacctg 660
ccacagggct tctctgccct ggagcctctg gtggatctgc caatcggcat caacatcaca 720
cggtttcaga ccctgctggc cctgcacaga agctacctga cccctggcga ctcctctagc 780
ggatggacag caggagcagc agcatactat gtgggctatc tgcagccacg gaccttcctg 840
ctgaagtaca acgagaatgg caccatcaca gacgccgtgg attgcgccct ggatccactg 900
tctgagacaa agtgtacact gaagagcttt acagtggaga agggcatcta tcagaccagc 960
aacttcaggg tgcagcccac agagtccatc gtgcgctttc caaatatcac caacctgtgc 1020
cccttcggcg aggtgtttaa tgccacaaga ttcgccagcg tgtacgcctg gaacaggaag 1080
cgcatctcca attgcgtggc cgactattct gtgctgtaca actctgccag cttctccacc 1140
tttaagtgct atggcgtgag ccccaccaag ctgaacgacc tgtgcttcac aaacgtgtac 1200
gccgattcct ttgtgatcag gggcgacgag gtgcgccaga tcgcaccagg acagaccggc 1260
aagatcgcag actacaacta taagctgccc gacgatttca caggctgcgt gatcgcctgg 1320
aattccaaca atctggattc taaagtgggc ggcaactaca attatctgta caggctgttc 1380
cgcaagtcta acctgaagcc ttttgagcgg gacatctcca ccgagatcta ccaggccggc 1440
tctacaccat gcaacggcgt ggagggcttc aattgttatt ttcccctgca gagctacggc 1500
ttccagccta ccaatggcgt gggctatcag ccatacagag tggtggtgct gtcttttgag 1560
ctgctgcacg caccagcaac cgtgtgcgga cctaagaaga gcacaaatct ggtgaagaac 1620
aagtgcgtga acttcaactt caacggcctg accggaacag gcgtgctgac cgagtccaac 1680
aagaagttcc tgccctttca gcagttcggc agggacatcg cagataccac agacgccgtg 1740
cgcgaccccc agacactgga gatcctggat atcacccctt gcagcttcgg cggcgtgtcc 1800
gtgatcaccc ctggaaccaa tacaagcaac caggtggccg tgctgtatca ggacgtgaac 1860

```
tgtacagagg tgccagtggc catccacgcc gatcagctga cccccacatg gcgggtgtac   1920

tccacaggct ctaacgtgtt ccagaccaga gcaggatgcc tgatcggagc agagcacgtg   1980

aacaatagct atgagtgcga catccccatc ggcgccggca tctgtgcctc ctaccagacc   2040

cagacaaact cccctcggag agccaggtct gtggcctctc agagcatcat cgcctatacc   2100

atgagcctgg gcgccgagaa ctccgtggcc tacagcaaca attccatcgc catccccacc   2160

aatttcacaa tctccgtgac cacagagatc ctgcccgtga gcatgaccaa gacaagcgtg   2220

gactgcacca tgtatatctg tggcgattcc acagagtgct ctaatctgct gctgcagtac   2280

ggctcttttt gtacacagct gaaccgcgcc ctgaccggaa tcgcagtgga gcaggacaag   2340

aatacccagg agtaa                                                    2355


<210> SEQ ID NO 21
<211> LENGTH: 4
<212> TYPE: PRT
<213> ORGANISM: Artificial
<220> FEATURE:
<223> OTHER INFORMATION: Synthetic construct

<400> SEQUENCE: 21

Arg Arg Ala Arg
1


<210> SEQ ID NO 22
<211> LENGTH: 4
<212> TYPE: PRT
<213> ORGANISM: Artificial
<220> FEATURE:
<223> OTHER INFORMATION: Synthetic construct

<400> SEQUENCE: 22

Ser Arg Ala Gly
1


<210> SEQ ID NO 23
<211> LENGTH: 987
<212> TYPE: PRT
<213> ORGANISM: Artificial
<220> FEATURE:
<223> OTHER INFORMATION: Synthetic construct

<400> SEQUENCE: 23

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125
```

```
Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
```

-continued 545 550 555 560

Pro Phe Gln Gln Phe Gly Arg Asp Ile Ala Asp Thr Thr Asp Ala Val
565 570 575

Arg Asp Pro Gln Thr Leu Glu Ile Leu Asp Ile Thr Pro Cys Ser Phe
580 585 590

Gly Gly Val Ser Val Ile Thr Pro Gly Thr Asn Thr Ser Asn Gln Val
595 600 605

Ala Val Leu Tyr Gln Asp Val Asn Cys Thr Glu Val Pro Val Ala Ile
610 615 620

His Ala Asp Gln Leu Thr Pro Thr Trp Arg Val Tyr Ser Thr Gly Ser
625 630 635 640

Asn Val Phe Gln Thr Arg Ala Gly Cys Leu Ile Gly Ala Glu His Val
645 650 655

Asn Asn Ser Tyr Glu Cys Asp Ile Pro Ile Gly Ala Gly Ile Cys Ala
660 665 670

Ser Tyr Gln Thr Gln Thr Asn Ser Pro Ser Arg Ala Arg Ser Val Ala
675 680 685

Ser Gln Ser Ile Ile Ala Tyr Thr Met Ser Leu Gly Ala Glu Asn Ser
690 695 700

Val Ala Tyr Ser Asn Asn Ser Ile Ala Ile Pro Thr Asn Phe Thr Ile
705 710 715 720

Ser Val Thr Thr Glu Ile Leu Pro Val Ser Met Thr Lys Thr Ser Val
725 730 735

Asp Cys Thr Met Tyr Ile Cys Gly Asp Ser Thr Glu Cys Ser Asn Leu
740 745 750

Leu Leu Gln Tyr Gly Ser Phe Cys Thr Gln Leu Asn Arg Ala Leu Thr
755 760 765

Gly Ile Ala Val Glu Gln Asp Lys Asn Thr Gln Glu Val Phe Ala Gln
770 775 780

Val Lys Gln Ile Tyr Lys Thr Pro Pro Ile Lys Asp Phe Gly Gly Phe
785 790 795 800

Asn Phe Ser Gln Ile Leu Pro Asp Pro Ser Lys Pro Ser Lys Arg Ser
805 810 815

Phe Ile Glu Asp Leu Leu Phe Asn Lys Val Thr Leu Ala Asp Ala Gly
820 825 830

Phe Ile Lys Gln Tyr Gly Asp Cys Leu Gly Asp Ile Ala Ala Arg Asp
835 840 845

Leu Ile Cys Ala Gln Lys Phe Asn Gly Leu Thr Val Leu Pro Pro Leu
850 855 860

Leu Thr Asp Glu Met Ile Ala Gln Tyr Thr Ser Ala Leu Leu Ala Gly
865 870 875 880

Thr Ile Thr Ser Gly Trp Thr Phe Gly Ala Gly Ala Ala Leu Gln Ile
885 890 895

Pro Phe Ala Met Gln Met Ala Tyr Arg Phe Asn Gly Ile Gly Val Thr
900 905 910

Gln Asn Val Leu Tyr Glu Asn Gln Lys Leu Ile Ala Asn Gln Phe Asn
915 920 925

Ser Ala Ile Gly Lys Ile Gln Asp Ser Leu Ser Ser Thr Ala Ser Ala
930 935 940

Leu Gly Lys Leu Gln Asp Val Val Asn Gln Asn Ala Gln Ala Leu Asn
945 950 955 960

Thr Leu Val Lys Gln Leu Ser Ser Asn Phe Gly Ala Ile Ser Ser Val
965 970 975

Leu Asn Asp Ile Leu Ser Arg Leu Asp Pro Pro
980 985

<210> SEQ ID NO 24
<211> LENGTH: 1642
<212> TYPE: PRT
<213> ORGANISM: Artificial
<220> FEATURE:
<223> OTHER INFORMATION: Synthetic construct

<400> SEQUENCE: 24

Met Cys Val Asn Leu Thr Thr Arg Thr Gln Leu Pro Pro Ala Tyr Thr
1 5 10 15

Asn Ser Phe Thr Arg Gly Val Tyr Tyr Pro Asp Lys Val Phe Arg Ser
20 25 30

Ser Val Leu His Ser Thr Gln Asp Leu Phe Leu Pro Phe Phe Ser Asn
35 40 45

Val Thr Trp Phe His Ala Ile His Val Ser Gly Thr Asn Gly Thr Lys
50 55 60

Arg Phe Asp Asn Pro Val Leu Pro Phe Asn Asp Gly Val Tyr Phe Ala
65 70 75 80

Ser Thr Glu Lys Ser Asn Ile Ile Arg Gly Trp Ile Phe Gly Thr Thr
85 90 95

Leu Asp Ser Lys Thr Gln Ser Leu Leu Ile Val Asn Asn Ala Thr Asn
100 105 110

Val Val Ile Lys Val Cys Glu Phe Gln Phe Cys Asn Asp Pro Phe Leu
115 120 125

Gly Val Tyr Tyr His Lys Asn Asn Lys Ser Trp Met Glu Ser Glu Phe
130 135 140

Arg Val Tyr Ser Ser Ala Asn Asn Cys Thr Phe Glu Tyr Val Ser Gln
145 150 155 160

Pro Phe Leu Met Asp Leu Glu Gly Lys Gln Gly Asn Phe Lys Asn Leu
165 170 175

Arg Glu Phe Val Phe Lys Asn Ile Asp Gly Tyr Phe Lys Ile Tyr Ser
180 185 190

Lys His Thr Pro Ile Asn Leu Val Arg Asp Leu Pro Gln Gly Phe Ser
195 200 205

Ala Leu Glu Pro Leu Val Asp Leu Pro Ile Gly Ile Asn Ile Thr Arg
210 215 220

Phe Gln Thr Leu Leu Ala Leu His Arg Ser Tyr Leu Thr Pro Gly Asp
225 230 235 240

Ser Ser Ser Gly Trp Thr Ala Gly Ala Ala Ala Tyr Tyr Val Gly Tyr
245 250 255

Leu Gln Pro Arg Thr Phe Leu Leu Lys Tyr Asn Glu Asn Gly Thr Ile
260 265 270

Thr Asp Ala Val Asp Cys Ala Leu Asp Pro Leu Ser Glu Thr Lys Cys
275 280 285

Thr Leu Lys Ser Phe Thr Val Glu Lys Gly Ile Tyr Gln Thr Ser Asn
290 295 300

Phe Arg Val Gln Pro Thr Glu Ser Ile Val Arg Phe Ala Thr Val Cys
305 310 315 320

Gly Pro Lys Lys Ser Thr Asn Leu Val Lys Asn Lys Cys Val Asn Phe
325 330 335

Asn Phe Asn Gly Leu Thr Gly Thr Gly Val Leu Thr Glu Ser Asn Lys
340 345 350

```
Lys Phe Leu Pro Phe Gln Gln Phe Gly Arg Asp Ile Ala Asp Thr Thr
        355                 360                 365

Asp Ala Val Arg Asp Pro Gln Thr Leu Glu Ile Leu Asp Ile Thr Pro
    370                 375                 380

Cys Ser Phe Gly Gly Val Ser Val Ile Thr Pro Gly Thr Asn Thr Ser
385                 390                 395                 400

Asn Gln Val Ala Val Leu Tyr Gln Asp Val Asn Cys Thr Glu Val Pro
                405                 410                 415

Val Ala Ile His Ala Asp Gln Leu Thr Pro Thr Trp Arg Val Tyr Ser
            420                 425                 430

Thr Gly Ser Asn Val Phe Gln Thr Arg Ala Gly Cys Leu Ile Gly Ala
        435                 440                 445

Glu His Val Asn Asn Ser Tyr Glu Cys Asp Ile Pro Ile Gly Ala Gly
    450                 455                 460

Ile Cys Ala Ser Tyr Gln Thr Gln Thr Asn Ser Pro Ser Arg Ala Gly
465                 470                 475                 480

Ser Val Ala Ser Gln Ser Ile Ile Ala Tyr Thr Met Ser Leu Gly Ala
                485                 490                 495

Glu Asn Ser Val Ala Tyr Ser Asn Asn Ser Ile Ala Ile Pro Thr Asn
            500                 505                 510

Phe Thr Ile Ser Val Thr Thr Glu Ile Leu Pro Val Ser Met Thr Lys
        515                 520                 525

Thr Ser Val Asp Cys Thr Met Tyr Ile Cys Gly Asp Ser Thr Glu Cys
    530                 535                 540

Ser Asn Leu Leu Leu Gln Tyr Gly Ser Phe Cys Thr Gln Leu Asn Arg
545                 550                 555                 560

Ala Leu Thr Gly Ile Ala Val Glu Gln Asp Lys Asn Thr Gln Glu Val
                565                 570                 575

Phe Ala Gln Val Lys Gln Ile Tyr Lys Thr Pro Pro Ile Lys Asp Phe
            580                 585                 590

Gly Gly Phe Asn Phe Ser Gln Ile Leu Pro Asp Pro Ser Lys Pro Ser
        595                 600                 605

Lys Arg Ser Phe Ile Glu Asp Leu Leu Phe Asn Lys Val Thr Leu Ala
    610                 615                 620

Asp Ala Gly Phe Ile Lys Gln Tyr Gly Asp Cys Leu Gly Asp Ile Ala
625                 630                 635                 640

Ala Arg Asp Leu Ile Cys Ala Gln Lys Phe Asn Gly Leu Thr Val Leu
                645                 650                 655

Pro Pro Leu Leu Thr Asp Glu Met Ile Ala Gln Tyr Thr Ser Ala Leu
            660                 665                 670

Leu Ala Gly Thr Ile Thr Ser Gly Trp Thr Phe Gly Ala Gly Ala Ala
        675                 680                 685

Leu Gln Ile Pro Phe Ala Met Gln Met Ala Tyr Arg Phe Asn Gly Ile
    690                 695                 700

Gly Val Thr Gln Asn Val Leu Tyr Glu Asn Gln Lys Leu Ile Ala Asn
705                 710                 715                 720

Gln Phe Asn Ser Ala Ile Gly Lys Ile Gln Asp Ser Leu Ser Ser Thr
                725                 730                 735

Ala Ser Ala Leu Gly Lys Leu Gln Asp Val Val Asn Gln Asn Ala Gln
            740                 745                 750

Ala Leu Asn Thr Leu Val Lys Gln Leu Ser Ser Asn Phe Gly Ala Ile
        755                 760                 765
```

```
Ser Ser Val Leu Asn Asp Ile Leu Ser Arg Leu Asp Pro Pro Glu Ala
    770                 775                 780

Glu Val Gln Ile Asp Arg Leu Ile Thr Gly Arg Leu Gln Ser Leu Gln
785                 790                 795                 800

Thr Tyr Val Thr Gln Gln Leu Ile Arg Ala Ala Glu Ile Arg Ala Ser
                805                 810                 815

Ala Asn Leu Ala Ala Thr Lys Met Ser Glu Cys Val Leu Gly Gln Ser
            820                 825                 830

Lys Arg Val Asp Phe Cys Gly Lys Gly Tyr His Leu Met Ser Phe Pro
        835                 840                 845

Gln Ser Ala Pro His Gly Val Val Phe Leu His Val Thr Tyr Val Pro
    850                 855                 860

Ala Gln Glu Lys Asn Phe Thr Thr Ala Pro Ala Ile Cys His Asp Gly
865                 870                 875                 880

Lys Ala His Phe Pro Arg Glu Gly Val Phe Val Ser Asn Gly Thr His
                885                 890                 895

Trp Phe Val Thr Gln Arg Asn Phe Tyr Glu Pro Gln Ile Ile Thr Thr
            900                 905                 910

Asp Asn Thr Phe Val Ser Gly Asn Cys Asp Val Val Ile Gly Ile Val
        915                 920                 925

Asn Asn Thr Val Tyr Asp Pro Leu Gln Pro Glu Leu Asp Ser Phe Lys
    930                 935                 940

Glu Glu Leu Asp Lys Tyr Phe Lys Asn His Thr Ser Pro Asp Val Asp
945                 950                 955                 960

Leu Gly Asp Ile Ser Gly Ile Asn Ala Ser Val Val Asn Ile Gln Lys
                965                 970                 975

Glu Ile Asp Arg Leu Asn Glu Val Ala Lys Asn Leu Asn Glu Ser Leu
            980                 985                 990

Ile Asp Leu Gln Glu Leu Gly Lys  Tyr Glu Gln Ser Asp  Asn Gly Pro
        995                 1000                1005

Gln Asn  Gln Arg Asn Ala Pro  Arg Ile Thr Phe Gly  Gly Pro Ser
    1010                 1015                 1020

Asp Ser  Thr Gly Ser Asn Gln  Asn Gly Glu Arg Ser  Gly Ala Arg
    1025                 1030                 1035

Ser Lys  Gln Arg Arg Pro Gln  Gly Leu Pro Asn Asn  Thr Ala Ser
    1040                 1045                 1050

Trp Phe  Thr Ala Leu Thr Gln  His Gly Lys Glu Asp  Leu Lys Phe
    1055                 1060                 1065

Pro Arg  Gly Gln Gly Val Pro  Ile Asn Thr Asn Ser  Ser Pro Asp
    1070                 1075                 1080

Asp Gln  Ile Gly Tyr Tyr Arg  Arg Ala Thr Arg Arg  Ile Arg Gly
    1085                 1090                 1095

Gly Asp  Gly Lys Met Lys Asp  Leu Ser Pro Arg Trp  Tyr Phe Tyr
    1100                 1105                 1110

Tyr Leu  Gly Thr Gly Pro Glu  Ala Gly Leu Pro Tyr  Gly Ala Asn
    1115                 1120                 1125

Lys Asp  Gly Ile Ile Trp Val  Ala Thr Glu Gly Ala  Leu Asn Thr
    1130                 1135                 1140

Pro Lys  Asp His Ile Gly Thr  Arg Asn Pro Ala Asn  Asn Ala Ala
    1145                 1150                 1155

Ile Val  Leu Gln Leu Pro Gln  Gly Thr Thr Leu Pro  Lys Gly Phe
    1160                 1165                 1170

Tyr Ala  Glu Gly Ser Arg Gly  Gly Ser Gln Ala Ser  Ser Arg Ser
```

```
    1175                1180                1185

Ser Ser  Arg Ser Arg Asn Ser  Ser Arg Asn Ser Thr  Pro Gly Ser
    1190                1195                1200

Ser Arg  Gly Thr Ser Pro Ala  Arg Met Ala Gly Asn  Gly Gly Asp
    1205                1210                1215

Ala Ala  Leu Ala Leu Leu Leu  Leu Asp Arg Leu Asn  Gln Leu Glu
    1220                1225                1230

Ser Lys  Met Ser Gly Lys Gly  Gln Gln Gln Gln Gly  Gln Thr Val
    1235                1240                1245

Thr Lys  Lys Ser Ala Ala Glu  Ala Ser Lys Lys Pro  Arg Gln Lys
    1250                1255                1260

Arg Thr  Ala Thr Lys Ala Tyr  Asn Val Thr Gln Ala  Phe Gly Arg
    1265                1270                1275

Arg Gly  Pro Glu Gln Thr Gln  Gly Asn Phe Gly Asp  Gln Glu Leu
    1280                1285                1290

Ile Arg  Gln Gly Thr Asp Tyr  Lys His Trp Pro Gln  Ile Ala Gln
    1295                1300                1305

Phe Ala  Pro Ser Ala Ser Ala  Phe Phe Gly Met Ser  Arg Ile Gly
    1310                1315                1320

Met Glu  Val Thr Pro Ser Gly  Thr Trp Leu Thr Tyr  Thr Gly Ala
    1325                1330                1335

Ile Lys  Leu Asp Asp Lys Asp  Pro Asn Phe Lys Asp  Gln Val Ile
    1340                1345                1350

Leu Leu  Asn Lys His Ile Asp  Ala Tyr Lys Thr Phe  Pro Pro Thr
    1355                1360                1365

Glu Pro  Lys Lys Asp Lys Lys  Lys Lys Ala Asp Glu  Thr Gln Ala
    1370                1375                1380

Leu Pro  Gln Arg Gln Lys Lys  Gln Gln Thr Val Thr  Leu Leu Pro
    1385                1390                1395

Ala Ala  Asp Leu Asp Asp Phe  Ser Lys Gln Leu Gln  Gln Ser Met
    1400                1405                1410

Ser Ser  Ala Asp Ser Thr Gln  Ala Ala Asp Ser Asn  Gly Thr Ile
    1415                1420                1425

Thr Val  Glu Glu Leu Lys Lys  Leu Leu Glu Gln Trp  Asn Leu Val
    1430                1435                1440

Ile Gly  Phe Leu Phe Leu Thr  Trp Ile Cys Leu Leu  Gln Phe Ala
    1445                1450                1455

Tyr Ala  Asn Arg Asn Arg Phe  Leu Tyr Ile Ile Lys  Leu Ile Phe
    1460                1465                1470

Leu Trp  Leu Leu Trp Pro Val  Thr Leu Ala Cys Phe  Val Leu Ala
    1475                1480                1485

Ala Val  Tyr Arg Ile Asn Trp  Ile Thr Gly Gly Ile  Ala Ile Ala
    1490                1495                1500

Met Ala  Cys Leu Val Gly Leu  Met Trp Leu Ser Tyr  Phe Ile Ala
    1505                1510                1515

Ser Phe  Arg Leu Phe Ala Arg  Thr Arg Ser Met Trp  Ser Phe Asn
    1520                1525                1530

Pro Glu  Thr Asn Ile Leu Leu  Asn Val Pro Leu His  Gly Thr Ile
    1535                1540                1545

Leu Thr  Arg Pro Leu Leu Glu  Ser Glu Leu Val Ile  Gly Ala Val
    1550                1555                1560

Ile Leu  Arg Gly His Leu Arg  Ile Ala Gly His His  Leu Gly Arg
    1565                1570                1575
```

Cys Asp Ile Lys Asp Leu Pro Lys Glu Ile Thr Val Ala Thr Ser
1580 1585 1590

Arg Thr Leu Ser Tyr Tyr Lys Leu Gly Ala Ser Gln Arg Val Ala
1595 1600 1605

Gly Asp Ser Gly Phe Ala Ala Tyr Ser Arg Tyr Arg Ile Gly Asn
1610 1615 1620

Tyr Lys Leu Asn Thr Asp His Ser Ser Ser Ser Asp Asn Ile Ala
1625 1630 1635

Leu Leu Val Gln
1640

<210> SEQ ID NO 25
<211> LENGTH: 1593
<212> TYPE: PRT
<213> ORGANISM: Artificial
<220> FEATURE:
<223> OTHER INFORMATION: Synthetic construct

<400> SEQUENCE: 25

Met Cys Val Asn Leu Thr Thr Arg Thr Gln Leu Pro Pro Ala Tyr Thr
1 5 10 15

Asn Ser Phe Thr Arg Gly Val Tyr Tyr Pro Asp Lys Val Phe Arg Ser
20 25 30

Ser Val Leu His Ser Thr Gln Asp Leu Phe Leu Pro Phe Phe Ser Asn
35 40 45

Val Thr Trp Phe His Ala Ile His Val Ser Gly Thr Asn Gly Thr Lys
50 55 60

Arg Phe Asp Asn Pro Val Leu Pro Phe Asn Asp Gly Val Tyr Phe Ala
65 70 75 80

Ser Thr Glu Lys Ser Asn Ile Ile Arg Gly Trp Ile Phe Gly Thr Thr
85 90 95

Leu Asp Ser Lys Thr Gln Ser Leu Leu Ile Val Asn Asn Ala Thr Asn
100 105 110

Val Val Ile Lys Val Cys Glu Phe Gln Phe Cys Asn Asp Pro Phe Leu
115 120 125

Gly Val Tyr Tyr His Lys Asn Asn Lys Ser Trp Met Glu Ser Glu Phe
130 135 140

Arg Val Tyr Ser Ser Ala Asn Asn Cys Thr Phe Glu Tyr Val Ser Gln
145 150 155 160

Pro Phe Leu Met Asp Leu Glu Gly Lys Gln Gly Asn Phe Lys Asn Leu
165 170 175

Arg Glu Phe Val Phe Lys Asn Ile Asp Gly Tyr Phe Lys Ile Tyr Ser
180 185 190

Lys His Thr Pro Ile Asn Leu Val Arg Asp Leu Pro Gln Gly Phe Ser
195 200 205

Ala Leu Glu Pro Leu Val Asp Leu Pro Ile Gly Ile Asn Ile Thr Arg
210 215 220

Phe Gln Thr Leu Leu Ala Leu His Arg Ser Tyr Leu Thr Pro Gly Asp
225 230 235 240

Ser Ser Ser Gly Trp Thr Ala Gly Ala Ala Ala Tyr Tyr Val Gly Tyr
245 250 255

Leu Gln Pro Arg Thr Phe Leu Leu Lys Tyr Asn Glu Asn Gly Thr Ile
260 265 270

Thr Asp Ala Val Asp Cys Ala Leu Asp Pro Leu Ser Glu Thr Lys Cys
275 280 285

```
Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Ala Thr Val Cys
305                 310                 315                 320

Gly Pro Lys Lys Ser Thr Asn Leu Val Lys Asn Lys Cys Val Asn Phe
                325                 330                 335

Asn Phe Asn Gly Leu Thr Gly Thr Gly Val Leu Thr Glu Ser Asn Lys
            340                 345                 350

Lys Phe Leu Pro Phe Gln Gln Phe Gly Arg Asp Ile Ala Asp Thr Thr
        355                 360                 365

Asp Ala Val Arg Asp Pro Gln Thr Leu Glu Ile Leu Asp Ile Thr Pro
    370                 375                 380

Cys Ser Phe Gly Gly Val Ser Val Ile Thr Pro Gly Thr Asn Thr Ser
385                 390                 395                 400

Asn Gln Val Ala Val Leu Tyr Gln Asp Val Asn Cys Thr Glu Val Pro
                405                 410                 415

Val Ala Ile His Ala Asp Gln Leu Thr Pro Thr Trp Arg Val Tyr Ser
            420                 425                 430

Thr Gly Ser Asn Val Phe Gln Thr Arg Ala Gly Cys Leu Ile Gly Ala
        435                 440                 445

Glu His Val Asn Asn Ser Tyr Glu Cys Asp Ile Pro Ile Gly Ala Gly
    450                 455                 460

Ile Cys Ala Ser Tyr Gln Thr Gln Thr Asn Ser Pro Ser Arg Ala Gly
465                 470                 475                 480

Ser Val Ala Ser Gln Ser Ile Ile Ala Tyr Thr Met Ser Leu Gly Ala
                485                 490                 495

Glu Asn Ser Val Ala Tyr Ser Asn Asn Ser Ile Ala Ile Pro Thr Asn
            500                 505                 510

Phe Thr Ile Ser Val Thr Thr Glu Ile Leu Pro Val Ser Met Thr Lys
        515                 520                 525

Thr Ser Val Asp Cys Thr Met Tyr Ile Cys Gly Asp Ser Thr Glu Cys
    530                 535                 540

Ser Asn Leu Leu Leu Gln Tyr Gly Ser Phe Cys Thr Gln Leu Asn Arg
545                 550                 555                 560

Ala Leu Thr Gly Ile Ala Val Glu Gln Asp Lys Asn Thr Gln Glu Val
                565                 570                 575

Phe Ala Gln Val Lys Gln Ile Tyr Lys Thr Pro Pro Ile Lys Asp Phe
            580                 585                 590

Gly Gly Phe Asn Phe Ser Gln Ile Leu Pro Asp Pro Ser Lys Pro Ser
        595                 600                 605

Lys Arg Ser Phe Ile Glu Asp Leu Leu Phe Asn Lys Val Thr Leu Ala
    610                 615                 620

Asp Ala Gly Phe Ile Lys Gln Tyr Gly Asp Cys Leu Gly Asp Ile Ala
625                 630                 635                 640

Ala Arg Asp Leu Ile Cys Ala Gln Lys Phe Asn Gly Leu Thr Val Leu
                645                 650                 655

Pro Pro Leu Leu Thr Asp Glu Met Ile Ala Gln Tyr Thr Ser Ala Leu
            660                 665                 670

Leu Ala Gly Thr Ile Thr Ser Gly Trp Thr Phe Gly Ala Gly Ala Ala
        675                 680                 685

Leu Gln Ile Pro Phe Ala Met Gln Met Ala Tyr Arg Phe Asn Gly Ile
    690                 695                 700
```

```
Gly Val Thr Gln Asn Val Leu Tyr Glu Asn Gln Lys Leu Ile Ala Asn
705                 710                 715                 720

Gln Phe Asn Ser Ala Ile Gly Lys Ile Gln Asp Ser Leu Ser Ser Thr
                725                 730                 735

Ala Ser Ala Leu Gly Lys Leu Gln Asp Val Val Asn Gln Asn Ala Gln
            740                 745                 750

Ala Leu Asn Thr Leu Val Lys Gln Leu Ser Ser Asn Phe Gly Ala Ile
        755                 760                 765

Ser Ser Val Leu Asn Asp Ile Leu Ser Arg Leu Asp Pro Pro Glu Ala
    770                 775                 780

Glu Val Gln Ile Asp Arg Leu Ile Thr Gly Arg Leu Gln Ser Leu Gln
785                 790                 795                 800

Thr Tyr Val Thr Gln Gln Leu Ile Arg Ala Ala Glu Ile Arg Ala Ser
                805                 810                 815

Ala Asn Leu Ala Ala Thr Lys Met Ser Glu Cys Val Leu Gly Gln Ser
            820                 825                 830

Lys Arg Val Asp Phe Cys Gly Lys Gly Tyr His Leu Met Ser Phe Pro
        835                 840                 845

Gln Ser Ala Pro His Gly Val Val Phe Leu His Val Thr Tyr Val Pro
    850                 855                 860

Ala Gln Glu Lys Asn Phe Thr Thr Ala Pro Ala Ile Cys His Asp Gly
865                 870                 875                 880

Lys Ala His Phe Pro Arg Glu Gly Val Phe Val Ser Asn Gly Thr His
                885                 890                 895

Trp Phe Val Thr Gln Arg Asn Phe Tyr Glu Pro Gln Ile Ile Thr Thr
            900                 905                 910

Asp Asn Thr Phe Val Ser Gly Asn Cys Asp Val Val Ile Gly Ile Val
        915                 920                 925

Asn Asn Thr Val Tyr Asp Pro Leu Gln Pro Glu Leu Asp Ser Phe Lys
    930                 935                 940

Glu Glu Leu Asp Lys Tyr Phe Lys Asn His Thr Ser Pro Asp Val Asp
945                 950                 955                 960

Leu Gly Asp Ile Ser Gly Ile Asn Ala Ser Val Val Asn Ile Gln Lys
                965                 970                 975

Glu Ile Asp Arg Leu Asn Glu Val Ala Lys Asn Leu Asn Glu Ser Leu
            980                 985                 990

Ile Asp Leu Gln Glu Leu Gly Lys  Tyr Glu Gln Ser Asp  Asn Gly Pro
        995                 1000                1005

Gln Asn  Gln Arg Asn Ala Pro  Arg Ile Thr Phe Gly  Gly Pro Ser
    1010                1015                1020

Asp Ser  Thr Gly Ser Asn Gln  Asn Gly Glu Arg Ser  Gly Ala Arg
    1025                1030                1035

Ser Lys  Gln Arg Arg Pro Gln  Gly Leu Pro Asn Asn  Thr Ala Ser
    1040                1045                1050

Trp Phe  Thr Ala Leu Thr Gln  His Gly Lys Glu Asp  Leu Lys Phe
    1055                1060                1065

Pro Arg  Gly Gln Gly Val Pro  Ile Asn Thr Asn Ser  Ser Pro Asp
    1070                1075                1080

Asp Gln  Ile Gly Tyr Tyr Arg  Arg Ala Thr Arg Arg  Ile Arg Gly
    1085                1090                1095

Gly Asp  Gly Lys Met Lys Asp  Leu Ser Pro Arg Trp  Tyr Phe Tyr
    1100                1105                1110

Tyr Leu  Gly Thr Gly Pro Glu  Ala Gly Leu Pro Tyr  Gly Ala Asn
```

```
    1115                1120                1125

Lys Asp  Gly Ile Ile Trp Val  Ala Thr Glu Gly Ala  Leu Asn Thr
    1130                1135                1140

Pro Lys  Asp His Ile Gly Thr  Arg Asn Pro Ala Asn  Asn Ala Ala
    1145                1150                1155

Ile Val  Leu Gln Leu Pro Gln  Gly Thr Thr Leu Pro  Lys Gly Phe
    1160                1165                1170

Tyr Ala  Glu Gly Ser Arg Gly  Gly Ser Gln Ala Ser  Ser Arg Ser
    1175                1180                1185

Ser Ser  Arg Ser Arg Asn Ser  Ser Arg Asn Ser Thr  Pro Gly Ser
    1190                1195                1200

Ser Arg  Gly Thr Ser Pro Ala  Arg Met Ala Gly Asn  Gly Gly Asp
    1205                1210                1215

Ala Ala  Leu Ala Leu Leu Leu  Leu Asp Arg Leu Asn  Gln Leu Glu
    1220                1225                1230

Ser Lys  Met Ser Gly Lys Gly  Gln Gln Gln Gln Gly  Gln Thr Val
    1235                1240                1245

Thr Lys  Lys Ser Ala Ala Glu  Ala Ser Lys Lys Pro  Arg Gln Lys
    1250                1255                1260

Arg Thr  Ala Thr Lys Ala Tyr  Asn Val Thr Gln Ala  Phe Gly Arg
    1265                1270                1275

Arg Gly  Pro Glu Gln Thr Gln  Gly Asn Phe Gly Asp  Gln Glu Leu
    1280                1285                1290

Ile Arg  Gln Gly Thr Asp Tyr  Lys His Trp Pro Gln  Ile Ala Gln
    1295                1300                1305

Phe Ala  Pro Ser Ala Ser Ala  Phe Phe Gly Met Ser  Arg Ile Gly
    1310                1315                1320

Met Glu  Val Thr Pro Ser Gly  Thr Trp Leu Thr Tyr  Thr Gly Ala
    1325                1330                1335

Ile Lys  Leu Asp Asp Lys Asp  Pro Asn Phe Lys Asp  Gln Val Ile
    1340                1345                1350

Leu Leu  Asn Lys His Ile Asp  Ala Tyr Lys Thr Phe  Pro Pro Thr
    1355                1360                1365

Glu Pro  Lys Lys Asp Lys Lys  Lys Lys Ala Asp Glu  Thr Gln Ala
    1370                1375                1380

Leu Pro  Gln Arg Gln Lys Lys  Gln Gln Thr Val Thr  Leu Leu Pro
    1385                1390                1395

Ala Ala  Asp Leu Asp Asp Phe  Ser Lys Gln Leu Gln  Gln Ser Met
    1400                1405                1410

Ser Ser  Ala Asp Ser Thr Gln  Ala Ala Asp Ser Asn  Gly Thr Ile
    1415                1420                1425

Thr Val  Glu Glu Leu Lys Lys  Leu Leu Glu Gln Asn  Arg Asn Arg
    1430                1435                1440

Phe Leu  Tyr Ile Ile Lys Leu  Thr Leu Ala Cys Phe  Val Leu Ala
    1445                1450                1455

Ala Val  Asn Trp Ile Thr Gly  Gly Leu Met Trp Leu  Ser Tyr Phe
    1460                1465                1470

Ile Ala  Arg Thr Arg Ser Met  Trp Ser Phe Asn Pro  Glu Thr Asn
    1475                1480                1485

Ile Leu  Leu Asn Val Pro Leu  His Gly Thr Ile Leu  Thr Arg Pro
    1490                1495                1500

Leu Leu  Glu Ser Glu Leu Val  Ile Gly Ala Val Ile  Leu Arg Gly
    1505                1510                1515
```

```
His Leu Arg Ile Ala Gly His His Leu Gly Arg Cys Asp Ile Lys
    1520                1525                1530

Asp Leu Pro Lys Glu Ile Thr Val Ala Thr Ser Arg Thr Leu Ser
    1535                1540                1545

Tyr Tyr Lys Leu Gly Ala Ser Gln Arg Val Ala Gly Asp Ser Gly
    1550                1555                1560

Phe Ala Ala Tyr Ser Arg Tyr Arg Ile Gly Asn Tyr Lys Leu Asn
    1565                1570                1575

Thr Asp His Ser Ser Ser Ser Asp Asn Ile Ala Leu Leu Val Gln
    1580                1585                1590


<210> SEQ ID NO 26
<211> LENGTH: 1369
<212> TYPE: PRT
<213> ORGANISM: Artificial
<220> FEATURE:
<223> OTHER INFORMATION: Synthetic construct

<400> SEQUENCE: 26

Met Thr Asn Ser Arg Ile Lys Ala Ser Met Pro Thr Thr Ile Ala Lys
1               5                   10                  15

Asn Thr Val Lys Ser Val Gly Lys Phe Cys Leu Glu Ala Ser Phe Asn
            20                  25                  30

Tyr Leu Lys Ser Pro Asn Phe Ser Lys Leu Ile Asn Ile Ile Ile Trp
        35                  40                  45

Phe Leu Leu Leu Ser Val Cys Leu Gly Ser Leu Ile Tyr Ser Thr Ala
    50                  55                  60

Ala Leu Gly Val Leu Met Ser Asn Leu Gly Met Pro Ser Tyr Cys Thr
65                  70                  75                  80

Gly Tyr Arg Glu Gly Tyr Leu Asn Ser Thr Asn Val Thr Ile Ala Thr
                85                  90                  95

Tyr Cys Thr Gly Ser Ile Pro Cys Ser Val Cys Leu Ser Gly Leu Asp
            100                 105                 110

Ser Leu Asp Thr Tyr Pro Ser Leu Glu Thr Ile Gln Ile Thr Ile Ser
        115                 120                 125

Ser Phe Lys Trp Asp Leu Thr Ala Phe Gly Leu Val Ala Glu Trp Phe
    130                 135                 140

Leu Ala Tyr Ile Leu Phe Thr Arg Phe Phe Tyr Val Leu Gly Leu Ala
145                 150                 155                 160

Ala Ile Met Gln Leu Phe Phe Ser Tyr Phe Ala Val His Phe Ile Ser
                165                 170                 175

Asn Ser Trp Leu Met Trp Leu Ile Ile Asn Leu Val Gln Met Ala Pro
            180                 185                 190

Ile Ser Ala Met Val Arg Met Tyr Ile Phe Phe Ala Ser Phe Tyr Tyr
        195                 200                 205

Val Trp Lys Ser Tyr Val His Val Val Asp Gly Cys Asn Ser Ser Thr
    210                 215                 220

Cys Met Met Cys Tyr Lys Arg Asn Arg Ala Thr Arg Val Glu Cys Thr
225                 230                 235                 240

Thr Ile Val Asn Gly Val Arg Arg Ser Phe Tyr Val Tyr Ala Asn Gly
                245                 250                 255

Gly Lys Gly Phe Cys Lys Leu His Asn Trp Asn Cys Val Asn Cys Asp
            260                 265                 270

Thr Phe Cys Ala Gly Ser Thr Phe Ile Ser Asp Glu Val Ala Arg Asp
        275                 280                 285
```

```
Leu Ser Leu Gln Phe Lys Arg Pro Ile Asn Pro Thr Asp Gln Ser Ser
    290                 295                 300

Tyr Ile Val Asp Ser Val Thr Val Lys Asn Gly Ser Ile His Leu Tyr
305                 310                 315                 320

Phe Asp Lys Ala Gly Gln Lys Thr Tyr Glu Arg His Ser Leu Ser His
                325                 330                 335

Phe Val Asn Leu Asp Asn Leu Arg Ala Asn Asn Thr Lys Gly Ser Leu
            340                 345                 350

Pro Ile Asn Val Ile Val Phe Asp Gly Lys Ser Lys Cys Glu Glu Ser
        355                 360                 365

Ser Ala Lys Ser Ala Ser Val Tyr Tyr Ser Gln Leu Met Cys Gln Pro
    370                 375                 380

Ile Leu Leu Leu Asp Gln Ala Leu Val Ser Asp Val Gly Asp Ser Ala
385                 390                 395                 400

Glu Val Ala Val Lys Met Phe Asp Ala Tyr Val Asn Thr Phe Ser Ser
                405                 410                 415

Thr Phe Asn Val Pro Met Glu Lys Leu Lys Thr Leu Val Ala Thr Ala
            420                 425                 430

Glu Ala Glu Leu Ala Lys Asn Val Ser Leu Asp Asn Val Leu Ser Thr
        435                 440                 445

Phe Ile Ser Ala Ala Arg Gln Gly Phe Val Asp Ser Asp Val Glu Thr
    450                 455                 460

Lys Asp Val Val Glu Cys Leu Lys Leu Ser His Gln Ser Asp Ile Glu
465                 470                 475                 480

Val Thr Gly Asp Ser Cys Asn Asn Tyr Met Leu Thr Tyr Asn Lys Val
                485                 490                 495

Glu Asn Met Thr Pro Arg Asp Leu Gly Ala Cys Ile Asp Cys Ser Ala
            500                 505                 510

Arg His Ile Asn Ala Gln Val Ala Lys Ser His Asn Ile Ala Leu Ile
        515                 520                 525

Trp Asn Val Lys Asp Phe Met Ser Leu Ser Glu Gln Leu Arg Lys Gln
    530                 535                 540

Ile Arg Ser Ala Ala Lys Lys Asn Asn Leu Pro Phe Lys Leu Thr Cys
545                 550                 555                 560

Ala Thr Thr Arg Gln Val Val Asn Val Val Thr Thr Lys Ile Ala Leu
                565                 570                 575

Lys Gly Gly Lys Ile Val Asn Asn Trp Leu Lys Gln Leu Ile Lys Val
            580                 585                 590

Thr Leu Val Phe Leu Phe Val Ala Ala Ile Phe Tyr Leu Ile Thr Pro
        595                 600                 605

Val His Val Met Ser Lys His Thr Asp Phe Ser Ser Glu Ile Ile Gly
    610                 615                 620

Tyr Lys Ala Ile Asp Gly Gly Val Thr Arg Asp Ile Ala Ser Thr Asp
625                 630                 635                 640

Thr Cys Phe Ala Asn Lys His Ala Asp Phe Asp Thr Trp Phe Ser Gln
                645                 650                 655

Arg Gly Gly Ser Tyr Thr Asn Asp Lys Ala Cys Pro Leu Ile Ala Ala
            660                 665                 670

Val Ile Thr Arg Glu Val Gly Phe Val Val Pro Gly Leu Pro Gly Thr
        675                 680                 685

Ile Leu Arg Thr Thr Asn Gly Asp Phe Leu His Phe Leu Pro Arg Val
    690                 695                 700
```

```
Phe Ser Ala Val Gly Asn Ile Cys Tyr Thr Pro Ser Lys Leu Ile Glu
705                 710                 715                 720

Tyr Thr Asp Phe Ala Thr Ser Ala Cys Val Leu Ala Ala Glu Cys Thr
                725                 730                 735

Ile Phe Lys Asp Ala Ser Gly Lys Pro Val Pro Tyr Cys Tyr Asp Thr
            740                 745                 750

Asn Val Leu Glu Gly Ser Val Ala Tyr Glu Ser Leu Arg Pro Asp Thr
        755                 760                 765

Arg Tyr Val Leu Met Asp Gly Ser Ile Ile Gln Phe Pro Asn Thr Tyr
    770                 775                 780

Leu Glu Gly Ser Val Arg Val Val Thr Thr Phe Asp Ser Glu Tyr Cys
785                 790                 795                 800

Arg His Gly Thr Cys Glu Arg Ser Glu Ala Gly Val Cys Val Ser Thr
                805                 810                 815

Ser Gly Arg Trp Val Leu Asn Asn Asp Tyr Tyr Arg Ser Leu Pro Gly
            820                 825                 830

Val Phe Cys Gly Val Asp Ala Val Asn Leu Leu Thr Asn Met Phe Thr
        835                 840                 845

Pro Leu Ile Gln Pro Ile Gly Ala Leu Asp Ile Ser Ala Ser Ile Val
    850                 855                 860

Ala Gly Gly Ile Val Ala Ile Val Val Thr Cys Leu Ala Tyr Tyr Phe
865                 870                 875                 880

Met Arg Phe Arg Arg Ala Phe Gly Glu Tyr Ser His Val Val Ala Phe
                885                 890                 895

Asn Thr Leu Leu Phe Leu Met Ser Phe Thr Val Leu Cys Leu Thr Pro
            900                 905                 910

Val Tyr Ser Phe Leu Pro Gly Val Tyr Ser Val Ile Tyr Leu Tyr Leu
        915                 920                 925

Thr Phe Tyr Leu Thr Asn Asp Val Ser Phe Leu Ala His Ile Gln Trp
    930                 935                 940

Met Val Met Phe Thr Pro Leu Val Pro Phe Trp Ile Thr Ile Ala Tyr
945                 950                 955                 960

Ile Ile Cys Ile Ser Thr Lys His Phe Tyr Trp Phe Phe Ser Asn Tyr
                965                 970                 975

Leu Lys Arg Arg Val Val Phe Asn Gly Val Ser Phe Ser Thr Phe Glu
            980                 985                 990

Glu Ala Ala Leu Cys Thr Phe Leu  Leu Asn Lys Glu Met  Tyr Leu Lys
        995                 1000                1005

Leu Arg  Ser Asp Val Leu Leu  Pro Leu Thr Gln Tyr  Asn Arg Tyr
    1010                1015                1020

Leu Ala  Leu Tyr Asn Lys Tyr  Lys Tyr Phe Ser Gly  Ala Met Asp
    1025                1030                1035

Thr Thr  Ser Tyr Arg Glu Ala  Ala Cys Cys His Leu  Ala Lys Ala
    1040                1045                1050

Leu Asn  Asp Phe Ser Asn Ser  Gly Ser Asp Val Leu  Tyr Gln Pro
    1055                1060                1065

Pro Gln  Thr Ser Ile Thr Ser  Ala Val Leu Gln Ser  Ala Val Lys
    1070                1075                1080

Arg Thr  Ile Lys Gly Thr His  His Trp Leu Leu Leu  Thr Ile Leu
    1085                1090                1095

Thr Ser  Leu Leu Val Leu Val  Gln Ser Thr Gln Trp  Ser Leu Phe
    1100                1105                1110

Phe Phe  Leu Tyr Glu Asn Ala  Phe Leu Pro Phe Ala  Met Gly Ile
```

```
    1115                1120                1125

Ile Ala  Met Ser Ala Phe Ala  Met Met Phe Val Lys  His Lys His
    1130                1135                1140

Ala Phe  Leu Cys Leu Phe Leu  Leu Pro Ser Leu Ala  Thr Val Ala
    1145                1150                1155

Tyr Phe  Asn Met Val Tyr Met  Pro Ala Ser Trp Val  Met Arg Ile
    1160                1165                1170

Met Thr  Trp Leu Asp Met Val  Asp Thr Ser Leu Ser  Gly Phe Lys
    1175                1180                1185

Leu Lys  Asp Cys Val Met Tyr  Ala Ser Ala Val Val  Leu Leu Ile
    1190                1195                1200

Leu Met  Thr Ala Arg Thr Val  Tyr Asp Asp Gly Ala  Arg Arg Val
    1205                1210                1215

Trp Thr  Leu Met Asn Val Leu  Thr Leu Val Tyr Lys  Val Tyr Tyr
    1220                1225                1230

Gly Asn  Ala Leu Asp Gln Ala  Ile Ser Met Trp Ala  Leu Ile Ile
    1235                1240                1245

Ser Val  Thr Ser Asn Tyr Ser  Gly Val Val Thr Thr  Val Met Phe
    1250                1255                1260

Leu Ala  Arg Gly Ile Val Phe  Met Cys Val Glu Tyr  Cys Pro Ile
    1265                1270                1275

Phe Phe  Ile Thr Gly Asn Thr  Leu Gln Cys Ile Met  Leu Val Tyr
    1280                1285                1290

Cys Phe  Leu Gly Tyr Phe Cys  Thr Cys Tyr Phe Gly  Leu Phe Cys
    1295                1300                1305

Leu Leu  Asn Arg Tyr Phe Arg  Leu Thr Leu Gly Val  Tyr Asp Tyr
    1310                1315                1320

Leu Val  Ser Thr Gln Glu Phe  Arg Tyr Met Asn Ser  Gln Gly Leu
    1325                1330                1335

Leu Pro  Pro Lys Asn Ser Ile  Asp Ala Phe Lys Leu  Asn Ile Lys
    1340                1345                1350

Leu Leu  Gly Val Gly Gly Lys  Pro Cys Ile Lys Val  Ala Thr Val
    1355                1360                1365

Gln


<210> SEQ ID NO 27
<211> LENGTH: 1025
<212> TYPE: PRT
<213> ORGANISM: Artificial
<220> FEATURE:
<223> OTHER INFORMATION: Synthetic construct

<400> SEQUENCE: 27

Met Thr Asn Ser Arg Ile Lys Ala Ser Met Pro Thr Thr Ile Ala Lys
1               5                   10                  15

Asn Thr Val Lys Ser Val Gly Lys Phe Cys Leu Glu Ala Ser Phe Asn
            20                  25                  30

Tyr Leu Lys Ser Pro Asn Phe Ser Lys Leu Ile Asn Leu Met Ser Asn
        35                  40                  45

Leu Gly Met Pro Ser Tyr Cys Thr Gly Tyr Arg Glu Gly Tyr Leu Asn
    50                  55                  60

Ser Thr Asn Val Thr Ile Ala Thr Tyr Cys Thr Gly Ser Ile Pro Cys
65                  70                  75                  80

Ser Val Cys Leu Ser Gly Leu Asp Ser Leu Asp Thr Tyr Pro Ser Leu
                85                  90                  95
```

```
Glu Thr Ile Gln Ile Thr Ile Ser Ser Phe Lys Trp Asp Leu Thr Ala
            100                 105                 110

Phe Gly Leu Val Ala Glu Trp Ser Tyr Phe Ala Val His Phe Ile Ser
        115                 120                 125

Asn Ser Trp Leu Met Trp Leu Ile Ile Asn Leu Lys Ser Tyr Val His
    130                 135                 140

Val Val Asp Gly Cys Asn Ser Ser Thr Cys Met Met Cys Tyr Lys Arg
145                 150                 155                 160

Asn Arg Ala Thr Arg Val Glu Cys Thr Thr Ile Val Asn Gly Val Arg
                165                 170                 175

Arg Ser Phe Tyr Val Tyr Ala Asn Gly Gly Lys Gly Phe Cys Lys Leu
            180                 185                 190

His Asn Trp Asn Cys Val Asn Cys Asp Thr Phe Cys Ala Gly Ser Thr
        195                 200                 205

Phe Ile Ser Asp Glu Val Ala Arg Asp Leu Ser Leu Gln Phe Lys Arg
    210                 215                 220

Pro Ile Asn Pro Thr Asp Gln Ser Ser Tyr Ile Val Asp Ser Val Thr
225                 230                 235                 240

Val Lys Asn Gly Ser Ile His Leu Tyr Phe Asp Lys Ala Gly Gln Lys
                245                 250                 255

Thr Tyr Glu Arg His Ser Leu Ser His Phe Val Asn Leu Asp Asn Leu
            260                 265                 270

Arg Ala Asn Asn Thr Lys Gly Ser Leu Pro Ile Asn Val Ile Val Phe
        275                 280                 285

Asp Gly Lys Ser Lys Cys Glu Glu Ser Ser Ala Lys Ser Ala Ser Val
    290                 295                 300

Tyr Tyr Ser Gln Leu Met Cys Gln Pro Ile Leu Leu Leu Asp Gln Ala
305                 310                 315                 320

Leu Val Ser Asp Val Gly Asp Ser Ala Glu Val Ala Val Lys Met Phe
                325                 330                 335

Asp Ala Tyr Val Asn Thr Phe Ser Ser Thr Phe Asn Val Pro Met Glu
            340                 345                 350

Lys Leu Lys Thr Leu Val Ala Thr Ala Glu Ala Glu Leu Ala Lys Asn
        355                 360                 365

Val Ser Leu Asp Asn Val Leu Ser Thr Phe Ile Ser Ala Ala Arg Gln
    370                 375                 380

Gly Phe Val Asp Ser Asp Val Glu Thr Lys Asp Val Val Glu Cys Leu
385                 390                 395                 400

Lys Leu Ser His Gln Ser Asp Ile Glu Val Thr Gly Asp Ser Cys Asn
                405                 410                 415

Asn Tyr Met Leu Thr Tyr Asn Lys Val Glu Asn Met Thr Pro Arg Asp
            420                 425                 430

Leu Gly Ala Cys Ile Asp Cys Ser Ala Arg His Ile Asn Ala Gln Val
        435                 440                 445

Ala Lys Ser His Asn Ile Ala Leu Ile Trp Asn Val Lys Asp Phe Met
    450                 455                 460

Ser Leu Ser Glu Gln Leu Arg Lys Gln Ile Arg Ser Ala Ala Lys Lys
465                 470                 475                 480

Asn Asn Leu Pro Phe Lys Leu Thr Cys Ala Thr Thr Arg Gln Val Val
                485                 490                 495

Asn Val Val Thr Thr Lys Ile Ala Leu Lys Gly Gly Lys Ile Val Asn
            500                 505                 510
```

```
Asn Trp Ser Lys His Thr Asp Phe Ser Ser Glu Ile Ile Gly Tyr Lys
        515                 520                 525

Ala Ile Asp Gly Gly Val Thr Arg Asp Ile Ala Ser Thr Asp Thr Cys
    530                 535                 540

Phe Ala Asn Lys His Ala Asp Phe Asp Thr Trp Phe Ser Gln Arg Gly
545                 550                 555                 560

Gly Ser Tyr Thr Asn Asp Lys Ala Cys Pro Leu Ile Ala Ala Val Ile
                565                 570                 575

Thr Arg Glu Val Gly Phe Val Val Pro Gly Leu Pro Gly Thr Ile Leu
            580                 585                 590

Arg Thr Thr Asn Gly Asp Phe Leu His Phe Leu Pro Arg Val Phe Ser
        595                 600                 605

Ala Val Gly Asn Ile Cys Tyr Thr Pro Ser Lys Leu Ile Glu Tyr Thr
    610                 615                 620

Asp Phe Ala Thr Ser Ala Cys Val Leu Ala Ala Glu Cys Thr Ile Phe
625                 630                 635                 640

Lys Asp Ala Ser Gly Lys Pro Val Pro Tyr Cys Tyr Asp Thr Asn Val
                645                 650                 655

Leu Glu Gly Ser Val Ala Tyr Glu Ser Leu Arg Pro Asp Thr Arg Tyr
            660                 665                 670

Val Leu Met Asp Gly Ser Ile Ile Gln Phe Pro Asn Thr Tyr Leu Glu
        675                 680                 685

Gly Ser Val Arg Val Val Thr Thr Phe Asp Ser Glu Tyr Cys Arg His
    690                 695                 700

Gly Thr Cys Glu Arg Ser Glu Ala Gly Val Cys Val Ser Thr Ser Gly
705                 710                 715                 720

Arg Trp Val Leu Asn Asn Asp Tyr Tyr Arg Ser Leu Pro Gly Val Phe
                725                 730                 735

Cys Gly Val Pro Leu Ile Gln Pro Ile Gly Ala Leu Asp Arg Phe Arg
            740                 745                 750

Arg Ala Phe Gly Glu Tyr Ser His Ser Phe Leu Pro Gly His Ile Gln
        755                 760                 765

Trp Met Val Met Phe Thr Pro Leu Trp Phe Phe Ser Asn Tyr Leu Lys
    770                 775                 780

Arg Arg Val Asn Lys Glu Met Tyr Leu Lys Leu Arg Ser Asp Val Leu
785                 790                 795                 800

Leu Pro Leu Thr Gln Tyr Asn Arg Tyr Leu Ala Leu Tyr Asn Lys Tyr
                805                 810                 815

Lys Tyr Phe Ser Gly Ala Met Asp Thr Thr Ser Tyr Arg Glu Ala Ala
            820                 825                 830

Cys Cys His Leu Ala Lys Ala Leu Asn Asp Phe Ser Asn Ser Gly Ser
        835                 840                 845

Asp Val Leu Tyr Gln Pro Pro Gln Thr Ser Ile Thr Ser Ala Val Leu
    850                 855                 860

Gln Ser Ala Val Lys Arg Thr Ile Lys Gly Thr His Leu Tyr Glu Asn
865                 870                 875                 880

Ala Lys His Lys His Ala Phe Ser Trp Val Met Arg Ile Met Thr Trp
                885                 890                 895

Leu Asp Met Val Asp Thr Ser Leu Ser Gly Phe Lys Leu Lys Asp Cys
            900                 905                 910

Asp Asp Gly Ala Arg Arg Val Trp Thr Leu Met Asn Val Leu Thr Leu
        915                 920                 925

Val Ala Leu Asp Gln Ala Ile Ser Met Trp Ala Leu Ile Ile Ser Val
```

930 935 940

Arg Gly Ile Val Phe Met Cys Val Glu Tyr Cys Cys Thr Cys Tyr Phe
945 950 955 960

Gly Leu Phe Cys Leu Leu Asn Arg Tyr Phe Arg Leu Thr Leu Gly Val
965 970 975

Tyr Asp Tyr Leu Val Ser Thr Gln Glu Phe Arg Tyr Met Asn Ser Gln
980 985 990

Gly Leu Leu Pro Pro Lys Asn Ser Ile Asp Ala Phe Lys Leu Asn Ile
995 1000 1005

Lys Leu Leu Gly Val Gly Gly Lys Pro Cys Ile Lys Val Ala Thr
1010 1015 1020

Val Gln
1025

<210> SEQ ID NO 28
<211> LENGTH: 987
<212> TYPE: PRT
<213> ORGANISM: Artificial
<220> FEATURE:
<223> OTHER INFORMATION: Synthetic construct

<400> SEQUENCE: 28

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro

```
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Lys Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ser Arg Ala Arg Ser Val Ala
        675                 680                 685
```

```
Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro
            980                 985
```

<210> SEQ ID NO 29
<211> LENGTH: 987
<212> TYPE: PRT
<213> ORGANISM: Artificial
<220> FEATURE:
<223> OTHER INFORMATION: Synthetic construct

<400> SEQUENCE: 29

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60
```

```
Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Asn Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480
```

```
Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ser Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
```

900 905 910

Gln Asn Val Leu Tyr Glu Asn Gln Lys Leu Ile Ala Asn Gln Phe Asn
915 920 925

Ser Ala Ile Gly Lys Ile Gln Asp Ser Leu Ser Ser Thr Ala Ser Ala
930 935 940

Leu Gly Lys Leu Gln Asp Val Val Asn Gln Asn Ala Gln Ala Leu Asn
945 950 955 960

Thr Leu Val Lys Gln Leu Ser Ser Asn Phe Gly Ala Ile Ser Ser Val
965 970 975

Leu Asn Asp Ile Leu Ser Arg Leu Asp Pro Pro
980 985

<210> SEQ ID NO 30
<211> LENGTH: 987
<212> TYPE: PRT
<213> ORGANISM: Artificial
<220> FEATURE:
<223> OTHER INFORMATION: Synthetic construct

<400> SEQUENCE: 30

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala

-continued

```
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Tyr Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ser Arg Ala Arg Ser Val Ala
        675                 680                 685

Ser Gln Ser Ile Ile Ala Tyr Thr Met Ser Leu Gly Ala Glu Asn Ser
    690                 695                 700
```

Val Ala Tyr Ser Asn Asn Ser Ile Ala Ile Pro Thr Asn Phe Thr Ile
705 710 715 720

Ser Val Thr Thr Glu Ile Leu Pro Val Ser Met Thr Lys Thr Ser Val
725 730 735

Asp Cys Thr Met Tyr Ile Cys Gly Asp Ser Thr Glu Cys Ser Asn Leu
740 745 750

Leu Leu Gln Tyr Gly Ser Phe Cys Thr Gln Leu Asn Arg Ala Leu Thr
755 760 765

Gly Ile Ala Val Glu Gln Asp Lys Asn Thr Gln Glu Val Phe Ala Gln
770 775 780

Val Lys Gln Ile Tyr Lys Thr Pro Pro Ile Lys Asp Phe Gly Gly Phe
785 790 795 800

Asn Phe Ser Gln Ile Leu Pro Asp Pro Ser Lys Pro Ser Lys Arg Ser
805 810 815

Phe Ile Glu Asp Leu Leu Phe Asn Lys Val Thr Leu Ala Asp Ala Gly
820 825 830

Phe Ile Lys Gln Tyr Gly Asp Cys Leu Gly Asp Ile Ala Ala Arg Asp
835 840 845

Leu Ile Cys Ala Gln Lys Phe Asn Gly Leu Thr Val Leu Pro Pro Leu
850 855 860

Leu Thr Asp Glu Met Ile Ala Gln Tyr Thr Ser Ala Leu Leu Ala Gly
865 870 875 880

Thr Ile Thr Ser Gly Trp Thr Phe Gly Ala Gly Ala Ala Leu Gln Ile
885 890 895

Pro Phe Ala Met Gln Met Ala Tyr Arg Phe Asn Gly Ile Gly Val Thr
900 905 910

Gln Asn Val Leu Tyr Glu Asn Gln Lys Leu Ile Ala Asn Gln Phe Asn
915 920 925

Ser Ala Ile Gly Lys Ile Gln Asp Ser Leu Ser Ser Thr Ala Ser Ala
930 935 940

Leu Gly Lys Leu Gln Asp Val Val Asn Gln Asn Ala Gln Ala Leu Asn
945 950 955 960

Thr Leu Val Lys Gln Leu Ser Ser Asn Phe Gly Ala Ile Ser Ser Val
965 970 975

Leu Asn Asp Ile Leu Ser Arg Leu Asp Pro Pro
980 985

<210> SEQ ID NO 31
<211> LENGTH: 16
<212> TYPE: PRT
<213> ORGANISM: Artificial
<220> FEATURE:
<223> OTHER INFORMATION: Synthetic construct

<400> SEQUENCE: 31

Trp Leu Gln Gly Leu Leu Leu Leu Gly Thr Val Ala Cys Ser Ile Ser
1 5 10 15

<210> SEQ ID NO 32
<211> LENGTH: 6
<212> TYPE: PRT
<213> ORGANISM: Artificial
<220> FEATURE:
<223> OTHER INFORMATION: Synthetic construct

<400> SEQUENCE: 32

Gly Gly Gly Gly Gly Gly

```
1               5


<210> SEQ ID NO 33
<211> LENGTH: 5
<212> TYPE: PRT
<213> ORGANISM: Artificial
<220> FEATURE:
<223> OTHER INFORMATION: Synthetic construct

<400> SEQUENCE: 33

Gly Gly Gly Gly Thr
1               5


<210> SEQ ID NO 34
<211> LENGTH: 6
<212> TYPE: PRT
<213> ORGANISM: Artificial
<220> FEATURE:
<223> OTHER INFORMATION: Synthetic construct

<400> SEQUENCE: 34

Gly Gly Gly Pro Pro Pro
1               5


<210> SEQ ID NO 35
<211> LENGTH: 7
<212> TYPE: PRT
<213> ORGANISM: Artificial
<220> FEATURE:
<223> OTHER INFORMATION: Synthetic construct

<400> SEQUENCE: 35

Gly Gly Gly Ala Pro Pro Pro
1               5
```